United States Patent
Mastaitis et al.

(10) Patent No.: US 12,371,475 B2
(45) Date of Patent: Jul. 29, 2025

(54) NUCLEIC ACIDS ENCODING ANCHOR MODIFIED ANTIBODIES AND USES THEREOF

(71) Applicant: Regeneron Pharmaceuticals, Inc., Tarrytown, NY (US)

(72) Inventors: Jason Mastaitis, Yorktown Heights, NY (US); Andrew J. Murphy, Croton-on-Hudson, NY (US); John McWhirter, Savannah, GA (US); Vera Voronina, North Bethesda, MD (US); Jesper Gromada, Concord, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 316 days.

(21) Appl. No.: 17/555,616

(22) Filed: Dec. 20, 2021

(65) Prior Publication Data

US 2022/0195014 A1   Jun. 23, 2022

Related U.S. Application Data

(60) Provisional application No. 63/219,402, filed on Jul. 8, 2021, provisional application No. 63/129,893, filed on Dec. 23, 2020.

(51) Int. Cl.
| | | |
|---|---|---|
| C07K 16/00 | (2006.01) | |
| A01K 67/0275 | (2024.01) | |
| C07K 14/58 | (2006.01) | |
| C07K 14/72 | (2006.01) | |
| C07K 16/26 | (2006.01) | |
| C12N 9/22 | (2006.01) | |
| C12N 15/11 | (2006.01) | |
| C12N 15/90 | (2006.01) | |

(52) U.S. Cl.
CPC .......... *C07K 16/00* (2013.01); *A01K 67/0275* (2013.01); *C07K 14/58* (2013.01); *C07K 14/72* (2013.01); *C07K 16/26* (2013.01); *C12N 9/22* (2013.01); *C12N 15/11* (2013.01); *C12N 15/907* (2013.01); *A01K 2217/07* (2013.01); *A01K 2227/105* (2013.01); *A01K 2267/01* (2013.01); *C07K 2317/56* (2013.01); *C07K 2317/76* (2013.01); *C12N 2310/20* (2017.05)

(58) Field of Classification Search
CPC .. C07K 16/00; C07K 2319/02; C07K 14/723; C07K 2317/56; C07K 14/58
See application file for complete search history.

(56) References Cited

U.S. PATENT DOCUMENTS

| | | | |
|---|---|---|---|
| 5,569,825 A | 10/1996 | Lonberg et al. | |
| 5,633,425 A | 5/1997 | Lonberg et al. | |
| 5,698,679 A | 12/1997 | Nemazee et al. | |
| 5,731,168 A | 3/1998 | Carter et al. | |
| 5,770,429 A | 6/1998 | Lonberg et al. | |
| 5,807,706 A | 9/1998 | Carter et al. | |
| 5,814,318 A | 9/1998 | Lonberg et al. | |
| 5,821,333 A | 10/1998 | Carter et al. | |
| 6,075,181 A | 6/2000 | Kucherlapati et al. | |
| 6,114,598 A | 9/2000 | Kucherlapati et al. | |
| 6,150,584 A | 11/2000 | Kucherlapati et al. | |
| 6,586,251 B2 | 7/2003 | Economides et al. | |
| 6,596,541 B2 | 7/2003 | Murphy et al. | |
| 6,998,514 B2 | 2/2006 | Bruggemann et al. | |
| 7,582,298 B2 | 9/2009 | Stevens et al. | |
| 7,642,228 B2 | 1/2010 | Carter et al. | |
| 7,795,494 B2 | 9/2010 | Ghayur | |
| 7,910,798 B2 | 3/2011 | Tanamachi et al. | |
| 8,232,449 B2 | 7/2012 | Tanamachi et al. | |
| 8,502,018 B2 | 8/2013 | Murphy et al. | |
| 8,642,835 B2 | 2/2014 | Macdonald et al. | |
| 8,679,785 B2 | 3/2014 | Carter et al. | |

(Continued)

FOREIGN PATENT DOCUMENTS

| | | |
|---|---|---|
| EP | 3128009 B1 | 7/2020 |
| WO | 2007/117410 A2 | 10/2007 |

(Continued)

OTHER PUBLICATIONS

Alt et al. "Immunoglobulin genes in transgenic mice," Trends Genet., 1985, 1:231-236.
Altschul et al., "Basic Local Alignment Search Tool," J. Mol. Biol., 1990, 215(3): 403-410.
Altschul and Gish, "[27] Local Alignment Statistics," Methods in Enzymol., 1996, 266:460-480.
Altschul et al., "Gapped BLAST and PSI-BLAST: a new generation of protein database search programs," Nucleic Acids Res., 1997, 25:3389-3402.
Auerbach et al. "Establishment and Chimera Analysis of 129/SvEv- and C57BL/6-Derived. Mouse Embryonic Stem Cell Lines," Biotechniques, 2000, 29(5):1024-1028, 1030, 1032.

(Continued)

*Primary Examiner* — Daniel E Kolker
*Assistant Examiner* — Maureen Varina Driscoll
(74) *Attorney, Agent, or Firm* — FisherBroyles, LLP; Rita S. Wu; Elysa Goldberg

(57) ABSTRACT

Described herein are anchor-modified immunoglobulin polypeptides, wherein the anchor moors the immunoglobulin polypeptide to a receptor of interest. The anchor-modified immunoglobulin polypeptides are generally characterized at the N-terminus with an anchor, e.g., the receptor binding portion of a ligand that binds a receptor. Non-human animals genetically modified with recombinant immunoglobulin segments that encode the anchor-modified immunoglobulin polypeptides are capable of making the anchor-modified immunoglobulin polypeptides. Such non-human animals also provided, along with methods and compositions for making and using the non-human animals. Methods for producing anchor-modified immunoglobulins from non-human animals are also provided, as well as anchor-modified immunoglobulins generated therefrom.

27 Claims, 23 Drawing Sheets

Specification includes a Sequence Listing.

(56) References Cited

U.S. PATENT DOCUMENTS

| | | |
|---|---|---|
| 8,697,940 B2 | 4/2014 | Macdonald et al. |
| 8,703,485 B2 | 4/2014 | Buelow |
| 8,754,287 B2 | 6/2014 | Macdonald et al. |
| 8,791,323 B2 | 7/2014 | Murphy et al. |
| 8,809,051 B2 | 8/2014 | Jakobovits et al. |
| 8,907,157 B2 | 12/2014 | Buelow |
| 9,035,128 B2 | 5/2015 | Macdonald et al. |
| 9,145,588 B2 | 9/2015 | Throsby et al. |
| 9,204,624 B2 | 12/2015 | McWhirter et al. |
| 9,206,263 B2 | 12/2015 | Macdonald et al. |
| 9,226,484 B2 | 1/2016 | Macdonald et al. |
| 9,301,510 B2 | 4/2016 | McWhirter et al. |
| 9,332,742 B2 | 5/2016 | McWhirter et al. |
| 9,334,334 B2 | 5/2016 | McWhirter et al. |
| 9,447,177 B2 | 9/2016 | Bradley et al. |
| 9,516,868 B2 | 12/2016 | Macdonald et al. |
| 9,551,124 B2 | 1/2017 | Bourgeois |
| 9,580,491 B2 | 2/2017 | Green et al. |
| 9,796,788 B2 | 10/2017 | McWhirter et al. |
| 9,801,362 B2 | 10/2017 | McWhirter et al. |
| 9,969,814 B2 | 5/2018 | McWhirter et al. |
| 10,130,081 B2 | 11/2018 | McWhirter et al. |
| 10,143,186 B2 | 12/2018 | McWhirter et al. |
| 2003/0232395 A1* | 12/2003 | Hufton ............ C12N 15/81 435/254.2 |
| 2007/0004909 A1 | 1/2007 | Johnson et al. |
| 2009/0060910 A1 | 3/2009 | Johnson et al. |
| 2010/0146647 A1 | 6/2010 | Logtenberg et al. |
| 2011/0195454 A1 | 8/2011 | McWhirter et al. |
| 2012/0021409 A1 | 1/2012 | McWhirter et al. |
| 2012/0164068 A1* | 6/2012 | Hudson ............... A61P 9/00 424/1.49 |
| 2012/0192300 A1 | 7/2012 | Babb et al. |
| 2013/0045492 A1 | 2/2013 | Babb et al. |
| 2013/0096287 A1* | 4/2013 | Macdonald ......... A61P 31/10 536/23.53 |
| 2013/0167256 A1 | 6/2013 | Green et al. |
| 2013/0185821 A1 | 7/2013 | Babb et al. |
| 2013/0195849 A1 | 8/2013 | Spreter von Kreudenstein et al. |
| 2013/0198880 A1 | 8/2013 | McWhirter et al. |
| 2013/0219535 A1 | 8/2013 | Wabl et al. |
| 2013/0302836 A1 | 11/2013 | McWhirter et al. |
| 2013/0326647 A1 | 12/2013 | Macdonald et al. |
| 2013/0333057 A1* | 12/2013 | Macdonald ........ A01K 67/0276 800/21 |
| 2014/0013456 A1 | 1/2014 | McWhirter et al. |
| 2015/0059009 A1 | 2/2015 | McWhirter et al. |
| 2015/0113668 A1 | 4/2015 | Bruggemann et al. |
| 2015/0289489 A1 | 10/2015 | Macdonald et al. |
| 2015/0313193 A1 | 11/2015 | McWhirter et al. |
| 2015/0376628 A1 | 12/2015 | Schoenherr et al. |
| 2016/0145646 A1 | 5/2016 | Frendewey et al. |
| 2016/0177339 A1 | 6/2016 | Voronina et al. |
| 2018/0125043 A1 | 5/2018 | Guo et al. |
| 2018/0244804 A1 | 8/2018 | Macdonald et al. |

FOREIGN PATENT DOCUMENTS

| | | |
|---|---|---|
| WO | 2008/124086 A2 | 10/2008 |
| WO | 2008/151081 A1 | 12/2008 |
| WO | 2009/114400 A1 | 9/2009 |
| WO | 2009/157771 A2 | 12/2009 |
| WO | 2010/039900 A2 | 4/2010 |
| WO | 2011/004192 A1 | 1/2011 |
| WO | 2011/097603 A1 | 8/2011 |
| WO | 2011/123708 A2 | 10/2011 |
| WO | 2011/163314 A1 | 12/2011 |
| WO | 2012/148873 A2 | 11/2012 |
| WO | 2013/134263 A1 | 9/2013 |
| WO | 2013/184761 A1 | 12/2013 |
| WO | 2014/093908 A2 | 6/2014 |
| WO | 2014/160179 A1 | 10/2014 |
| WO | 2014/160202 A1 | 10/2014 |
| WO | 2017/210586 A1 | 12/2017 |
| WO | 2019/113065 A1 | 6/2019 |
| WO | WO-2020072937 A1 * | 4/2020 |

OTHER PUBLICATIONS

Azzazy and Highsmith "Phage display technology: clinical applications and recent innovations," Clin. Biochem., 2002, 35:425-445.

Barbié and Lefranc, "The Human Immunoglobulin Kappa Variable (IGKV) Genes and Joining (IGKJ) Segments," Exp. Clin. Immunogenet., 1998, 15:171-183.

Collins and Bercik, "Intestinal bacteria influence brain activity in healthy humans," Nature Reviews, Gastroenterology & Hepatology, Jun. 2013, 10:326-327.

Dechiara et al. "VelociMouse: Fully ES Cell-Derived FO-Generation Mice Obtained from the Injection of ES Cells into Eight-Cell-Stage Embryos," Methods Mol. Biol., 2009, 530:311-324.

Dechiara et al. "Producing Fully ES Cell-Derived Mice from Eight-Cell Stage Embryo Injections," Methods Enzymol., 2010, 476:285-294.

Festing et al. "Revised nomenclature for strain 129 mice," Mammalian Genome, 1999, 10:836.

Frendewey et al. "The Loss-of-Allele Assay for ES Cell Screening and Mouse Genotyping," Methods Enzymol., 2010, 476:295-307.

Gavilondo and Larrick, "Antibody Engineering at the Millennium," BioTechniques, 2002, 29:128-145.

Gonnet et al., "Exhaustive Matching of the Entire Protein Sequence Database," Science, Jun. 5, 1992, 256:1443-1445.

Green et al. "Antigen-specific human monoclonal antibodies from mice engineered with human Ig heavy and light chain YACs," Nat. Genet., 1994, 7:13-21.

He et al. "Structural Determinants of Natriuretic Peptide Receptor Specificity and Degeneracy," J. Mol. Biol., 2006, 361:698-714.

Hiom and Gellert, "Assembly of a 12/23 Paired Signal Complex: A Critical Control Point in V(D)J Recombination," Mol. Cell., 1998, 1(7):1011-1019.

Hoogenboom, "Designing and optimizing library selection strategies for generating high-affinity antibodies," TIB Tech., 1997, 15:62-70.

Hoogenboom and Chames, "Natural and designer binding sites made by phage display technology," Immunology Today, 2000, 21:371-378.

Jakobovits et al. "From XenoMouse technology to panitumumab, the first fully human antibody product from transgenic mice," Nat. Biotechnol., 2007, 25:1134-1143.

Jaubert et al. "Three new allelic mouse mutations that cause skeletal overgrowth involve the natriuretic peptide receptor C gene (Npr3)," PNAS, 1999, 96(18) 10278-10283.

Kellermann and Green "Antibody discovery: the use of transgenic mice to generate human monoclonal antibodies for therapeutics," Current Opinion in Biotechnology, 2002, 13:593-597.

Kitano et al., "Production of polyclonal antibody specific for human natriuretic peptide receptor B," Journal of Immunological Methods, Elsevier Science Publishers B.V., Amsterdam, NL, Aug. 14, 1996, 194(2):147-153.

Lakso et al., "Targeted oncogene activation by site-specific recombination in transgenic mice," Proc. Natl. Acad. Sci. USA, 1992, 89:6232-6236.

Lee et al. "Complete humanization of the mouse immunoglobulin loci enables efficient therapeutic antibody discovery," Nature Biotechnology, 2014, 32(4):356 (12 pages).

Lefranc, "Nomenclature of the Human Immunoglobulin Heavy (IGH) Genes," Exp. Clin. Immunogenet., 2001, 18:100-116.

Lefranc et al., "IMGT unique numbering for immunoglobulin and T cell receptor variable domains and Ig superfamily V-like domains," Dev. Comp. Immunol., 2003, 27:55-77.

Lefranc and Lefranc "Immunoglobulins or Antibodies: IMGT® Bridging Genes, Structures and Functions," Biomedicines, 2020, 8(319):1-117.

Li et al. "Minimization of a Peptide Hormone," Science, 1995, 270:1657-1660.

(56) References Cited

OTHER PUBLICATIONS

Little et al. Of mice and men: hybridoma and recombinant antibodies, Immunology Today, 2000, 21(8):364-370.
Lonberg et al. "Antigen-specific human antibodies from mice comprising four distinct genetic modifications," Nature, 1994, 368:856-859.
Macdonald et al. "Precise and in situ genetic humanization of 6 Mb of mouse immunoglobulin genes," Proc. Natl. Acad. Sci. USA, 2014, 111:5147-5152 with supplemental pages (18 pages).
Mangiafico et al. "Neutral endopeptidase inhibition and the natriuretic peptide system: an evolving strategy in cardiovascular therapeutics," European Heart Journal, 2013, 34:886-893.
Martinez and Lefranc "The Mouse (*Mus musculus*) Immunoglobulin Kappa Variable (IGKV) Genes and Joining (IGKJ) Segments," Exp. Clin. Immunogenet., 1998, 15:184-193.
Matsukawa et al., "The natriuretic peptide clearance receptor locally modulates the physiological effects of the natriuretic peptide system," Proc. Natl. Acad. Sci. USA, 1999, 96:7403-7408.
Misono "Natriuretic peptides and their receptors," Febs J., 2011, 278:1791.
Misono et al. "Structure, signaling mechanism and regulation of the natriuretic peptide receptor guanylate cyclase," Febs J., 2011, 278:1818-1829.
Murphy et al., "Mice with megabase humanization of their immunoglobulin genes generate antibodies as efficiently as normal mice," Proc. Natl. Acad. Sci. U. S. A., 2014, 111(14):5153-5158 with supplemental pages (12 pages).
O'Gorman et al, "Recombinase-Mediated Gene Activation and Site-Specific Integration in Mammalian Cells," Science, 1991, 251:1351-1355.
Pallarès et al., "The Human Immunoglobulin Lambda Variable (IGLV) Genes and Joining (IGLJ) Segments," Exp. Clin. Immunogenet., 1998, 15:8-18.
Pallarès et al.,"The Human Immunoglobulin Heavy Variable Genes," Exp. Clin. Immunogenet., 1999, 16:36-60.
Pandit et al. "Natriuretic peptides: Diagnostic and therapeutic use," Ind. J. Endocrinol. Metab., 2011, 15(4):S345-S353.
Potter et al., "Natriuretic Peptides, Their Receptors, and Cyclic Guanosine Monophosphate-Dependent Signaling Functions," Endocrine Reviews, 2006, 27(1):47-72.
Poueymirou et al. "F0 generation mice fully derived from gene-targeted embryonic stem cells allowing immedite phenotypic analyses," Nat. Biotechnol., 2007, 25:91-99.
Ramsden et al., "Conservation of sequence in recombination signal sequence spacers," Nuc. Acids Res., 1994, 22(10):1785-1796.
Ruiz et al. "The Human Immunoglobulin Heavy Diversity (IGHD) and Joining (IGHJ) Segments," Exp. Clin. Immunogenet., 1999, 16:173-184.
Taylor et al., "A transgenic mouse that expresses a diversity of human sequence heavy chain and light chain immunoglobulins," Nucl. Acids Res., 1992, 20:6287-6295.
Tian et al. "Induction of HIV Neutralizing Antibody Lineages in Mice with Diverse Precursor Repertoires," Cell, 2016, 166:1471-1484.
Tomizuka et al. "Double trans-chromosomic mice: maintenance of two individual human chromosome fragments containing Ig heavy and kappa loci and expression of fully human antibodies," PNAS USA, 2000, 97:722-727.
Tscheuschner et al. "Fast Confirmation of Antibody Identity by MALDI-TOF MS Fingerprints," Antibodies, 2020, 9(2):8 (17 pages).
Valenzuela et al. "High-throughput engineering of the mouse genome coupled with high-resolution expression analysis," Nature Biotech., 2003, 21(6):652-659.
Wang and Stollar "Human immunoglobulin variable region gene analysis by single cell RT-PCR," Journal of Immunological Methods, 2000, 244:217-225.
Wu et al., "Structure and Function of Peptide-Binding G Protein-Coupled Receptors," J. Mol. Biol., 2017, 429:2726-2745.
Zhang et al., "Pentamerization of Single-domain Antibodies from Phage Libraries: A Novel Strategy for the Rapid Generation of High-avidity Antibody Reagents," Journal of Molecular Biology, Academic Press, United Kingdom, Jan. 2, 2004, 335(1):49-56.
Written Opinion of the International Searching Authority and International Search Report with respect to PCT/US2021/064263, dated Apr. 28, 2022.

* cited by examiner

NUCLEIC ACIDS ENCODING ANCHOR MODIFIED ANTIBODIES AND USES THEREOF

CROSS-REFERENCE TO RELATED APPLICATIONS

This application claims the benefit under 35 USC § 119(e) of U.S. Provisional Application Ser. No. 63/129,893, filed Dec. 23, 2020, and U.S. Provisional Application Ser. No. 63/219,402, filed Jul. 8, 2021 each of which applications is hereby incorporated by reference.

SEQUENCE LISTING

The Sequence Listing written in file 10507US01_ST25.txt is 47 kilobytes, was created on Dec. 17, 2021, and is hereby incorporated in its entirety by reference.

BACKGROUND

Monoclonal antibody products have revolutionized the biopharmaceutical industry and achieved significant advances in the treatment of several diseases. Despite these advances and the knowledge gained by the use of monoclonal antibodies for therapeutic use, diseases linked to targets that are difficult for monoclonal antibodies to bind and/or access persist, which highlights the need for different approaches for developing effective treatments.

SUMMARY

Disclosed herein is the recognition that it is desirable to engineer non-human animals as improved in vivo systems for identifying and developing new antibody-based therapeutics and, in some embodiments, antibodies (e.g., monoclonal antibodies and/or fragments thereof), which can be used for the treatment of a variety of diseases. The nucleic acids, non-human animals, methods, and polypeptides disclosed herein relate to anchor-modified immunoglobulins. An anchor as described herein generally comprises the receptor binding portion of a non-immunoglobulin polypeptide that binds a cognate receptor. Anchors appended to immunoglobulin help to increase the affinity of the immunoglobulin to the cognate receptor of the anchor, thus improving the binding properties of the immunoglobulin. Described herein are nucleic acid molecules that encode anchor-modified immunoglobulins and/or may be used to modify non-human animals such that the non-human animals may make anchor-modified immunoglobulins de novo.

An anchor-modified immunoglobulin described herein may be encoded, at least in part, by a variable region (V) segment, e.g., an immunoglobulin (Ig) heavy chain variable region ($V_H$) segment or an Ig light chain variable region ($V_L$) segment, modified to encode the anchor in between and in operable linkage to: an Ig leader sequence and the framework (FR) and complementarity determining region (CDR) sequences of a germline V segment.

Accordingly, nucleic acid molecules, including targeting vectors and non-human animal genomes, comprising the unrearranged or rearranged modified Ig V segment are also described. Also described are non-human animal genomes, non-human animal cells, and non-human animals that comprise the nucleic acid molecules described herein.

A recombinant nucleic acid molecule described herein may comprise a modified immunoglobulin (Ig) variable (V) segment that encodes an anchor modified Ig polypeptide, wherein the modified Ig V segment comprises a nucleic acid sequence encoding the anchor between a nucleic acid sequence encoding an Ig signal peptide and a nucleic acid sequence encoding the framework region (FR) 1, complementarity determining region (CDR)1, FR2, CDR2, FR3, and CDR3 of a germline Ig V segment or a variant thereof, wherein the anchor-modified Ig polypeptide comprises in operable linkage: (i) the Ig signal peptide, (ii) the anchor, and (iii) the FR1, CDR1, FR2, CDR2, FR3, and CDR3 of the germline Ig V segment or a variant thereof, wherein the anchor comprises a receptor binding portion of a non-immunoglobulin polypeptide of interest that binds a cognate receptor, and optionally wherein the recombinant nucleic acid molecule lacks any other V segments. The recombinant nucleic acid molecules described herein may also comprise one or more (un)rearranged Ig diversity (D) segment(s), one or more (un)rearranged Ig joining (J) segment(s) and/or one or more Ig constant region (C) genes.

In some embodiments, the Ig signal peptide is the Ig signal peptide of the germline Ig V segment, or variant thereof. In some embodiments, the Ig signal peptide comprises the sequence MDWTWRFLFVVAAATGVQS (SEQ ID NO:7). In some embodiments, the anchor comprises a linker that links the receptor binding portion of a non-immunoglobulin polypeptide of interest to the FR1, CDR1, FR2, CDR2, FR3, and CDR3 of the germline Ig V segment, or a variant thereof. In some linker embodiments, the linker comprises the sequence GGGGS (SEQ ID NO:5)

In some embodiments, the germline Ig V segment or variant thereof, is a germline Ig heavy chain variable ($V_H$) segment or variant thereof, e.g., is a human (h) germline Ig V segment or variant thereof, e.g., a germline human (h) $V_H$1-2 segment, a germline h$V_H$1-3 segment, a germline h$V_H$1-8 segment, a germline h$V_H$1 18 segment, a germline h$V_H$1-24 segment, a germline h$V_H$1-45 segment, a germline h$V_H$1-46 segment, a germline h$V_H$1-58 segment, a germline h$V_H$1-69 segment, a germline h$V_H$2-5 segment, a germline h$V_H$2-26 segment, a germline h$V_H$2-70 segment, a germline h$V_H$3-7 segment, a germline h$V_H$3-9 segment, a germline h$V_H$3-11 segment, a germline h$V_H$3 13 segment, a germline h$V_H$3-15 segment, a germline h$V_H$3-16 segment, a germline h$V_H$3-20 segment, a germline h$V_H$3-21 segment, a germline h$V_H$3-23 segment, a germline h$V_H$3-30 segment, a germline h$V_H$3-30-3 segment, a germline h$V_H$3-30-5 segment, a germline h$V_H$3-33 segment, a germline h$V_H$3-35 segment, a germline h$V_H$3-38 segment, a germline h$V_H$3-43 segment, a germline h$V_H$3-48 segment, a germline h$V_H$3-49 segment, a germline h$V_H$3-53 segment, a germline h$V_H$3-64 segment, a germline h$V_H$3-66 segment, a germline h$V_H$3-72 segment, a germline h$V_H$3-73 segment, a germline h$V_H$3-74 segment, a germline h$V_H$4-4 segment, a germline h$V_H$4-28 segment, a germline h$V_H$4-30-1 segment, a germline h$V_H$4 30-2 segment, a germline h$V_H$4-30-4 segment, a germline h$V_H$4-31 segment, a germline h$V_H$4-34 segment, a germline h$V_H$4-39 segment, a germline h$V_H$4-59 segment, a germline h$V_H$4-61 segment, a germline h$V_H$5-51 segment, a germline h$V_H$6-1 segment, a germline h$V_H$7-4-1 segment, a germline h$V_H$7-81 segment, or variants thereof. In some embodiments, the germline Ig V segment or variant thereof is a germline h$V_H$1-69 segment or variant thereof. In some embodiments, the variant is an allelic variant.

In some embodiments, a recombinant nucleic acid molecule may comprise a heavy chain variable region locus, e.g., may comprise in operable linkage and from 5' to 3': (I) the modified Ig $V_H$ segment, (II) one or a plurality of Ig heavy chain diversity ($D_H$) segments, and (III) one or a plurality of Ig heavy chain joining ($J_H$) segments. In some embodiments, the one or a plurality of Ig $D_H$ segments of (II) comprises one, a plurality of, or all human Ig $D_H$ segments, and/or the one or a plurality of Ig $J_H$ segments of (III) comprises one, a plurality of, or all human Ig $J_H$ segments. In some embodiments, the one or a plurality of Ig $D_H$ segments of (II) and the one or a plurality of Ig $J_H$ gene segments of (III) are recombined and form a rearranged Ig $D_H/J_H$ sequence such that the recombinant nucleic acid molecule comprises in operable linkage and from 5' to 3': the modified Ig $V_H$ gene segment and the rearranged Ig $D_H/J_H$ sequence.

In some embodiments, the modified Ig $V_H$ gene segment and the rearranged Ig $D_H/J_H$ sequence are recombined and form a rearranged Ig $V_H/D_H/J_H$ sequence that encodes an anchor modified Ig heavy chain variable domain, wherein the anchor modified Ig heavy chain variable domain comprises in operable linkage: (i) the Ig signal peptide, (ii) the anchor, and (iii) the FR1, complementarity determining region (CDR) 1, FR2, CDR2, FR3, CDR3, and FR4 encoded by the rearranged Ig $V_H/D_H/J_H$ sequence.

In some embodiments, the modified Ig $V_H$ segment is an unrearranged modified Ig $V_H$ gene segment.

In some embodiments, a recombinant nucleic acid disclosed herein further comprises a nucleic acid sequence encoding an Ig heavy chain constant region ($C_H$), wherein the nucleic acid sequence encoding an Ig $C_H$ is downstream of and operably linked to (I) the modified Ig $V_H$ segment, (II) the one or a plurality of Ig $D_H$ segments, and (III) the one or a plurality of Ig $J_H$ segments. In some embodiments, the nucleic acid sequence encoding an Ig $C_H$ comprises an Igµ gene that encodes an IgM isotype, an Igδ gene that encodes an IgD isotype, an Igγ gene that encodes an IgG isotype, an Igα gene that encodes an IgA isotype, and/or an Igε gene that encodes an IgE isotype. In some embodiments, a recombinant nucleic acid molecule described herein comprises a nucleic acid sequence encoding an anchor-modified Ig heavy chain, wherein the anchor-modified Ig heavy chain comprises in operable linkage: (i) the Ig signal peptide, (ii) the anchor, (iii) an Ig heavy chain variable domain comprising the FR1, CDR1, FR2, CDR2, FR3, CDR3, and FR4 encoded by a rearranged Ig $V_H/D_H/J_H$ sequence, and (iv) an Ig $C_H$. In some embodiments, the Ig $C_H$ is a non-human Ig $C_H$, e.g., a rodent Ig $C_H$, e.g., a rat Ig $C_H$ or a mouse Ig $C_H$.

In some embodiments, the germline Ig V segment or variant thereof is a germline Ig light chain variable ($V_L$) segment or variant thereof. In some embodiments, a recombinant nucleic acid molecule may comprise a light chain variable region locus, e.g., may comprise in operable linkage and from 5' to 3': (I) the modified Ig $V_L$ segment, and (II) one or a plurality of Ig light chain joining ($J_L$) segments.

In some embodiments the modified Ig $V_L$ segment and the one or a plurality of Ig $J_L$ segments are recombined and form a rearranged Ig $V_L/J_L$ sequence that encodes an anchor modified Ig light chain variable domain, wherein the anchor modified Ig light chain variable domain comprises in operable linkage: (i) the Ig signal peptide, (ii) the anchor, and (iii) the FR1, CDR1, FR2, CDR2, FR3, CDR3, and FR4 encoded by the rearranged Ig $V_L/J_L$ sequence.

In some embodiments, a recombinant nucleic acid molecule may comprise a light chain variable region locus and a nucleic acid sequence encoding an Ig light chain constant region ($C_L$), wherein the nucleic acid sequence encoding an Ig $C_L$ is downstream of and operably linked to: (I) the modified Ig $V_L$ segment and (II) the one or a plurality of Ig light chain joining ($J_L$) segments. In some embodiments, the anchor-modified Ig light chain comprises in operable linkage: (i) the Ig signal peptide, (ii) the anchor, (iii) an Ig light chain variable domain comprising the FR1, CDR1, FR2, CDR2, FR3, CDR3, and FR4 encoded by a rearranged Ig $V_L/J_L$ sequence, and (iv) an Ig $C_L$. In some embodiments, the Ig $C_L$ is a non-human Ig $C_L$, e.g., a rodent Ig $C_L$, e.g., a rat Ig $C_L$ or a mouse Ig $C_L$.

In some light chain variable region locus embodiments, the germline Ig $V_L$ segment or variant thereof is a germline Ig light chain variable kappa (Vκ) segment or variant thereof. Accordingly, in some embodiments, a recombinant nucleic acid molecule described herein comprises in operable linkage and from 5' to 3': (I) the modified Ig Vκ segment, and (II) one or a plurality of Ig light chain joining kappa (Jκ) segments. In some embodiments, a recombinant nucleic acid molecule described herein comprises in operable linkage and from 5' to 3': (I) the modified Ig Vκ segment, (II) one or a plurality of Ig light chain joining kappa (Jκ) and (III) a nucleic acid sequence encoding an Ig light chain constant kappa region (Cκ).

In some light chain variable region locus embodiments, the germline Ig $V_L$ segment or variant thereof is a germline Ig light chain variable lambda (Vλ) segment or variant thereof. Accordingly, in some embodiments, a recombinant nucleic acid molecule described herein comprises in operable linkage and from 5' to 3': (I) the modified Ig Vλ segment and (II) one or a plurality of Ig light chain joining lambda (Jλ) segments. In some embodiments, a recombinant nucleic acid molecule described herein comprises in operable linkage and from 5' to 3': (I) the modified Ig Vλ segment, (II) one or a plurality of Ig light chain joining lambda (Jλ) segments, and a nucleic acid sequence encoding an Ig light chain constant lambda region (Cλ).

In some embodiments, a recombinant nucleic acid molecule described herein comprises the sequence set forth as SEQ ID NO:8 or a degenerate variant thereof, or SEQ ID NO:10 or a degenerate variant thereof.

Targeting vectors, non-human animal cells (e.g., host cells, embryonic stem cells, etc.), and non-human animals comprising the nucleic acid molecules are also described.

Targeting vectors comprising the recombinant nucleic acid molecule embodiments disclosed herein are also described. In some targeting vector embodiments, the targeting vector further comprises 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule upstream of and in operable linkage to a non-human Ig $C_H$ at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof. In some embodiments, upon homologous recombination between the targeting vector and the non-human Ig heavy chain locus, the recombinant nucleic acid molecule replaces a non-human $V_H$ segment at the non-human Ig heavy chain locus. In some embodiments, upon homologous recombination between the targeting vector and the non-human Ig heavy chain locus, the recombinant nucleic acid molecule replaces one or more non-human $V_H$ segments, all non-human $D_H$ segments, and all non-human $J_H$ segments at the non-human Ig heavy chain locus. In some embodiments, upon homologous recombination between the targeting vector and the non-human Ig heavy chain locus, the recombinant nucleic acid molecule replaces all but one non-human $V_H$ segment or all non-human $V_H$ segments, all non-human $D_H$ segments, and all non-human $J_H$ segments at the non-human Ig heavy chain locus. In some embodiments, upon homologous recombination between the targeting vector and the non-human Ig heavy chain locus, the targeted non-human Ig heavy chain locus comprises the recombinant nucleic acid molecule in operable linkage to a non-human Ig heavy chain regulatory sequence at the non-human Ig heavy chain locus. In some embodiments, a targeting vector comprises a recombinant nucleic acid molecule described herein and 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule in operable linkage to a non-human Ig heavy chain regulatory sequence at the non-human Ig heavy chain locus, optionally wherein the non-human Ig heavy chain locus is an endogenous rodent Ig heavy chain locus in a rodent or rodent cell (e.g., a rodent embryonic stem cell) and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof, and optionally wherein upon homologous recombination between the targeting vector and the non-human Ig heavy chain locus, the recombinant nucleic acid molecule replaces one or more non-human $V_H$ segments, all non-human $D_H$ gene segments, all non-human $J_H$ gene segments, and one or more non-human $C_H$ genes at the non-human Ig heavy chain locus. In some embodiments, the 5' homology arm comprises a sequence set forth as SEQ ID NO:11 and/or the 3' homology arm comprises a sequence set forth as SEQ ID NO:12.

In some targeting vector embodiments, a targeting vector comprises a recombinant nucleic acid molecule described herein and 5' and 3' homology arms that target a non-human Ig light chain locus such that upon homologous recombination between the targeting vector and the non-human Ig light chain locus, the targeted non-human Ig light chain locus comprises the recombinant nucleic acid molecule upstream of and in operable linkage to a non-human Ig CL at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof. In some embodiments, upon homologous recombination between the targeting vector and the non-human Ig light chain locus, the recombinant nucleic acid molecule replaces a non-human $V_L$ segment at the non-human Ig light chain locus. In some embodiments, upon homologous recombination between the targeting vector and the non-human Ig light chain locus, the recombinant nucleic acid molecule replaces one or more non-human $V_L$ segments and all non-human $J_L$ segments at the non-human Ig light chain locus. In some embodiments, upon homologous recombination between the targeting vector and the non-human Ig light chain locus, the recombinant nucleic acid molecule replaces all non-human $V_L$ segments and all non-human $J_H$ segments at the non-human Ig light chain locus. In some embodiments, upon homologous recombination between the targeting vector and the non-human Ig light chain locus, the targeted non-human Ig heavy chain locus comprises the recombinant nucleic acid molecule in operable linkage to a non-human Ig light chain regulatory sequence at the Ig light chain locus. In some embodiments, a targeting vector described herein comprises a nucleic acid molecule described herein and 5' and 3' homology arms that target a non-human Ig light chain locus such that upon homologous recombination between the targeting vector and the non-human Ig light chain locus, the targeted non-human Ig light chain locus comprises the recombinant nucleic acid molecule in operable linkage to a non-human Ig light chain regulatory sequence at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof, and optionally wherein upon homologous recombination between the targeting vector and the non-human Ig light chain locus, the recombinant nucleic acid molecule replaces non-human $V_L$ segments, all non-human $J_L$ gene segments, and the non-human CL gene at the non-human Ig light chain locus.

In some targeting vector embodiments, a targeting vector comprises a recombinant nucleic acid molecule described herein and 5' and 3' homology arms that target a non-human Ig light chain κ locus such that upon homologous recombination between the targeting vector and the non-human Ig light chain κ locus, the targeted non-human Ig light chain κ locus comprises the recombinant nucleic acid molecule upstream of and in operable linkage to a non-human Ig Cκ at the non-human Ig light chain κ locus, optionally wherein the non-human Ig light chain κ locus is an endogenous rodent Ig light chain κ locus and/or wherein the non-human Ig light chain κ locus comprises a human or humanized immunoglobulin light chain variable region, a deletion of endogenous Ig Vκ and/or Jκ gene segments, or a combination thereof. In some embodiments, upon homologous recombination between the targeting vector and the non-human Ig light chain κ locus, the recombinant nucleic acid molecule replaces a non-human Vκ segment at the non-human Ig light chain κ locus. In some embodiments, upon homologous recombination between the targeting vector and the non-human Ig light chain κ locus, the recombinant nucleic acid molecule replaces one or more non-human Vκ segments and all non-human Jκ segments at the non-human Ig light chain κ locus. In some embodiments, upon homologous recombination between the targeting vector and the non-human Ig light chain κ locus, the recombinant nucleic acid molecule replaces all non-human Vκ segments and all non-human Jκ segments at the non-human Ig light chain κ locus. In some embodiments, upon homologous recombination between the targeting vector and the non-human Ig light chain κ locus, the targeted non-human Ig light chain κ locus comprises the recombinant nucleic acid molecule in operable linkage to a non-human Ig light chain κ regulatory sequence at the Ig light chain κ locus. In some targeting vector embodiments, a targeting vector comprises a recombinant nucleic acid molecule described herein and 5' and 3' homology arms that target a non-human Ig light chain κ locus such that upon homologous recombination between the targeting vector and the non-human Ig light chain κ locus, the targeted non-human Ig light chain κ locus comprises the recombinant nucleic acid molecule in operable linkage to a non-human Ig light chain κ regulatory sequence at the Ig light chain κ locus, optionally wherein upon homologous recombination between the targeting vector and the non-human Ig light chain κ locus, the recombinant nucleic acid molecule replaces non-human Vκ segments, all non-human Jκ gene segments, and the non-human Cκ gene at the non-human Ig light chain κ locus.

In some targeting vector embodiments, a targeting vector comprises a recombinant nucleic acid molecule described herein and 5' and 3' homology arms that target a non-human Ig light chain λ locus such that upon homologous recombination between the targeting vector and the non-human Ig light chain λ locus, the targeted non-human Ig light chain λ locus comprises the recombinant nucleic acid molecule upstream of and in operable linkage to a non-human Ig Cλ at the non-human Ig light chain locus, optionally wherein the non-human Ig light chain λ locus is an endogenous rodent Ig light chain λ locus and/or wherein the non-human Ig light chain λ locus comprises a human or humanized immunoglobulin light chain variable region, a deletion of endogenous Ig Vλ and/or gene segments, or a combination thereof. In some embodiments, upon homologous recombination between the targeting vector and the non-human Ig light chain λ locus, the recombinant nucleic acid molecule replaces a non-human Vλ segment at the non-human Ig light chain λ locus. In some embodiments, upon homologous recombination between the targeting vector and the non-human Ig light chain λ locus, the recombinant nucleic acid molecule replaces one or more non-human Vλ segments and all non-human segments at the non-human Ig light chain locus. In some embodiments, upon homologous recombination between the targeting vector and the non-human Ig light chain λ locus, the recombinant nucleic acid molecule replaces all non-human Vλ segments and all non-human segments at the non-human Ig light chain λ locus. In some embodiments, upon homologous recombination between the targeting vector and the non-human Ig light chain λ locus, the targeted non-human Ig light chain λ locus comprises the recombinant nucleic acid molecule in operable linkage to a non-human Ig light chain λ regulatory sequence at the Ig light chain λ locus. In some embodiments, a targeting vector comprises a recombinant nucleic acid molecule as described herein and 5' and 3' homology arms that target a non-human Ig light chain λ locus such that upon homologous recombination between the targeting vector and the non-human Ig light chain λ locus, the targeted non-human Ig light chain λ locus comprises the recombinant nucleic acid molecule in operable linkage to a non-human Ig light chain λ regulatory sequence at the Ig light chain λ locus. In some embodiments, upon homologous recombination between the targeting vector and the non-human Ig light chain λ locus, the recombinant nucleic acid molecule replaces non-human Vλ segments, all non-human Jλ gene segments, and the non-human Cλ gene at the non-human Ig light chain λ locus.

Also described herein are non-human animal genomes comprising a recombinant nucleic acid molecule and/or a targeting vector as described herein. In some non-human animal genome embodiments, the non-human animal genome comprises a recombinant nucleic acid molecule as described herein at an endogenous Ig locus of the non-human animal genome, e.g., the non-human animal genome comprises a targeting vector as described herein, wherein the targeting vector comprises 5' and 3' homology arms that target the endogenous Ig locus. In some embodiments, the non-human animal genome is a rodent genome. In some embodiments, the non-human animal genome is a rat genome. In some embodiments, the non-human animal genome is a mouse genome.

Also described herein are a non-human animal or a non-human animal cell comprising a recombinant nucleic acid molecule, a targeting vector, and/or a non-human animal genome as described herein. In some non-human animal embodiments, a non-human animal as described herein comprises a recombinant nucleic acid molecule, targeting vector, or non-human animal genome as described herein in its germline, e.g., in a germ cell, e.g., is capable of passing the recombinant nucleic acid molecule, a targeting vector, and/or a non-human animal genome as described herein to its offspring.

Also described are the methods of using of recombinant nucleic acid molecules, e.g., targeting vectors, as described herein in vitro to make a non-human cell, a non-human embryo, and/or non-human animal. In some embodiments, an in vitro method of modifying an isolated cell comprises introducing into the isolated cell a recombinant nucleic acid molecule as described herein, e.g., by contacting the cell with a targeting vector as described herein. In some method embodiments, the cell is a host cell. In some method embodiments, the cell is an embryonic stem (ES) cell. In some embodiments, cell as described herein or made according to a method described herein is a rodent cell, e.g., wherein the rodent cell is a rat cell or a mouse cell.

Also described are the methods of using of the nucleic acid molecules, the non-human cells, and/or the non-human animals as described herein to make anchor-modified antigen-binding proteins. Also described are non-human animal embryos and non-human animals which may comprise and/or be developed (e.g., generated) from an embryonic stem cell as described herein. Such embryos or non-human animals may be developed by a method comprising implanting ES cell as described herein into an embryo, and/or implanting an embryo comprising the ES cell into a suitable host and maintaining the host under suitable conditions during development of the ES cell or the embryo into viable progeny.

In some non-human animal embodiments as described herein (e.g., embodiments wherein a non-human animal comprises a recombinant nucleic acid molecule, targeting vector, and/or genome as described herein and/or is generated according to a method as described herein), a non-human animal comprises in comparison to a control non-human animal: (a) a comparable number of mature B cells in the spleen, (b) a comparable number of kappa positive B cells in the spleen, (c) a comparable number of lambda positive B cells in the spleen, (d) a comparable level of serum IgG and/or (e) a comparable level of serum IgM. In some embodiments, a non-human animal as described herein is capable of mounting an immune response comparable to a control non-human animal. In some embodiments, a non-human animal as described herein comprises a plurality of antigen-binding proteins that each comprises an anchor and/or is derived from a recombinant nucleic acid molecule, targeting vector, and/or non-human animal as described herein. In some embodiments, a non-human animal as described herein further comprises the cognate receptor of a non-immunoglobulin polypeptide of interest, the receptor binding portion of which non-immunoglobulin polypeptide of interest serves as the anchor. In some non-human animal embodiments, a non-human animal as described herein comprises a plurality of antigen-binding proteins that each specifically binds the cognate receptor of the non-immunoglobulin polypeptide of interest, the receptor binding portion of which non-immunoglobulin polypeptide of interest serves as the anchor.

As described herein, a non-immunoglobulin polypeptide of interest (the receptor binding portion of which non-immunoglobulin polypeptide of interest serves as an anchor) may comprise atrial natriuretic peptide (ANP). In some embodiments, the c-terminal tail of ANP (e.g., NSFRY (SEQ ID NO:3)) may serve as an anchor for a cognate receptor. In some embodiments the cognate receptor comprises a natriuretic peptide receptor (NPR), e.g., NPR3, or portion thereof.

In some non-human animal embodiments, wherein the non-human animal as described herein is immunized with the cognate receptor (optionally wherein the cognate receptor comprises a natriuretic peptide receptor (NPR), e.g., NPR3) of the non-immunoglobulin polypeptide of interest (e.g., ANP) of which the receptor binding portion (e.g., NSFRY (SEQ ID NO:3)) serves as an anchor as described herein, a non-human animal as described herein further comprises a plurality of antigen binding proteins that bind the cognate receptor, each of which comprises a KD of less than $1 \times 10^9$ and/or a t½ of greater than 30 minutes. In some embodiments, at least 15% of the plurality of antigen-binding proteins are able to block and/or block binding of the cognate receptor to the non-immunoglobulin polypeptide of interest. In some embodiments, more than 50% of the plurality of antigen binding proteins bind the cognate receptor expressed on a cell surface.

In some non-human animal embodiments described herein, the non-human animal is a rodent. In some non-human animal embodiments described herein, the non-human animal is a rat. In some non-human embodiments, the non-human animal is a mouse.

Also described are the anchor-modified antigen-binding proteins encoded by the nucleic acid molecules described herein or made by the non-human animals described herein.

Described herein are methods of producing an antigen-binding protein or obtaining a nucleic acid encoding same, the method comprising (i) immunizing a non-human animal described herein or made according to a method described herein (e.g., a non-human animal comprising a modified immunoglobulin (Ig) variable (V) segment that encodes an anchor modified Ig polypeptide) with an antigen (e.g., the cognate receptor of a non-immunoglobulin polypeptide of interest, wherein the receptor binding portion of the non-immunoglobulin polypeptide of interest serves as the anchor), and (ii) allowing the non-human animal to produce an immune response to the antigen including an antibody, or nucleic acid encoding same, that binds the antigen. Some embodiments further comprise recovering the antigen binding protein, or nucleic acid encoding same, from the non-human animal or a non-human animal cell, e.g., a B cell, and optionally fusing the B cell with a myeloma cell to form a hybridoma. Some embodiments further comprise cloning the recovered nucleic acid into an expression construct, and optionally expressing the expression construct in a host cell. In some cloning embodiments, the method further comprises cloning the recovered nucleic acid, wherein the recovered nucleic acid encodes an Ig variable domain, in frame with a human Ig constant region encoding sequence. Also described herein are the B cells, hybridomas fused with the B cells, or the host cells expressing the nucleic acids recovered from the B cells. In some embodiments, the mass of each antigen binding protein confirms the presence of the anchor-modified Ig polypeptide. In some embodiments, the mass of each antigen-binding protein is determined by Matrix-Assisted Laser Desorption Ionization-Time of Flight Mass Spectrometry. In some embodiments, the mass of each antigen binding protein confirms the presence of the anchor-modified Ig polypeptide and the mass of each antigen-binding protein is determined by Matrix-Assisted Laser Desorption Ionization-Time of Flight Mass Spectrometry.

Also described herein are anchor-modified Ig polypeptides that are (a) encoded by a recombinant nucleic acid molecule described herein, a targeting vector described herein, or a non-human animal genome described herein, (b) expressed by a non-human animal or non-human animal cell described herein, (c) expressed by the non-human animal or non-human animal cell made according to a method described herein, and/or (d) produced by any method described herein.

Other features, objects, and advantages of the non-human animals, cells, nucleic acids and compositions disclosed herein are apparent in the detailed description of certain embodiments that follows. It should be understood, however, that the detailed description, while indicating certain embodiments, is given by way of illustration only, not limitation.

BRIEF DESCRIPTION OF THE DRAWINGS

The Drawings included herein, which is composed of the following Figures, are for illustration purposes only and not for limitation.

FIGS. 5A-B provides (A) the total number of cells per spleen (y-axis), the number of CD19$^+$ cells/spleen (y-axis) or (B) the percentage of lymphocytes (CD19$^+$ cells) per spleen (y-axis) of mice modified with the ANP-modified $V_H$1-69 segment (ANP) or control VELOCIMMUNE® animals comprising humanized Ig loci (control). FIGS. 5C-5D provides (C) the total number of mature B cells (CD19$^+$IgD$^{hi}$IgM$^{int}$) and transitional B cells (CD19$^+$IgD$^{int}$IgM$^{hi}$) per spleen (y-axis) or (D) the percentage of mature B cells (CD19$^+$IgD$^{hi}$IgM$^{int}$) and transitional B cells (CD19$^+$IgD$^{int}$IgM$^{hi}$) per spleen (y-axis) of mice modified with the ANP-modified $V_H$1-69 segment (ANP) or control VELOCIMMUNE® animals comprising humanized Ig loci (control). FIGS. 5E-F provides (E) the total number of CD19$^+$kappa$^+$ cells and CD19$^+$lambda$^+$ cells per spleen (y-axis) or (F) the percentage of CD19$^+$κ$^+$ cells and CD19$^+$λ$^+$ cells per spleen (y-axis) of mice modified with the ANP-modified $V_H$1-69 segment (ANP) or control VELOCIMMUNE® animals comprising humanized Ig loci (control).

FIGS. 6A-B provides (A) the total number of cells per femur (y-axis) and the number of CD19$^+$ B cells per femur (y-axis) or (B) the percentage of lymphocytes (CD19$^+$ cells) per femur (y-axis) of mice modified with the ANP-modified $V_H$1-69 segment (ANP) or control VELOCIMMUNE® animals comprising humanized Ig loci (control). FIGS. 6C-D provides (C) the total number of CD43$^+$ckit$^+$ pro-B cells per femur (y-axis) and the number of CD43$^-$ckit$^-$ pre-B cells per femur (y-axis) or (D) the percentage of CD43$^+$ckit$^+$ pro-B cells or CD43$^-$ckit$^-$ pre-B cells per femur of mice modified with the ANP-modified $V_H$1-69 segment (ANP) or control VELOCIMMUNE® animals comprising humanized Ig loci (control). FIG. 6E-F provides (E) the total number of immature B cells and mature B cells per femur (y-axis) or (F) the percentage of immature B cells and mature B cells per femur (y-axis) of mice modified with the ANP-modified $V_H$1-69 segment (ANP) or control VELOCIMMUNE® animals comprising humanized Ig loci (control).

DEFINITIONS

Figure 1:
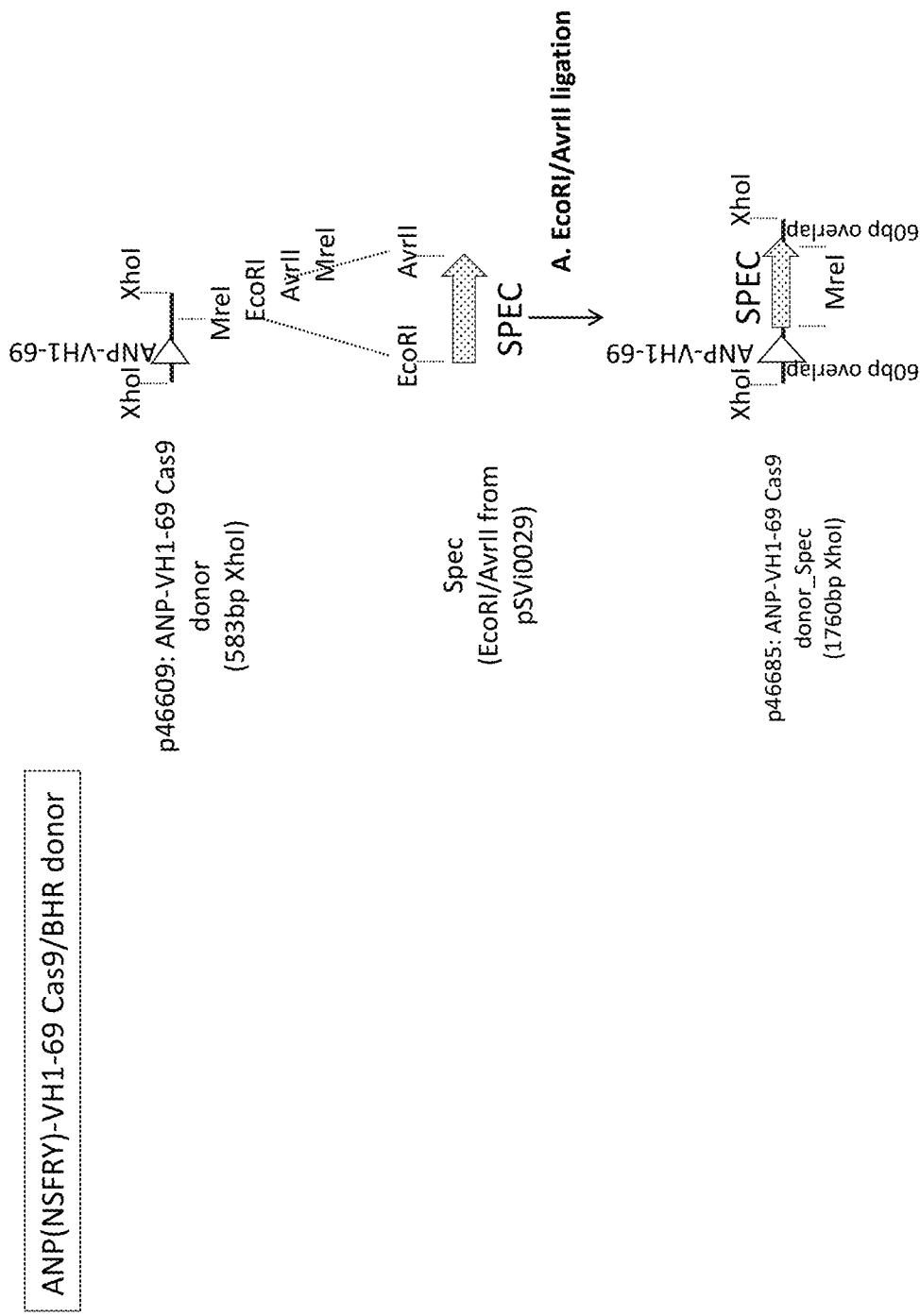
FIG. 1 shows an illustration, not to scale, of an exemplary non-limiting embodiment of an ANP-modified $V_H$ gene segment useful as donor DNA for Cas9/GA modification. Also shown are restriction recognition sites (XhoI, MreI, EcoRI, AvrII, MreI) and the Spectinomycin resistance gene (SPEC). In this nonlimiting embodiment, the human $V_H$1-69 gene segment is modified with the sequence encoding the C-terminal tail (NSFRY; SEQ ID NO:3) of atrial natriuretic protein (ANP) to form donor DNA comprising an ANP-modified $V_H$1-69 gene segment. Generally, unfilled shapes represent human sequences, filled shapes represent murine sequences, and dotted shapes represent non-human and non-murine sequences.

The scope of the present invention is defined by the claims appended hereto and is not limited by particular embodiments described herein; those skilled in the art, reading the present disclosure, will be aware of various modifications that may be equivalent to such described embodiments, or otherwise within the scope of the claims. In general, terminology is in accordance with its understood meaning in the art, unless clearly indicated otherwise. Explicit definitions of certain terms are provided herein and below; meanings of these and other terms in particular instances throughout this specification will be clear to those skilled in the art from context. Additional definitions for the following terms and other terms are set forth throughout the specification. References cited within this specification, or relevant portions thereof, are incorporated herein by reference in their entireties.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

As used in this application, the terms "about" and "approximately" are used as equivalents. Any numerals used in this application with or without about/approximately are meant to cover any normal fluctuations, e.g., +/−5%, appreciated by one of ordinary skill in the relevant art.

Administration: refers to the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc.

For example, in some embodiments, administration to an animal subject (e.g., to a human or a rodent) may be bronchial (including by bronchial instillation), buccal, enteral, intradermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time. In some embodiments, an antibody produced by a non-human animal disclosed herein can be administered to a subject (e.g., a human subject or rodent). In some embodiments, a pharmaceutical composition includes an antibody produced by a non-human animal disclosed herein. In some embodiments, a pharmaceutical composition can include a buffer, a diluent, an excipient, or any combination thereof. In some embodiments, a pharmaceutical composition including an antibody produced by a non-human animal disclosed herein can be included in a container for storage or administration, for example, a vial, a syringe (e.g., an IV syringe), or a bag (e.g., an IV bag).

Affinity: refers to the strength of the interaction between an antigen-binding protein and its binding partner, e.g., between an antibody and a specific epitope. An antibody that specifically binds to an epitope typically has a $K_D$ with respect to its target epitope of about $10^{-9}$M or lower (e.g., about $1 \times 10^{-9}$M, $1 \times 10^{-10}$ M, $1 \times 10^{-11}$M, or about $1 \times 10^{-12}$ M). $K_D$ may be measured by surface plasmon resonance, e.g., BIACORE™; enzyme linked immunoassay (ELISA) or other well-known methods.

Antibody: refers to an immunoglobulin antigen-binding protein. A tetrameric antibody comprises four polypeptide immunoglobulin (Ig) chains, e.g., two Ig heavy (H) chains and two Ig light (L) chains inter-connected by disulfide bonds. Each heavy chain comprises an Ig heavy chain variable domain and an Ig heavy chain constant region or domain ($C_H$). The heavy chain constant region comprises three domains, $C_H1$, $C_H2$ and $C_H3$. Each Ig light chain comprises an Ig light chain variable domain and an Ig light chain constant region ($C_L$).

The Ig heavy chain variable domain and Ig light chain variable domain may each be further subdivided into regions of hypervariability, termed complementarity determining regions (CDR), interspersed with regions that are more conserved, termed framework regions (FR). Each of the Ig heavy chain variable domain and the light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3).

Antigen-binding protein refers to immunoglobulins, antibody, antibodies, binding protein and the like, e.g., monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies, and epitope-binding fragments of any of the above. The terms "antibody" and "antibodies" also refer to covalent diabodies such as those disclosed in U.S. Pat. Appl. Pub. 20070004909, incorporated herein by reference in its entirety, and Ig-DARTS such as those disclosed in U.S. Pat. Appl. Pub. 20090060910, incorporated herein by reference in its entirety.

Biologically active: refers to a characteristic of any agent that has activity in a biological system, in vitro or in vivo (e.g., in an organism). For instance, an agent that, when present in an organism, has a biological effect within that organism is considered to be biologically active.

In particular embodiments where a protein or polypeptide is biologically active, a portion of that protein or polypeptide that confers at least one biological activity of the protein or polypeptide is typically referred to as a "biologically active" portion.

Cognate: refers to two biomolecules that typically interact (for example, a receptor and its ligand).

Comparable: refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Conservative: refers to a conservative amino acid substitution, i.e., a substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a non-immunoglobulin polypeptide of interest to bind to its cognate receptor. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine.

In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, hereby incorporated by reference in its entirety. In some embodiments, a substitution is a moderately conservative substitution wherein the substitution has a nonnegative value in the PAM250 log-likelihood matrix.

Control: refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" may refer to a "control animal." A "control animal" may have a modification as described herein, a modification that is different as described herein, or no modification (i.e., a wild-type animal). In one experiment, a "test" (i.e., a variable being tested) is applied. In a second experiment, the "control," the variable being tested is not applied. A control may be a positive control or a negative control.

In some embodiments, a control is a historical control (i.e., of a test or assay performed previously, or an amount or result that is previously known). In some embodiments, a control is or comprises a printed or otherwise saved record.

Degenerate variant of a reference nucleic acid molecule encodes a polypeptide that has an identical amino acid sequence as that encoded by the reference nucleic acid and has a substantially identical nucleic acid sequence to the reference nucleic acid molecule but for differences due to the degeneracy of the genetic code.

Disruption: refers to the result of a homologous recombination event with a DNA molecule (e.g., with an endogenous homologous sequence such as a gene or gene locus).

In some embodiments, a disruption may achieve or represent an insertion, deletion, substitution, replacement, missense mutation, or a frame-shift of a DNA sequence(s), or any combination thereof. Insertions may include the insertion of entire genes, fragments of genes, e.g., exons, which may be of an origin other than the endogenous sequence (e.g., a heterologous sequence), or coding sequences derived or isolated from a particular gene of interest. In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter the sequence of a gene or an encoded gene product (e.g., an encoded protein). In some embodiments, a disruption may alter sequence of a chromosome or chromosome position in a genome. In some embodiments, a disruption may truncate or fragment a gene or an encoded gene product (e.g., an encoded protein). In some embodiments, a disruption may extend a gene or an encoded gene product. In some such embodiments, a disruption may achieve assembly of a fusion protein. In some embodiments, a disruption may affect level, but not activity, of a gene or gene product. In some embodiments, a disruption may affect activity, but not level, of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product. In some embodiments, a significant effect can be measured by, e.g., but not limited to, a Student's T-test.

Endogenous locus or endogenous gene: refers to a genetic locus found in a parent or reference organism (or cell) prior to introduction of an alteration, disruption, deletion, insertion, modification, substitution or replacement as described herein.

In some embodiments, an endogenous locus comprises a sequence, in whole or in part, found in nature. In some embodiments, the endogenous locus is a wild-type locus. In some embodiments, a reference organism is a wild-type organism. In some embodiments, a reference organism is an engineered organism. In some embodiments, a reference organism is a laboratory-bred organism (whether wild-type or engineered).

Endogenous promoter: refers to a promoter that is naturally associated, e.g., in a wild-type organism, with an endogenous gene or genetic locus.

Engineered: refers, in general, to the aspect of having been manipulated by the hand of man. As is common practice and is understood by those in the art, progeny of an engineered polynucleotide or cell are typically still referred to as "engineered" even though the actual manipulation was performed on a prior entity. Furthermore, as will be appreciated by those skilled in the art, a variety of methodologies are available through which "engineering" as described herein may be achieved. A polynucleotide may be considered to be "engineered" when two or more sequences that are not linked together in that order in nature are manipulated by the hand of man to be directly linked to one another in the engineered polynucleotide. In some embodiments, an engineered polynucleotide may comprise a regulatory sequence, which is found in nature in operative linkage with a first coding sequence but not in operative linkage with a second coding sequence, linked by the hand of man so that it is operatively linked with the second coding sequence. Alternatively, or additionally, in some embodiments, first and second nucleic acid sequences that each encodes polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed).

In some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc.). Alternatively, or additionally, in some embodiments, "engineering" may involve use of in vitro chemical synthesis methodologies and/or recombinant nucleic acid technologies such as, for example, for example, nucleic acid amplification (e.g., via the polymerase chain reaction) hybridization, mutation, transformation, transfection, etc., and/or any of a variety of controlled mating methodologies. As will be appreciated by those skilled in the art, a variety of established such techniques (e.g., for recombinant DNA, oligonucleotide synthesis, and tissue culture and transformation (e.g., electroporation, lipofection, etc.) are well known in the art and described in various general and more specific references that are cited and/or discussed throughout the present specification. See e.g., Sambrook et al., Molecular Cloning: A Laboratory Manual (2d ed., Cold Spring Harbor Laboratory Press, Cold Spring Harbor, N.Y., 1989; incorporated herein in its entirety by reference).

Gene: refers to a DNA sequence in a chromosome that codes for a product (e.g., an RNA product and/or a polypeptide product). For the purpose of clarity, the term "gene" generally refers to a portion of a nucleic acid that encodes a polypeptide; the term may optionally encompass regulatory sequences, as will be clear from context to those of ordinary skill in the art. This definition is not intended to exclude application of the term "gene" to non-protein-coding expression units but rather to clarify that, in most cases, the term, as used in this document refers to a polypeptide-coding nucleic acid.

In some embodiments, a gene includes coding sequence (i.e., sequence that encodes a particular product). In some embodiments, a gene includes non-coding sequence. In some embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.).

The variable domains of immunoglobulin antigen receptors, e.g., antibodies, are encoded in sets of gene segments, also referred to herein as "segments" that are sequentially situated along the chromosome and undergo somatic recombination to form a complete variable domain exon. The configuration of human gene segments that are inherited, e.g., the germline configuration of human gene segments, e.g., the order of human gene segments in the germline genome (e.g., the genome passed down to the next generation) of a human, may be found at Lefranc, M.-P., Exp. Clin. Immunogenet., 18, 100-116 (2001), incorporated herein in its entirety by reference, which also shows functional gene segments and pseudogenes found within the human immunoglobulin heavy chain locus in germline configuration. Gene segments are classified as variable (V) gene segments (each of which may also be individually referred to as a V segment), diversity (D) gene segments (each of which may also be individually referred to as a D segment), or joining (J) gene segments (each of which may also be individually referred to as a J segment). There are multiple copies of each type of gene segment in the germline DNA, but only one is expressed for each type of receptor chain in a receptor-bearing lymphocyte A series of recombination events, involving several genetic components, serves to assemble immunoglobulins from ordered arrangement of gene segments (e.g., V, D and J). This assembly of gene segments is known to be imprecise and, therefore, immunoglobulin diversity is achieved both by combination of different gene segments and formation of unique junctions through imprecise joining. Further diversity is generated through a process known as somatic hypermutation in which the variable region sequence of immunoglobulins is altered to increase affinity and specificity for antigen. Reference to an Ig gene segment herein, e.g., an Ig V segment, includes variants of the germline Ig V segment. A variant of a germline Ig segment, e.g., a germline Ig V segment includes a polymorphic, e.g., allelic, variant thereof, a somatically hypermutated variant thereof, a recombined variant thereof, and a degenerate variant thereof.

Sequence polymorphisms of the coding region of an Ig segment, e.g., the sequences of allelic variants of a germline Ig segment, are described in Pallarès, N. et al. (1998) *Exp. Clin. Immunogenet.*, 15, 8-18; Barbié, V. and Lefranc, M.-P. (1998) *Exp. Clin. Immunogenet.*, 15, 171-183; Martinez, C. and Lefranc, M.-P. (1998) *Exp. Clin. Immunogenet.*, 15, 184-193; Pallarès, N. et al. (1999) *Exp. Clin. Immunogenet.*, 16, 36-60 (1999), and Ruiz, M. et al. (1999) *Exp. Clin. Immunogenet.*, 16, 173-184, each of which is incorporated herein in its entirety by reference. Representation of allelic germline Ig segments may also be found in two formats on the worldwide web (www) at imgt.org/IMGTrepertoire/Proteins/#B, which displays the alignments of all known sequences assigned to the different alleles, by comparison to the allele*01, and imgt.org/IMGTrepertoire/Proteins/#C, which provides descriptions of the nucleotide mutations and corresponding amino acid changes of the different alleles, by comparison to the allele*01. See also EP Patent No. 3 128 009, incorporated herein in its entirety by reference.

An Ig V segment may be considered a recombined or somatically hypermutated variant of a germline Ig V segment if it comprises, for one or more of the following regions: FR1, FR2 and/or FR3, at least 80%, at least 85%, at least 90%, at least 95%, at least 98%, or at least 99% nucleic acid sequence homology to the germline segment, or encodes an amino acid that has at least 80%, at least 85%, at least 90%, at least 95%, at least 98%, or at least 99% amino acid sequence homology to an amino acid sequence encoded by the germline Ig V segment.

In some embodiments, an Ig V segment may be considered a recombined or somatically hypermutated variant of a germline Ig V segment if it comprises, for one or more of the following regions: FR1, FR2 and/or FR3, between 80%-99% nucleic acid sequence homology to the germline segment. In some embodiments, an Ig V segment may be considered a recombined or somatically hypermutated variant of a germline Ig V segment if it comprises, for one or more of the following regions: FR1, FR2 and/or FR3, between 85%-99% nucleic acid sequence homology to the germline segment. In some embodiments, an Ig V segment may be considered a recombined or somatically hypermutated variant of a germline Ig V segment if it comprises, for one or more of the following regions: FR1, FR2 and/or FR3, between 90%-99% nucleic acid sequence homology to the germline segment. In some embodiments, an Ig V segment may be considered a recombined or somatically hypermutated variant of a germline Ig V segment if it comprises, for one or more of the following regions: FR1, FR2 and/or FR3, between 95%-99% nucleic acid sequence homology to the germline segment.

An Ig V segment may be considered a recombined or somatically hypermutated variant of a germline Ig V segment if it encodes, for one or more of the following regions: FR1, FR2 and/or FR3, an amino acid that has between 80%-99% amino acid sequence homology to an amino acid sequence encoded by the germline Ig V segment. An Ig V segment may be considered a recombined or somatically hypermutated variant of a germline Ig V segment if it encodes, for one or more of the following regions: FR1, FR2 and/or FR3, an amino acid that has between 85%-99% amino acid sequence homology to an amino acid sequence encoded by the germline Ig V segment. An Ig V segment may be considered a recombined or somatically hypermutated variant of a germline Ig V segment if it encodes, for one or more of the following regions: FR1, FR2 and/or FR3, an amino acid that has between 90%-99% amino acid sequence homology to an amino acid sequence encoded by the germline Ig V segment. An Ig V segment may be considered a recombined or somatically hypermutated variant of a germline Ig V segment if it encodes, for one or more of the following regions: FR1, FR2 and/or FR3, an amino acid that has between 95%-99% amino acid sequence homology to an amino acid sequence encoded by the germline Ig V segment.

The immunoglobulin molecule is a Y-shaped polypeptide composed of two identical heavy and two identical light chains, each of which have two structural components: one variable domain and one constant domain. It is the variable domains of heavy and light chains that are formed by the assembly of gene segments, while constant domains are fused to variable domains through RNA splicing. Although the mechanism of assembling (or joining) gene segments is similar for heavy and light chains, only one joining event is required for light chains (i.e., V to J) while two are required for heavy chains (i.e., D to J and V to DJ).

Generally, an immunoglobulin heavy chain variable domain is encoded by variable domain exon formed by the somatic recombination of an immunoglobulin heavy chain variable ($V_H$) gene segment (also referred to as a $V_H$ segment) recombined with an immunoglobulin heavy chain diversity (DO gene segment (also referred to as a $D_H$ segment) and an immunoglobulin heavy chain joining $J_H$ gene segment (also referred to as a $J_H$ segment). An immunoglobulin light chain variable domain is generally encoded by a variable domain exon formed by the somatic recombination of an immunoglobulin light chain variable ($V_L$) gene segment (also referred to as a $V_L$ segment) with an immunoglobulin light chain joining ($J_L$) gene segment (also referred to as a $J_L$ segment).

The assembly of gene segments for heavy and light chain variable regions (referred to respectively as VDJ recombination and VJ recombination) is guided by conserved non-coding DNA sequences that flank each gene segment, termed recombination signal sequences (RSSs), which ensure DNA rearrangements at precise locations relative to V, D and J coding sequences (see, e.g., Ramsden, D. A. et al., 1994, Nuc. Acids Res. 22(10):1785-96; incorporated herein in its entirety by reference). Each RSS consists of a conserved block of seven nucleotides (heptamer) that is contiguous with a coding sequence (e.g., a V, D or J segment) followed by a spacer (either 12 bp or 23 bp) and a second conserved block of nine nucleotides (nonamer). Although considerable sequence divergence in the 12 bp or 23Bp spacer among individuals is tolerated, the length of these sequences typically does not vary. Recombination between immunoglobulin gene segments follows a rule commonly referred to as the 12/23 rule, in which gene segments flanked by an RSS with a 12 bp spacer (or 12 mer) are typically joined to a gene segment flanked by a 23 bp spacer (or 23 mer; see, e.g., Hiom, K. and M. Gellert, 1998, Mol. Cell. 1(7):1011-9; incorporated herein in its entirety by reference).

Unless otherwise indicated or unless it would be evident to one of ordinary skill in the art that a contradiction or inconsistency would arise, an unrearranged gene segment without reference to an RSS is presumed to comprise the two RSS with which the gene segment is naturally associated, e.g., flanked by, operably linked to, etc. In some embodiments, an unrearranged gene segment herein may comprise a gene segment in its germline (e.g., wildtype) configuration, e.g., a germline $V_H$ gene segment and a germline $J_H$ gene segment are each flanked on both sides by 23 mer RSS. In contrast, a germline $D_H$ gene segment, e.g., an unrearranged $D_H$ gene segment, is flanked on each side by a 12 mer RSS.

As such, an unrearranged gene segment may also refer to a gene segment in its germline configuration, including any RSS associated with such germline configuration. Moreover, a plurality of gene segments in their germline configuration generally refers to the not only each individual gene segment being in its germline (e.g., unrearranged) configuration, but also the order and/or location of the functional gene segments. See, e.g., Lefranc, M.-P., Exp. Clin. Immunogenet., 18, 100-116 (2001); incorporated herein in its entirety by reference, for the germline configuration of human V, D and J gene segments.

Each V segment comprises a nucleic acid sequence that encodes an Ig signal or leader (L) peptide operably linked to a nucleic acid sequence that encodes the FR1, CDR1, FR2, CDR2, FR3, and part of the CDR3 of an immunoglobulin variable domain. Each D gene segment contributes to the CDR3 of an immunoglobulin heavy chain variable domain. Each J gene segment also contributes to the CDR3 and FR4 of an immunoglobulin variable domain. The amino acid positions of the FR1, CDR1, FR2, CDR2, FR3, CDR3, and FR4 based on a unique numbering described in Lefranc et al. (2003) Dev. Comp. Immunol. 27:55-77 and can also be viewed on www.imgt.org.

Heterologous: refers to an agent or entity from a different source. For example, when used in reference to a polypeptide, gene, or gene product present in a particular cell or organism, the term clarifies that the relevant polypeptide or fragment thereof, gene or fragment thereof, or gene product or fragment thereof: (1) was engineered by the hand of man; (2) was introduced into the cell or organism (or a precursor thereof) through the hand of man (e.g., via genetic engineering); and/or (3) is not naturally produced by or present in the relevant cell or organism (e.g., the relevant cell type or organism type). Another example includes a polypeptide or fragment thereof, gene or fragment thereof, or gene product or fragment thereof that is normally present in a particular native cell or organism, but has been modified, for example, by mutation or placement under the control of non-naturally associated and, in some embodiments, non-endogenous regulatory elements (e.g., a promoter).

Host cell: refers to a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not be identical to the parent cell, but are still included within the scope of the term "host cell".

In some embodiments, a host cell is or comprises a prokaryotic or eukaryotic cell. In embodiments, a host cell is or comprises a mammalian cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *Escherichia coli, Bacillus* spp., *Streptomyces* spp., etc.), mycobacteria cells, fungal cells, yeast cells (e.g., *Saccharomyces cerevisiae, Schizosaccharomyces pombe, Pichia pastoris, Pichia methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas.

In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6® cell). In some embodiments, a host cell is or comprises an isolated cell. In some embodiments, a host cell is part of a tissue. In some embodiments, a host cell is part of an organism.

Humanized: refers to a molecule (e.g., a nucleic acid, protein, etc.) that was non-human in origin and for which a portion has been replaced with a corresponding portion of a corresponding human molecule in such a manner that the modified (e.g., humanized) molecule retains its biological function and/or maintains the structure that performs the retained biological function. In contrast "human" and the like encompasses molecules having only a human origin, e.g., human nucleotides or protein comprising only human nucleotide and amino acid sequences respectively. The term "human(ized)" is used to reflect that the human(ized) molecule may be (a) a human molecule or (b) a humanized molecule.

Identity: in connection with a comparison of sequences, refers to identity as determined by a number of different algorithms known in the art that can be used to measure nucleotide and/or amino acid sequence identity.

In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

Immunoglobulin refers to a class of polypeptides, and nucleic acids encoding the polypeptides, that are present in serum or are expressed on B cells of the immune system, which function as antibodies, e.g., antigen-binding proteins.

A non-immunoglobulin polypeptide refers to ligands, e.g., polypeptides, that binds a cognate receptor. Exemplary and well-known non-immunoglobulin polypeptide:cognate receptor pairs include, but are not limited to, e.g., those non-immunoglobulin polypeptides that bind cognate G-protein coupled receptors (GPCRs) Exemplary GPCRs include, but are not limited to chemokine receptors, glucagon receptors (e.g., GLP1:GLP1R), calcitonin receptors, melanocortin receptors. These and other cognate GPCRs, including the non-immunoglobulin polypeptides that bind the same, are well-known in the art. See, e.g., Wu et al. (2017) *J. Mol. Biol.* 429:2726-45, which is incorporated herein in its entirety by reference. Additional non-limiting and exemplary non-immunoglobulin polypeptide (ligand):cognate receptor pairs include a. ligands that bind cognate receptor tyrosine kinases, e.g., ligands such as but not limited to epidermal growth factor (EGF), insulin, platelet derived growth factor (PDGF), vascular endothelial growth factor (VEGF), fibroblast growth factor (FGF), etc.
b. DLL:Notch receptor pairs,
c. B7:CD28/CLTA4/PD1 receptor pairs,
d. semaphorin:plexin receptor pairs,
e. PCSK9/LDLR pairs,
f. HLA:LILR pairs,
g. HLA:KIR pairs,
h. RGD-ligands:integrin pairs,
i. Amylin:CALCR/RAMP, e.g., RAMP1/2/3, pairs
j. Natriuretic peptides (e.g., ANP, BNP, CNP, etc.): natriuretic peptide receptors (NPR, NPR3, etc.) pairs, etc.

A ligand:receptor pair may include proteases and inhibitors.

In vitro: refers to events that occur in an artificial environment, e.g., in a test tube or reaction vessel, in cell culture, etc., rather than within a multi-cellular organism.

In vivo: refers to events that occur within a multi-cellular organism, such as a human and/or a non-human animal. In the context of cell-based systems, the term may be used to refer to events that occur within a living cell (as opposed to, for example, in vitro systems).

Isolated: refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10 or more of the other components with which they were initially associated. In some embodiments, isolated agents are at least about 80% or more pure. A substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients.

To give but one example, in some embodiments, a biological polymer such as a polypeptide or polynucleotide that occurs in nature is considered to be "isolated" when: (a) by virtue of its origin or source of derivation is not associated with some or all of the components that accompany it in its native state in nature; (b) it is substantially free of other polypeptides or nucleic acids of the same species from the species that produces it in nature; or (c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively, or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

Leader Sequence or Signal Peptide: refers to an immunoglobulin signal or leader (L) peptide that guides an immunoglobulin heavy or light chain through the endoplasmic reticulum and that is subsequently cleaved from the heavy or light chain before assembly of the final antibody. It may also refer to the nucleic acid sequence that encodes the signal or leader peptide. Each V gene segment comprises a leader sequence encoded by exon 1 and exon 2 of the segment (see, e.g., FIG. 2) that is immediately upstream of the exon 2 sequence encoding the FR1, CDR1, FR2, CDR2, FR3 and CDR3 of the germline Ig V segment. Ig signal or leader sequences are well-known in the art. See, e.g., Lefranc et al. (2003) Dev. Comp. Immunol. 27:55-77, incorporated herein in its entirety by reference and can also be viewed on the worldwide web (www) with the address imgt.org. See also Lefranc and Lefranc (2020) *Biomedicines* 8(9):1-117.

Non-human animal: refers to any vertebrate organism that is not a human. A non-human animal may be a cyclostome, a bony fish, a cartilaginous fish (e.g., a shark or a ray), an amphibian, a reptile, a mammal, and a bird. In some embodiments, a non-human mammal may be a primate, a goat, a sheep, a pig, a dog, a cow, or a rodent. In some embodiments, a non-human animal may be a rat or a mouse.

Nucleic acid in its broadest sense, refers to any compound and/or substance that is or can be incorporated into an oligonucleotide chain and is generally interchangeable with nucleic acid molecule, nucleic acid sequence, nucleotide molecule, nucleotide molecule, which terms are also interchangeable with each other.

In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively, or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" has a nucleotide sequence that encodes polypeptide fragment (e.g., a peptide). In some embodiments, a "nucleic acid" includes one or more introns. In some embodiments, a "nucleic acid" includes one or more exons. In some embodiments, a "nucleic acid" includes one or more coding sequences. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide or fragment thereof. In some embodiments, a "nucleic acid" has enzymatic activity.

Operably linked: refers to a juxtaposition wherein the components described are in a relationship permitting them to function in their intended manner.

In other embodiments, operable linkage does not require contiguity. For example, unrearranged variable region gene segments "operably linked" to each other are capable of rearranging to form a rearranged variable region gene, which unrearranged variable region gene segments may not necessarily be contiguous with one another. Unrearranged variable region gene segments operably linked to each other and to a contiguous constant region gene are capable of rearranging to form a rearranged variable region gene that is expressed in conjunction with the constant region gene as a polypeptide chain of an antigen binding protein. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest.

The term "expression control sequence", refers to polynucleotide sequences, which are necessary to affect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site and transcription termination sequence, while in eukaryotes typically, such control sequences include promoters and transcription termination sequence. The term "control sequences" is intended to include components whose presence is essential for expression and processing and can also include additional components whose presence is advantageous, for example, leader sequences and fusion partner sequences.

Physiological conditions: has its art-understood meaning referencing conditions under which cells or organisms live and/or reproduce. In some embodiments, the term refers to conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20–40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiological conditions. In some embodiments, physiological conditions are encountered in an organism (e.g., non-human animal).

Polypeptide: refers to any polymeric chain of amino acids.

In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man. In some embodiments, a polypeptide may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Recombinant: refers to nucleic acids and/or polypeptides that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., 1997 TIB Tech. 15:62-70; Hoogenboom H., and Chames P., 2000, Immunology Today 21:371-378; Azzazy H., and Highsmith W. E., 2002, Clin. Biochem. 35:425-445; Gavilondo J. V., and Larrick J. W., 2002, BioTechniques 29:128-145), antibodies isolated from an animal (e.g., a mouse) that is transgenic for human immunoglobulin genes (see e.g., Taylor, L. D., et al., 1992, Nucl. Acids Res. 20:6287-6295; Little M. et al., 2000, Immunology Today 21:364-370; Kellermann S. A. and Green L. L., 2002, Current Opinion in Biotechnology 13:593-597; Murphy, A. J., et al., 2014, Proc. Natl. Acad. Sci. U.S.A 111(14):5153-5158; each of which is incorporated herein in its entirety by reference) or polypeptides prepared, expressed, created or isolated by any other means that involves splicing selected sequence elements to one another.

In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide comprises sequences found in the genome (or polypeptide) of a source organism of interest (e.g., human, mouse, etc.). In some embodiments, a recombinant polypeptide comprises sequences that occur in nature separately from one another (i.e., from two or more different organisms, for example, human and non-human portions) in two different organisms (e.g., a human and a non-human organism). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptide sequences, may not naturally exist within the genome of a non-human animal in vivo.

Reference: refers to a standard or control agent, animal, cohort, individual, population, sample, sequence or value against which an agent, animal, cohort, individual, population, sample, sequence or value of interest is compared. A "reference" or "control" may refer to a "reference animal" or "control animal". A "reference animal" may have a modification as described herein, a modification that is different as described herein or no modification (i.e., a wild-type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

In some embodiments, a reference agent, animal, cohort, individual, population, sample, sequence or value is tested and/or determined substantially simultaneously with the testing or determination of the agent, animal, cohort, individual, population, sample, sequence or value of interest. In some embodiments, a reference agent, animal, cohort, individual, population, sample, sequence or value is a historical reference, optionally embodied in a tangible medium. In some embodiments, a reference may refer to a control. "VELOCIMMUNE® control" and the like, e.g., "control VELOCIMMUNE®," or "control" as a reference animal refers to a VELOCIMMUNE® mouse comprising humanized heavy and kappa variable region loci, where the mice are capable of breeding. These VELOCIMMUNE® control mice are generally described in Macdonald et al (2014) Proc. Natl. Acad. Sci. USA 111:5147-52 and supplemental information, which is hereby incorporated by reference in its entirety.

Somatic Recombination: refers to the recombination of $V_H$, $D_H$, and $J_H$ gene segments at an immunoglobulin heavy chain locus or the recombination of $V_L$ and $J_L$ gene segments at an immunoglobulin light chain locus. Somatic recombination occurs prior to antigen contact ad during B cell development in the bone marrow. At a heavy chain locus, one $D_H$ and one $J_H$ are randomly recombined with the removal of all intervening DNA in a process referred to as D-J joining. Next, a random $V_H$ segment is recombined to the rearranged $D_H J_H$ segment. Recombination at an immunoglobulin light chain locus occurs in a similar manner. A $V_L$ gene segment and a $J_L$ gene segment are combined are recombined during a process referred to as V-J joining, with removal of all the DNA between them.

Substantially: refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used to capture the potential lack of completeness inherent in many biological and chemical phenomena.

Substantial homology: refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | Nonpolar | Neutral | 1.8 |
|---|---|---|---|---|---|
| Arginine | Arg | R | Polar | Positive | -4.5 |
| Asparagine | Asn | N | Polar | Neutral | -3.5 |
| Aspartic acid | Asp | D | Polar | Negative | -3.5 |
| Cysteine | Cys | C | Nonpolar | Neutral | 2.5 |
| Glutamic acid | Glu | E | Polar | Negative | -3.5 |
| Glutamine | Gln | Q | Polar | Neutral | -3.5 |
| Glycine | Gly | G | Nonpolar | Neutral | -0.4 |
| Histidine | His | H | Polar | Positive | -3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | -3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | -1.6 |
| Serine | Ser | S | Polar | Neutral | -0.8 |

-continued

| Threonine | Thr | T | Polar | Neutral | -0.7 |
|---|---|---|---|---|---|
| Tryptophan | Trp | W | Nonpolar | Neutral | -0.9 |
| Tyrosine | Tyr | Y | Polar | Neutral | -1.3 |
| Valine | Val | V | Nonpolar | Neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410; Altschul, S. F. et al., 1996, Methods in Enzymol. 266:460-80; Altschul, S. F. et al., 1997, Nucleic Acids Res., 25:3389-402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying homologous sequences, the programs mentioned above typically provide an indication of the degree of homology.

In some embodiments, two sequences are considered to be substantially homologous if at least 95% or more of their corresponding residues are homologous over a relevant stretch of residues. In some embodiments, the relevant stretch is a complete sequence. In some embodiments, the relevant stretch is at least 9 or more residues. In some embodiments, the relevant stretch includes contiguous residues along a complete sequence. In some embodiments, the relevant stretch includes discontinuous residues along a complete sequence, for example, noncontiguous residues brought together by the folded conformation of a polypeptide or a portion thereof. In some embodiments, the relevant stretch is at least 10 or more residues.

Substantial identity: refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410; Altschul, S. F. et al., 1996, Methods in Enzymol. 266:460-80; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying identical sequences, the programs mentioned above typically provide an indication of the degree of identity.

In some embodiments, two sequences are considered to be substantially identical if at least 95% or more of their corresponding residues are identical over a relevant stretch of residues. In some embodiments, the relevant stretch is a complete sequence. In some embodiments, the relevant stretch is at least 10 or more residues.

Targeting vector or targeting construct: refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included.

In some embodiments, a targeting construct as described herein further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct as described herein further comprises a gene of interest in whole or in part, wherein the gene of interest is a heterologous gene that encodes a polypeptide, in whole or in part, that has a similar function as a protein encoded by an endogenous sequence. In some embodiments, a targeting construct as described herein further comprises a humanized gene of interest, in whole or in part, wherein the humanized gene of interest encodes a polypeptide, in whole or in part, that has a similar function as a polypeptide encoded by an endogenous sequence. In some embodiments, a targeting construct (or targeting vector) may comprise a nucleic acid sequence manipulated by the hand of man. For example, in some embodiments, a targeting construct (or targeting vector) may be constructed to contain an engineered or recombinant polynucleotide that contains two or more sequences that are not linked together in that order in nature yet manipulated by the hand of man to be directly linked to one another in the engineered or recombinant polynucleotide.

Transgene or transgene construct: refers to a nucleic acid sequence (encoding e.g., a polypeptide of interest, in whole or in part) that has been introduced into a cell by the hand of man such as by the methods described herein. A transgene could be partly or entirely heterologous, i.e., foreign, to the transgenic animal or cell into which it is introduced. A transgene can include one or more transcriptional regulatory sequences and any other nucleic acid, such as introns or promoters, which may be necessary for expression of a selected nucleic acid sequence. A transgene can include one or more selectable markers that allow for subsequent selection of progeny (e.g., cells) that have taken up the transgene.

Transgenic animal, transgenic non-human animal or $Tg^+$: are used interchangeably herein and refer to any non-naturally occurring non-human animal in which one or more of the cells of the non-human animal contain heterologous nucleic acid and/or gene encoding a polypeptide of interest, in whole or in part.

In some embodiments, a heterologous nucleic acid sequence and/or gene is introduced into the cell, directly or indirectly by introduction into a precursor cell, by way of deliberate genetic manipulation, such as by microinjection or by infection with a recombinant virus. The term genetic manipulation does not include classic breeding techniques, but rather is directed to introduction of recombinant DNA molecule(s). This molecule may be integrated within a chromosome, or it may be extrachromosomally replicating DNA. The term "$Tg^+$" includes animals that are heterozygous or homozygous for a heterologous nucleic acid and/or gene, and/or animals that have single or multi-copies of a heterologous nucleic acid and/or gene.

Targeting vector: refers to a nucleic acid molecule capable of transporting a nucleic acid of interest to which it is associated, particularly for targeted insertion of the nucleic acid of interest into another nucleic acid molecule, e.g., donor plasmid, non-human animal genome, etc.

In some embodiment, vectors are capable of extra-chromosomal replication and/or expression of nucleic acids to which they are linked in a host cell such as a eukaryotic and/or prokaryotic cell. Vectors capable of directing the expression of operably linked genes are referred to herein as "expression vectors" or "constructs".

Wild-type: has its art-understood meaning that refers to an entity having a structure and/or activity as found in nature in a "normal" (as contrasted with mutant, diseased, engineered, altered, etc.) state or context. Those of ordinary skill in the art will appreciate that wild-type genes and polypeptides often exist in multiple different forms (e.g., alleles).

Other features, objects, and advantages of the present invention are apparent in the detailed description of some embodiments that follows. It should be understood, however, that the detailed description, while indicating some embodiments of the present invention, is given by way of illustration only, not limitation. Various changes and modifications within the scope of the invention will become apparent to those skilled in the art from the detailed description.

DETAILED DESCRIPTION

Although antibody-based therapeutics offer significant promise in the treatment of several diseases, development of particularly effective antibody agents that bind intractable targets remains a challenge. Described herein are anchor-modified immunoglobulins (Ig) and modified Ig V segments that encode them, where the anchor comprises at least the receptor binding portion of a ligand (e.g., a non-immunoglobulin polypeptide) that binds a cognate receptor. Animals comprising the modified Ig V segments may generate a diverse repertoire of anchor-modified immunoglobulins in response to immunization with a receptor cognate to the anchor.

Without being bound by theory, it is thought that the anchor acts to increase the affinity of an antibody created de novo in an animal in response to antigenic challenge with the cognate receptor, e.g., by binding to the cognate receptor simultaneously with an antibody that specifically binds the cognate receptor and/or allowing affinity maturation of those antibodies that would not normally be expanded, without the anchor, in response to antigenic challenge with the cognate receptor. Accordingly, the diverse repertoire of immunoglobulins produced by non-human animals disclosed herein may comprise anchor-modified immunoglobulins that bind the cognate receptor with high affinity, thereby increasing the population of immunoglobulins from which a lead candidate against the previously intractable target may be discovered.

Nucleic Acid Molecules Including Targeting Vectors and Animal Genomes, Etc.

An anchor-modified immunoglobulin described herein may be encoded, at least in part, by a variable region (V) segment, e.g., an immunoglobulin (Ig) heavy chain variable region ($V_H$) segment or an Ig light chain variable region ($V_L$) segment, modified to encode the anchor in between and in operable linkage to: an Ig leader sequence, and the framework (FR) and complementarity determining region (CDR) sequences of a germline Ig V segment. The nucleic acid sequences encoding immunoglobulin (Ig) signal peptides and the nucleic acid sequences of germline V segments, e.g., human germline V segments, are well-known in the art, as are the amino acid sequences so encoded. See, e.g., Lefranc, M.-P., *Exp. Clin. Immunogenet.*, 18, 100-116 (2001), incorporated herein in its entirety by reference and the website found in the worldwide web (www) at the address imgt.org.

A nucleic acid molecule, including targeting vectors, and animal genomes as described herein may comprise a nucleic acid sequence encoding any Ig signal peptide of a germline V segment. In some embodiments a modified Ig V segment comprises a nucleic acid sequence encoding a signal peptide of a first germline Ig V segment, a nucleic acid sequence encoding an anchor, and a nucleic acid encoding the framework region (FR) 1, complementarity determining region (CDR)1, FR2, CDR2, FR3, and CDR3 of a second germline Ig V segment, wherein the first germline Ig V segment and the second germline Ig V segment are different germline Ig V segments. In some embodiments, a modified Ig V segment comprises a nucleic acid sequence encoding a signal peptide of a first germline Ig V segment, a nucleic acid sequence encoding an anchor, and a nucleic acid encoding the framework region (FR) 1, complementarity determining region (CDR)1, FR2, CDR2, FR3, and CDR3 of a second germline Ig V segment, wherein the first germline Ig V segment and the second germline Ig V segment are the same germline Ig V segment. In some embodiments, the Ig signal peptide comprises the sequence MDWTWRFLFVVAAATGVQS (SEQ ID NO:7).

The amino acid sequences of human (h) germline V segments (e.g., human germline variable heavy chain ($hV_H$ or hIGVH) segments, human germline variable kappa ($hV\kappa$ or hIGKV) segments, and human germline variable lambda ($hV\lambda$ or hIGLV) segments and murine (m) germline V segments (e.g., mouse germline variable heavy chain ($mV_H$ or mIGVH) segments, mouse germline variable kappa ($mV\kappa$ or mIGKV) segments, and mouse germline variable lambda ($mV\lambda$ or mIGLV) segments may be found at the worldwide web (www) addresses imgt.org/IMGTrepertoire/Proteins/SequenceLogos/human/ and imgt.org/IMGTrepertoire/Proteins/SequenceLogos/mouse/, each of which is incorporated herein in its entirety by reference.

In some embodiments, the germline Ig V segment or variant thereof (e.g., that encodes FR1, CDR1, FR2, CDR2, FR3, and CDR3 of a modified Ig V segment as described herein) is a human (h) germline Ig V segment or variant thereof, e.g., a germline human (h) $V_H1$-2 segment, a germline $hV_H1$-3 segment, a germline $hV_H1$-8 segment, a germline $hV_H1$ 18 segment, a germline $hV_H1$-24 segment, a germline $hV_H1$-45 segment, a germline $hV_H1$-46 segment, a germline $hV_H1$-58 segment, a germline $hV_H1$-69 segment, a germline $hV_H2$-5 segment, a germline $hV_H2$-26 segment, a germline $hV_H2$ 70 segment, a germline $hV_H3$-7 segment, a germline $hV_H3$-9 segment, a germline $hV_H3$ 11 segment, a germline $hV_H3$ 13 segment, a germline $hV_H3$-15 segment, a germline $hV_H3$-16 segment, a germline $hV_H3$-20 segment, a germline $hV_H3$-21 segment, a germline $hV_H3$-23 segment, a germline $hV_H3$-30 segment, a germline $hV_H3$-30-3 segment, a germline $hV_H3$-30-5 segment, a germline $hV_H3$-33 segment, a germline $hV_H3$-35 segment, a germline $hV_H3$-38 segment, a germline $hV_H3$-43 segment, a germline $hV_H3$-48 segment, a germline $hV_H3$-49 segment, a germline $hV_H3$-53 segment, a germline $hV_H3$-64 segment, a germline $hV_H3$-66 segment, a germline $hV_H3$-72 segment, a germline $hV_H3$-73 segment, a germline $hV_H3$-74 segment, a germline $hV_H4$-4 segment, a germline $hV_H4$-28 segment, a germline $hV_H4$-30-1 segment, a germline $hV_H4$ 30-2 segment, a germline $hV_H4$-30-4 segment, a germline $hV_H4$-31 segment, a germline $hV_H4$-34 segment, a germline $hV_H4$-39 segment, a germline $hV_H4$-59 segment, a germline $hV_H4$-61 segment, a germline $hV_H5$-51 segment, a germline $hV_H6$-1 segment, a germline $hV_H7$-4-1 segment, a germline $hV_H7$-81 segment, or variants thereof. In some embodiments, the germline Ig V segment or variant thereof is a germline $hV_H1$-69 segment or variant thereof.

On some embodiments, a nucleic acid molecule as described herein comprises only the modified Ig $hV_H$ segment, e.g., does not comprise any additional $hV_H$ segments or variants thereof.

In some embodiments, a nucleic acid molecule as described herein further comprises, in addition to the modified Ig $hV_H$ segment, additional $hV_H$ segments, e.g., one of, more than one of, or each of $V_H1$-2, $hV_H1$-3, $hV_H1$-8, $hV_H1$ 18, $hV_H1$-24, $hV_H1$-45, $hV_H1$-46, $hV_H1$-58, $hV_H1$-69, $hV_H2$-5, $hV_H2$-26, $hV_H2$ 70, $hV_H3$-7, $hV_H3$-9, $hV_H3$ 11, $hV_H3$ 13, $hV_H3$-15, $hV_H3$-16, $hV_H3$-20, $hV_H3$-21, $hV_H3$-23, $hV_H3$-30, $hV_H3$-30-3, $hV_H3$-30-5, $hV_H3$-33, $hV_H3$-35, $hV_H3$-38, $hV_H3$-43, $hV_H3$-48, $hV_H3$-49, $hV_H3$-53, $hV_H3$-64, $hV_H3$-66, $hV_H3$-72, $hV_H3$-73, $hV_H3$-74, $hV_H4$-4, $hV_H4$-28, $hV_H4$-30-1, $hV_H4$ 30-2, $hV_H4$-30-4, $hV_H4$-31, $hV_H4$-34, $hV_H4$-39, $hV_H4$-59, $hV_H4$-61, $hV_H5$-51, $hV_H6$-1, $hV_H7$-4-1, $hV_H7$-81 and variants thereof. In some embodiments comprising more than one of, or each of, the $V_H1$-2, $hV_H1$-3, $hV_H1$-8, $hV_H1$ 18, $hV_H1$-24, $hV_H1$-45, $hV_H1$-46, $hV_H1$-58, $hV_H1$-69, $hV_H2$-5, $hV_H2$-26, $hV_H2$ 70, $hV_H3$-7, $hV_H3$-9, $hV_H3$ 11, $hV_H3$ 13, $hV_H3$-15, $hV_H3$-16, $hV_H3$-20, $hV_H3$-21, $hV_H3$-23, $hV_H3$-30, $hV_H3$-30-3, $hV_H3$-30-5, $hV_H3$-33, $hV_H3$-35, $hV_H3$-38, $hV_H3$-43, $hV_H3$-48, $hV_H3$-49, $hV_H3$-53, $hV_H3$-64, $hV_H3$-66, $hV_H3$-72, $hV_H3$-73, $hV_H3$-74, $hV_H4$-4, $hV_H4$-28, $hV_H4$-30-1, $hV_H4$ 30-2, $hV_H4$-30-4, $hV_H4$-31, $hV_H4$-34, $hV_H4$-39, $hV_H4$-59, $hV_H4$-61, $hV_H5$-51, $hV_H6$-1, $hV_H7$-4-1, and $hV_H7$-81 segments, the $hV_H$ segments are in germline configuration.

In some embodiments, a nucleic acid molecule as described herein (e.g., a targeting vector, a non-human animal genome, etc.) may comprise an Ig heavy chain variable region, e.g., may comprise in addition to the anchor-modified V segment, additional (un)rearranged $V_H$, $D_H$ and/or $J_H$ gene segments, and in some embodiments, additional (un)rearranged $hV_H$, $hD_H$ and/or $hJ_H$ gene segments. In some embodiments, a nucleic acid molecule (e.g., a targeting vector, a non-human animal genome, etc.) as described herein comprises only one (un)rearranged $hV_H$ segment, one or more (un)rearranged $hD_H$ segment, and one or more (un)rearranged $hJ_H$ segment, wherein the only one (un)rearranged $hV_H$ segment is a modified $hV_H$ segment comprising a nucleic acid sequence encoding an anchor as described herein.

In some embodiments, a recombinant nucleic acid (e.g., a targeting vector, a non-human animal genome, etc.) as described herein comprises one or more human $D_H$ segments, e.g., one of, more than one of, or each of $hD_H1$-1, $hD_H1$-7, $hD_H1$-14, $hD_H1$-20, $hD_H1$-26, $hD_H2$-2, $hD_H2$-8, $hD_H2$-15, $hD_H2$-21, $hD_H3$-3, $hD_H3$-9, $hD_H3$-10, $hD_H3$-16, $hD_H3$-22, $hD_H4$-$hD_H4$-11, $hD_H4$-17, $hD_H4$-23, $hD_H5$-5, $hD_H5$-12, $hD_H5$-18, $hD_H5$-24, $hD_H6$-6, $hD_H6$-13, $hD_H6$-19, $hD_H6$-25, $hD_H7$-27, and variants thereof. In some embodiments comprising more than one of, or each of, the $hD_H1$-1, $hD_H1$-7, $hD_H1$-14, $hD_H1$-20, $hD_H1$-26, $hD_H2$-2, $hD_H2$-8, $hD_H2$-15, $hD_H2$-21, $hD_H3$-3, $hD_H3$-9, $hD_H3$-10, $hD_H3$-16, hD$_H$3-22, hD$_H$4-4, hD$_H$4-11, hD$_H$4-17, hD$_H$4-23, hD$_H$5-5, hD$_H$5-12, hD$_H$5-18, hD$_H$5-24, hD$_H$6-6, hD$_H$6-13, hD$_H$6-19, hD$_H$6-25, and hD$_H$7-27, the hD$_H$ segments are in germline configuration.

In some embodiments, a recombinant nucleic acid (e.g., a targeting vector, a non-human animal genome, etc.) as described herein comprises one or more human J$_H$ segments, e.g., one of, more than one of, or each of hJ$_H$1, hJ$_H$2, hJ$_H$3, hJ$_H$4, hJ$_H$5, hJ$_H$6, and variants thereof. In some embodiments comprising more than one of, or each of, the hJ$_H$1, hJ$_H$2, hJ$_H$3, hJ$_H$4, hJ$_H$5, and hJ$_H$6, segments, the hJ$_H$ segments are in germline configuration.

In some embodiments, a recombinant nucleic acid molecule (e.g., a targeting vector, a non-human animal genome, etc.) as described herein may comprise a heavy chain variable region locus, e.g., may comprise in operable linkage and from 5' to 3': (I) the modified Ig V$_H$ segment, (II) one or a plurality of Ig heavy chain diversity (D$_H$) segments, and (III) one or a plurality of all Ig heavy chain joining (J$_H$) segments. In some embodiments, the one or a plurality of Ig D$_H$ segments of (II) comprises one, a plurality of, or all human Ig D$_H$ segments, and/or the one or a plurality of Ig J$_H$ segments of (III) comprises one, a plurality of, or all human Ig J$_H$ segments. In some embodiments, the one or a plurality of Ig D$_H$ segments of (II) and the one or a plurality of Ig J$_H$ gene segments of (III) are recombined and form a rearranged Ig D$_H$/J$_H$ sequence such that the recombinant nucleic acid molecule comprises in operable linkage and from 5' to 3': the modified Ig V$_H$ gene segment and the rearranged Ig D$_H$/J$_H$ sequence.

In some embodiments, the Ig V$_H$ gene segment and the rearranged Ig D$_H$/J$_H$ sequence are recombined and form a rearranged Ig V$_H$/D$_H$/J$_H$ sequence that encodes an anchor modified Ig heavy chain variable domain, wherein the anchor modified Ig heavy chain variable domain comprises in operable linkage: (i) the Ig signal peptide, (ii) the anchor, and (iii) the FR1, complementarity determining region (CDR) 1, FR2, CDR2, FR3, CDR3, and FR4 encoded by the rearranged Ig V$_H$/D$_H$/J$_H$ sequence.

In some embodiments, the modified Ig V$_H$ segment is an unrearranged modified Ig V$_H$ gene segment.

In some embodiments, a recombinant nucleic acid (e.g., a targeting vector, a non-human animal genome, etc.) as described herein further comprises a nucleic acid sequence encoding an Ig heavy chain constant region (C$_H$), wherein the nucleic acid sequence encoding an Ig C$_H$ is downstream of and operably linked to (I) the modified Ig V$_H$ segment, (II) the one or a plurality of Ig D$_H$ segments, and (III) the one or a plurality of Ig J$_H$ segments. In some embodiments, the nucleic acid sequence encodes an Ig C$_H$ comprises an Igμ gene that encodes an IgM isotype, an Igδ gene that encodes an IgD isotype, an Igγ gene that encodes an IgG isotype, an Igα gene that encodes an IgA isotype, and/or an Igε gene that encodes an IgE isotype. In some embodiments, a recombinant nucleic acid molecule described herein comprises a nucleic acid sequence encoding an anchor-modified Ig heavy chain, wherein the anchor-modified Ig heavy chain comprises in operable linkage: (i) the Ig signal peptide, (ii) the anchor, (iii) an Ig heavy chain variable domain comprising the FR1, CDR1, FR2, CDR2, FR3, CDR3, and FR4 encoded by a rearranged Ig V$_H$/D$_H$/J$_H$ sequence, and (iv) an Ig C$_H$. In some embodiments, the Ig C$_H$ is a non-human Ig C$_H$, e.g., a rodent Ig C$_H$, e.g., a rat Ig C$_H$ or a mouse Ig C$_H$.

In some embodiments, the germline Ig V segment or variant thereof (e.g., that encodes FR1, CDR1, FR2, CDR2, FR3, and CDR3 of a modified Ig V segment as described herein) is a germline Ig light chain variable (V$_L$) segment or variant thereof. In some embodiments, a recombinant nucleic acid molecule may comprise a light chain variable region locus, e.g., may comprise in operable linkage and from 5' to 3': (I) the modified Ig V$_L$ segment, and (II) one or a plurality of Ig light chain joining (J$_L$) segments. In some embodiments the modified Ig V$_L$ segment and the one or a plurality of Ig J$_L$ segments are recombined and form a rearranged Ig V$_L$/J$_L$ sequence that encodes an anchor modified Ig light chain variable domain, wherein the anchor modified Ig light chain variable domain comprises in operable linkage: (i) the Ig signal peptide, (ii) the anchor, and (iii) the FR1, CDR1, FR2, CDR2, FR3, CDR3, and FR4 encoded by the rearranged Ig V$_L$/J$_L$ sequence. In some embodiments, a recombinant nucleic acid molecule may comprise a light chain variable region locus and a nucleic acid sequence encoding an Ig light chain constant region (C$_L$), wherein the nucleic acid sequence encoding an Ig C$_L$ is downstream of and operably linked to: (I) the modified Ig V$_L$ segment and (II) the one or a plurality of Ig light chain joining (J$_L$) segments. In some embodiments, the anchor-modified Ig light chain comprises in operable linkage: (i) the Ig signal peptide, (ii) the anchor, (iii) an Ig light chain variable domain comprising the FR1, CDR1, FR2, CDR2, FR3, CDR3, and FR4 encoded by a rearranged Ig V$_L$/J$_L$ sequence, and (iv) an Ig C$_L$. In some embodiments, the Ig C$_L$ is a non-human Ig C$_L$, e.g., a rodent Ig C$_L$, e.g., a rat Ig C$_L$ or a mouse Ig C$_L$.

In some embodiments, the germline Ig V segment or variant thereof (e.g., that encodes FR1, CDR1, FR2, CDR2, FR3, and CDR3 of a modified Ig V segment as described herein) is a germline Ig light chain variable kappa (Vκ) segment or variant thereof, e.g., a human Vκ segment, e.g., is a hVκ1-5 segment, a hVκ1-6 segment, a hVκ1-8 segment, a hVκ1D-8 segment, a hVκ1-9 segment, a hVκ1-12 segment, a hVκ1D-12 segment, a hVκ1-13 segment, a hVκ1D-13 segment, a hVκ1-16 segment, a hVκ1D-16 segment, a hVκ1-17 segment, a hVκ1D-17 segment, a hVκ1-27 segment, a hVκ1-33 segment, a hVκ1D-33 segment, a hVκ1-37 segment, a hVκ1D-37 segment, a hVκ1-39 segment, a hVκ1D-39, a hVκ1-NL1 segment, a hVκ1D-42 segment, a hVκ1D-43 segment, a hVκ2-4 segment, a hVκ2-18 segment, a hVκ2D-18 segment, a hVκ2-24 segment, a hVκ2D-24 segment, a hVκ2-28 segment, a hVκ2D-28 segment, a hVκ2-29 segment, a hVκ2D-29 segment, a hVκ2-30 segment, a hVκ2D-30 segment, a hVκ2-40 segment, a hVκ2D-40 segment, a hVκ2D-26 segment, a hVκ3-7 segment, a hVκ3D-7 segment, a hVκ3-11 segment, a hVκ3D-11 segment, a hVκ3-15 segment, a hVκ3D-15 segment, a hVκ3-20 segment, a hVκ3D-20 segment, a hVκ4-1 segment, a hVκ5-2 segment, a hVκ6-21 segment, a hVκ6D-21 segment, a hVκ6D-41 segment, a hVκ7-3 segment, and variants thereof. In some embodiments, a nucleic acid molecule as described herein further comprises, in addition to the modified Ig hVκ segment, additional hVκ segments, e.g., one of, more than one of, or each of a hVκ1D-8 segment, a hVκ1-9 segment, a hVκ1-12 segment, a hVκ1D-12 segment, a hVκ1-13 segment, a hVκ1D-13 segment, a hVκ1-16 segment, a hVκ1D-16 segment, a hVκ1-17 segment, a hVκ1D-17 segment, a hVκ1-27 segment, a hVκ1-33 segment, a hVκ1D-33 segment, a hVκ1-37 segment, a hVκ1D-37 segment, a hVκ1-39 segment, a hVκ1D-39, a hVκ1-NL1 segment, a hVκ1D-42 segment, a hVκ1D-43 segment, a hVκ2-4 segment, a hVκ2-18 segment, a hVκ2D-18 segment, a hVκ2-24 segment, a hVκ2D-24 segment, a hVκ2-28 segment, a hVκ2D-28 segment, a hVκ2-29 segment, a hVκ2D-29 segment, a hVκ2-30 segment, a hVκ2D-30 segment, a hVκ2-40 segment, a hVκ2D-40 segment, a hVκ2D-

26 segment, a hVκ3-7 segment, a hVκ3D-7 segment, a hVκ3-11 segment, a hVκ3D-11 segment, a hVκ3-15 segment, a hVκ3D-15 segment, a hVκ3-20 segment, a hVκ3D-20 segment, a hVκ4-1 segment, a hVκ5-2 segment, a hVκ6-21 segment, and a hVκ6D-21 segment. In some embodiments comprising more than one of, or each of, a hVκ1D-8 segment, a hVκ1-9 segment, a hVκ1-12 segment, a hVκ1D-12 segment, a hVκ1-13 segment, a hVκ1D-13 segment, a hVκ1-16 segment, a hVκ1D-16 segment, a hVκ1-17 segment, a hVκ1D-17 segment, a hVκ1-27 segment, a hVκ1-33 segment, a hVκ1D-33 segment, a hVκ1-37 segment, a hVκ1D-37 segment, a hVκ1-39 segment, a hVκ1D-39, a hVκ1-NL1 segment, a hVκ1D-42 segment, a hVκ1D-43 segment, a hVκ2-4 segment, a hVκ2-18 segment, a hVκ2D-18 segment, a hVκ2-24 segment, a hVκ2D-24 segment, a hVκ2-28 segment, a hVκ2D-28 segment, a hVκ2-29 segment, a hVκ2D-29 segment, a hVκ2-30 segment, a hVκ2D-30 segment, a hVκ2-40 segment, a hVκ2D-40 segment, a hVκ2D-26 segment, a hVκ3-7 segment, a hVκ3D-7 segment, a hVκ3-11 segment, a hVκ3D-11 segment, a hVκ3-15 segment, a hVκ3D-15 segment, a hVκ3-20 segment, a hVκ3D-20 segment, a hVκ4-1 segment, a hVκ5-2 segment, a hVκ6-21 segment, and a hVκ6D-21 segment, the hVκ segments are in germline configuration.

In some embodiments, a nucleic acid molecule as described herein (e.g., a targeting vector, a non-human animal genome, etc.) may comprise an Ig light chain κ variable region, e.g., may comprise in addition to the anchor-modified hVκ segment, additional (un)rearranged Jκ segments, and in some embodiments, additional (un)rearranged hJκ gene segments. Accordingly, in some embodiments, a recombinant nucleic acid molecule described herein comprises in operable linkage and from 5' to 3': (I) the modified Ig Vκ segment, and (II) one or a plurality of Ig light chain joining kappa Jκ segments. In some embodiments, a recombinant nucleic acid (e.g., a targeting vector, a non-human animal genome, etc.) as described herein comprises one or more human $J_κ$ segments, e.g., one of, more than one of, or each of hJκ1, hJκ2, hJκ3, hJκ4, hJκ5, and variants thereof. In some embodiments comprising more than one of, or each of, the hJκ1, hJκ2, hJκ3, hJκ4, hJκ5 segments, the hJκ segments are in germline configuration.

Additionally, in some embodiments, a recombinant nucleic acid molecule described herein comprises in operable linkage and from 5' to 3': (I) the modified Ig Vκ segment, and (II) one or a plurality of Ig light chain joining kappa (Jκ) and a nucleic acid sequence encoding an Ig light chain constant kappa region (Cκ).

In some embodiments, the germline Ig V segment or variant thereof (e.g., that encodes FR1, CDR1, FR2, CDR2, FR3, and CDR3 of a modified Ig V segment as described herein) is a germline Ig light chain variable lambda (Vλ) segment or variant thereof, e.g., a human Vλ segment, e.g., a hVλ1-36 segment, a hVλ1-40 segment, a hVλ1-41 segment, a hVλ1-44 segment, a hVλ1-47 segment, a hVλ1-50 segment, a hVλ1-51 segment, a hVλ1-62 segment, a hVλ2-5 segment, a hVλ2-8 segment, a hVλ2-11 segment, a hVλ2-14 segment, a hVλ2-18 segment, a hVλ2-23 segment, a hVλ2-33 segment, hVλ2-34 segment, a hVλ3-1 segment, a hVλ3-9 segment, a hVλ3-10 segment, a hVλ3-12 segment, a hVλ3-13 segment, a hVλ3-16 segment, a hVλ3-19 segment, a hVλ3-21 segment, a hVλ3-22 segment, a hVλ3-25 segment, a hVλ3-27 segment, a hVλ3-31 segment, a hVλ3-32 segment, a hVλ4-3 segment, a hVλ4-60 segment, a hVλ4-69 segment, a hVλ5-37 segment, a hVλ5-39 segment, a hVλ5-45 segment, a hVλ5-48 segment, a hVλ5-52 segment, a hVλ6-57 segment, a hVλ7-43 segment, a hVλ7-46 segment, a hVλ8-61 segment, a hVλ9-49 segment, a hVλ10-54 segment, a hVλ11-55 segment, and variants thereof. In some embodiments, a nucleic acid molecule as described herein further comprises, in addition to the modified Ig hVλ segment, additional hVλ segments, e.g., one of, more than one of, or each of a hVλ1-36 segment, a hVλ1-40 segment, a hVλ1-41 segment, a hVλ1-44 segment, a hVλ1-47 segment, a hVλ1-50 segment, a hVλ1-51 segment, a hVλ1-62 segment, a hVλ2-5 segment, a hVλ2-8 segment, a hVλ2-11 segment, a hVλ2-14 segment, a hVλ2-18 segment, a hVλ2-23 segment, a hVλ2-33 segment, hVλ2-34 segment, a hVλ3-1 segment, a hVλ3-9 segment, a hVλ3-10 segment, a hVλ3-12 segment, a hVλ3-13 segment, a hVλ3-16 segment, a hVλ3-19 segment, a hVλ3-21 segment, a hVλ3-22 segment, a hVλ3-25 segment, a hVλ3-27 segment, a hVλ3-31 segment, a hVλ3-32 segment, a hVλ4-3 segment, a hVλ4-60 segment, a hVλ4-69 segment, a hVλ5-37 segment, a hVλ5-39 segment, a hVλ5-45 segment, a hVλ5-48 segment, a hVλ5-52 segment, a hVλ6-57 segment, a hVλ7-43 segment, a hVλ7-46 segment, a hVλ8-61 segment, a hVλ9-49 segment, a hVλ10-54 segment, and a hVλ11-55 segment. In some embodiments comprising more than one of, or each of, a hVλ1-36 segment, a hVλ1-40 segment, a hVλ1-41 segment, a hVλ1-44 segment, a hVλ1-47 segment, a hVλ1-50 segment, a hVλ1-51 segment, a hVλ1-62 segment, a hVλ2-5 segment, a hVλ2-8 segment, a hVλ2-11 segment, a hVλ2-14 segment, a hVλ2-18 segment, a hVλ2-23 segment, a hVλ2-33 segment, hVλ2-34 segment, a hVλ3-1 segment, a hVλ3-9 segment, a hVλ3-10 segment, a hVλ3-12 segment, a hVλ3-13 segment, a hVλ3-16 segment, a hVλ3-19 segment, a hVλ3-21 segment, a hVλ3-22 segment, a hVλ3-25 segment, a hVλ3-27 segment, a hVλ3-31 segment, a hVλ3-32 segment, a hVλ4-3 segment, a hVλ4-60 segment, a hVλ4-69 segment, a hVλ5-37 segment, a hVλ5-39 segment, a hVλ5-45 segment, a hVλ5-48 segment, a hVλ5-52 segment, a hVλ6-57 segment, a hVλ7-43 segment, a hVλ7-46 segment, a hVλ8-61 segment, a hVλ9-49 segment, a hVλ10-54 segment, a hVλ11-55 segment, the hVλ segments are in germline configuration.

In some embodiments, a nucleic acid molecule as described herein (e.g., a targeting vector, a non-human animal genome, etc.) may comprise an Ig light chain λ variable region, e.g., may comprise in addition to the anchor-modified hVλ segment, additional (un)rearranged segments, and in some embodiments, additional (un)rearranged hJλ gene segments. Accordingly, in some embodiments, a recombinant nucleic acid molecule described herein comprises in operable linkage and from 5' to 3': (I) the modified Ig Vλ segment, and (II) one or a plurality of Ig light chain joining kappa segments. In some embodiments, a recombinant nucleic acid (e.g., a targeting vector, a non-human animal genome, etc.) as described herein comprises one or more human segments, e.g., one of, more than one of, or each of hJλ1, hJλ2, hJλ3, hJλ4, hJλ5, hJλ6, hJλ7 segments and variants thereof. In some embodiments comprising more than one of, or each of, the hJλ1, hJλ2, hJλ3, hJλ4, hJλ5, hJλ6, hJλ7 segments, the hJλ segments are in germline configuration. In some embodiments, a recombinant nucleic acid molecule described herein comprises in operable linkage and from 5' to 3': (I) the modified Ig Vλ segment, (II) one or a plurality of Ig light chain joining lambda (Jλ) segments, and a nucleic acid sequence encoding an Ig light chain constant lambda region (Cλ).

Anchors

As described herein, anchors comprise ligands (or portions thereof) that bind to cognate receptors. In some embodiments, a ligand may be a non-immunoglobulin polypeptide. Accordingly, as described herein, an anchor may comprise a non-immunoglobulin polypeptide, e.g., a receptor binding portion of the non-immunoglobulin polypeptide. The anchor modifications described herein may be useful to increase the affinity of antigen-binding proteins, e.g., antibodies, to intractable receptors.

Exemplary and well-known non-immunoglobulin polypeptide:cognate receptor pairs include, but are not limited to, e.g., those non-immunoglobulin polypeptides that bind cognate G-protein coupled receptors (GPCRs) Exemplary GPCRs include, but are not limited to chemokine receptors, glucagon receptors (e.g., GLP1:GLP1R), calcitonin receptors, melanocortin receptors. These and other cognate GPCRs, including the non-immunoglobulin polypeptides that bind the same, are well-known in the art. See, e.g., Wu et al. (2017) *J. Mol. Biol.* 429:2726-45, which is incorporated herein in its entirety by reference. Additional non-limiting and exemplary non-immunoglobulin polypeptide (ligand):cognate receptor pairs include a. ligands that bind cognate receptor tyrosine kinases, e.g., ligands such as but not limited to epidermal growth factor (EGF), insulin, platelet derived growth factor (PDGF), vascular endothelial growth factor (VEGF), fibroblast growth factor (FGF), etc.
b. DLL:Notch receptor pairs,
c. B7:CD28/CLTA4/PD1 receptor pairs,
d. semaphorin:plexin receptor pairs,
e. PCSK9/LDLR pairs,
f. HLA:LILR pairs,
g. HLA:KIR pairs,
h. RGD-ligands:integrin pairs,
i. Natriuretic peptides (e.g., ANP, BNP, CNP, etc.): natriuretic peptide receptors (NPR, NPR3, etc.) pairs, etc.

A ligand:receptor pair may include proteases and inhibitors.

In some embodiments, an anchor comprises a natriuretic peptide (NP), e.g., a receptor binding portion of an NP. NPs comprise at least eight structurally related amino acid peptides stored as three different prohormones: atrial natriuretic peptide (ANP) prohormone, B-type natriuretic peptide (BNP) prohormone, and C-type natriuretic peptide (CNP) prohormone. Dendroaspis natriuretic peptide, a D-type natriuretic peptide (DNP) has recently been discovered, and its role in humans still remains unclear.

The ANP prohormone (proANP) is a 126 amino acid polypeptide that is expressed primarily by cardiomyocytes and gives rise to several peptides with blood pressure lowering properties, natriuretic properties, diuretic properties, and/or kaliuretic properties. These peptides derived from the ANP prohormone are identified by their amino acid sequences beginning at the N-terminal end of the ANP prohormone: e.g., proANP 1-30 comprises a long-acting NP, proANP 31-67 comprises a vessel dilator, proANP 79-98 comprises a kaliuretic peptide, and amino acids 99-126 (also referred to as ANP), inter alia. Within the kidney, proANP is processed differently, resulting in an additional four amino acids being added to the N-terminus, e.g., proANP 95-126 (also referred to as urodilatin).

The BNP prohormone (proBNP) is a 108-amino acid polypeptide, also expressed primarily by cardiomyocytes. The BNP prohormone is processed within the human heart to form BNP (e.g., amino acids 77-108 of its 108 amino acid prohormone), and NT-proBNP (e.g., amino acids 1-76, both of which circulate in humans. BNP is a reliable biomarker of ventricular dilatation. Pandit et al. (2011) *Ind. J. Endocrinol. Metab.* 15(4) S345-53, incorporated herein in its entirety by reference.

Unlike the ANP and BNP, CNP is primarily expressed by endothelial and renal epithelial cells. Two CNP molecules have been identified in the circulation. Also, although CNP appears to lack natriuretic function, CNP likely serves as a regulator of vascular tone and growth in a paracrine or autocrine manner, and there is some indication that CNP may play a role in bone growth.

NPs exert their biological functions by specific binding to cell-surface receptors. Three specific receptors have been identified in mammalian tissues: two guanylyl cyclase-coupled receptors (GC-A and GC-B, also referred to as NP receptor (NPR)-A and NPR-B, respectively). NPR-A and NPR-B act through activation of the cGMP-dependent signaling cascade. In contrast, the third type C receptor (also referred to as NPR-C) is not coupled to guanylyl cyclase and appears to be mainly involved in clearance of NPs. All three receptors bind ANP, BNP, and CNP with different affinities. The rank order of ligand selectivity for GC-A is ANP≥BNP>>CNP, for GC-B is CNP>>ANP≥BNP, and for NPR-C is ANP>CNP>BNP. Jaubert et al. (1999) *PNAS* 96(18) 10278-283, incorporated herein in its entirety by reference.

NP receptors may be useful targets for the treatment of hypertension and cardiovascular disease. However, while ANP and BNP have important diuretic, natriuretic and hypotensive properties, CNP may play a role in bone growth. As such, any antibody-based targeting of NP receptors must be mindful of the differential binding affinities of the receptors for the NPs.

In some embodiments, an anchor comprises the sequence ANP or a portion thereof. A nucleic acid sequence encoding human ANP is set forth as NCBI accession number NM_006172.4 and SEQ ID NO:1 herein. An amino acid sequence of human ANP is set forth as NCBI accession number NP 006163 and SEQ ID NO:2 herein. In some embodiments, an anchor described herein comprises the receptor binding portion of ANP, e.g., the C-terminal tail of ANP. In some embodiments, the receptor binding portion of ANP comprises the amino acid sequence NSFRY (SEQ ID NO:3).

Linkers

In some embodiments, an anchor comprises a linker that links the receptor binding portion of a non-immunoglobulin polypeptide of interest to the FR1, CDR1, FR2, CDR2, FR3, and CDR3 of the germline Ig V segment, or a variant thereof. In some embodiments, the linker may be one amino acid in length. In some embodiments, the linker may be two amino acids in length. In some embodiments, the linker may be three amino acids in length. In some embodiments, the linker may be four amino acids in length, e.g., the linker may comprise the sequence GLSG (SEQ ID NO:13). In some embodiments, the linker may be five amino acids in length, e.g., may comprise the sequence GGGGS (SEQ ID NO:5). I In some embodiments, the linker may be six amino acids in length, e.g., may comprise a sequence of GLSGSG (SEQ ID NO:14). In some embodiments, the linker may be seven amino acids in length. In some embodiments, the linker may comprise a sequence of GLSGLSGS (SEQ ID NO:15). In some embodiments, the linker may be nine amino acids in length. In some embodiments, the linker may be ten amino acids in length, e.g., may comprise a sequence of GLSGLSGLSG (SEQ ID NO:16) or GLSGGSGLSG (SEQ ID NO:17). In some embodiments, the first and second linkers are identical in length, and are each more than ten amino acids in length.

In some embodiments, a recombinant nucleic acid molecule described herein comprises the sequence set forth as SEQ ID NO:8 or a degenerate variant thereof, or SEQ ID NO:10 or a degenerate variant thereof.

Targeting Vectors

Further provided are targeting vectors to be employed in the methods for making the genetically modified non-human animals, cells, tissues or embryos provided herein.

In one embodiment, a targeting vector is provided that comprises an insert nucleic acid, e.g., a recombinant nucleic acid molecule comprising a modified Ig V segment as described herein, flanked by 5' and 3' homology arms that can undergo homologous recombination with a locus of interest, e.g., an Ig heavy or light chain variable region locus. The targeting vectors and examples of components of the targeting vectors (i.e. insert nucleic acids, polynucleotides of interest, expression cassettes, etc.) are described in detail herein below.

A homology arm and a target site (i.e., cognate genomic region) "complement" or are "complementary" to one another when the two regions share a sufficient level of sequence identity to one another to act as substrates for a homologous recombination reaction. By "homology" is meant DNA sequences that are either identical or share sequence identity to a corresponding or "complementary" sequence. The sequence identity between a given target site and the corresponding homology arm found on the targeting vector can be any degree of sequence identity that allows for homologous recombination to occur. For example, the amount of sequence identity shared by the homology arm of the targeting vector (or a fragment thereof) and the target site (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a complementary region of homology between the homology arm and the complementary target site can be of any length that is sufficient to promote homologous recombination at the cleaved recognition site. For example, a given homology arm and/or complementary target site can comprise complementary regions of homology that are at least 5-10 kb, 5-15 kb, 10-20 kb, 20-30 kb, 30-40 kb, 40-50 kb, 50-60 kb, 60-70 kb, 70-80 kb, 80-90 kb, 90-100 kb, 100-110 kb, 110-120 kb, 120-130 kb, 130-140 kb, 140-150 kb, 150-160 kb, 160-170 kb, 170-180 kb, 180-190 kb, 190-200 kb, 200 kb to 300 kb in length or greater (such as described in the vectors described elsewhere herein) such that the homology arm has sufficient homology to undergo homologous recombination with the corresponding target sites within the genome of the cell. For ease of reference the homology arms are referred to herein as a 5' and a 3' homology arm. This terminology relates to the relative position of the homology arms to the insert nucleic acid within the targeting vector.

The homology arms of the targeting vector are therefore designed to be complementary to a target site with the targeted locus. Thus, the homology arms can be complementary to a locus that is native to the cell, or alternatively they can be complementary to a region of a heterologous or exogenous segment of DNA that was integrated into the genome of the cell, including, but not limited to, transgenes, expression cassettes, or heterologous or exogenous regions of genomic DNA. Alternatively, the homology arms of the targeting vector can be complementary to a region of a human artificial chromosome or any other engineered genomic region contained in an appropriate host cell. Still further, the homology arms of the targeting vector can be complementary to or be derived from a region of a BAC library, a cosmid library, or a P1 phage library. Thus, in specific embodiments, the homology arms of the targeting vector are complementary to a eukaryotic, non-human, mammalian, non-human mammalian, human, rodent, mouse or rat genomic locus that is native, heterologous or exogenous to a given cell. In one embodiment, the homology arms are derived from a synthetic DNA.

In some targeting vector embodiments, the targeting vector further comprises 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule (e.g., a recombinant nucleic acid molecule comprising a modified Ig $V_H$ segment, and optionally Ig $D_H$ and/or Ig $J_H$ segments) upstream of and in operable linkage to a non-human Ig $C_H$ at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof. In some embodiments, upon homologous recombination between the targeting vector and the non-human Ig heavy chain locus, the recombinant nucleic acid molecule replaces a non-human $V_H$ segment at the non-human Ig heavy chain locus. In some embodiments, upon homologous recombination between the targeting vector and the non-human Ig heavy chain locus, the recombinant nucleic acid molecule replaces one or more non-human $V_H$ segments, all non-human $D_H$ segments, and all non-human $J_H$ segments at the non-human Ig heavy chain locus. In some embodiments, upon homologous recombination between the targeting vector and the non-human Ig heavy chain locus, the recombinant nucleic acid molecule replaces all but one non-human $V_H$ segment or all non-human $V_H$ segments, all non-human $D_H$ segments, and all non-human $J_H$ segments at the non-human Ig heavy chain locus. In some embodiments, upon homologous recombination between the targeting vector and the non-human Ig heavy chain locus, the targeted non-human Ig heavy chain locus comprises the recombinant nucleic acid molecule in operable linkage to a non-human Ig heavy chain regulatory sequence at the non-human Ig heavy chain locus.

In some embodiments, a targeting vector comprises a recombinant nucleic acid molecule described herein and 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule (e.g., a recombinant nucleic acid molecule comprising a modified Ig $V_H$ segment, and optionally Ig $D_H$ segment(s), Ig $J_H$ segment(s) and/or Ig $C_H$ gene(s)) in operable linkage to a non-human Ig heavy chain regulatory sequence at the non-human Ig heavy chain locus, optionally wherein the non-human Ig heavy chain locus is an endogenous rodent Ig heavy chain locus in a rodent or rodent cell (e.g., a rodent embryonic stem cell) and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof, and optionally wherein upon homologous recombination between the targeting vector and the non-human Ig heavy chain locus, the recombinant nucleic acid molecule replaces one or more non-human $V_H$ segments, all non-human $D_H$ gene segments, all non-human $J_H$ gene segments, and one or more non-human $C_H$ genes at the non-human Ig heavy chain locus.

In some embodiments, the 5' homology arm comprises a sequence set forth as SEQ ID NO:12 and/or the 3' homology arm comprises a sequence set forth as SEQ ID NO:13.

In some targeting vector embodiments, a targeting vector comprises a recombinant nucleic acid molecule described herein and 5' and 3' homology arms that target a non-human Ig light chain locus such that upon homologous recombination between the targeting vector and the non-human Ig light chain locus, the targeted non-human Ig light chain locus comprises the recombinant nucleic acid molecule (e.g., a recombinant nucleic acid molecule comprising a modified Ig $V_L$ segment, and optionally Ig $J_L$ segment(s) as described herein) upstream of and in operable linkage to a non-human Ig $C_L$ at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof. In some embodiments, upon homologous recombination between the targeting vector and the non-human Ig light chain locus, the recombinant nucleic acid molecule replaces a non-human $V_L$ segment at the non-human Ig light chain locus. In some embodiments, upon homologous recombination between the targeting vector and the non-human Ig light chain locus, the recombinant nucleic acid molecule replaces one or more non-human $V_L$ segments and all non-human $J_L$ segments at the non-human Ig light chain locus. In some embodiments, upon homologous recombination between the targeting vector and the non-human Ig light chain locus, the recombinant nucleic acid molecule replaces all non-human $V_L$ segments and all non-human $J_H$ segments at the non-human Ig light chain locus. In some embodiments, upon homologous recombination between the targeting vector and the non-human Ig light chain locus, the targeted non-human Ig heavy chain locus comprises the recombinant nucleic acid molecule in operable linkage to a non-human Ig light chain regulatory sequence at the Ig light chain locus.

In some embodiments, a targeting vector described herein comprises a nucleic acid molecule described herein and 5' and 3' homology arms that target a non-human Ig light chain locus such that upon homologous recombination between the targeting vector and the non-human Ig light chain locus, the targeted non-human Ig light chain locus comprises the recombinant nucleic acid molecule (e.g., a recombinant nucleic acid molecule comprising a modified Ig $V_L$ segment, and optionally Ig $J_L$ segment(s) and/or an Ig $C_L$ gene as described herein) in operable linkage to a non-human Ig light chain regulatory sequence at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof, and optionally wherein upon homologous recombination between the targeting vector and the non-human Ig light chain locus, the recombinant nucleic acid molecule replaces non-human $V_L$ segments, all non-human $J_L$ gene segments, and the non-human $C_L$ gene at the non-human Ig light chain locus.

In some targeting vector embodiments, a targeting vector comprises a recombinant nucleic acid molecule described herein and 5' and 3' homology arms that target a non-human Ig light chain κ locus such that upon homologous recombination between the targeting vector and the non-human Ig light chain κ locus, the targeted non-human Ig light chain κ locus comprises the recombinant nucleic acid molecule (e.g., a recombinant nucleic acid molecule comprising a modified Ig Vκ segment, and optionally Ig Jκ segment(s) as described herein) upstream of and in operable linkage to a non-human Ig Cκ at the non-human Ig light chain κ locus, optionally wherein the non-human Ig light chain κ locus is an endogenous rodent Ig light chain κ locus and/or wherein the non-human Ig light chain κ locus comprises a human or humanized immunoglobulin light chain variable region, a deletion of endogenous Ig Vκ and/or Jκ gene segments, or a combination thereof. In some embodiments, upon homologous recombination between the targeting vector and the non-human Ig light chain κ locus, the recombinant nucleic acid molecule replaces a non-human Vκ segment at the non-human Ig light chain κ locus. In some embodiments, upon homologous recombination between the targeting vector and the non-human Ig light chain κ locus, the recombinant nucleic acid molecule replaces one or more non-human Vκ segments and all non-human Jκ segments at the non-human Ig light chain κ locus. In some embodiments, upon homologous recombination between the targeting vector and the non-human Ig light chain κ locus, the recombinant nucleic acid molecule replaces all non-human Vκ segments and all non-human Jκ segments at the non-human Ig light chain κ locus. In some embodiments, upon homologous recombination between the targeting vector and the non-human Ig light chain κ locus, the targeted non-human Ig light chain κ locus comprises the recombinant nucleic acid molecule in operable linkage to a non-human Ig light chain κ regulatory sequence at the Ig light chain κ locus.

In some targeting vector embodiments, a targeting vector comprises a recombinant nucleic acid molecule described herein and 5' and 3' homology arms that target a non-human Ig light chain κ locus such that upon homologous recombination between the targeting vector and the non-human Ig light chain κ locus, the targeted non-human Ig light chain κ locus comprises the recombinant nucleic acid molecule (e.g., a recombinant nucleic acid molecule comprising a modified Ig Vκ segment, and optionally Ig Jκ segment(s) and/or an Ig Cκ gene as described herein) in operable linkage to a non-human Ig light chain κ regulatory sequence at the Ig light chain κ locus, optionally wherein upon homologous recombination between the targeting vector and the non-human Ig light chain κ locus, the recombinant nucleic acid molecule replaces non-human Vκ segments, all non-human Jκ gene segments, and the non-human Cκ gene at the non-human Ig light chain κ locus.

In some targeting vector embodiments, a targeting vector comprises a recombinant nucleic acid molecule described herein and 5' and 3' homology arms that target a non-human Ig light chain λ locus such that upon homologous recombination between the targeting vector and the non-human Ig light chain λ locus, the targeted non-human Ig light chain λ locus comprises the recombinant nucleic acid molecule (e.g., a recombinant nucleic acid molecule comprising a modified Ig Vλ segment, and optionally Ig segment(s)) upstream of and in operable linkage to a non-human Ig Cλ at the non-human Ig light chain locus, optionally wherein the non-human Ig light chain λ locus is an endogenous rodent Ig light chain λ locus and/or wherein the non-human Ig light chain λ locus comprises a human or humanized immunoglobulin light chain variable region, a deletion of endogenous Ig Vλ and/or gene segments, or a combination thereof. In some embodiments, upon homologous recombination between the targeting vector and the non-human Ig light chain λ locus, the recombinant nucleic acid molecule replaces a non-human Vλ segment at the non-human Ig light chain λ locus. In some embodiments, upon homologous recombination between the targeting vector and the non-human Ig light chain λ locus, the recombinant nucleic acid molecule replaces one or more non-human Vλ segments and all non-human segments at the non-human Ig light chain locus. In some embodiments, upon homologous recombination between the targeting vector and the non-human Ig light chain λ locus, the recombinant nucleic acid molecule replaces all non-human Vλ segments and all non-human segments at the non-human Ig light chain λ locus. In some embodiments, upon homologous recombination between the targeting vector and the non-human Ig light chain λ locus, the targeted non-human Ig light chain λ locus comprises the recombinant nucleic acid molecule in operable linkage to a non-human Ig light chain λ regulatory sequence at the Ig light chain λ locus.

In some embodiments, a targeting vector comprises a recombinant nucleic acid molecule as described herein and 5' and 3' homology arms that target a non-human Ig light chain λ locus such that upon homologous recombination between the targeting vector and the non-human Ig light chain λ locus, the targeted non-human Ig light chain λ locus comprises the recombinant nucleic acid molecule (e.g., a recombinant nucleic acid molecule comprising a modified Ig Vλ segment, and optionally Ig segment(s) and/or an Ig Cλ gene as described herein) in operable linkage to a non-human Ig light chain λ regulatory sequence at the Ig light chain λ locus. In some embodiments, upon homologous recombination between the targeting vector and the non-human Ig light chain λ locus, the recombinant nucleic acid molecule replaces non-human Vλ segments, all non-human Jλ gene segments, and the non-human Cλ gene at the non-human Ig light chain λ locus.

In some embodiments, a targeting vector as described herein may further comprises a nucleotide sequence flanked with site-specific recombination target sequences. It is recognized any region or individual polynucleotide of interest within the targeting vector may also be flanked by such sites. The site-specific recombinase can be introduced into the cell by any means, including by introducing the recombinase polypeptide into the cell or by introducing a polynucleotide encoding the site-specific recombinase into the host cell. The polynucleotide encoding the site-specific recombinase can be located within the targeting vector or within a separate polynucleotide. The site-specific recombinase can be operably linked to a promoter active in the cell including, for example, an inducible promoter, a promoter that is endogenous to the cell, a promoter that is heterologous to the cell, a cell-specific promoter, a tissue-specific promoter, or a developmental stage-specific promoter. Site-specific recombination target sequences, which can flank the nucleotide sequence or any polynucleotide of interest in the targeting vector can include, but are not limited to, loxP, lox511, lox2272, lox66, lox71, loxM2, lox5171, FRT, FRT11, FRT71, attp, att, FRT, rox, or a combination thereof.

In some embodiments, the site-specific recombination sites flank a polynucleotide encoding a selection marker within the targeting vector. In such instances following integration of the targeting vector at the targeted locus, the nucleotide sequences between the site-specific recombination sites can be removed.

In some embodiments, a targeting vector as describe herein comprises a selection marker, which may be contained in a selection cassette. Such selection markers include, but are not limited, to neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. In one embodiment, the polynucleotide encoding the selection marker is operably linked to a promoter active in the cell. In one embodiment, the polynucleotide encoding the selection marker is flanked with site-specific recombination target sequences.

Non-Human Animal Genomes

Also described herein are non-human animal genomes comprising a recombinant nucleic acid molecule and/or a targeting vector as described herein. In some non-human animal genome embodiments, the non-human animal genome comprises a recombinant nucleic acid molecule as described herein at an endogenous Ig locus of the non-human animal genome, e.g., the non-human animal genome comprises a targeting vector as described herein, wherein the targeting vector comprises 5' and 3' homology arms that target the endogenous Ig locus. In some embodiments, the non-human animal genome is a rodent genome. In some embodiments, the non-human animal genome is a rat genome. In some embodiments, the non-human animal genome is a mouse genome.

In non-human animal genome embodiments, the genome comprises a non-human Ig heavy chain locus comprising the recombinant nucleic acid molecule (e.g., a recombinant nucleic acid molecule comprising a modified Ig $V_H$ segment, and optionally Ig $D_H$ and/or Ig $J_H$ segments) upstream of and in operable linkage to a non-human Ig $C_H$ at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof. In some embodiments, the recombinant nucleic acid molecule replaces a non-human $V_H$ segment at the non-human Ig heavy chain locus. In some embodiments, the recombinant nucleic acid molecule replaces one or more non-human $V_H$ segments, all non-human $D_H$ segments, and all non-human $J_H$ segments at the non-human Ig heavy chain locus. In some embodiments, the recombinant nucleic acid molecule replaces all but one non-human $V_H$ segment or all non-human $V_H$ segments, all non-human $D_H$ segments, and all non-human $J_H$ segments at the non-human Ig heavy chain locus. In some embodiments, the recombinant nucleic acid molecule is in operable linkage to a non-human Ig heavy chain regulatory sequence at the non-human Ig heavy chain locus.

In some embodiments, the non-human Ig heavy chain locus comprises the recombinant nucleic acid molecule (e.g., a recombinant nucleic acid molecule comprising a modified Ig $V_H$ segment, and optionally Ig $D_H$ segment(s), Ig $J_H$ segment(s) and/or Ig $C_H$ gene(s)) in operable linkage to a non-human Ig heavy chain regulatory sequence at the non-human Ig heavy chain locus, optionally wherein the non-human Ig heavy chain locus is an endogenous rodent Ig heavy chain locus in a rodent or rodent cell (e.g., a rodent embryonic stem cell) and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof, and optionally wherein the recombinant nucleic acid molecule replaces one or more non-human $V_H$ segments, all non-human $D_H$ gene segments, all non-human $J_H$ gene segments, and one or more non-human $C_H$ genes at the non-human Ig heavy chain locus.

In non-human animal genome embodiments, the genome comprises a non-human Ig light chain locus comprising the recombinant nucleic acid molecule (e.g., a recombinant nucleic acid molecule comprising a modified Ig $V_L$ segment, and optionally Ig $J_L$ segment(s) as described herein) upstream of and in operable linkage to a non-human Ig $C_L$ at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof. In some embodiments, the recombinant nucleic acid molecule replaces a non-human $V_L$ segment at the non-human Ig light chain locus. In some embodiments, the recombinant nucleic acid molecule replaces one or more non-human $V_L$ segments and all non-human $J_L$ segments at the non-human Ig light chain locus. In some embodiments, the recombinant nucleic acid molecule replaces all non-human $V_L$ segments and all non-human $J_H$ segments at the non-human Ig light chain locus. In some embodiments, the recombinant nucleic acid molecule is in operable linkage to a non-human Ig light chain regulatory sequence at the Ig light chain locus.

In non-human animal genome embodiments, the Ig light chain locus comprises the recombinant nucleic acid molecule (e.g., a recombinant nucleic acid molecule comprising a modified Ig $V_L$ segment, and optionally Ig $J_L$ segment(s) and/or an Ig $C_L$ gene as described herein) in operable linkage to a non-human Ig light chain regulatory sequence at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof, and optionally wherein the recombinant nucleic acid molecule replaces non-human $V_L$ segments, all non-human $J_L$ gene segments, and the non-human $C_L$ gene at the non-human Ig light chain locus.

In non-human animal genome embodiments, the genome comprises a non-human Ig light chain κ locus comprising the recombinant nucleic acid molecule (e.g., a recombinant nucleic acid molecule comprising a modified Ig Vκ segment, and optionally Ig Jκ segment(s) as described herein) upstream of and in operable linkage to a non-human Ig Cκ at the non-human Ig light chain κ locus, optionally wherein the non-human Ig light chain κ locus is an endogenous rodent Ig light chain κ locus and/or wherein the non-human Ig light chain κ locus comprises a human or humanized immunoglobulin light chain variable region, a deletion of endogenous Ig Vκ and/or Jκ gene segments, or a combination thereof. In some embodiments, the recombinant nucleic acid molecule replaces a non-human Vκ segment at the non-human Ig light chain κ locus. In some embodiments, the recombinant nucleic acid molecule replaces one or more non-human Vκ segments and all non-human Jκ segments at the non-human Ig light chain κ locus. In some embodiments, the recombinant nucleic acid molecule replaces all non-human Vκ segments and all non-human Jκ segments at the non-human Ig light chain κ locus. In some embodiments, recombinant nucleic acid molecule in operable linkage to a non-human Ig light chain κ regulatory sequence at the Ig light chain κ locus.

In some embodiments, the recombinant nucleic acid molecule (e.g., a recombinant nucleic acid molecule comprising a modified Ig Vκ segment, and optionally Ig Jκ segment(s) and/or an Ig Cκ gene as described herein) in operable linkage to a non-human Ig light chain κ regulatory sequence at the Ig light chain κ locus, optionally wherein the recombinant nucleic acid molecule replaces non-human Vκ segments, all non-human Jκ gene segments, and the non-human Cκ gene at the non-human Ig light chain κ locus.

In non-human animal genome embodiments, the genome comprises a non-human Ig light chain λ locus comprising a recombinant nucleic acid molecule (e.g., a recombinant nucleic acid molecule comprising a modified Ig Vλ segment, and optionally Ig Jλ segment(s)) upstream of and in operable linkage to a non-human Ig Cλ at the non-human Ig light chain locus, optionally wherein the non-human Ig light chain λ locus is an endogenous rodent Ig light chain λ locus and/or wherein the non-human Ig light chain λ locus comprises a human or humanized immunoglobulin light chain variable region, a deletion of endogenous Ig Vλ and/or gene segments, or a combination thereof. In some embodiments, the recombinant nucleic acid molecule replaces a non-human Vλ segment at the non-human Ig light chain λ locus. In some embodiments, the recombinant nucleic acid molecule replaces one or more non-human Vλ segments and all non-human segments at the non-human Ig light chain locus. In some embodiments, upon homologous recombination between the targeting vector and the non-human Ig light chain λ locus, the recombinant nucleic acid molecule replaces all non-human Vλ segments and all non-human segments at the non-human Ig light chain λ locus. In some embodiments, the recombinant nucleic acid molecule in operable linkage to a non-human Ig light chain λ regulatory sequence at the Ig light chain λ locus.

In some non-human animal genome embodiments, the non-human Ig light chain λ locus comprises the recombinant nucleic acid molecule (e.g., a recombinant nucleic acid molecule comprising a modified Ig Vλ segment, and optionally Ig Jλ segment(s) and/or an Ig Cλ gene as described herein) in operable linkage to a non-human Ig light chain λ regulatory sequence at the Ig light chain λ locus. In some embodiments, the recombinant nucleic acid molecule replaces non-human Vλ segments, all non-human Jλ gene segments, and the non-human Cλ gene at the non-human Ig light chain λ locus.

Non-Human Animal Cells, Non-Human Animals, and Methods of Making the Same

Non-Human Animals and Non-Human Animal Cells

Non-human animals and non-human animal cells are provided that express anchor-modified immunoglobulins, e.g., from Ig loci modified to comprise a recombinant nucleic acid molecule as described herein comprising a modified Ig V segment, e.g., an Ig heavy chain variable region ($V_H$) segment or an Ig light chain variable region ($V_L$) segment, modified to encode the anchor in between and in operable linkage to: an Ig leader sequence, and the framework (FR) and complementarity determining region (CDR) sequences of a germline V segment. Non-human animals, embryos, cells comprising the recombinant nucleic acid molecules, targeting constructs, and/or animal genomes described herein are thus provided.

In some non-human animal or non-human animal cell embodiments, the non-human animal or cell comprises a recombinant nucleic acid molecule as described herein (comprising a modified Ig V segment, e.g., an Ig heavy chain variable region ($V_H$) segment or an Ig light chain variable region ($V_L$) segment, modified to encode the anchor in between and in operable linkage to: an Ig leader sequence, and the framework (FR) and complementarity determining region (CDR) sequences of a germline V segment) randomly located within the genome of the animal. In some embodiments, the non-human animal comprises a recombinant nucleic acid molecule as described herein (comprising a modified Ig V segment, e.g., an Ig heavy chain variable region ($V_H$) segment or an Ig light chain variable region ($V_L$) segment, modified to encode the anchor in between and in operable linkage to: an Ig leader sequence, and the framework (FR) and complementarity determining region (CDR) sequences of a germline V segment) at an endogenous Ig locus of the non-human animal, e.g., the non-human animal comprises a targeting vector as described herein, wherein the targeting vector comprises 5' and 3' homology arms that target the endogenous Ig locus. In some embodiments, the non-human animal is a rodent. In some embodiments, the non-human animal cell is a rodent cell. In some embodiments, the non-human animal is a rat. In some embodiments, the non-human animal cell is a rat cell. In some embodiments, the non-human animal is a mouse. In some embodiments, the non-human animal cell is a mouse cell.

In embodiments, the non-human animals or non-human animal cell comprises an non-human Ig heavy chain locus comprising a recombinant nucleic acid molecule (e.g., a recombinant nucleic acid molecule comprising a modified Ig $V_H$ segment, and optionally Ig $D_H$ and/or Ig $J_H$ segments) upstream of and in operable linkage to a non-human Ig $C_H$ at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof. In some embodiments, the recombinant nucleic acid molecule replaces a non-human $V_H$ segment at the non-human Ig heavy chain locus. In some embodiments, the recombinant nucleic acid molecule replaces one or more non-human $V_H$ segments, all non-human $D_H$ segments, and all non-human $J_H$ segments at the non-human Ig heavy chain locus. In some embodiments, the recombinant nucleic acid molecule replaces all but one non-human $V_H$ segment or all non-human $V_H$ segments, all non-human $D_H$ segments, and all non-human $J_H$ segments at the non-human Ig heavy chain locus. In some embodiments, the recombinant nucleic acid molecule is in operable linkage to a non-human Ig heavy chain regulatory sequence at the non-human Ig heavy chain locus.

In some embodiments, the non-human Ig heavy chain locus comprises the recombinant nucleic acid molecule (e.g., a recombinant nucleic acid molecule comprising a modified Ig $V_H$ segment, and optionally Ig $D_H$ segment(s), Ig $J_H$ segment(s) and/or Ig $C_H$ gene(s)) in operable linkage to a non-human Ig heavy chain regulatory sequence at the non-human Ig heavy chain locus, optionally wherein the non-human Ig heavy chain locus is an endogenous rodent Ig heavy chain locus in a rodent or rodent cell (e.g., a rodent embryonic stem cell) and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof, and optionally wherein the recombinant nucleic acid molecule replaces one or more non-human $V_H$ segments, all non-human $D_H$ gene segments, all non-human $J_H$ gene segments, and one or more non-human $C_H$ genes at the non-human Ig heavy chain locus.

In some embodiments, the non-human animals or non-human animal cell comprises a non-human Ig light chain locus comprising the recombinant nucleic acid molecule (e.g., a recombinant nucleic acid molecule comprising a modified Ig $V_L$ segment, and optionally Ig $J_L$ segment(s) as described herein) upstream of and in operable linkage to a non-human Ig $C_L$ at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof. In some embodiments, the recombinant nucleic acid molecule replaces a non-human $V_L$ segment at the non-human Ig light chain locus. In some embodiments, the recombinant nucleic acid molecule replaces one or more non-human $V_L$ segments and all non-human $J_L$ segments at the non-human Ig light chain locus. In some embodiments, the recombinant nucleic acid molecule replaces all non-human $V_L$ segments and all non-human $J_H$ segments at the non-human Ig light chain locus. In some embodiments, the recombinant nucleic acid molecule is in operable linkage to a non-human Ig light chain regulatory sequence at the Ig light chain locus.

In some embodiments, the Ig light chain locus comprises the recombinant nucleic acid molecule (e.g., a recombinant nucleic acid molecule comprising a modified Ig $V_L$ segment, and optionally Ig $J_L$ segment(s) and/or an Ig $C_L$ gene as described herein) in operable linkage to a non-human Ig light chain regulatory sequence at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof, and optionally wherein the recombinant nucleic acid molecule replaces non-human $V_L$ segments, all non-human $J_L$ gene segments, and the non-human $C_L$ gene at the non-human Ig light chain locus.

In some embodiments, the non-human animals or non-human animal cell comprises a non-human Ig light chain κ locus comprising the recombinant nucleic acid molecule (e.g., a recombinant nucleic acid molecule comprising a modified Ig Vκ segment, and optionally Ig Jκ segment(s) as described herein) upstream of and in operable linkage to a non-human Ig Cκ at the non-human Ig light chain κ locus, optionally wherein the non-human Ig light chain κ locus is an endogenous rodent Ig light chain κ locus and/or wherein the non-human Ig light chain κ locus comprises a human or humanized immunoglobulin light chain variable region, a deletion of endogenous Ig Vκ and/or Jκ gene segments, or a combination thereof. In some embodiments, the recombinant nucleic acid molecule replaces a non-human Vκ segment at the non-human Ig light chain κ locus. In some embodiments, the recombinant nucleic acid molecule replaces one or more non-human Vκ segments and all non-human Jκ segments at the non-human Ig light chain κ locus. In some embodiments, the recombinant nucleic acid molecule replaces all non-human Vκ segments and all non-human Jκ segments at the non-human Ig light chain κ locus. In some embodiments, recombinant nucleic acid molecule in operable linkage to a non-human Ig light chain κ regulatory sequence at the Ig light chain κ locus.

In some embodiments, the recombinant nucleic acid molecule (e.g., a recombinant nucleic acid molecule comprising a modified Ig Vκ segment, and optionally Ig Jκ segment(s)

and/or an Ig Cκ gene as described herein) is in operable linkage to a non-human Ig light chain κ regulatory sequence at the Ig light chain κ locus, optionally wherein the recombinant nucleic acid molecule replaces non-human Vκ segments, all non-human Jκ gene segments, and the non-human Cκ gene at the non-human Ig light chain κ locus.

In some embodiments, the non-human animals or non-human animal cell comprises a non-human Ig light chain λ locus comprising a recombinant nucleic acid molecule (e.g., a recombinant nucleic acid molecule comprising a modified Ig Vλ segment, and optionally Ig segment(s)) upstream of and in operable linkage to a non-human Ig Cλ at the non-human Ig light chain locus, optionally wherein the non-human Ig light chain λ locus is an endogenous rodent Ig light chain λ locus and/or wherein the non-human Ig light chain λ locus comprises a human or humanized immunoglobulin light chain variable region, a deletion of endogenous Ig Vλ and/or gene segments, or a combination thereof. In some embodiments, the recombinant nucleic acid molecule replaces a non-human Vλ segment at the non-human Ig light chain λ locus. In some embodiments, the recombinant nucleic acid molecule replaces one or more non-human Vλ segments and all non-human segments at the non-human Ig light chain λ locus. In some embodiments, upon homologous recombination between the targeting vector and the non-human Ig light chain λ locus, the recombinant nucleic acid molecule replaces all non-human Vλ segments and all non-human segments at the non-human Ig light chain λ locus. In some embodiments, the recombinant nucleic acid molecule in operable linkage to a non-human Ig light chain λ regulatory sequence at the Ig light chain λ locus.

In some embodiments, the non-human Ig light chain λ locus comprises the recombinant nucleic acid molecule (e.g., a recombinant nucleic acid molecule comprising a modified Ig Vλ segment, and optionally Ig segment(s) and/or an Ig Cλ gene as described herein) in operable linkage to a non-human Ig light chain λ regulatory sequence at the Ig light chain λ locus. In some embodiments, the recombinant nucleic acid molecule replaces non-human Vλ segments, all non-human Jλ gene segments, and the non-human Cλ gene at the non-human Ig light chain λ locus.

Methods of Making Non-Human Animals or Non-Human Animal Cells

Also described are the methods of using of recombinant nucleic acid molecules, e.g., targeting vectors, as described herein to make an in vitro non-human cell, a non-human embryo, and/or non-human animal. In some embodiments, an in vitro method of modifying an isolated cell comprises introducing into the isolated cell a recombinant nucleic acid molecule as described herein, e.g., by contacting the cell with a targeting vector as described herein. In some method embodiments, the cell is a host cell. In some method embodiments, the cell is an embryonic stem (ES) cell. In some embodiments, cell as described herein or made according to a method described herein is a rodent cell, e.g., wherein the rodent cell is a rat cell or a mouse cell.

Also described are the methods of using of the nucleic acid molecules, the non-human cells, and/or the non-human animals as described herein to make anchor-modified antigen-binding proteins. Also described are non-human animal embryos and non-human animals which may comprise and/or be developed (e.g., generated) from an embryonic stem cell as described herein. Such embryos or non-human animals may be developed by a method comprising implanting ES cell as described herein into an embryo, and/or implanting an embryo comprising the ES cell into a suitable host and maintaining the host under suitable conditions during development of the ES cell or the embryo into viable progeny.

As described herein, a targeting vector may be used to target an Ig locus having a human or humanized immunoglobulin variable region. Immunoglobulin loci comprising human variable region gene segments are known in the art and can be found, for example, in U.S. Pat. Nos. 5,633,425; 5,770,429; 5,814,318; 6,075,181; 6,114,598; 6,150,584; 6,998,514; 7,795,494; 7,910,798; 8,232,449; 8,502,018; 8,697,940; 8,703,485; 8,754,287; 8,791,323; 8,809,051; 8,907,157; 9,035,128; 9,145,588; 9,206,263; 9,447,177; 9,551,124; 9,580,491 and 9,475,559, each of which is hereby incorporated by reference in its entirety, as well as in U.S. Pat. Pub. Nos. 20100146647, 20110195454, 20130167256, 20130219535, 20130326647, 20130096287, and 2015/0113668, each of which is hereby incorporated by reference in its entirety, and in PCT Pub. Nos. WO2007117410, WO2008151081, WO2009157771, WO2010039900, WO2011004192, WO2011123708 and WO2014093908, each of which are hereby incorporated by reference in its entirety.

In some embodiments, non-human animals as disclosed herein comprise exogenous fully human immunoglobulin transgenes comprising a modified Ig V segment as described herein, which are able to rearrange in precursor B cells in mice (Alt et al., 1985, Immunoglobulin genes in transgenic mice, Trends Genet 1:231-236; incorporated herein in its entirety by reference). In these embodiments, fully human immunoglobulin transgenes comprising modified Ig V segment as described herein may be (randomly) inserted and endogenous immunoglobulin genes may also be knocked-out (Green et al., 1994, Antigen-specific human monoclonal antibodies from mice engineered with human Ig heavy and light chain YACs, Nat Genet 7:13-21; Lonberg et al., 1994, Antigen-specific human antibodies from mice comprising four distinct genetic modifications, Nature 368:856-859; Jakobovits et al., 2007, From XenoMouse technology to panitumumab, the first fully human antibody product from transgenic mice, Nat Biotechnol 25:1134-1143; each of which publications is incorporated by reference in its entirety) e.g., wherein endogenous immunoglobulin heavy chain and κ light chain loci are inactivated, e.g., by targeted deletion of small but critical portions of each endogenous locus, followed by introduction of human immunoglobulin gene loci as randomly integrated large transgenes, or minichromosomes (Tomizuka et al., 2000, Double trans-chromosomic mice: maintenance of two individual human chromosome fragments containing Ig heavy and kappa loci and expression of fully human antibodies, PNAS USA 97:722-727; incorporated by reference in its entirety).

In some embodiments, human or humanized immunoglobulin heavy and light chain loci comprising modified Ig V segment as described herein are at endogenous immunoglobulin heavy and light chain loci, respectively. It has been shown that replacement of even a single endogenous $V_H$ gene segment with a human $V_H$ gene segment can result in an immune response comprising humanized immunoglobulin variable domain. See, e.g., Tien et al. (2016) Cell 166:1471-84; incorporated herein in its entirety by reference.

A method for a large in situ genetic replacement of the mouse germline immunoglobulin variable gene loci with human germline immunoglobulin variable gene loci while maintaining the ability of the mice to generate offspring has been previously described. See, e.g., U.S. Pat. Nos. 6,596,541 and 8,697,940, each of which is incorporated in its entirety by reference. Specifically, the precise replacement of six megabases of both the mouse heavy chain and κ light chain immunoglobulin variable gene loci with their human counterparts while leaving the mouse constant regions intact is described. As a result, mice have been created that have a precise replacement of their entire germline immunoglobulin variable repertoire with equivalent human germline immunoglobulin variable sequences, while maintaining mouse constant regions. The human variable regions are linked to mouse constant regions to form chimeric human-mouse immunoglobulin loci that rearrange and express at physiologically appropriate levels. The antibodies expressed are "reverse chimeras," i.e., they comprise human variable region sequences and mouse constant region sequences.

In some embodiments, mice having humanized immunoglobulin variable regions that express antibodies having human or humanized variable regions and mouse constant regions are called VELOCIMMUNE® mice. VELOCIMMUNE® humanized mice exhibit a fully functional humoral immune system that is essentially indistinguishable from that of wild-type mice. They display normal cell populations at all stages of B cell development. They exhibit normal lymphoid organ morphology. Antibody sequences of VELOCIMMUNE® mice exhibit normal V(D)J rearrangement and normal somatic hypermutation frequencies. Antibody populations in these mice reflect isotype distributions that result from normal class switching (e.g., normal isotype cis-switching). Immunizing VELOCIMMUNE® mice results in robust humoral immune responses that generate large, diverse antibody repertoires having human immunoglobulin variable domains suitable for use as therapeutic candidates. This platform provides a plentiful source of naturally affinity-matured human immunoglobulin variable region sequences for making pharmaceutically acceptable antibodies and other antigen-binding proteins. It is the precise replacement of mouse immunoglobulin variable sequences with human immunoglobulin variable sequences such that the human immunoglobulin variable sequences are operably linked with endogenous non-human constant region gene sequence(s) in a reverse chimeric manner that allows for making VELOCIMMUNE® mice.

Mice modified in a reverse chimeric manner include, but are not limited mice modified to comprise at an endogenous immunoglobulin locus a human(ized) variable region (e.g., comprising (D), J, and one or more human V gene segments) operably linked to an endogenous constant region, e.g.,
(a) at an endogenous heavy chain locus:
  (i) an unrearranged human(ized) immunoglobulin heavy chain variable region in operable linkage to an endogenous heavy chain constant region, wherein the unrearranged human(ized) immunoglobulin heavy chain variable region comprises a plurality of unrearranged human heavy chain variable region $V_H$ gene segments (e.g., all functional human unrearranged human $V_H$ gene segments), one or more unrearranged immunoglobulin heavy chain $D_H$ gene segments and one or more unrearranged immunoglobulin heavy chain $J_H$ gene segments,
  optionally wherein the one or more unrearranged immunoglobulin heavy chain $D_H$ gene segments and one or more unrearranged immunoglobulin heavy chain $J_H$ gene segments are one or more unrearranged human immunoglobulin heavy chain $D_H$ gene segments (e.g., all functional human $D_H$ gene segments) and/or one or more unrearranged human immunoglobulin heavy chain $J_H$ gene segments (e.g., all functional human $J_H$ gene segments);
  (ii) a restricted unrearranged human(ized) heavy chain variable region in operable linkage to an endogenous heavy chain constant region, wherein the restricted unrearranged human(ized) heavy chain variable region consists essentially of a single unrearranged human heavy chain variable region $V_H$ gene segment operably linked with one or more unrearranged immunoglobulin heavy chain $D_H$ gene segments and one or more unrearranged immunoglobulin heavy chain $J_H$ gene segments, optionally wherein the one or more unrearranged immunoglobulin heavy chain $D_H$ gene segments and one or more unrearranged immunoglobulin heavy chain $J_H$ gene segments are one or more unrearranged human immunoglobulin heavy chain $D_H$ gene segments and/or one or more unrearranged human immunoglobulin heavy chain $J_H$ gene segments, respectively;
  (iii) a histidine modified unrearranged human(ized) heavy chain variable region in operable linkage to an endogenous heavy chain constant region, wherein the histidine modified unrearranged human(ized) heavy chain variable region comprises an unrearranged immunoglobulin heavy chain variable gene sequence comprising in a complementarity determining region 3 (CDR3) encoding sequence a substitution of at least one non-histidine codon with a histidine codon or an insertion of at least one histidine codon; or
  (iv) a heavy chain only immunoglobulin encoding sequence comprising an unrearranged human(ized) heavy chain variable region in operable linkage to an endogenous heavy chain constant region, wherein the endogenous heavy chain constant region comprises (1) an intact endogenous IgM gene that encodes an IgM isotype that associates with light chain and (2) a non-IgM gene, e.g., an IgG gene, lacking a sequence that encodes a functional CH1 domain, wherein the non-IgM gene encodes a non-IgM isotype lacking a CH1 domain capable of covalently associating with a light chain constant domain;
  and/or
(b) at an endogenous light chain locus:
  (i) an unrearranged human(ized) immunoglobulin light chain variable region in operable linkage to an endogenous light chain constant region, wherein the unrearranged human(ized) immunoglobulin light chain variable region comprises a plurality of unrearranged human light chain variable region $V_L$ gene segments (e.g., all functional human unrearranged human $V_L$ gene segments) and one or more unrearranged immunoglobulin light chain $J_L$ gene segments,
  optionally wherein the one or more unrearranged immunoglobulin light chain $J_L$ gene segments are one or more unrearranged human immunoglobulin light chain $J_L$ gene segments (e.g., all functional human $J_HL$ gene segments),
  optionally wherein the endogenous immunoglobulin light chain locus is an endogenous immunoglobulin light chain kappa (κ) locus, the unrearranged human(ized) immunoglobulin light chain variable region comprises human variable κ ($V_κ$) and joining κ ($J_κ$) gene segments, and wherein the endogenous light chain constant region is an endogenous κ chain constant region sequence and/or wherein the endogenous immunoglobulin light chain locus is an endogenous immunoglobulin light chain lambda (λ), the unrearranged human(ized) immunoglobulin light chain variable region comprises human variable λ ($V_λ$) and joining λ ($J_λ$) gene segments, and the endogenous light chain constant region is an endogenous λ chain constant region sequence, optionally wherein the endogenous immunoglobulin light chain λ locus comprises (a) one or more human $V_λ$ gene segments, (b) one or more human $J_λ$ gene segments, and (c) one or more human $C_λ$ gene segments, wherein (a) and (b) are operably linked to (c) and a rodent immunoglobulin light chain constant ($C_λ$) gene segment, and wherein the endogenous immunoglobulin λ light chain locus further comprises: one or more rodent immunoglobulin λ light chain enhancers (Eλ), and one or more human immunoglobulin λ light chain enhancers (Eλ), optionally comprising three human Eλs;
(ii) a common light chain encoding sequence comprising a rearranged human(ized) light chain variable region sequence in operable linkage to an endogenous light chain constant region, wherein the rearranged human(ized) light chain variable region sequence comprises a human light chain variable region $V_L$ gene segment rearranged with an immunoglobulin light chain $J_L$ gene segment;
(iii) a restricted unrearranged human(ized) light chain variable region in operable linkage to an endogenous light chain constant region, wherein the restricted unrearranged human(ized) light chain variable region comprises no more than two unrearranged human immunoglobulin light chain variable ($V_L$) gene segments operably linked to one or more unrearranged human immunoglobulin light chain joining ($J_L$) gene segments;
(iv) a histidine modified unrearranged human(ized) light chain variable region in operable linkage to an endogenous light chain constant region, wherein the histidine modified unrearranged human(ized) light chain variable region comprises an unrearranged human(ized) immunoglobulin light chain variable gene sequence comprising in a complementarity determining region 3 (CDR3) encoding sequence a substitution of at least one non-histidine codon with a histidine codon or an insertion of at least one histidine codon; or
(v) a histidine modified rearranged human(ized) light chain variable region in operable linkage to an endogenous light chain constant region, wherein the histidine modified rearranged human(ized) light chain variable region comprises a rearranged human(ized) immunoglobulin light chain variable gene sequence comprising in a complementarity determining region 3 (CDR3) encoding sequence a substitution of at least one non-histidine codon with a histidine codon or an insertion of at least one histidine codon,
optionally wherein the mouse further comprises
(i) a human(ized) immunoglobulin heavy chain locus comprising a functional ADAM6 gene such that the mouse exhibits wildtype fertility of the non-human animal; and/or
(ii) an exogenous terminal deoxynucleotidyl transferase (TdT) gene for increased antigen receptor diversity, optionally such that at least 10% of the rearranged variable region genes comprise non-template additions,
which mice have been previously described. See, e.g., U.S. Pat. Nos. 8,697,940; 8,754,287; 9,204,624; 9,334,334; 9,801,362; 9,332,742; and 9,516,868; U.S. Patent Publications 20110195454, 20120021409, 20120192300, 20130045492; 20150289489; 20180125043; 20180244804; PCT Publication No. WO2019/113065, WO2017210586, and WO2011163314; Lee et al. (2014) *Nature Biotechnology* 32:356, each of which is incorporated herein in its entirety by reference.

A skilled artisan will readily recognize that any mouse or mouse cells (e.g., mouse ES cell modified in a reverse chimeric manner may be modified to comprise a modified Ig V segment as described herein. In some embodiments, the described herein is a genetically modified non-human animal whose genome, e.g., germline genome, comprises:

an endogenous immunoglobulin locus comprising an immunoglobulin heavy chain variable region comprising a modified $hV_H$ gene segment of the invention, a human $D_H$ gene segment, and a human $J_H$ gene segment, wherein the immunoglobulin heavy chain variable region is operably linked to a constant region, and/or an endogenous chain locus comprising an immunoglobulin light chain variable region comprising a modified $V_L$ segment of the invention and a human $J_L$ gene segment, wherein the immunoglobulin light chain variable region is operably linked to a constant region.

In some embodiments, a non-human animal, e.g., a rodent, e.g., a rat or a mouse, comprises in its genome a replacement of one or more endogenous $V_H$, $D_H$, and $J_H$ segments at an endogenous immunoglobulin heavy chain locus with one or more human $V_H$, $D_H$, and $J_H$ segments, wherein the one or more human $V_H$, $D_H$, and $J_H$ segments comprises a modified human $V_H$ gene segment as described herein and are operably linked to an endogenous immunoglobulin heavy chain gene; and optionally an unrearranged or rearranged human $V_L$ and human $J_L$ segment operably linked to a non-human, e.g., rodent, e.g., a mouse or rat, or human immunoglobulin light chain constant ($C_L$) region gene, e.g., at an endogenous non-human light chain locus.

In certain embodiments, the genetically modified non-human animals comprise in their genome, e.g., germline genome, an immunoglobulin locus (exogenous or endogenous) containing an immunoglobulin variable region comprising one or more unrearranged human immunoglobulin variable region gene segments including a modified Ig V gene segment as described herein and an immunoglobulin constant region comprising an immunoglobulin constant region gene and in which the one or more unrearranged human immunoglobulin variable region gene segments are operably linked to the immunoglobulin constant region gene.

Generally, a genetically modified immunoglobulin locus comprises an immunoglobulin variable region (comprising immunoglobulin variable region gene segments) operably linked to an immunoglobulin constant region. In some embodiments, the genetically modified immunoglobulin locus comprises one or more human unrearranged immunoglobulin heavy chain variable region gene segments, including a modified Ig $V_H$ gene segment as described herein, operably linked to a heavy chain constant region gene. In some embodiments, the genetically modified immunoglobulin locus comprises human unrearranged immunoglobulin variable region κ gene segments, including a modified Ig Vκ gene segment as described herein, operably linked to a κ chain constant region gene. In some embodiments, the genetically modified immunoglobulin locus comprises human unrearranged immunoglobulin variable region λ gene segments, including a modified Ig Vλ gene segment as described herein, operably linked to a κ chain constant region gene. In some embodiments, the genetically modified immunoglobulin locus comprises human unrearranged immunoglobulin variable region λ gene segments, including a modified Ig Vλ gene segment as described herein, operably linked to a λ chain constant region gene.

In certain embodiments, the non-human animal comprises at an endogenous heavy chain locus an unrearranged human (ized) immunoglobulin heavy chain variable region comprising a modified Ig $V_H$ gene segment as described herein in operable linkage to an endogenous heavy chain constant region, wherein immunoglobulin variable region contains one or more unrearranged human Ig heavy chain variable region gene segments. In some embodiments, the one or more unrearranged human Ig variable region gene segments comprises a modified Ig $V_H$ gene segment as described herein, one or more immunoglobulin heavy chain diversity (DO segments, and one or more immunoglobulin heavy chain joining (JO segments (optionally one or more unrearranged human $J_H$ segments). In some embodiments, the modified Ig $V_H$ gene segment as described herein is the only Ig $V_H$ segment present in the heavy chain variable region. In some embodiments, the unrearranged human Ig gene segments include all of the functional human $D_H$ gene segments. In some embodiments, the unrearranged human Ig gene segments include all of the functional human $J_H$ gene segments. Exemplary variable regions comprising Ig heavy chain gene segments are provided, for example, in Macdonald et al, Proc. Natl. Acad. Sci. USA 111:5147-52 and supplemental information, which is hereby incorporated by reference in its entirety.

In some embodiments, the non-human animals provided herein comprise at an endogenous heavy chain locus a restricted unrearranged human(ized) heavy chain variable region in operable linkage to an endogenous heavy chain constant region comprising at least a non-human IgM gene, wherein the restricted unrearranged human(ized) heavy chain variable region is characterized by a single human $V_H$ gene segment (e.g., a single modified Ig $V_H$ gene segment as described herein), a plurality of $D_H$ gene segments (e.g., human $D_H$ gene segments) and a plurality of $J_H$ gene segments (e.g. human $J_H$ gene segments), wherein the restricted immunoglobulin heavy chain locus is capable of rearranging and forming a plurality of distinct rearrangements, wherein each rearrangement is derived from the single human $V_H$ gene segment, one of the $D_H$ segments, and one of the $J_H$ segments, and wherein each rearrangement encodes a different heavy chain variable domain (e.g., as described in U.S. Pat. Pub. No. 20130096287, which is hereby incorporated by reference herein in its entirety). In some embodiments the single modified human $V_H$ gene segment is $V_H$1-2 or $V_H$1-69.

In certain embodiments, a non-human animal comprises at an endogenous light chain locus an unrearranged human (ized) immunoglobulin light chain variable region, including a modified Ig $V_L$ segment as described herein, in operable linkage to an endogenous light chain constant region. In some embodiments the unrearranged human(ized) immunoglobulin light chain variable region contains unrearranged human Ig κ variable region gene segments. In some embodiments, the unrearranged human(ized) immunoglobulin variable region comprises one or a plurality of unrearranged human Vκ segments, which may include a modified Ig Vκ segment as described herein, and one or more unrearranged human Jκ segments. In some embodiments, the unrearranged human immunoglobulin variable region gene segments comprise all of the human Jκ segments. In some embodiments, the immunoglobulin variable region gene segments comprise four functional Vκ segments and all human Jκ segments. In some embodiments, the immunoglobulin variable region gene segments comprise 16 functional Vκ segments and all human Jκ segments (e.g., all functional human Vκ segments and Jκ segments). In some embodiments, the unrearranged human immunoglobulin variable region gene segments comprise all of the human Vκ segments and all human Jκ segments. Exemplary variable regions comprising Ig κ gene segments are provided, for example, in Macdonald et al, Proc. Natl. Acad. Sci. USA 111:5147-52 and supplemental information, which is hereby incorporated by reference in its entirety.

In some embodiments, a restricted unrearranged human (ized) light chain variable region in operable linkage to an endogenous light chain constant region is characterized in that the unrearranged human(ized) light chain variable region comprises no more than two human $V_L$ gene segments and a plurality of $J_L$ gene segments (e.g., dual light chain mice, or DLC, as described in U.S. Pat. No. 9,796,788, which is hereby incorporated by reference herein in its entirety), one of which no more than two human $V_L$ gene segments may be a modified Ig $V_L$ segment as described herein. In some embodiments the $V_L$ gene segments are Vκ gene segments. In some embodiments the $V_L$ gene segments are Vλ gene segments. In some embodiments the Vκ gene segments are IGKV3-20 and IGKV1-39. In some embodiments, a non-human animal comprises exactly two unrearranged human Vκ gene segments and five unrearranged human Jκ gene segments operably linked to a mouse light chain constant region at the endogenous κ light chain loci of the mouse, optionally wherein the exactly two unrearranged human Vκ gene segments are a human Vκ1-39 gene segment and a human Vκ3-20 gene segment, wherein the five unrearranged human Jκ gene segments are a human Jκ 1 gene segment, a human Jκ 2 gene segment, a human Jκ 3 gene segment, a human Jκ 4 gene segment, and a human Jκ5 gene segment, wherein the unrearranged human kappa light chain gene segments are capable of rearranging and encoding human variable domains of an antibody, and optionally further wherein the non-human animal does not comprise an endogenous Vκ gene segment that is capable of rearranging to form an immunoglobulin light chain variable region.

In certain embodiments, the unrearranged human(ized) immunoglobulin light chain variable region in operable linkage to an endogenous light chain constant region contains unrearranged human Igλ variable region gene segments, including a modified Ig λ segment as described herein. In some embodiments, the unrearranged human immunoglobulin variable region gene segments comprise a plurality of human Vλ segments and one or more human Jλ segments. In some embodiment, the unrearranged human immunoglobulin variable region gene segments comprise one or more human Vλ segments, one or more human Jλ segments, and one or more human Cλ constant region sequences. In some embodiments, the unrearranged human immunoglobulin variable region gene segments comprise all of the human Vλ segments. In some embodiments, the unrearranged human immunoglobulin variable region gene segments comprise all of the human Jλ segments. Exemplary variable regions comprising Ig λ gene segments are provided, for example, U.S. Pat. Nos. 9,035,128 and 6,998,514, each of which is hereby incorporated by reference herein in its entirety. In some embodiments, the unrearranged human(ized) immunoglobulin light chain variable region in operable linkage to an endogenous light chain constant region comprises (a) one or more human Vλ gene segments, (b) one or more human Jλ gene segments, and (c) one or more human Cλ gene segments, wherein (a) and (b) are operably linked to (c) and an endogenous (e.g., rodent) Cλ gene segment, and wherein the endogenous immunoglobulin λ light chain locus further comprises: one or more rodent immunoglobulin λ light chain enhancers (Eλ), and one or more human immunoglobulin λ light chain enhancers (Eλ), optionally comprising three human Eλ.

In certain embodiments, the unrearranged human(ized) immunoglobulin light chain variable region in operable linkage to an endogenous light chain constant region comprises an unrearranged human Igλ variable region gene segments, e.g., a modified Ig λ segment as described herein, operably linked to an endogenous (e.g., rodent, e.g., rat or mouse) Cκ gene such that the non-human animal expresses an immunoglobulin light chain that comprises a human λ variable domain sequence derived from the Vλ and Jλ gene segments fused with an endogenous κ constant domain, see, e.g., U.S. Pat. No. 9,226,484, incorporated herein in its entirety by reference.

In some embodiments, a humanized immunoglobulin κ light chain locus, e.g., a humanized immunoglobulin endogenous κ locus, comprises one or more human Vλ gene segments (e.g. a modified human Vλ segments as described herein) and one or more human Jλ gene segments upstream of (e.g., operably linked to) a Cλ gene, e.g., which may replace an endogenous Cκ gene. In some embodiments, a Cλ gene is a rodent (e.g., rat or mouse) Cλ gene. In some embodiments, a Cλ gene is a mouse Cλ1 gene. In some embodiments, the Cλ gene comprises one or more human Cλ genes. In some embodiments, the one or more human Jλ gene segments and one or more Cλ genes of such a humanized immunoglobulin κ light chain locus are present in Jλ-Cλ clusters. In some embodiments, a genetically modified rodent (e.g., rat or mouse) is homozygous for such a humanized immunoglobulin κ light chain locus. In some embodiments, a genetically modified rodent (e.g., rat or mouse) is heterozygous for such a humanized immunoglobulin κ light chain locus. In some embodiments, a genetically modified rodent (e.g., rat or mouse), which comprises such a humanized immunoglobulin κ light chain locus, produces an antibody comprising, inter alia, λ light chains, where each λ light chain comprises a human λ light chain variable domain operably linked to a human λ light chain constant domain, e.g., in response to antigenic stimulation.

In some embodiments, the immunoglobulin variable region comprising unrearranged human immunoglobulin variable region gene segments also includes human immunoglobulin variable region intergenic sequences. In some embodiments, the immunoglobulin variable region includes non-human (e.g., rodent, rat, mouse) Ig variable region intergenic sequences. In some embodiments, the intergenic sequence is of endogenous species origin.

In some embodiments, the immunoglobulin variable region is a rearranged light variable region (a universal light chain variable region). In some embodiments, the rearranged Ig light chain variable region gene is a human rearranged Ig light chain variable region gene. Exemplary rearranged Ig light chain variable regions are provided in, e.g., U.S. Pat. Nos. 9,969,814; 10,130,181; and 10,143,186 and U.S. Patent Pub. Nos. 20120021409, 20120192300, 20130045492, 20130185821, 20130302836, and 20150313193, each of which are hereby incorporated by reference herein in its entirety. In some embodiments, the non-human organism ("universal light chain" organism) comprising a universal light chain variable region is used to produce bispecific antibodies. In some embodiments, a common light chain encoding sequence comprises a single rearranged human immunoglobulin light chain Vκ/Jκ sequence operably linked to an endogenous light chain constant region. In some embodiments, the single rearranged human immunoglobulin light chain Vκ/Jκ sequence is modified such that the single rearranged human immunoglobulin light chain sequence encodes an anchor as described herein operably linked to the universal light chain. In some embodiments, the single rearranged human immunoglobulin light chain Vκ/Jκ sequence is either (i) a human Vκ1-39/Jκ5 sequence comprising a human Vκ/Jκ gene segment fused to a human Jκ5 gene segment, or (ii) a human Vκ3-20/Jκ1 sequence comprising a human Vκ3-20 gene segment fused to a human Jκ1 gene segment.

In some embodiments, the immunoglobulin variable region is a light chain and/or a heavy chain immunoglobulin variable region that includes insertions and/or replacements of histidine codons designed to introduce pH-dependent binding properties to the antibodies generated in such non-human organism. In some of such embodiments, the histidine codons are inserted and/or replaced in the nucleic acid sequences encoding CDR3. Various such light and/or heavy immunoglobulin loci are provided in U.S. Pat. Nos. 9,301,510; 9,334,334; and 9,801,362 and U.S. Patent Application Publication No. 20140013456, each of which is incorporated herein by reference in its entirety. In some embodiments, the histidine modified rearranged human(ized) light chain variable region in operable linkage to an endogenous light chain constant region comprises a single rearranged human immunoglobulin light chain variable region gene sequence comprising human Vκ and Jκ segment sequences, optionally wherein the Vκ segment sequence is derived from a human Vκ1-39 or Vκ3-20 gene segment, and wherein the single rearranged human immunoglobulin light chain variable region gene sequence comprises a substitution of at least one non-histidine codon of the Vκ segment sequence with a histidine codon that is expressed at a position selected from the group consisting of 105, 106, 107, 108, 109, 111 and a combination thereof (according to IMGT numbering). In some embodiments, the histidine modified unrearranged human(ized) heavy chain variable region in operable linkage to an endogenous heavy chain constant region comprises an unrearranged human(ized) immunoglobulin heavy chain variable gene sequence comprising in a complementarity determining region 3 (CDR3) encoding sequence (e.g., in a modified (human) $V_H$ gene segment as described herein) a substitution of at least one non-histidine codon with a histidine codon or an insertion of at least one histidine codon. In some embodiments, the unrearranged human (ized) immunoglobulin heavy chain variable gene sequence comprises unrearranged human $V_H$ (e.g., a modified (human) $V_H$ segment as described herein), unrearranged human $D_H$ or synthetic $D_H$, and unrearranged human $J_H$ gene segments, optionally wherein the unrearranged human $V_H$ segment (e.g., modified (human) $V_H$ segment as described herein) comprises the substitution of at least one non-histidine codon with a histidine codon or an insertion of at least one histidine codon. In some embodiments, the histidine modified unrearranged human(ized) light chain variable region in operable linkage to an endogenous heavy chain constant region comprises unrearranged $V_L$ and unrearranged $J_L$ gene segments. In some embodiments, the histidine modified unrearranged human(ized) light chain variable region comprises no more than two unrearranged human $V_L$ (e.g., no more than two Vκ gene segments) and one or more unrearranged human $J_L$ (e.g., Jκ) gene segment (s), wherein each of the no more than two human $V_L$ gene segments comprises in a CDR3 encoding sequence a substitution of at least one non-histidine codon with a histidine codon or an insertion of at least one histidine codon. In some embodiments, the no more than two unrearranged human Vκ gene segments are human Vκ1-39 and Vκ3-20 gene segments each comprising one or more substitutions of a non-histidine codon with a histidine codon, and wherein the human Vκ and Jκ gene segments are capable of rearranging and the human Vκ and Jκ gene segments encode a human light chain variable domain comprising one or more histidines at a position selected from the group consisting of 105, 106, 107, 108, 109, 111 (according to IGMT numbering), and a combination thereof, wherein the one or more histidines are derived from the one or more substitutions.

In some embodiments, the immunoglobulin constant region comprises a heavy chain constant region gene. In some embodiments, the heavy chain constant region gene is a human heavy chain constant region gene. In some embodiments, the heavy chain constant region gene is of endogenous species origin. In some embodiments, the heavy chain constant region gene is a mouse constant region gene or a rat constant region gene. In some embodiments, the constant region gene is a mixture of human and non-human sequence. For example, in some embodiments, the constant region gene encodes a human CH1 region and a non-human (e.g., endogenous species origin, mouse, rat) CH2 and/or CH3 region. In some embodiments, the heavy chain constant region gene is an Cµ, Cδ, Cγ (Cγ1, Cγ2, Cγ3, Cγ4), Cα or Cε constant region gene. In some embodiments, the constant region gene is an endogenous constant region gene. In some embodiments, the constant region gene encodes a mutated CH1 region so that the non-human animal expresses heavy chain only antibodies (see, e.g., U.S. Pat. No. 8,754,287, U.S. Patent Application Publication No. 2015/0289489, each of which is incorporated herein by reference in its entirety). In some embodiments, e.g., where the goal is to generate heavy chains to make bispecific antibodies (e.g., in universal or dual light chain organisms), the Fc domains of the heavy chains comprise modifications to facilitate heavy chain heterodimer formation and/or to inhibit heavy chain homodimer formation. Such modifications are provided, for example, in U.S. Pat. Nos. 5,731,168; 5,807,706; 5,821,333; 7,642,228 and 8,679,785 and in U.S. Pat. Pub. No. 2013/0195849, each of which is hereby incorporated by reference herein in its entirety.

In some embodiments, the immunoglobulin constant region comprises a light chain constant region gene. In some embodiments, the light chain constant region gene is a κ constant region gene. In some embodiments, the light chain constant region gene is a λ constant region gene. In some embodiments, the light chain constant region gene is of endogenous species origin. In some embodiments, the light chain constant region gene is a mouse constant region gene or a rat constant region gene. In some embodiments, the light chain constant region gene is a mixture of human and non-human sequence.

In some embodiments, the immunoglobulin variable region comprising human variable region gene segments and the immunoglobulin constant region gene to which the variable region gene segments are operably linked are located at an endogenous immunoglobulin locus. In some embodiments, the endogenous immunoglobulin locus is an endogenous heavy chain locus. In some embodiments, the endogenous immunoglobulin locus is an endogenous κ locus. In some embodiments, the endogenous immunoglobulin locus is an endogenous λ locus. In some embodiments, the constant region gene to which the human variable region gene segments are operably linked is an endogenous constant region gene.

In some embodiments, one or more of the endogenous immunoglobulin loci or a portion of the one or more endogenous loci (e.g., a variable region and/or a constant region) in the genome of the non-human animal provided herein is inactivated. Endogenous immunoglobulin variable region gene loci and portions thereof can be inactivated using any method known in the art, including, but not limited to, the deletion of the locus or a portion thereof from the genome of the organism, the replacement of a locus or a portion thereof with a different nucleic acid sequence, the inversion of a portion of the locus and/or the displacement of a portion of the locus to another position in the genome of the non-human organism. In some embodiments the inactivation of the locus is only a partial inactivation. In some embodiments, the variable region of the locus is inactivated but the constant region remains functional (e.g., because it is operably linked to non-endogenous variable region gene segments).

In some embodiments, the genetically modified non-human animal includes an inactivated endogenous immunoglobulin heavy chain locus. In some embodiments, the endogenous immunoglobulin heavy chain locus or a portion thereof is inactivated by deletion, replacement, displacement and/or inversion of at least part of the endogenous variable region of the endogenous heavy chain locus. In some embodiments, the at least part of the variable region of the endogenous heavy chain locus that is deleted, replaced, displaced, and/or inverted comprises the J segments of the variable region. In some embodiments, the endogenous immunoglobulin heavy chain locus or portion thereof is inactivated by deletion, replacement, displacement and/or inversion of at least part of the endogenous constant region of the endogenous heavy chain locus. In some embodiments, the at least part of the constant region of the endogenous heavy chain locus that is deleted, replaced, displaced, and/or inverted comprises the Oµ gene of the endogenous constant region.

In some embodiments, the genetically modified non-human animal includes an inactivated endogenous immunoglobulin κ chain locus. In some embodiments, the endogenous immunoglobulin κ chain locus or a portion thereof is inactivated by deletion, replacement, displacement and/or inversion of at least part of the endogenous variable region of the endogenous κ chain locus. In some embodiments, the at least part of the variable region of the endogenous κ chain locus that is deleted, replaced, displaced, and/or inverted comprises the J segments of the variable region. In some embodiments, the endogenous immunoglobulin κ chain locus or portion thereof is inactivated by deletion, replacement, displacement and/or inversion of at least part of the endogenous constant region of the endogenous κ chain locus. In some embodiments, the at least part of the constant region of the endogenous κ chain locus that is deleted, replaced, displaced, and/or inverted comprises the Cκ gene of the endogenous constant region.

In some embodiments, the genetically modified non-human animal includes an inactivated endogenous immunoglobulin λ chain locus. In some embodiments, the endogenous immunoglobulin λ chain locus or a portion thereof is inactivated by deletion, replacement, displacement and/or inversion of at least part of an endogenous variable region of the endogenous λ chain locus. In some embodiments, the at least part of at least one V-J-C gene cluster in the endogenous λ chain locus is deleted, replaced, displaced, and/or inverted. In some embodiments, the endogenous immunoglobulin λ chain locus or portion thereof is inactivated by deletion, replacement, displacement and/or inversion of at least part of an endogenous constant region of the endogenous λ chain locus. In some embodiments, the at least part of the constant region of the endogenous λ chain locus that is deleted, replaced, displaced, and/or inverted comprises a C gene of the endogenous constant region.

In various embodiments, the immunoglobulin locus modifications do not affect fertility of the non-human animal. In some embodiments, the heavy chain locus comprises a functional, e.g., endogenous ADAM6a gene, ADAM6b gene, or both, and the genetic modification does not affect the expression and/or function of the endogenous ADAM6a gene, ADAM6b gene, or both. In some embodiments, the genome of the genetically modified non-human animal further comprises an ectopically located functional, e.g., endogenous ADAM6a gene, ADAM6b gene, or both. Exemplary non-human animals expressing exogenous ADAM6a and/or ADAM6b are described in U.S. Pat. Nos. 8,642,835 and 8,697,940, each of which is hereby incorporated by reference in its entirety.

In some embodiments, the genetically modified non-human animal further comprises and expresses an exogenous terminal deoxynucleotidyl transferase (TdT) for increased antigen receptor diversity. Exemplary non-human animals expressing exogenous TdT are described in PCT Publication WO 2017210586, which is hereby incorporated by reference in its entirety.

In some embodiments, a transcriptional control element includes a RAG1 transcriptional control element, a RAG2 transcriptional control element, an immunoglobulin heavy chain transcriptional control element, an immunoglobulin λ light chain transcriptional control element, an immunoglobulin 1 light chain transcriptional control element, or any combination thereof.

In some embodiments, the genome of a provided non-human animal further comprises one or more human immunoglobulin heavy and/or light chain genes (see, e.g., U.S. Pat. Nos. 8,502,018; 8,642,835; 8,697,940; 8,791,323; and U.S. Patent Application Publication Nos. 2013/0096287 A1 and 2018/0125043 A1; and PCT Publication No. WO2019/113065, each of which are herein incorporated by reference in their entireties). Alternatively, a recombinant nucleic acid molecule comprising a modified Ig V segment as described herein may be introduced into an embryonic stem cell of a different modified strain such as, e.g., a VELOCIMMUNE® strain (see, e.g., U.S. Pat. No. 8,502,018 or 8,642,835; herein incorporated by reference in their entireties). In some embodiments, non-human animals as described herein may be prepared by introducing a targeting vector as described herein, into a cell from a modified strain. To give but one example, a targeting vector as described herein may be introduced into a non-human animal as described in U.S. Pat. Nos. 8,642,835 and 8,697,940; herein incorporated by reference in their entireties, which non-human animal expresses antibodies that have fully human variable regions and mouse constant regions. In some embodiments, non-human animals as described herein are prepared to further comprise human immunoglobulin genes (variable and/or constant region genes). In some embodiments, non-human animals as described herein comprise a modified Ig V segment as described herein, and genetic material from a heterologous species (e.g., humans), wherein the genetic material encodes, in whole or in part, one or more human heavy and/or light chain variable regions.

The non-human animals as described herein may be prepared as described above, or using methods known in the art, to comprise additional human or humanized genes, oftentimes depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired.

For example, as described herein, non-human animals comprising a modified Ig V segment as described herein may further comprise (e.g., via cross-breeding or multiple gene targeting strategies) one or more modifications as described U.S. Patent Application Publication Nos. 2011-0195454 A1, 2012-0021409 A1, 2012-0192300 A1, 2013-0045492 A1, 2013-0185821 A1, 2013-0198880 A1, 2013-0302836 A1, 2015-0059009 A1; International Patent Application Publication Nos. WO 2011/097603, WO 2012/148873, WO 2013/134263, WO 2013/184761, WO 2014/160179, WO 2014/160202; all of which are hereby incorporated by reference in their entireties.

A transgenic founder non-human animal can be identified based upon the presence of a modified Ig V segment in its genome and/or expression of anchor-modified antibodies that comprise amino acids corresponding to a receptor binding portion of a non-immunoglobulin polypeptide that binds a cognate receptor. A transgenic founder non-human animal can then be used to breed additional non-human animals carrying the modified Ig V segment thereby creating a series of non-human animals each carrying one or more copies of a modified Ig V segment. Moreover, transgenic non-human animals carrying a modified Ig V segment can further be bred to other transgenic non-human animals carrying other transgenes (e.g., human immunoglobulin genes) as desired.

Transgenic non-human animals may also be produced to contain selected systems that allow for regulated or directed expression of the transgene. Exemplary systems include the Cre/loxP recombinase system of bacteriophage P1 (see, e.g., Lakso, M. et al., 1992, Proc. Natl. Acad. Sci. USA 89:6232-6236, which is incorporated by reference in its entirety) and the FLP/Frt recombinase system of *S. cerevisiae* (O'Gorman, S. et al, 1991, Science 251:1351-1355; each of which is incorporated by reference in its entirety). Such animals can be provided through the construction of "double" transgenic animals, e.g., by mating two transgenic animals, one containing a transgene comprising a selected modification (e.g., a modified Ig V segment) and the other containing a transgene encoding a recombinase (e.g., a Cre recombinase).

Although embodiments employing a modified Ig v segment in a mouse (i.e., a mouse with a modified human $V_H$ segment, $D_H$, and $J_H$ gene segments, all of which are operably linked with one or more murine heavy chain constant region genes) are extensively discussed herein, other non-human animals that comprise a modified Ig v segment are also provided. Such non-human animals include any of those which can be genetically modified to express anchor-modified immunoglobulins as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Methods for modifying a non-human animal genome (e.g., a pig, cow, rodent, chicken, etc.) include, e.g., employing a zinc finger nuclease (ZFN), a transcription activator-like effector nuclease (TALEN) or a Cas protein (i.e., a CRISPR/Cas system) to modify a genome to include a modified Ig V segment as described herein. Guidance for methods for modifying the germline genome of a non-human animal can be found in, e.g., U.S. Patent Application Publication Nos. 2015-0376628 A1, US 2016-0145646 A1 and US 2016-0177339 A1; incorporated herein by reference in their entireties.

In some embodiments, a non-human animal as described herein is a mammal. In some embodiments, a non-human animal as described herein is a small mammal, e.g., of the superfamily Dipodoidea or Muroidea. In some embodiments, a genetically modified animal as described herein is a rodent. In some embodiments, a rodent as described herein is selected from a mouse, a rat, and a hamster. In some embodiments, a rodent as described herein is selected from the superfamily Muroidea. In some embodiments, a genetically modified animal as described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, a genetically modified rodent as described herein is selected from a true mouse or rat (family Muridae), a gerbil, a spiny mouse, and a crested rat. In some embodiments, a genetically modified mouse as described herein is from a member of the family Muridae. In some embodiment, a non-human animal as described herein is a rodent. In some embodiments, a rodent as described herein is selected from a mouse and a rat. In some embodiments, a non-human animal as described herein is a mouse.

In some embodiments, a non-human animal as described herein is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, a mouse of the present invention is a 129-strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5):1024-1028, 1030, 1032; herein incorporated by reference in its entirety). In some embodiments, a genetically modified mouse as described herein is a mix of an aforementioned 129 strain and an aforementioned C57BL/6 strain. In some embodiments, a mouse as described herein is a mix of aforementioned 129 strains, or a mix of aforementioned BL/6 strains. In some embodiments, a 129 strain of the mix as described herein is a 129S6 (129/SvEvTac) strain. In some embodiments, a mouse as described herein is a BALB strain, e.g., BALB/c strain. In some embodiments, a mouse as described herein is a mix of a BALB strain and another aforementioned strain.

In some embodiments, a non-human animal as described herein is a rat. In some embodiments, a rat as described herein is selected from a Wistar rat, an LEA strain, a Sprague Dawley strain, a Fischer strain, F344, F6, and Dark Agouti. In some embodiments, a rat strain as described herein is a mix of two or more strains selected from the group consisting of Wistar, LEA, Sprague Dawley, Fischer, F344, F6, and Dark Agouti.

Methods of Producing Anchor-Modified Immunoglobulins and Anchor-Modified Immunoglobulins Several in vitro and in vivo technologies have been developed for the production of antibody-based therapeutics. In particular, in vivo technologies have featured the production of transgenic animals (i.e., rodents) containing human immunoglobulin genes either randomly incorporated into the genome of the animal (e.g., see U.S. Pat. No. 5,569,825, incorporated by reference in its entirety) or precisely placed at an endogenous immunoglobulin locus in operable linkage with endogenous immunoglobulin constant regions of the animal (e.g., see U.S. Pat. Nos. 8,502,018; 8,642,835; 8,697,940; and 8,791,323; each of which is incorporated by reference in its entirety). Both approaches have been productive in producing promising antibody therapeutic candidates for use in humans. Further, both approaches have the advantage over in vitro approaches in that antibody candidates are chosen from antibody repertoires generated in vivo, which includes selection for affinity and specificity for antigen within the internal milieu of the host's immune system. In this way, antibodies bind to naturally presented antigen (within relevant biological epitopes and surfaces) rather than artificial environments or in silico predictions that can accompany in vitro technologies. Despite the robust antibody repertoires produced from in vivo technologies, antibodies to complex (e.g., viruses, channel polypeptides) or cytoplasmic antigens remains difficult. Further, generating antibodies to polypeptides that share a high degree of sequence identity between species (e.g., human and mouse) remains a challenge due to immune tolerance.

Thus, the present invention is, among other things, based on the recognition that the construction of an in vivo system characterized by the production of antibodies having an anchor to help moor the immunoglobulin to an antigen of interest (e.g., the cognate receptor of the anchor) and increase the affinity thereof to the antigen, either by contributing to the avidity of the molecule via its own affinity to its cognate receptor and/or by allowing somatic hypermutation of a larger repertoire of immunoglobulins capable of recognizing the cognate receptor.

Provided non-human animals may be employed for making a human antibody, where the human antibody comprises variable domains derived from one or more variable region nucleic acid sequences encoded by genetic material of a cell of a non-human animal as described herein. For example, a provided non-human animal is immunized with an antigen of interest (e.g., a receptor that is cognate to the anchor) under conditions and for a time sufficient that the non-human animal develops an immune response to said antigen of interest. Antibodies are isolated from the non-human animal (or one or more cells, for example, one or more B cells) and characterized using various assays measuring, for example, affinity, specificity, epitope mapping, ability for blocking ligand-receptor interaction, inhibition receptor activation, etc. In some embodiments, antibodies produced by provided non-human animals comprise one or more human variable domains that are derived from one or more human variable region nucleotide sequences isolated from the non-human animal.

Non-human animals as described herein provide an improved in vivo system and source of biological materials (e.g., cells) for producing human antibodies that are useful for a variety of assays. In some embodiments, provided non-human animals are used to develop therapeutics that target one or more receptors of a ligand receptor pair, as described herein. In some embodiments, provided non-human animals are used to identify, screen and/or develop candidate therapeutics (e.g., antibodies, etc.) that bind one or more G-protein-coupled receptor (GPCR) polypeptides. In some embodiments, provided non-human animals are used to screen and develop candidate therapeutics (e.g., antibodies, etc.) that block activity of one or more receptor tyrosine kinases, one or more human GPCR polypeptides, one or more Notch receptors, one or more of CD28, CTLA4, and PD1, a plexin receptor, a LDLR, an LILR, a KIR, and integrin, or an NPR, e.g., NPR3. In some embodiments, provided non-human animals are used to determine the binding profile of antagonists and/or agonists of one or more human GPCR polypeptides, one or more Notch receptors, one or more of CD28, CTLA4, and PD1, a plexin receptor, a LDLR, an LILR, a KIR, and integrin, or an NPR, e.g., NPR3. In some embodiments, provided non-human animals are used to determine the epitope or epitopes of one or more candidate therapeutic antibodies that bind one or more human GPCR polypeptides, one or more Notch receptors, one or more of CD28, CTLA4, and PD1, a plexin receptor, a LDLR, an LILR, a KIR, and integrin, or an NPR, e.g., NPR3.

In some embodiments, provided non-human animals are used to determine the pharmacokinetic profiles of antibodies. In some embodiments, one or more provided non-human animals and one or more control or reference non-human animals are each exposed to one or more candidate therapeutic antibodies at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection, e.g., using an intravenous fluid bag. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In some embodiments, provided non-human animals express antibodies, thus cells, cell lines, and cell cultures can be generated to serve as a source of antibodies for use in binding and functional assays, e.g., to assay for binding or function of an antagonist or agonist, particularly where the antagonist or agonist is specific for a human polypeptide sequence or epitope or, alternatively, specific for a human polypeptide sequence or epitope that functions in ligand-receptor interaction (binding). In some embodiments, epitopes bound by candidate therapeutic antibodies or siRNAs can be determined using cells isolated from provided non-human animals.

In some embodiments, cells from provided non-human animals can be isolated and used on an ad hoc basis or can be maintained in culture for many generations. In some embodiments, cells from a provided non-human animal are immortalized (e.g., via use of a virus) and maintained in culture indefinitely (e.g., in serial cultures).

In some embodiments, non-human animals as described herein provide an in vivo system for the generation of antibody variants that binds a human target antigen. Such variants include antibodies having a desired functionality, specificity, low cross-reactivity to a common epitope shared by two or more human target antigens. In some embodiments, provided non-human animals are employed to generate panels of antibodies to generate a series of antibody variants that are screened for a desired or improved functionality.

In some embodiments, non-human animals as described herein provide an in vivo system for generating antibody libraries. Such libraries provide a source for heavy and light chain variable region sequences that may be grafted onto different Fc regions based on a desired effector function and/or used as a source for affinity maturation of the variable region sequence using techniques known in the art (e.g., site-directed mutagenesis, error-prone PCR, etc.).

Kits

The present invention further provides a pack or kit comprising one or more containers filled with at least one non-human animal, non-human cell, DNA fragment, and/or targeting vector as described herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both, or a contract that governs the transfer of materials and/or biological products (e.g., a non-human animal or non-human cell as described herein) between two or more entities.

Non-limiting embodiments are described below:

Embodiment 1. A recombinant nucleic acid molecule comprising a modified immunoglobulin (Ig) variable (V) segment that encodes an anchor-modified Ig polypeptide,
wherein the modified Ig V segment comprises a nucleic acid sequence encoding the anchor between a nucleic acid sequence encoding an Ig signal peptide and a nucleic acid sequence encoding the framework region (FR) 1, complementarity determining region (CDR)1, FR2, CDR2, FR3, and CDR3 of a germline Ig V segment, or a variant thereof,
wherein anchor modified Ig polypeptide comprises in operable linkage:
(i) the Ig signal peptide,
(ii) the anchor, and
(iii) the FR1, CDR1, FR2, CDR2, FR3, and CDR3 of the germline Ig V segment, or a variant thereof,
wherein the anchor comprises a receptor binding portion of a non-immunoglobulin polypeptide of interest that binds a cognate receptor, and
optionally wherein the nucleic acid molecule lacks any other V segments.

Embodiment 2. The recombinant nucleic acid molecule of embodiment 1, wherein the Ig signal peptide is the Ig signal peptide of the germline Ig V segment, or variant thereof.

Embodiment 3. The recombinant nucleic acid molecule of embodiment 1 or embodiment 2, wherein the germline Ig V segment or variant thereof is a germline Ig heavy chain variable ($V_H$) segment or variant thereof such that
the modified Ig V segment is a modified Ig $V_H$ segment that comprises the nucleic acid sequence encoding the anchor between the nucleic acid sequence encoding an Ig signal peptide and a nucleic acid sequence encoding the framework region (FR) 1, complementarity determining region (CDR)1, FR2, CDR2, FR3, and CDR3 of the germline Ig $V_H$ segment or a variant thereof, and
the anchor modified Ig polypeptide comprises in operable linkage:
(i) the Ig signal peptide,
(ii) the anchor, and
(iii) the FR1, CDR1, FR2, CDR2, FR3, and CDR3 of the germline Ig $V_H$ segment or a variant thereof.

Embodiment 4. The recombinant nucleic acid molecule of any one of embodiments 1-3, wherein the germline Ig V segment or variant thereof is a germline human (h) $V_H$1-2 segment, a germline $hV_H$1-3 segment, a germline $hV_H$1-8 segment, a germline $hV_H$1-18 segment, a germline $hV_H$1-24 segment, a germline $hV_H$1-45 segment, a germline $hV_H$1-46 segment, a germline $hV_H$1-58 segment, a germline $hV_H$1-69 segment, a germline $hV_H$2-5 segment, a germline $hV_H$2-26 segment, a germline $hV_H$2-70 segment, a germline $hV_H$3-7 segment, a germline $hV_H$3-9 segment, a germline $hV_H$3-11 segment, a germline $hV_H$3-13 segment, a germline $hV_H$3-15 segment, a germline $hV_H$3-16 segment, a germline $hV_H$3-20 segment, a germline $hV_H$3-21 segment, a germline $hV_H$3-23 segment, a germline $hV_H$3-30 segment, a germline $hV_H$3-30-3 segment, a germline $hV_H$3-30-5 segment, a germline $hV_H$3-33 segment, a germline $hV_H$3-35 segment, a germline $hV_H$3-38 segment, a germline $hV_H$3-43 segment, a germline $hV_H$3-48 segment, a germline $hV_H$3-49 segment, a germline $hV_H$3-53 segment, a germline $hV_H$3-64 segment, a germline $hV_H$3-66 segment, a germline $hV_H$3-72 segment, a germline $hV_H$3-73 segment, a germline $hV_H$3-74 segment, a germline $hV_H$4-4 segment, a germline $hV_H$4-28 segment, a germline $hV_H$4-30-1 segment, a germline $hV_H$4-30-2 segment, a germline $hV_H$4-30-4 segment, a germline $hV_H$4-31 segment, a germline $hV_H$4-34 segment, a germline $hV_H$4-39 segment, a germline $hV_H$4-59 segment, a germline $hV_H$4-61 segment, a germline $hV_H$5-51 segment, a germline $hV_H$6-1 segment, a germline $hV_H$7-4-1 segment, a germline $hV_H$7-81 segment, or variants thereof.

Embodiment 5. The recombinant nucleic acid molecule of any one of embodiments 1-4, wherein the germline Ig V segment or variant thereof is a germline $hV_H$1-69 segment or variant thereof, optionally wherein the Ig signal peptide comprises the sequence MDWTWRFLFVVAAATGVQS (SEQ ID NO:7).

Embodiment 6. The recombinant nucleic acid molecule of any one of embodiments 3-5, comprising in operable linkage and from 5' to 3':
(I) the modified Ig $V_H$ segment,
(II) one or a plurality of Ig heavy chain diversity (DO segments, and
(III) one or a plurality of Ig heavy chain joining ($J_H$) segments.

Embodiment 7. The recombinant nucleic acid molecule of embodiment 6, wherein
the one or a plurality of Ig $D_H$ segments of (II) comprises one, a plurality of, or all human Ig $D_H$ segments, and/or
the one or a plurality of Ig $J_H$ segments of (III) comprises one, a plurality of, or all human Ig $J_H$ segments.

Embodiment 8. The recombinant nucleic acid molecule of embodiment 6 or embodiment 7, wherein the one or a plurality of Ig $D_H$ segments of (II) and the one or a plurality of Ig $J_H$ gene segments of (III) are recombined and form a rearranged Ig $D_H/J_H$ sequence such that the recombinant nucleic acid molecule comprises in operable linkage and from 5' to 3':
the modified Ig $V_H$ gene segment and
the rearranged Ig $D_H/J_H$ sequence.

Embodiment 9. The recombinant nucleic acid molecule of embodiment 8, wherein the modified Ig $V_H$ gene segment and the rearranged Ig $D_H/J_H$ sequence are recombined and form a rearranged Ig $V_H/D_H/J_H$ sequence that encodes an anchor modified Ig heavy chain variable domain,
wherein the anchor modified Ig heavy chain variable domain comprises in operable linkage:
(i) the Ig signal peptide,
(ii) the anchor, and
(iii) the FR1, complementarity determining region (CDR) 1, FR2, CDR2, FR3, CDR3, and FR4 encoded by the rearranged Ig $V_H/D_H/J_H$ sequence.

Embodiment 10. The recombinant nucleic acid molecule of any one of embodiments 3-8, wherein the modified Ig $V_H$ segment is an unrearranged modified Ig $V_H$ gene segment.

Embodiment 11. The recombinant nucleic acid molecule of any one of embodiments 6-10, further comprising a nucleic acid sequence encoding an Ig heavy chain constant region ($C_H$),
wherein the nucleic acid sequence encoding an Ig $C_H$ is downstream of and operably linked to
(I) the modified Ig $V_H$ segment,
(II) the one or a plurality of Ig $D_H$ segments, and
(III) the one or a plurality of Ig $J_H$ segments.

Embodiment 12. The recombinant nucleic acid molecule of embodiment 11, wherein the nucleic acid sequence encoding an Ig $C_H$ comprises an Iv gene that encodes an IgM isotype, an Igδ gene that encodes an IgD isotype, an Igγ gene that encodes an IgG isotype, an Igα gene that encodes an IgA isotype, and/or an Igε gene that encodes an IgE isotype.

Embodiment 13. The recombinant nucleic acid molecule of any one of embodiments 3-12, comprising a nucleic acid sequence encoding an anchor-modified Ig heavy chain, wherein the anchor-modified Ig heavy chain comprises in operable linkage:
(i) the Ig signal peptide,
(ii) the anchor,
(iii) an Ig heavy chain variable domain comprising the FR1, CDR1, FR2, CDR2, FR3, CDR3, and FR4 encoded by a rearranged Ig $V_H/D_H/J_H$ sequence, and
(iv) an Ig $C_H$.

Embodiment 14. The recombinant nucleic acid molecule of any one of embodiments 11-13, wherein the Ig $C_H$ is a non-human Ig $C_H$.

Embodiment 15. The recombinant nucleic acid molecule of embodiment 14, wherein the non-human Ig $C_H$ is a rodent Ig $C_H$.

Embodiment 16. The recombinant nucleic acid molecule of embodiment 15, wherein the non-human Ig $C_H$ is a rat Ig $C_H$.

Embodiment 17. The recombinant nucleic acid molecule of embodiment 15, wherein the non-human Ig $C_H$ is a mouse Ig $C_H$.

Embodiment 18. The recombinant nucleic acid molecule of embodiment 1 or embodiment 2, wherein the germline Ig V gene segment or variant thereof is a germline Ig light chain variable ($V_L$) segment or a variant thereof such that the modified Ig V segment is a modified Ig $V_L$ segment that comprises the nucleic acid sequence encoding the anchor between the nucleic acid sequence encoding an Ig signal peptide and a nucleic acid sequence encoding the framework region (FR) 1, complementarity determining region (CDR)1, FR2, CDR2, FR3, and CDR3 of the germline Ig $V_L$ segment or a variant thereof, and the anchor modified Ig polypeptide comprises in operable linkage:
(i) the Ig signal peptide,
(ii) the anchor, and
(iii) the FR1, CDR1, FR2, CDR2, FR3, and CDR3 of the germline Ig $V_L$ segment or a variant thereof.

Embodiment 19. The recombinant nucleic acid molecule of embodiment 18, comprising in operable linkage and from 5' to 3':
(I) the modified Ig $V_L$ segment, and
(II) one or a plurality of Ig light chain joining ($J_L$) segments.

Embodiment 20. The recombinant nucleic acid molecule of embodiment 19, wherein the modified Ig $V_L$ segment and the one or a plurality of Ig $J_L$ segments are recombined and form a rearranged Ig $V_L/J_L$ sequence that encodes an anchor modified Ig light chain variable domain,
wherein the anchor modified Ig light chain variable domain comprises in operable linkage:
(i) the Ig signal peptide,
(ii) the anchor, and
(iii) the FR1, CDR1, FR2, CDR2, FR3, CDR3, and FR4 encoded by the rearranged Ig $V_L/J_L$ sequence.

Embodiment 21. The recombinant nucleic acid molecule of embodiment 19 or embodiment 20, further comprising a nucleic acid sequence encoding an Ig light chain constant region (CO,
wherein the nucleic acid sequence encoding an Ig $C_L$ is downstream of and operably linked to:
(I) the modified Ig $V_L$ segment and
(II) the one or a plurality of Ig light chain joining ($J_L$) segments.

Embodiment 22. The recombinant nucleic acid molecule of any one of embodiments 18-21, comprising a nucleic acid sequence encoding an anchor-modified Ig light chain, wherein the anchor-modified Ig light chain comprises in operable linkage:
(i) the Ig signal peptide,
(ii) the anchor,
(iii) an Ig light chain variable domain comprising the FR1, CDR1, FR2, CDR2, FR3, CDR3, and FR4 encoded by a rearranged Ig $V_L/J_L$ sequence, and
(iv) an Ig $C_L$.

Embodiment 23. The recombinant nucleic acid molecule of embodiment 21 or embodiment 22, wherein the Ig $C_L$ is a non-human Ig $C_L$.

Embodiment 24. The recombinant nucleic acid molecule of embodiment 23, wherein the non-human Ig $C_L$ is a rodent Ig $C_L$.

Embodiment 25. The recombinant nucleic acid molecule of embodiment 23, wherein the non-human Ig $C_L$ is a rat Ig $C_L$.

Embodiment 26. The recombinant nucleic acid molecule of embodiment 23, wherein the non-human Ig $C_L$ is a mouse Ig $C_L$.

Embodiment 27. The recombinant nucleic acid molecule of any one of embodiments 18-26, wherein the germline Ig $V_L$ segment or variant thereof is a germline Ig light chain variable kappa (Vκ) segment or variant thereof such that the modified Ig V segment is a modified Ig Vκ segment that comprises the nucleic acid sequence encoding the anchor between the nucleic acid sequence encoding an Ig signal peptide and a nucleic acid sequence encoding the framework region (FR) 1, complementarity determining region (CDR)1, FR2, CDR2, FR3, and CDR3 of the germline Ig Vκ segment or a variant thereof, and the anchor modified Ig polypeptide comprises in operable linkage:
(i) the Ig signal peptide,
(ii) the anchor, and
(iii) the FR1, CDR1, FR2, CDR2, FR3, and CDR3 of the germline Ig Vκ segment or a variant thereof.

Embodiment 28. The recombinant nucleic acid molecule of embodiment 27, comprising in operable linkage and from 5' to 3':
(I) the modified Ig Vκ segment, and
(II) one or a plurality of Ig light chain joining kappa (Jκ) segments.

Embodiment 29. The recombinant nucleic acid molecule of embodiment 28, further comprising a nucleic acid sequence encoding an Ig light chain constant kappa region (Cκ),
wherein the nucleic acid sequence encoding an Ig Cκ is downstream of and operably linked to:
(I) the modified Ig Vκ segment, and
(II) the one or a plurality of Ig Jκ segments.

Embodiment 30. The recombinant nucleic acid molecule of any one of embodiments 18-26, wherein the germline Ig $V_L$ segment or variant thereof is a germline Ig light chain variable lambda (Vλ) segment or variant thereof such that the modified Ig V segment is a modified Ig Vλ segment that comprises the nucleic acid sequence encoding the anchor between the nucleic acid sequence encoding an Ig signal peptide and a nucleic acid sequence encoding the framework region (FR) 1, complementarity determining region (CDR)1, FR2, CDR2, FR3, and CDR3 of the germline Ig Vλ segment or a variant thereof, and the anchor modified Ig polypeptide comprises in operable linkage:
(i) the Ig signal peptide,
(ii) the anchor, and
(iii) the FR1, CDR1, FR2, CDR2, FR3, and CDR3 of the germline Ig Vλ segment or a variant thereof.

Embodiment 31. The recombinant nucleic acid molecule of embodiment 30, comprising in operable linkage and from 5' to 3':

(I) the modified Ig Vλ segment, and
(II) one or a plurality of Ig light chain joining lambda (Jλ) segments.

Embodiment 32. The recombinant nucleic acid molecule of embodiment 31, further comprising a nucleic acid sequence encoding an Ig light chain constant lambda region (Cλ),
wherein the nucleic acid sequence encoding an Ig Cλ is downstream of and operably linked to:
(I) the modified Ig Vλ segment, and
(II) the one or a plurality of Ig segments.

Embodiment 33. The recombinant nucleic acid molecule of any one of embodiments 1-32, wherein the anchor comprises a linker that links the receptor binding portion of a non-immunoglobulin polypeptide of interest to the FR1, CDR1, FR2, CDR2, FR3, and CDR3 of the germline Ig V segment, or a variant thereof.

Embodiment 34. The recombinant acid molecule of embodiment 33, wherein the linker comprises the sequence GGGGS (SEQ ID NO:5)

Embodiment 35. The recombinant nucleic acid molecule of any one of embodiments 1-34, wherein the anchor comprises the natriuretic peptide receptor (NPR) binding portion of a natriuretic peptide (NP).

Embodiment 36. The recombinant nucleic acid molecule of embodiment 35, wherein the NPR binding portion of the NP comprises the C-terminal tail of the NP.

Embodiment 37. The recombinant nucleic acid molecule of embodiment 35 or embodiment 36, wherein the NP is atrial natriuretic peptide (ANP).

Embodiment 38. The recombinant nucleic acid molecule of any one of embodiments 1-37, wherein the anchor comprises the sequence NSFRY (SEQ ID NO:3).

Embodiment 39. The recombinant nucleic acid molecule of any one of embodiments 1-38, comprising a sequence selected from the group consisting of the sequence set forth as SEQ ID NO:8 or a degenerate variant thereof, sequence set forth as SEQ ID NO:10 or a degenerate variant thereof, SEQ ID NO:11 of a degenerate variant thereof, and SEQ ID NO:12 or a degenerate variant thereof.

Embodiment 40. A targeting vector comprising the recombinant nucleic acid molecule of any one of embodiments 1-10 and 33-39, wherein the targeting vector further comprises 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule upstream of and in operable linkage to a non-human Ig $C_H$ at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof.

Embodiment 41. The targeting vector of embodiment 40, wherein upon homologous recombination between the targeting vector and the non-human Ig heavy chain locus, the recombinant nucleic acid molecule replaces a non-human $V_H$ segment at the non-human Ig heavy chain locus.

Embodiment 42. The targeting vector of embodiment 40 or embodiment 41, wherein upon homologous recombination between the targeting vector and the non-human Ig heavy chain locus, the recombinant nucleic acid molecule replaces one or more non-human $V_H$ segments, all non-human $D_H$ segments, and all non-human $J_H$ segments at the non-human Ig heavy chain locus.

Embodiment 43. The targeting vector of any one of embodiments 40-42, wherein upon homologous recombination between the targeting vector and the non-human Ig heavy chain locus, the recombinant nucleic acid molecule replaces all but one non-human $V_H$ segment or all non-human $V_H$ segments, all non-human $D_H$ segments, and all non-human $J_H$ segments at the non-human Ig heavy chain locus.

Embodiment 44. The targeting vector of any one of embodiments 40-43, wherein upon homologous recombination between the targeting vector and the non-human Ig heavy chain locus, the targeted non-human Ig heavy chain locus comprises the recombinant nucleic acid molecule in operable linkage to a non-human Ig heavy chain regulatory sequence at the non-human Ig heavy chain locus.

Embodiment 45. The targeting vector of any one of embodiments 40-44, wherein the 5' homology arm comprises a sequence set forth as SEQ ID NO:11 and/or the 3' homology arm comprises a sequence set forth as SEQ ID NO:12.

Embodiment 46. A targeting vector comprising the recombinant nucleic acid molecule of any one of embodiments 1-17 and 33-39, wherein the targeting vector further comprises 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule in operable linkage to a non-human Ig heavy chain regulatory sequence at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof.

Embodiment 47. The targeting vector of embodiment 46, wherein upon homologous recombination between the targeting vector and the non-human Ig heavy chain locus, the recombinant nucleic acid molecule replaces one or more non-human $V_H$ segments, all non-human $D_H$ gene segments, all non-human $J_H$ gene segments, and one or more non-human $C_H$ genes at the non-human Ig heavy chain locus.

Embodiment 48. A targeting vector comprising the recombinant nucleic acid molecule of any one of embodiments 1-2, 18-20, 27-28, 30-31, and 33-38, wherein the targeting vector further comprises 5' and 3' homology arms that target a non-human Ig light chain locus such that upon homologous recombination between the targeting vector and the non-human Ig light chain locus, the targeted non-human Ig light chain locus comprises the recombinant nucleic acid molecule upstream of and in operable linkage to a non-human Ig $C_L$ at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof Embodiment 49. The targeting vector of embodiment 48, wherein upon homologous recombination between the targeting vector and the non-human Ig light chain locus, the recombinant nucleic acid molecule replaces a non-human $V_L$ segment at the non-human Ig light chain locus.

Embodiment 50. The targeting vector of embodiment 48 or embodiment 49, wherein upon homologous recombination between the targeting vector and the non-human Ig light chain locus, the recombinant nucleic acid molecule replaces one or more non-human $V_L$ segments and all non-human $J_L$ segments at the non-human Ig light chain locus.

Embodiment 51. The targeting vector of any one of embodiments 48-50, wherein upon homologous recombination between the targeting vector and the non-human Ig light chain locus, the recombinant nucleic acid molecule replaces all non-human $V_L$ segments and all non-human $J_H$ segments at the non-human Ig light chain locus.

Embodiment 52. The targeting vector of any one of embodiments 48-51, wherein upon homologous recombination between the targeting vector and the non-human Ig light chain locus, the targeted non-human Ig heavy chain locus comprises the recombinant nucleic acid molecule in operable linkage to a non-human Ig light chain regulatory sequence at the Ig light chain locus.

Embodiment 53. A targeting vector comprising the recombinant nucleic acid molecule of any one of embodiments 1-2, 18-38 wherein the targeting vector further comprises 5' and 3' homology arms that target a non-human Ig light chain locus such that upon homologous recombination between the targeting vector and the non-human Ig light chain locus, the targeted non-human Ig light chain locus comprises the recombinant nucleic acid molecule in operable linkage to a non-human Ig light chain regulatory sequence at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof.

Embodiment 54. The targeting vector of embodiment 53, wherein upon homologous recombination between the targeting vector and the non-human Ig light chain locus, the recombinant nucleic acid molecule replaces non-human $V_L$ segments, all non-human $J_L$ gene segments, and the non-human $C_L$ gene at the non-human Ig light chain locus.

Embodiment 55. A targeting vector comprising the recombinant nucleic acid molecule of any one of embodiments 1-2, 18-20, 27-28, and 33-38, wherein the targeting vector further comprises 5' and 3' homology arms that target a non-human Ig light chain κ locus such that upon homologous recombination between the targeting vector and the non-human Ig light chain κ locus, the targeted non-human Ig light chain κ locus comprises the recombinant nucleic acid molecule upstream of and in operable linkage to a non-human Ig Cκ at the non-human Ig light chain κ locus, optionally wherein the non-human Ig light chain κ locus is an endogenous rodent Ig light chain κ locus and/or wherein the non-human Ig light chain κ locus comprises a human or humanized immunoglobulin light chain variable region, a deletion of endogenous Ig Vκ and/or Jκ gene segments, or a combination thereof.

Embodiment 56. The targeting vector of embodiment 55, wherein upon homologous recombination between the targeting vector and the non-human Ig light chain κ locus, the recombinant nucleic acid molecule replaces a non-human Vκ segment at the non-human Ig light chain κ locus.

Embodiment 57. The targeting vector of embodiment 55 or embodiment 56, wherein upon homologous recombination between the targeting vector and the non-human Ig light chain κ locus, the recombinant nucleic acid molecule replaces one or more non-human Vκ segments and all non-human Jκ segments at the non-human Ig light chain κ locus.

Embodiment 58. The targeting vector of any one of embodiments 55-57, wherein upon homologous recombination between the targeting vector and the non-human Ig light chain κ locus, the recombinant nucleic acid molecule replaces all non-human Vκ segments and all non-human Jκ segments at the non-human Ig light chain κ locus.

Embodiment 59. The targeting vector of any one of embodiments 55-58, wherein upon homologous recombination between the targeting vector and the non-human Ig light chain κ locus, the targeted non-human Ig light chain κ locus comprises the recombinant nucleic acid molecule in operable linkage to a non-human Ig light chain κ regulatory sequence at the Ig light chain κ locus.

Embodiment 60. A targeting vector comprising the recombinant nucleic acid molecule of any one of embodiments 1-2 and 18-29, wherein the targeting vector further comprises 5' and 3' homology arms that target a non-human Ig light chain κ locus such that upon homologous recombination between the targeting vector and the non-human Ig light chain κ locus, the targeted non-human Ig light chain κ locus comprises the recombinant nucleic acid molecule in operable linkage to a non-human Ig light chain κ regulatory sequence at the Ig light chain κ locus.

Embodiment 61. The targeting vector of embodiment 60, wherein upon homologous recombination between the targeting vector and the non-human Ig light chain κ locus, the recombinant nucleic acid molecule replaces non-human Vκ segments, all non-human Jκ gene segments, and the non-human Cκ gene at the non-human Ig light chain κ locus.

Embodiment 62. A targeting vector comprising the recombinant nucleic acid molecule of any one of embodiments 1-2, 18-20, 30-31, and 33-38, wherein the targeting vector further comprises 5' and 3' homology arms that target a non-human Ig light chain λ locus such that upon homologous recombination between the targeting vector and the non-human Ig light chain λ locus, the targeted non-human Ig light chain λ locus comprises the recombinant nucleic acid molecule upstream of and in operable linkage to a non-human Ig Cλ at the non-human Ig light chain locus, optionally wherein the non-human Ig light chain λ locus is an endogenous rodent Ig light chain λ locus and/or wherein the non-human Ig light chain λ locus comprises a human or humanized immunoglobulin light chain variable region, a deletion of endogenous Ig Vλ and/or Jλ gene segments, or a combination thereof.

Embodiment 63. The targeting vector of embodiment 62, wherein upon homologous recombination between the targeting vector and the non-human Ig light chain λ locus, the recombinant nucleic acid molecule replaces a non-human Vλ segment at the non-human Ig light chain λ locus.

Embodiment 64. The targeting vector of embodiment 62 or embodiment 63, wherein upon homologous recombination between the targeting vector and the non-human Ig light chain λ locus, the recombinant nucleic acid molecule replaces one or more non-human Vλ segments and all non-human Jλ segments at the non-human Ig light chain locus.

Embodiment 65. The targeting vector of any one of embodiments 62-64, wherein upon homologous recombination between the targeting vector and the non-human Ig light chain λ locus, the recombinant nucleic acid molecule replaces all non-human Vλ segments and all non-human Jλ segments at the non-human Ig light chain λ locus.

Embodiment 66. The targeting vector of any one of embodiments 62-65, wherein upon homologous recombination between the targeting vector and the non-human Ig light chain λ locus, the targeted non-human Ig light chain λ locus comprises the recombinant nucleic acid molecule in operable linkage to a non-human Ig light chain λ regulatory sequence at the Ig light chain λ locus.

Embodiment 67. A targeting vector comprising the recombinant nucleic acid molecule of any one of embodiments 1-2, 18-26, and 30-38, wherein the targeting vector further comprises 5' and 3' homology arms that target a non-human Ig light chain λ locus such that upon homologous recombination between the targeting vector and the non-human Ig light chain λ locus, the targeted non-human Ig light chain λ locus comprises the recombinant nucleic acid molecule in operable linkage to a non-human Ig light chain λ regulatory sequence at the Ig light chain λ locus.

Embodiment 68. The targeting vector of embodiment 67, wherein upon homologous recombination between the targeting vector and the non-human Ig light chain λ locus, the recombinant nucleic acid molecule replaces non-human Vλ segments, all non-human Jλ gene segments, and the non-human Cλ gene at the non-human Ig light chain λ locus.

Embodiment 69. A non-human animal genome comprising the recombinant nucleic acid molecule of any one of embodiments 1-39 or the targeting vector of any one of embodiments 40-68, optionally wherein the non-human animal is a rodent, optionally wherein the rodent is a rat or a mouse.

Embodiment 70. The non-human animal genome of embodiment 69, wherein the recombinant nucleic acid is at an endogenous Ig locus of the non-human animal genome.

Embodiment 71. A non-human animal or a non-human animal cell comprising the recombinant nucleic acid molecule of any one of embodiments 1-39, the targeting vector of any one of embodiments 40-68, or the non-human animal genome of embodiment 69 or embodiment 70.

Embodiment 72. The non-human animal or non-human animal cell of embodiment 71, wherein the recombinant nucleic acid molecule, the targeting vector, or the non-human animal genome is in the germline of the non-human animal or non-human animal cell.

Embodiment 73. An in vitro method of modifying an isolated cell comprising introducing into the isolated cell the recombinant nucleic acid molecule of any one of embodiments 1-39.

Embodiment 74. The in vitro method of embodiment 73, wherein introducing comprises contacting the cell with the targeting vector of any one of embodiments 40-68.

Embodiment 75. The in vitro method of embodiment 73 or embodiment 74, wherein the cell is a host cell.

Embodiment 76. The in vitro method of embodiment 73 or embodiment 74, wherein the cell is an embryonic stem (ES) cell.

Embodiment 77. The in vitro method of any one of embodiments 73-76, wherein the cell is a rodent cell, optionally wherein the rodent cell is a rat cell or a mouse cell.

Embodiment 78. A non-human animal embryo generated from the embryonic stem cell of embodiment 76.

Embodiment 79. A non-human animal generated from the embryonic stem cell of embodiment 76

Embodiment 80. A method of making a non-human animal comprising implanting the ES cell of embodiment 76 or an embryo comprising the ES cell into a suitable host and maintaining the host under suitable conditions during development of the ES cell or the embryo into viable progeny.

Embodiment 81. The non-human animal of any one of embodiments 71-72 and 79 or the non-human animal made according to the method of embodiment 80, wherein the non-human animal comprises, in comparison to a control non-human animal:
(a) a comparable number of mature B cells in the spleen,
(b) a comparable number of kappa positive B cells in the spleen,
(c) a comparable number of lambda positive B cells in the spleen,
(d) a comparable level of serum IgG and/or
(e) a comparable level of serum IgM.

Embodiment 82. The non-human animal of any one of embodiments 71-72, 79 and 81, or the non-human animal made according to the method of embodiment 80, wherein the non-human animal is capable of mounting an immune response comparable to a control non-human animal.

Embodiment 83. The non-human animal of any one of embodiments 71-72, 79, and 81-82, or the non-human animal made according to the method of embodiment 80, comprising a plurality of antigen-binding proteins that each comprises the anchor-modified Ig polypeptide, optionally:
wherein the mass of each antigen-binding protein confirms the presence of the anchor-modified Ig polypeptide,
wherein the mass of each antigen-binding protein is determined by Matrix-Assisted Laser Desorption Ionization-Time of Flight Mass Spectrometry, or
wherein the mass of each antigen-binding protein confirms the presence of the anchor-modified Ig polypeptide and the mass of each antigen-binding protein is determined by Matrix-Assisted Laser Desorption Ionization-Time of Flight Mass Spectrometry.

Embodiment 84. The non-human animal of any one of embodiments 71-72, 79 and 81-83, or the non-human animal made according to the method of embodiment 80, wherein the non-human animal further comprises the cognate receptor of the non-immunoglobulin polypeptide of interest.

Embodiment 85. The non-human animal of any one of embodiments 71-72, 79, and 81-84, or the non-human animal made according to the method of embodiment 80, comprising a plurality of antigen-binding proteins that each comprises the anchor-modified Ig polypeptide and specifically binds the cognate receptor of the non-immunoglobulin polypeptide of interest, optionally:
wherein the mass of each antigen-binding protein confirms the presence of the anchor-modified Ig polypeptide,
wherein the mass of each antigen-binding protein is determined by Matrix-Assisted Laser Desorption Ionization-Time of Flight Mass Spectrometry, or
wherein the mass of each antigen-binding protein confirms the presence of the anchor-modified Ig polypeptide and the mass of each antigen-binding protein is determined by Matrix-Assisted Laser Desorption Ionization-Time of Flight Mass Spectrometry.

Embodiment 86. The non-human animal of any one of embodiments 84-85, wherein the cognate receptor is a natriuretic peptide receptor (NPR).

Embodiment 87. The non-human animal of any one of embodiments 84-86, wherein each of the plurality of antigen-binding proteins comprises a KD of less than $1 \times 10^9$ and/or a t½ of greater than 30 minutes.

Embodiment 88. The non-human animal of any one of embodiments 84-87, wherein at least 15% of the plurality of antigen-binding proteins block binding of the cognate receptor to the non-immunoglobulin polypeptide of interest.

Embodiment 89. The non-human animal of any one of embodiments 84-88, wherein more than 50% of the plurality of antigen-binding proteins bind the cognate receptor expressed on a cell surface.

Embodiment 90. The non-human animal of any one of embodiments 71-72, 79, and 81-89, or the non-human animal made according to the method of embodiment 80, wherein the non-human animal is a rodent, optionally wherein the rodent is a rat or a mouse.

Embodiment 91. A method of producing an antigen-binding protein or obtaining a nucleic acid encoding same, the method comprising
immunizing the non-human animal of any one of embodiments 71-72, 79, and 81-90 or the non-human animal made according to the method of embodiment 80 with an antigen,
allowing the non-human animal to produce the antigen-binding protein that comprises the anchor-modified Ig polypeptide, or nucleic acid encoding same, that binds the antigen, optionally:
wherein the mass of the antigen-binding protein confirms the presence of the anchor-modified Ig polypeptide,
wherein the mass of the antigen-binding protein is determined by Matrix-Assisted Laser Desorption Ionization-Time of Flight Mass Spectrometry, or
wherein the mass of the antigen-binding protein confirms the presence of the anchor-modified Ig polypeptide and the mass of the antigen-binding protein is determined by Matrix-Assisted Laser Desorption Ionization-Time of Flight Mass Spectrometry.

Embodiment 92. The method of embodiment 91, further comprising recovering the antigen binding protein, or nucleic acid encoding same, from the non-human animal or a non-human animal cell.

Embodiment 93. The method of embodiment 92, wherein the non-human animal cell is a B cell or a hybridoma.

Embodiment 94. The non-human animal cell recovered according to the method of embodiment 91.

Embodiment 95. The non-human animal of embodiment 94, wherein the non-human animal cell is a B cell.

Embodiment 96. The non-human animal cell of embodiment 94 or 95, wherein the B cell is a mouse B cell.

Embodiment 97. A hybridoma cell comprising the non-human animal cell of any one of embodiments 94-95 fused with a myeloma cell.

Embodiment 98. An anchor-modified Ig polypeptide encoded by the recombinant nucleic acid molecule of any one of embodiments 1-39, the targeting vector of any one of embodiments 40-68, the non-human animal genome of any one of embodiments 69-70, expressed by the non-human animal or non-human animal cell of any one of embodiments 71-72 and 81-90, expressed by the non-human animal or non-human animal cell made according to the method of any one of embodiments 73-76 and 80, or made according to the method of any one of embodiments 91-93, optionally:
wherein the mass of each antigen-binding protein confirms the presence of the anchor-modified Ig polypeptide,
wherein the mass of each antigen-binding protein is determined by Matrix-Assisted Laser Desorption Ionization-Time of Flight Mass Spectrometry, or
wherein the mass of each antigen-binding protein confirms the presence of the anchor-modified Ig polypeptide and the mass of each antigen-binding protein is determined by Matrix-Assisted Laser Desorption Ionization-Time of Flight Mass Spectrometry.

Embodiment 99. The anchor-modified Ig polypeptide of embodiment 98 comprising an amino acid sequence set forth as SEQ ID NO:3 at its N-terminus.

Other features of the described embodiments will become apparent in the course of the following descriptions of exemplary embodiments, which are given for illustration and are not intended to be limiting thereof.

EXAMPLES

The following examples are provided so as to describe to those of ordinary skill in the art how to make and use methods and compositions disclosed herein and are not intended to limit the scope of what the inventors regard as their invention. Unless indicated otherwise, temperature is indicated in Celsius, and pressure is at or near atmospheric.

Example 1. Construction of an Immunoglobulin Variable Region Comprising an ANP-Modified Immunoglobulin Variable Region Gene Segment This non-limiting example illustrates the construction of a targeting vector for integration of an anchor-modified immunoglobulin (Ig) variable region (V) gene segment into an immunoglobulin variable region of an immunoglobulin locus. As described below, the coding sequence of the ANP C-terminal tail is placed in operable linkage with an Ig V gene segment, which modified Ig V segment may be placed in operable linkage with Ig joining (J) gene segments, and if appropriate Ig diversity (D) gene segments, so that upon V(D)J recombination, antibodies comprising ANP C-terminal tails at the N-terminus of an immunoglobulin polypeptide chain are expressed.

A targeting vector containing an ANP-modified $V_H$ gene segment for insertion into an immunoglobulin heavy chain variable region was created using VELOCIGENE® technology (see, e.g., U.S. Pat. No. 6,586,251 and Valenzuela et al., 2003, Nature Biotech. 21(6):652-659; herein incorporated by reference) and molecular biology techniques known in the art. A non-limiting exemplary strategy for constructing a targeting vector using sequences encoding the C-terminal tail of ANP is set forth in FIGS. 1-2.

Figure 2:
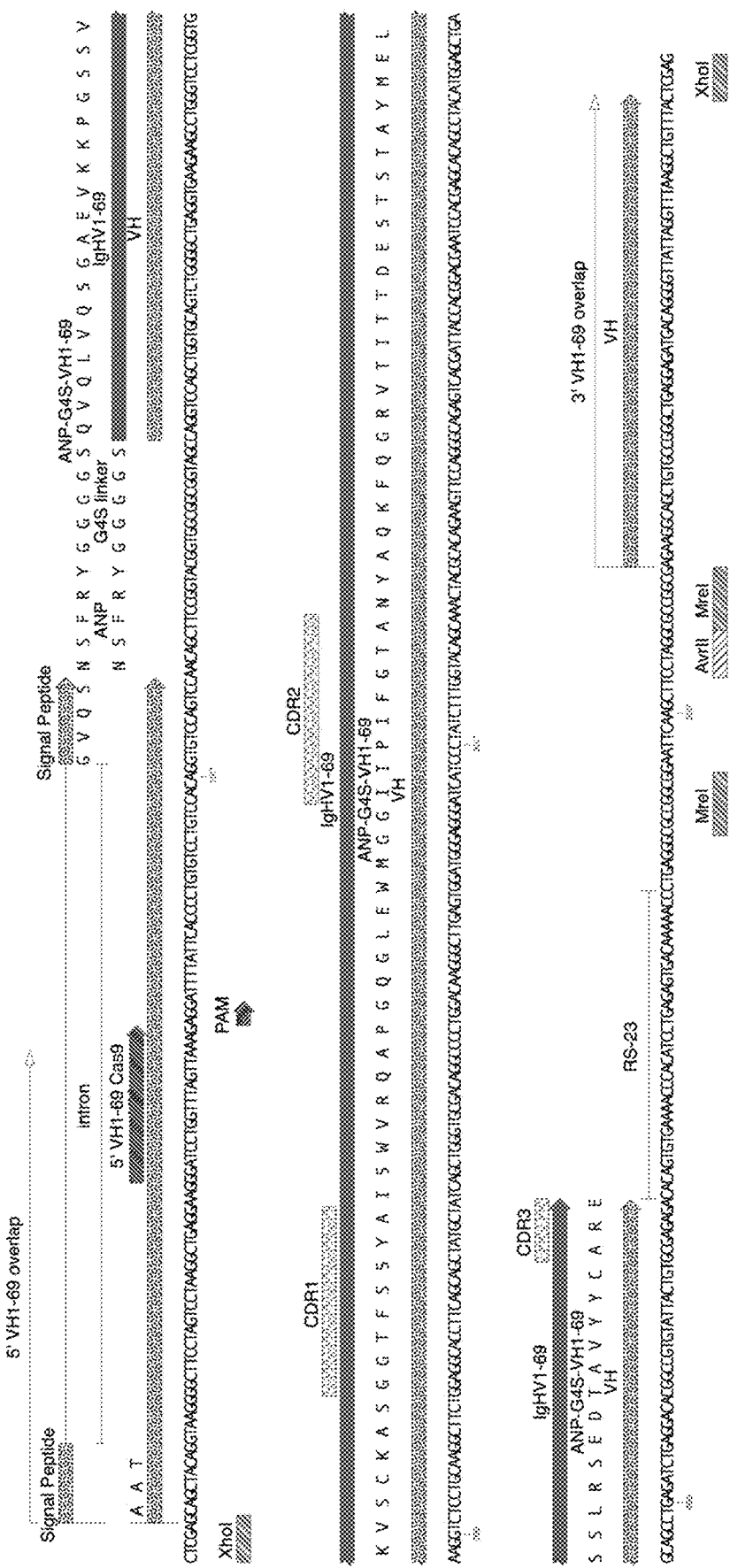
FIG. 2 shows an exemplary non-limiting embodiment of a DNA donor (set forth as SEQ ID NO:10) used to modify the $V_H$1-69 gene in BAC clone VI504. The following features are shown:
a sense DNA sequence that includes
  (a) the last 7 codons of the bipartite signal peptide (see split arrow labeled "signal peptide") encoded by a germline human $V_H$1-69 segment; a nucleotide sequence encoding the entirety of the signal polypeptide is set forth as SEQ ID NO:6; and amino acid sequence of the entirety of the signal polypeptide is set forth as SEQ ID NO:7,
  (b) the germline Ig $V_H$1-69 segment including exon 1, intron 1, and exon 2 (see the split arrows labeled "$V_H$" immediately above the DNA sequence)
  (c) intron 1 of the germline Ig $V_H$1-69 segment ("intron"),
  (d) the nucleotide sequence encoding a C-terminus tail of atrial natriuretic peptide (ANP) (SEQ ID NO:3) and a G4S linker (SEQ ID NO:5),
  (e) the portion of the germline $V_H$1-69 segment that that encodes the FR1, CDR1 (patterned box), FR2, CDR2 (patterned box), FR3 and CDR3 (patterned box), and the amino acid sequence of same (see split arrows labeled IgHV1-69), and
  (e) the 23-mer recombination signal sequence (RS-23 split),
a conceptual translation of the ANP-modified $V_H$1-69 segment which includes the leader sequence (labeled ANP-G4S-VH1-69),
the crRNA binding sites used to cut VI504 with Cas9 in vitro (labeled 5' VH1-69 Cas9 and PAM), the 5' and 3' overlaps used for Gibson Assembly of the donor with VI504 (black lines with arrows labeled "5'VH1-69 overlap" and 3' VH1-69 overlap, respectively), and restriction enzyme sites indicated by diagonally striped boxes below the sequences: EcoRI and AvrII sites used to ligate a spectinomycin-resistance cassette into the donors, XhoI sites used to remove the donor from the pUC vector backbone, and MreI sites used to remove the Spec cassette from the modified BAC prior to seamless repair by joiner oligo-mediated Gibson Assembly.

A donor DNA fragment comprising the C-terminal tail of ANP inserted into the germline $V_H$1-69 gene segment via a sequence encoding a peptide linker was made by de novo DNA synthesis (Blue Heron Biotech, Bothell, WA). FIG. 1 shows the "p466090" ANP-$V_H$1-69 Cas9 donor fragment. A spectinomycin-resistance cassette "SPEC" was ligated into the EcoRI and AvrII sites of donor plasmid p46609 to make plasmid p46685 (FIG. 1). Shown in FIG. 2 is a more detailed illustration of the resulting donor plasmid p46609.

Figure 3:
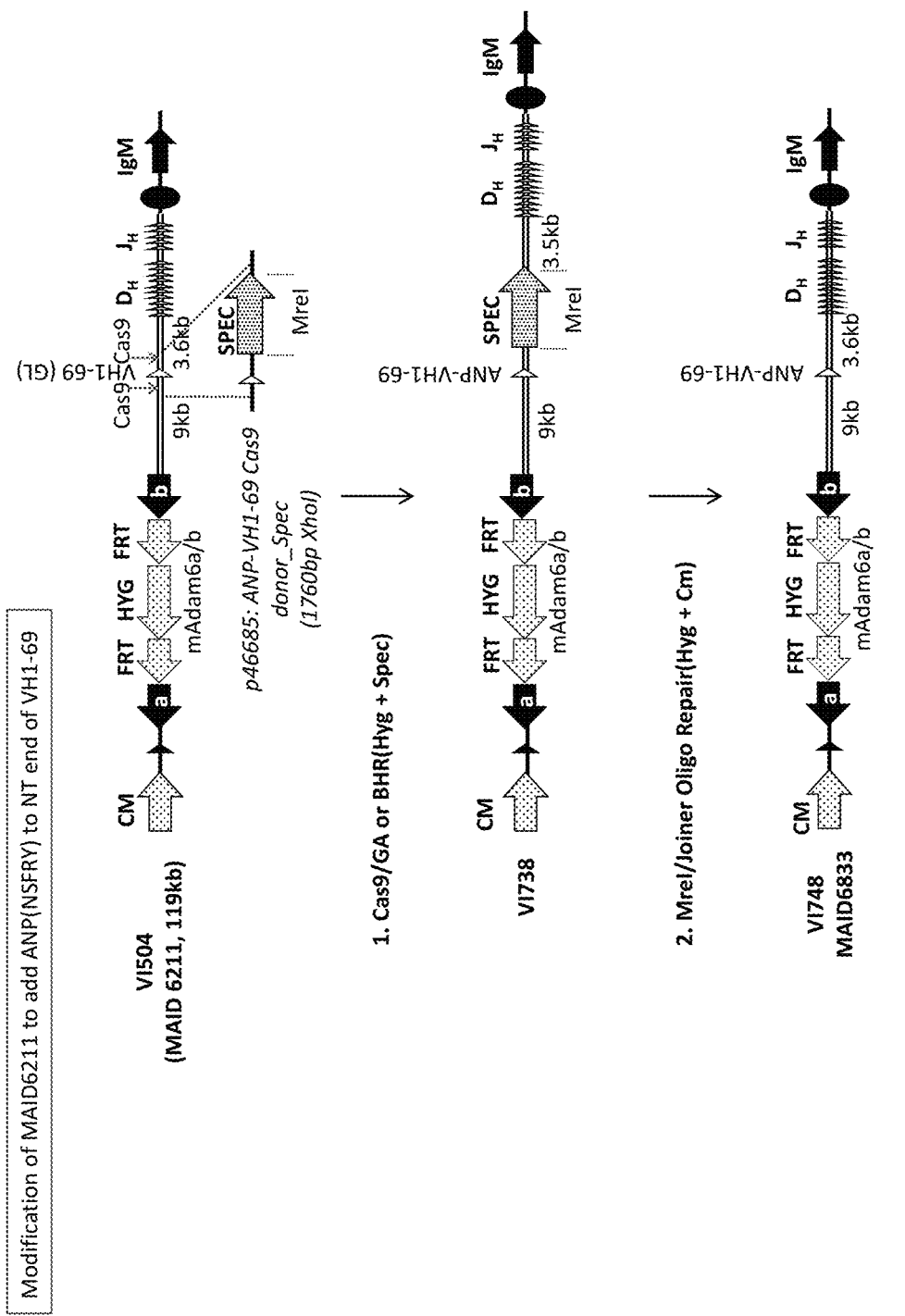
FIG. 3 shows an illustration, not to scale, of a non-limiting exemplary embodiment of inserting the ANP-modified $V_H$1-69 segment into BAC clone VI504 according to Example 1 to create a targeting vector VI748. Generally, unfilled shapes represent human sequences (e.g., the unfilled triangles representing the human $V_H$1-69 segment, the human $D_H$ segments, and the human $J_H$ segments), filled shapes represent murine sequences (e.g., a filled triangle representing an endogenous murine $V_H$ segment (unlabeled), filled arrows representing murine Adam6a "a" and Adam6b "b" genes, a filled oval representing an Ig enhancer, and a filled arrow representing a murine Igμ gene "IgM"), and dotted shapes represent non-human and non-murine sequences (e.g., a chloramphenicol resistance gene "CM", site-specific recombinase recognition sites "Frt sites, a hygromycin resistance gene "HYG", and a spectinomycin resistance gene "SPEC").

The donor fragment was used to modify BAC clone VI504 (MAID6211). See FIG. 2. BAC clone VI504 comprises, from 5' to 3', a ~20 kb 5' mouse homology arm, a ~15 kb I-CeuI-AscI fragment containing the mouse Adam6a gene "a", a Frt-Ub-Hyg-Frt cassette, and the mouse Adam6b gene "b", a ~9 kb AscI-AsiSI fragment containing the germline human $V_H$1-69 gene, a ~60 kb fragment containing the human $D_H$ and human $J_H$ genes, and a ~8 kb 3' mouse homology arm containing the mouse IgH intronic enhancer (filled oval), the IgM switch region, and part of the mouse IgM gene (FIG. 3).

In step 1, VI504 was digested in vitro with Cas9 complexed with a mixture of two gRNAs that cut 5' and 3' of the human germline $V_H$1-69 gene. The resulting 3' and 5' ends have 60 bp overlaps with the ends of p46685. The XhoI fragments of p46685 were then assembled with VI504 (MAID6211) by Gibson Assembly to make VI738. In step 2, VI738 was digested with MreI to remove the spectinomycin-resistance cassette. The BAC was then repaired by joiner oligo-mediated Gibson Assembly, leaving a seamless junction (ΔMreI) to make the final LTVECs VI748 (MAID6833). The LTVEC was identical to VI504 except for the insertion of the ANP-G4S codons in VI748.

Correct assembly of the donor fragments described and targeted replacement of the germline (GL) $V_H$1-69 gene segment of BAC clone VI504 with the NP-modified $V_H$1-69 gene segment as described here was confirmed by sequencing and polymerase chain reaction throughout the construction of the targeting vector using primers set forth in Table 1.

TABLE 1

| Step | Junction | Primer Name | Primer Sequence (SEQ ID NO:) | Jxn PCR(bp) |
|---|---|---|---|---|
| A. EcoRI/AvrII ligation of pSVi0029 into p46609 to make p46685 | | | | |
| Jxn PCR | EcoRI | 5' detect $V_H$1-69 FR3 | ACAGAAGTTCCA GGGCAGAG (SEQ ID NO: 18) | 302 |
| | | 3' up detect spec | TGTCCACTGGGT TCGTGCCTT (SEQ ID NO: 19) | |
| Jxn PCR | AvrII | 5' down detect spec | CAGTATCAGCCC GTCATACTT (SEQ ID NO: 20) | 197 |
| | | 3' $V_H$1-69 overlap detect | TAACCCCTGTCA TCTCCTC (SEQ ID NO: 21) | |
| 1. Cas9/GA of VI504 (MAID6211) + p46685 = VI738 | | | | |
| Cas9 | | 5' DNA Target(PAM) | GGATCCTGGTTT AGTTAAAG(AGG) (SEQ ID NO: 22) | |
| | | 5' $V_H$1-69 Cas9 crRNA | GGAUCCUGGUUU AGUUAAAGGUUU UAGAGCUAUGCU GUUUUG (SEQ ID NO: 23) | |
| | | 3' DNA Target(PAM) | GACAAAAACCCT GAGGGAGA(AGG) (SEQ ID NO: 24) | |
| | | 3 $V_H$1-69 Cas9 crRNA | GACAAAAACCCU GAGGGAGAGUUU UAGAGCUAUGCU GUUUUG (SEQ ID NO: 25) | |

TABLE 1-continued

| Step | Junction | Primer Name | Primer Sequence (SEQ ID NO:) | Jxn PCR(bp) |
|---|---|---|---|---|
| Jxn PCR | 5' V$_H$1-69 | 5' up detect V$_H$1-69 | CTGTGAAATACC CTGCCTC (SEQ ID NO: 26) | 797 |
|  |  | 3' up detect spec | TGTCCACTGGGT TCGTGCCTT (SEQ ID NO: 27) |  |
| Jxn PCR | 3' V$_H$1-69 | 5' down detect spec | CAGTATCAGCCC GTCATACTT (SEQ ID NO: 28) | 631 |
|  |  | 3' down detect M1116(h70) | CCCCCTCTTGCT CTCTTTCT (SEQ ID NO: 29) |  |
| 2. Deletion of MreI_Spec from VI738 by Joiner Oligo-mediated GA = VI748/ MAID6822 |  |  |  |  |
| Joiner Oligo |  | V$_H$1-69 MreI del Joiner Oligo | GTGAAAACCCAC ATCCTGAGAGTG ACAAAAACCCTG AGGGAGAAGGCA GCTGTGCCGGGC TGAGGAGATGAC AGGGGTTA (SEQ ID NO: 30) |  |
| Jxn PCR | ΔMreI | 5' detect V$_H$1-69 FR3 | ACAGAAGTTCCA GGGCAGAG (SEQ ID NO: 31) | 634 |
|  |  | 3' down detect M1116(h70) | CCCCCTCTTGCT CTCTTTCT (SEQ ID NO: 32) |  |

Example 2. Generation of Rodents Comprising an NP-Modified V$_H$ Gene Segment

This example demonstrates the production of non-human animals (e.g., rodents) whose genome comprises an immunoglobulin heavy chain variable region that includes an NP-modified V$_H$ gene segment, e.g., a V$_H$ gene segment comprising a C-terminal tail of ANP.

Figure 4:
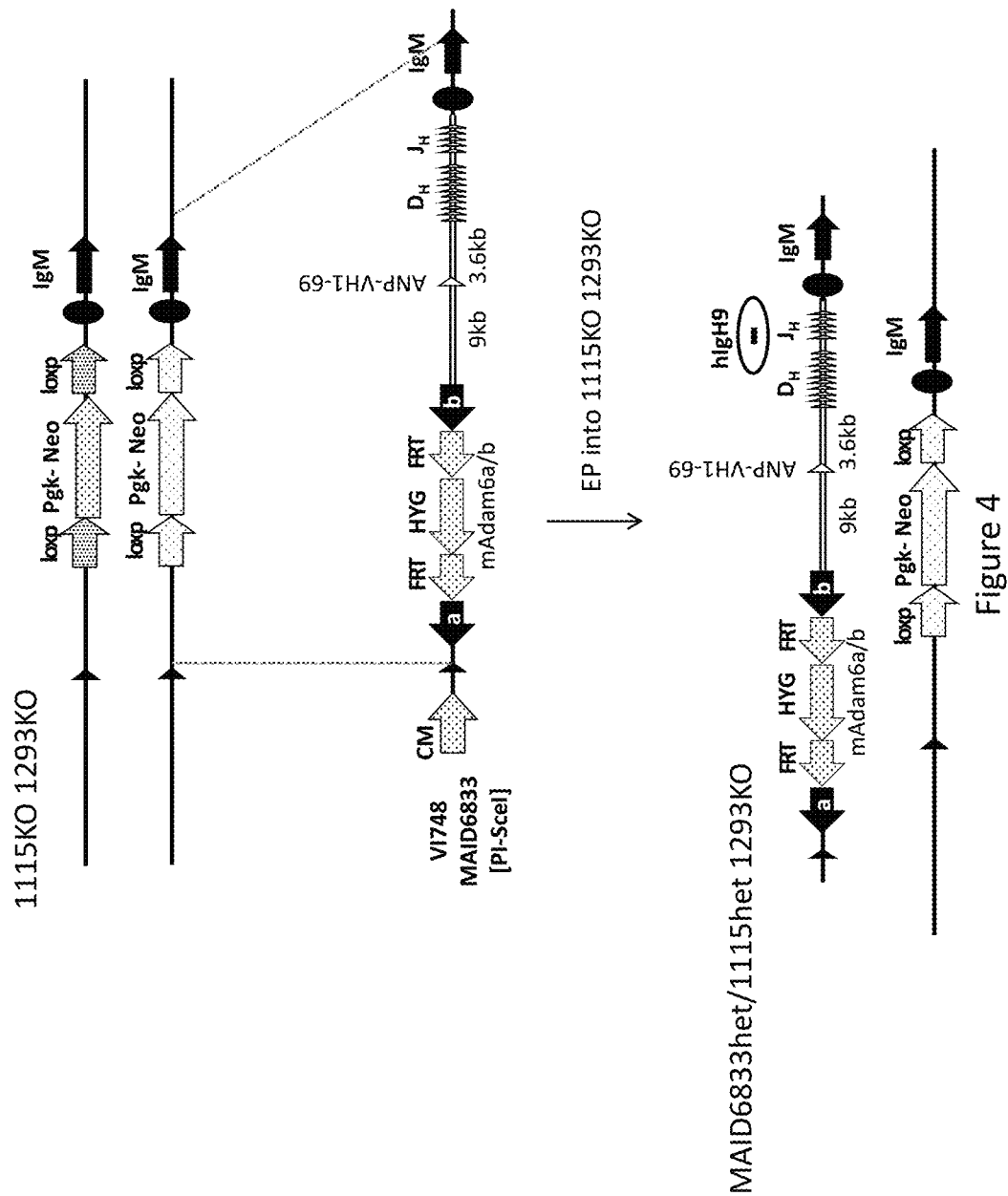
FIG. 4 shows an illustration, not to scale, of a non-limiting exemplary embodiment of inserting the targeting vector into an immunoglobulin heavy chain variable region locus in the genome of mouse ES cells via electroporation. After electroporation, this non-limiting exemplary embodiment retains an endogenous $V_H$ segment depicted as a filled triangle upstream of the Adam6a ("a") gene. Generally, unfilled shapes represent human sequences (e.g., the unfilled triangles representing the human $V_H$1-69 segment, the human $D_H$ segments, and the human $J_H$ segments), filled shapes represent murine sequences (e.g., a filled triangle representing an endogenous murine $V_H$ segment (unlabeled), filled arrows representing murine Adam6a "a" and Adam6b "b" genes, a filled oval representing an Ig enhancer, and a filled arrow representing a murine Igμ gene "IgM"), and dotted shapes represent non-human and non-murine sequences (e.g., a chloramphenicol resistance gene "CM", site-specific recombinase recognition sites "Frt sites, a hygromycin resistance gene "HYG", and a spectinomycin resistance gene "SPEC")
Figure 5A:
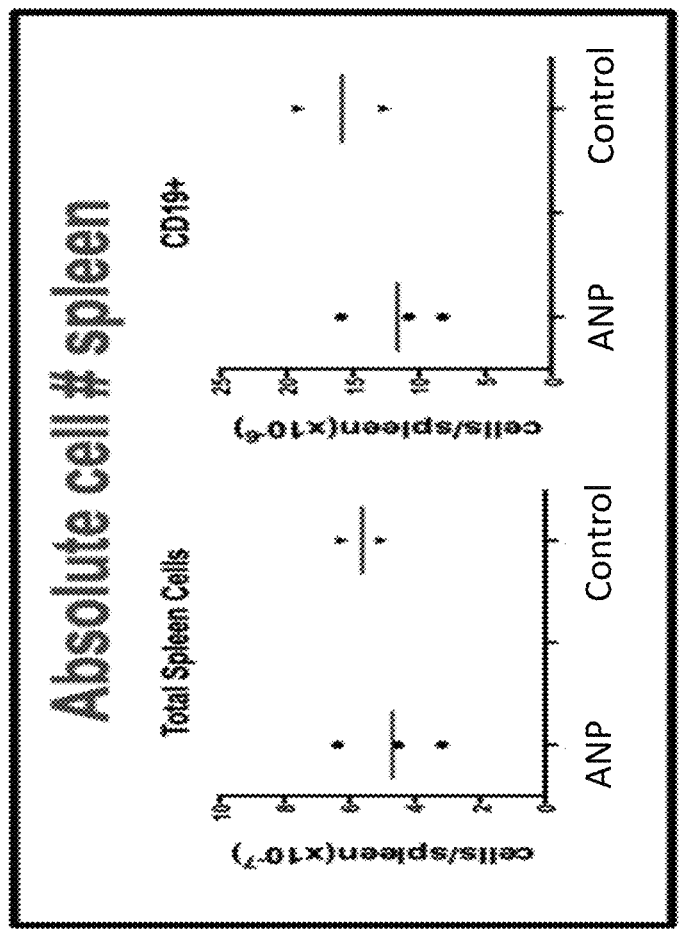
FIGS. 5A-5F show results, in connection with a non-limiting embodiment of the invention, graphs comparing populations splenoctyes from ANP-VH1-69 modified mice with control VELOCIMMUNE® mice.
Figure 5B:
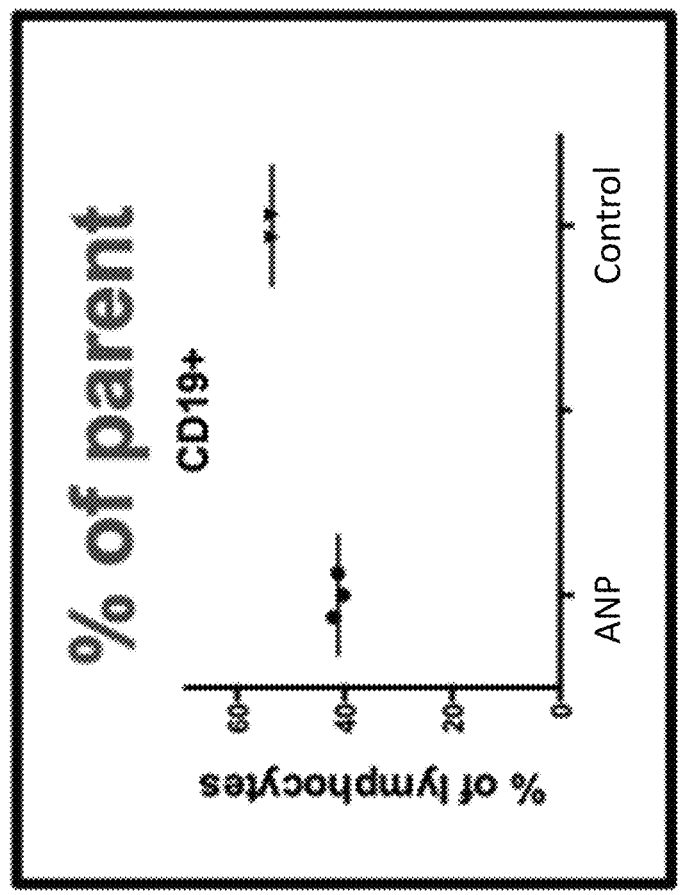
Figure 5C:
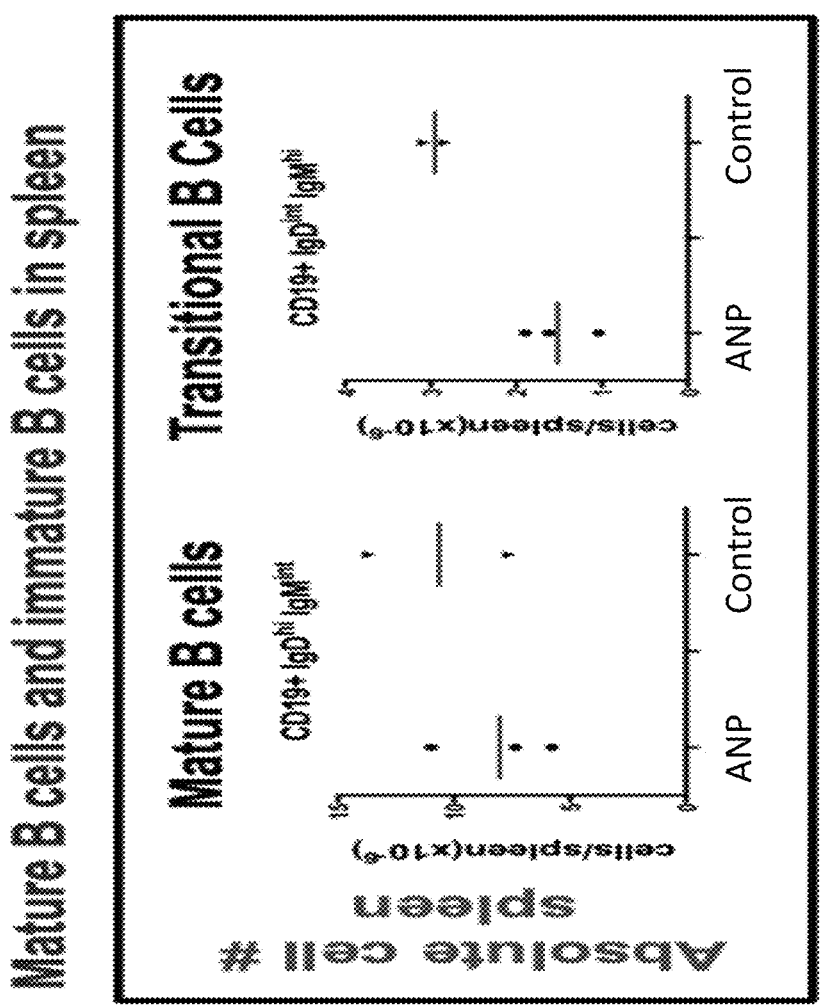
Figure 5D:
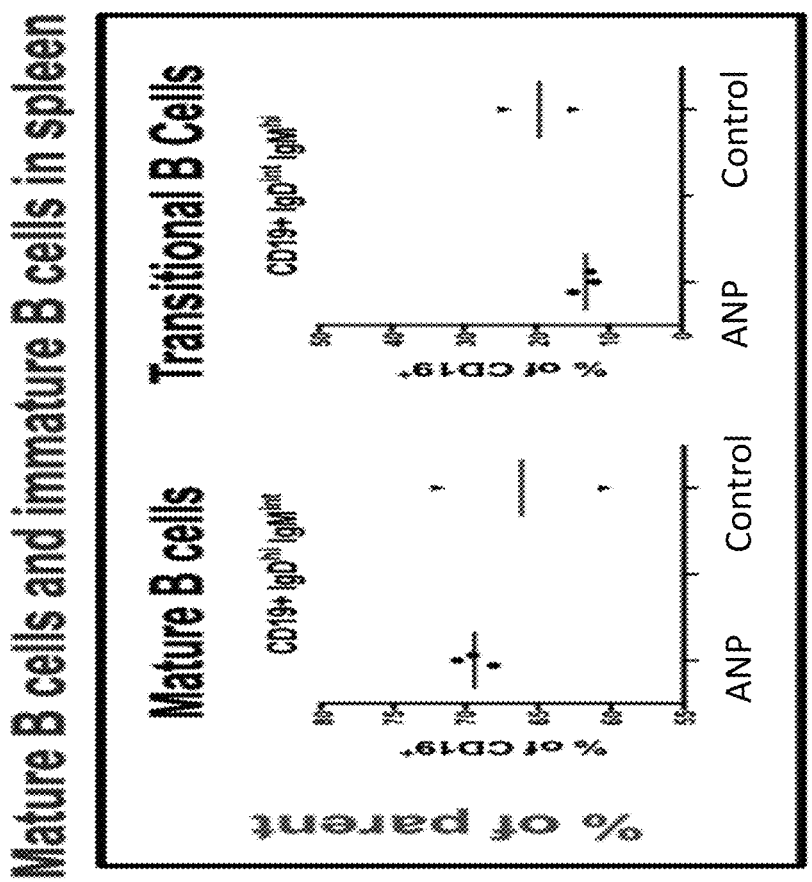
Figure 5E:
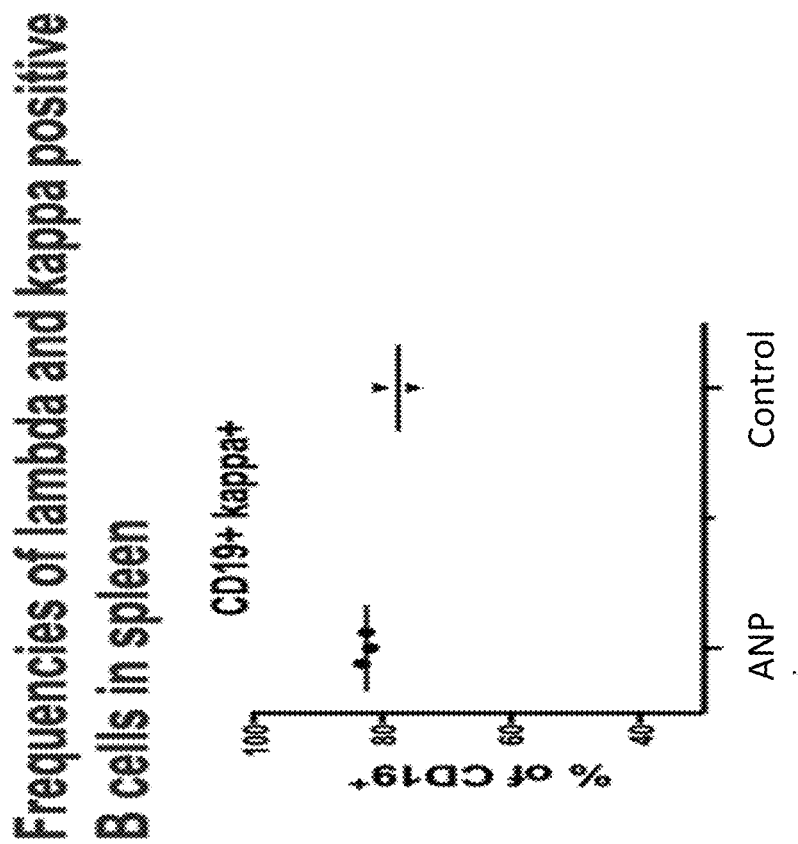
Figure 5F:
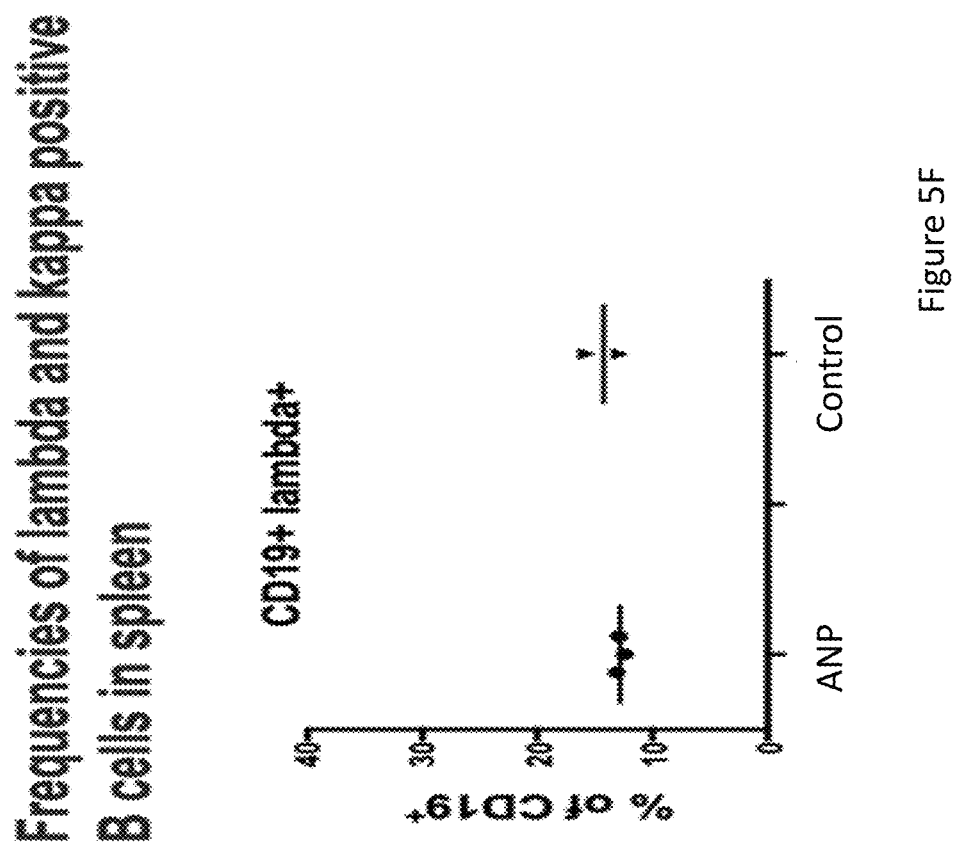
Figure 6A:
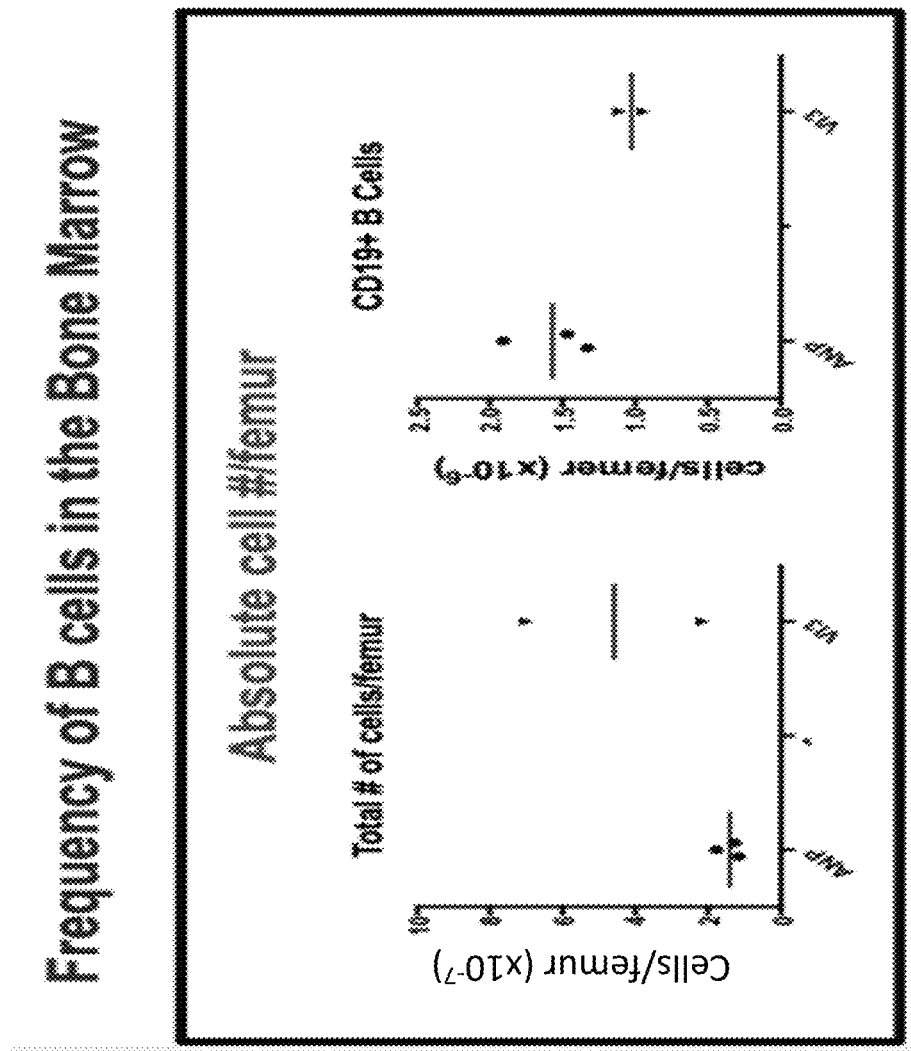
FIGS. 6A-6F shows results, in connection with a non-limiting embodiment of the invention, graphs comparing populations bone marrow cells isolated from femurs of ANP-V$_H$1-69 modified mice with control VELOCIMMUNE® mice.
Figure 6B:
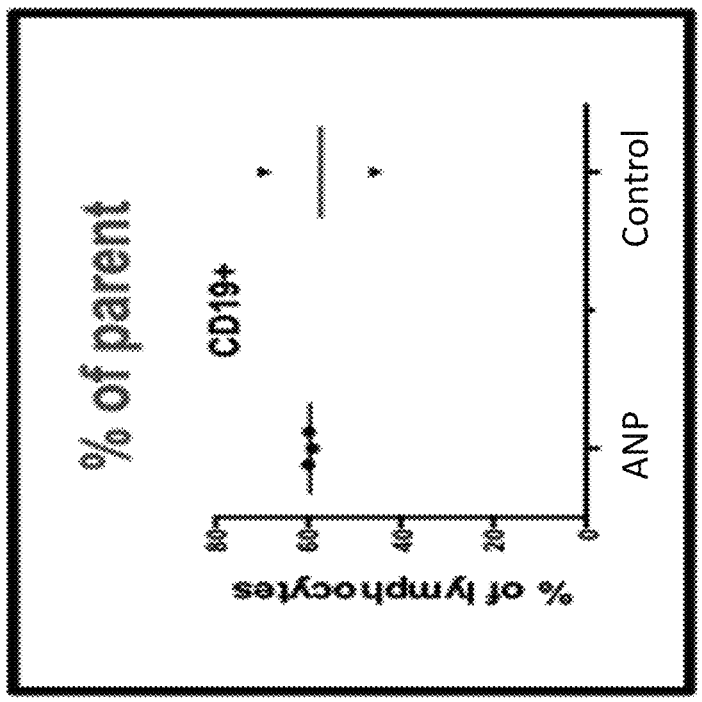
Figure 6C:
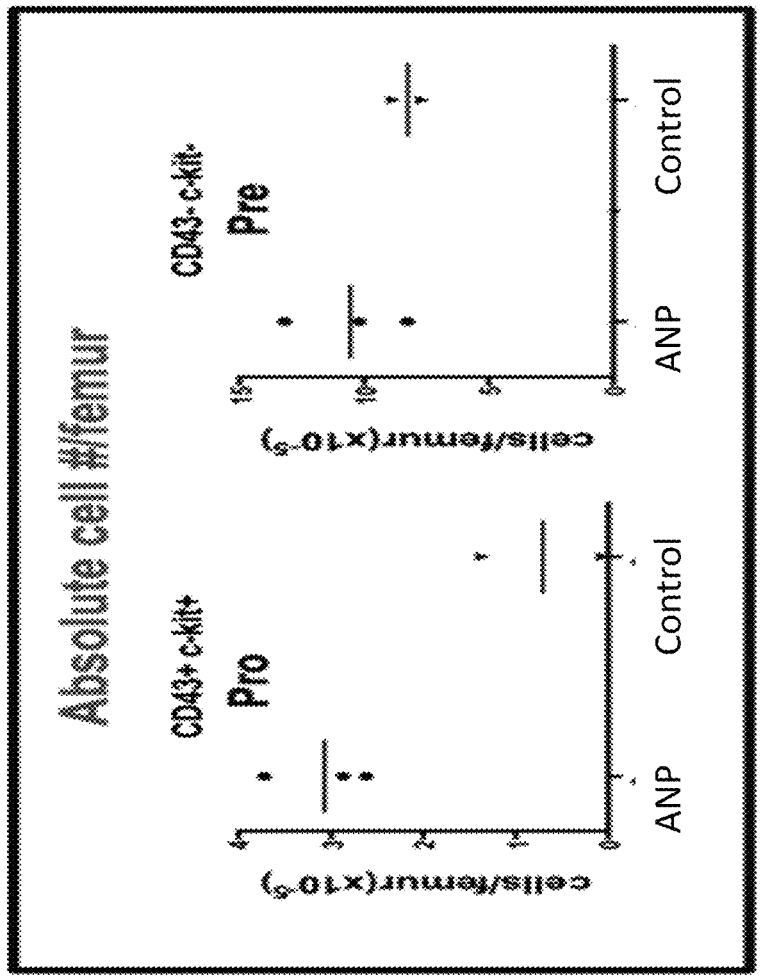
Figure 6D:
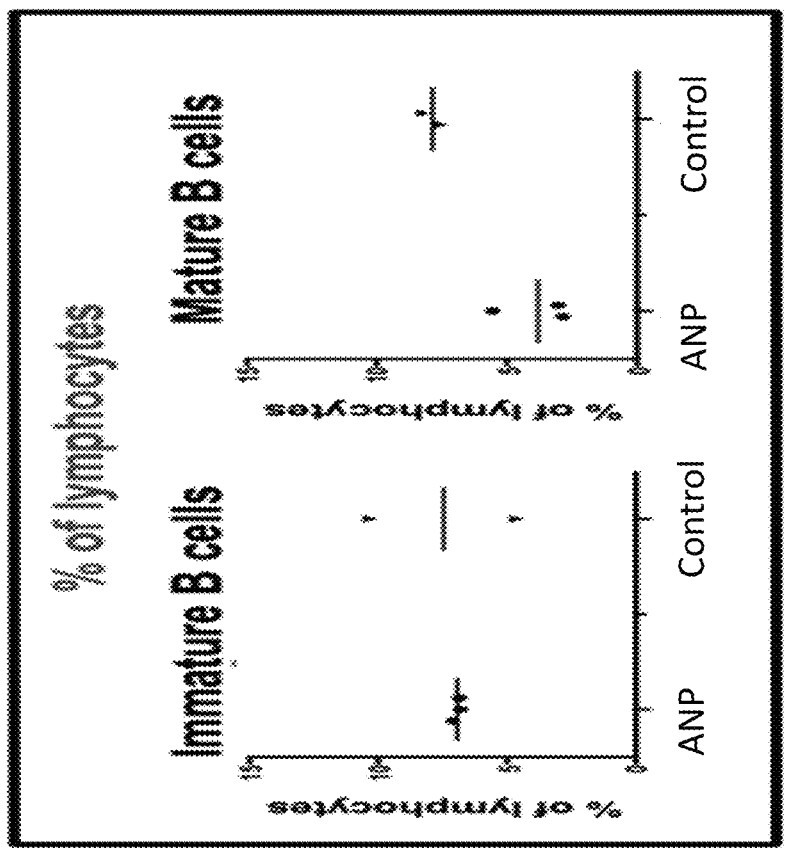
Figure 6E:
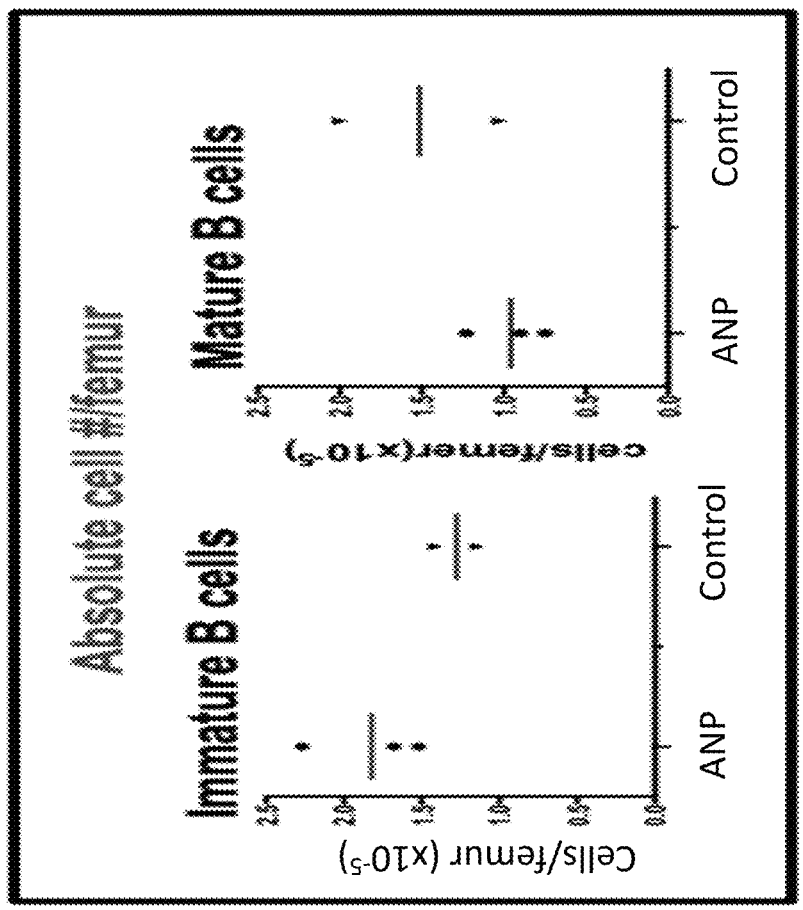
Figure 6F:
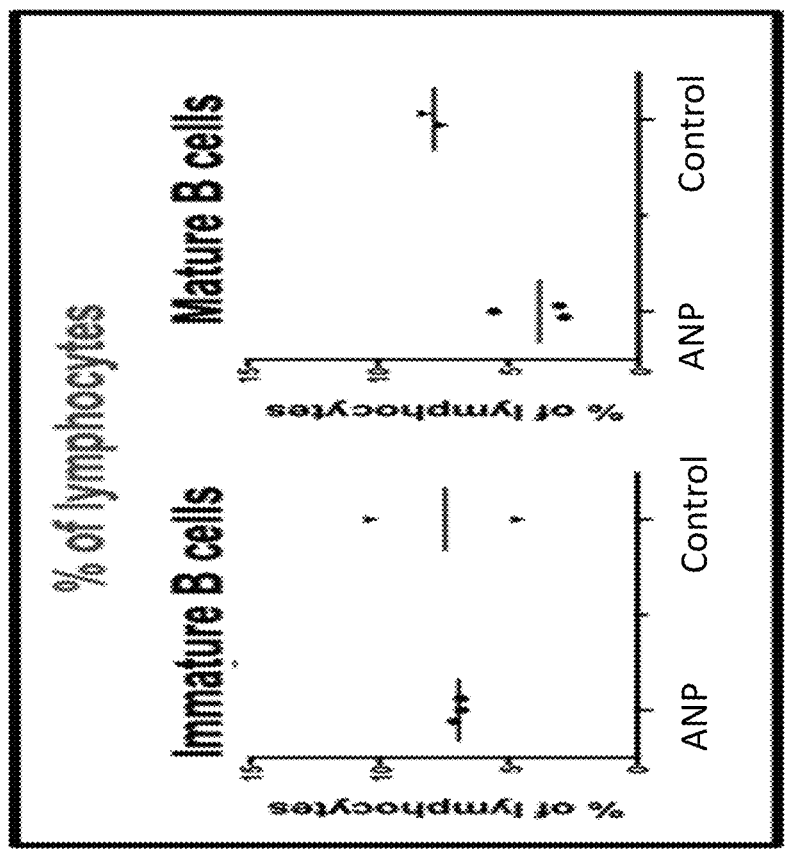

The V1748 targeting vector was linearized and electroporated into mouse embryonic stem cells having a genome that was homozygous for an endogenous Ig heavy chain variable region locus comprising a deletion of all endogenous V$_H$, D$_H$, and J$_H$ segments except for the most 5' V$_H$1-86 segment (1115KO), and for an endogenous Ig light chain variable region κ locus comprising a replacement of all endogenous Vκ and Jκ segments with the complete repertoire of human Vκ and Jκ segments. The Ig heavy chain locus of the ES cell (with a 50% Balb, 25% C57BL/6, 25% 129 background) used for electroporation of each targeting vector is depicted in FIG. 4. After electroporation, the electroporated cells were cultured in selection medium. Drug-resistant colonies were picked 10 days after electroporation and screened by TAQMAN™ and karyotyping for correct targeting as previously described (Valenzuela et al., supra; Frendewey, D. et al., 2010, Methods Enzymol. 476:295-307, which are incorporated herein by reference in their entireties) using a primer/probe sets that detected proper integration of the anchor modified V$_H$1-69 gene segment.

Forward Primer:
(SEQ ID NO: 34)
TGTGTCCTGTCCACAGGTG

Probe:
(SEQ ID NO: 35)
CCAGTCCAACAGTTCCGGTACG

Reverse Primer:
(SEQ ID NO: 36)
CAGCTGGACCTGGCTACC

The VELOCIMOUSE® method (DeChiara, T. M. et al., 2010, Methods Enzymol. 476:285-294; DeChiara, T. M., 2009, Methods Mol. Biol. 530:311-324; Poueymirou et al., 2007, Nat. Biotechnol. 25:91-99; which are incorporated by reference in their entireties herein) was used, in which targeted ES cells were injected into uncompacted 8-cell stage Swiss Webster embryos, to produce healthy fully ES cell-derived FO generation mice that are heterozygous for the anchor (ANP) modified V$_H$ segment and that express anchor (ANP) modified antibodies. Such modified mice are referred to herein as ANP-V$_H$1-69 modified mice.

The drug selection cassette may optionally be removed by the subsequent addition of a recombinase (e.g., by Cre treatment) or by breeding to a Cre deleter mouse strain (see, e.g., International Patent Application Publication No. WO 2009/114400, incorporated herein in its entirety by reference) in order to remove any loxed selected cassette introduced by the targeting construct that is not removed, e.g., at the ES cell stage or in the embryo. Optionally, the selection cassette is retained in the mice.

Example 3. Immune Phenotyping of Rodents by Flow Cytometric Analysis

To determine the immune phenotype of ANP-$V_H$1-69 modified mice, bone marrow and splenic B cells were analyzed by flow cytometry. For this study, two VELOCIMMUNE® control mice (see, e.g., U.S. Pat. Nos. 8,502,018; 8,642,835; 8,697,940, each of which is herein incorporated by reference in its entirety) and three ANP-$V_H$1-69 modified mice described in Example 2 were sacrificed and their spleens and bone marrow were harvested. Bone marrow was collected from femurs by centrifugation at 8,000 rpm for 2 minutes. Spleens were dissociated for single cell suspensions. Red blood cells from the spleen and bone marrow preparations were lysed with ACK lysis buffer, followed by washing with DPBS containing 2% FBS. Isolated cells (a total of 1×10$^6$) were incubated with anti-mouse CD16/CD32 (clone 2.4G2, BD) on ice for 10 minutes, followed by labeling with the antibody panels described in Table 2 for 30 minutes on ice.

TABLE 2

Panels of Abs used for flow cytometry

| Antigen | Clone | Source |
|---|---|---|
| Bone Marrow Maturation Ab Panel | | |
| CD43 | 1B11 | BioLegend |
| c-Kit | 2B8 | BioLegend |
| IgM | II/41 | eBioscience |
| IgD | 11-26c.2a | BioLegend |
| B220 | RA3-6B2 | eBioscience |
| CD19 | ID3 | BD |
| CD3 | 17-A2 | BioLegend |
| Bone marrow and spleen kappa/lambda panel | | |
| IgK | 187.1 | BD |
| IgL | RML-42 | BioLegend |
| IgM | II/41 | eBioscience |
| IgD | 11-26c.2a | BioLegend |
| CD3 | 17A2 | BioLegend |
| B220 | RA3-6B2 | eBioscience |
| CD19 | ID3 | BD |
| Spleen maturation panel | | |
| CD23 | B3B4 | BioLegend |
| CD93 | AA4.1 | BioLegend |
| IgM | II/41 | eBioscience |
| IgD | 11-26c.2a | BioLegend |
| CD19 | ID3 | BD |
| CD21/35 | 7G6 | BD |
| B220 | RA3-6B2 | eBioscience |

Following staining, cells were washed and fixed in 2% formaldehyde. Data acquisition was performed on a BD LSRFortessa flow cytometer and analyzed with FlowJo. Subsets of cells were identified using the following strategies. Bone marrow maturation: immature B cells (B220int IgM+), mature B cells (B220high IgM+), pro-B cells (IgM− B220int, c-KitintCD43high), pre-B cells (IgM− B220int, c-Kit-CD43int). Spleen and bone marrow kappa/lambda: B cells (CD19+CD3−), T cells (CD3+CD19−), IgK+ B cells (CD19+ IgK+ IgL−), IgL+ B cells (CD19+ IgK− IgL+). Spleen maturation: mature B cells (CD19+, B220+CD93−), follicular B cells (CD19+, B220+CD93−, CD21/35int IgMint/+), marginal zone B cells (CD19+, B220+CD93−, CD21/35+ IgM+), transitional B cells (CD19+, B220+ CD93+), T1 B cells (CD19+, B220+CD93+, IgM+CD23−), T2 B cells (CD19+, B220+CD93+, IgM+CD23+), and T3 B cells (CD19+, B220+CD93+, IgMint CD23+).

As shown in FIGS. 5A-5F, in the spleen, there were similar levels B cells in ANP-$V_H$1-69 modified mice as compared with the VELOCIMMUNE® control mice. The frequency of mature B cells in ANP-$V_H$1-69 modified mice appear to be similar to those observed in VELOCIMMUNE® control mice, however there was a slight decrease in immature cells in ANP-$V_H$1-69 modified mice as compared with VELOCIMMUNE® control mice. In the spleen, the frequencies of lambda and kappa positive B cells are similar in ANP-$V_H$1-69 modified mice as compared with VELOCIMMUNE® control mice.

As shown in FIGS. 6A-6F, in the bone marrow, there were similar levels of B cells in ANP-$V_H$1-69 modified mice as compared with VELOCIMMUNE® control mice. In the bone marrow, there were more pro-B cells and less pre-B cells in ANP-$V_H$1-69 modified mice as compared to VELOCIMMUNE® control mice. There are less mature and more immature B cells in the bone marrow of ANP-$V_H$1-69 modified mice as compared to VELOCIMMUNE® control mice.

To further immune phenotype ANP-$V_H$1-69 modified mice, levels of mouse IgG were analyzed via Western blot. For the assay, blood was drawn from a subset of ANP-$V_H$1-69 modified mice and VELOCIMMUNE® control mice. Serum was collected in serum separator tubes (BD), incubated for 30 minutes, and separated from blood by centrifugation at 9000 rcf for five minutes at 4° C. Mouse sera was diluted 1:25 in PBS and then ran on 4-20% Novex Tris-Glycine gels under non-reducing conditions. Gels were transferred to Polyvinylidene difluoride (PVDF) membranes according to manufacturer's specifications (BioRad Trans-Blot Transfer System). Blots were then blocked overnight with 10% nonfat milk in Tris-Buffered Saline with 0.05% Tween-20 (TBST, Sigma). PVDF membranes were incubated with anti-mouse IgG-HRP (Thermo/Pierce, Cat #31432) diluted 1:20,000 in 4% nonfat milk in TBST for one hour at room temperature. Blots were then washed five times for five minutes per wash and subsequently developed for one minute with Amersham ECL Western Blotting Detection Reagent (GE Healthcare Life Sciences) according to manufacturer's specifications. Blots were then imaged using a GE Healthcare ImageQuant LAS-4000 Cooled CCD Camera Gel Documentation System. Images were captured at 15 second intervals until 20 images were captured or images were fully exposed, whichever came first.

Figure 7:
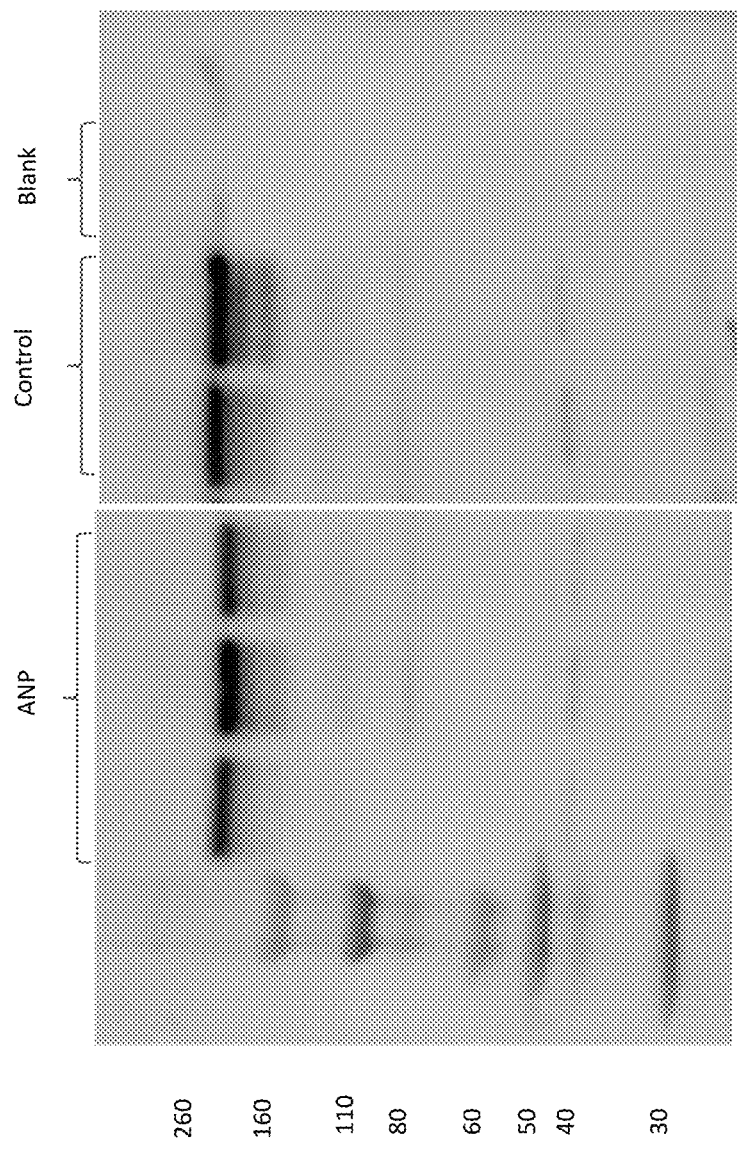
FIG. 7 shows results, in connection with a non-limiting embodiment of the invention, serum IgG levels from ANP-V$_H$1-69 modified animals with control VELOCIMMUNE® control animals analyzed by Western Blot analysis.

As shown in FIG. 7, the serum IgG levels were comparable between the ANP-$V_H$1-69 modified mice and VELOCIMMUNE® control mice as measured by Western blot. This result suggests the ANP mice Designer V mice have normal Ab levels as compared with VELOCIMMUNE® control mice.

To further immune phenotype ANP-$V_H$1-69 modified mice, levels of total serum IgM and IgG were measured by ELISA. For the ELISA, plates were coated with 1 μg/mL of anti-mouse IgM+ IgG+ IgA (Clone Ab102445, Abcam) overnight at 4° C. Plates were then washed in DPBS with 0.1% Tween-20 and blocked for 1 hour at room temperature in 1% BSA in DPBS. Serum for either ANP-$V_H$1-69 modified mice or VELOCIMMUNE® control mice and mouse IgM standard (Biolegend, Cat #401604) or mouse IgG standard (Sigma, Cat #18765) were serially diluted in 1% BSA in DPBS and incubated for 1 hour at room temperature. After incubation, plates were washed in DPBS with 0.1% Tween-20 and IgM or IgG were detected using either anti-mouse IgM− HRP (Southern Biotech, Cat #1021-05) or anti-mouse IgG-HRP (Southern Biotech, Cat #1030-05). Further washes were performed and then TMB substrate (BD) was added. After allowing for color development, the reaction was stopped with 1N Sulfuric acid and absorbance was read at 450 nm on a SpectraMax plate reader. Standard plots were generated in GraphPad Prism using nonlinear regression (curve fit, four parameter) of the IgM or IgG standards and serum IgM and IgG levels were quantified.

Figure 8A:
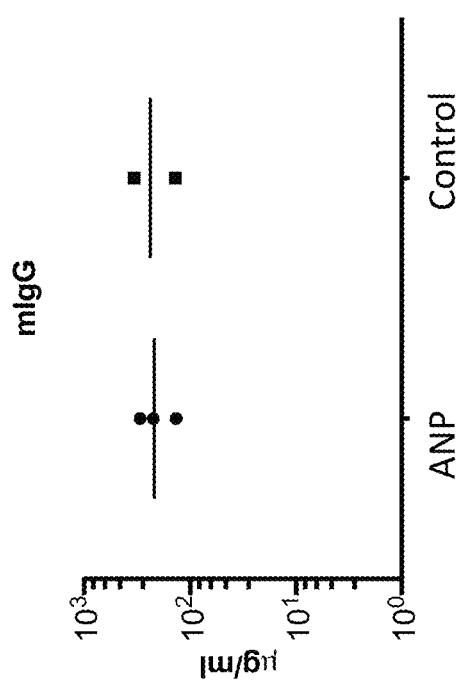
FIGS. 8A-B shows results, in connection with a non-limiting embodiment of the invention, the concentration (m/mL; y-axis) of (A) serum mouse (m) IgG or (B) serum mIgM isolated from ANP-V$_H$1-69 modified animals (ANP) or control VELOCIMMUNE® animals comprising humanized Ig loci (control).
Figure 8B:
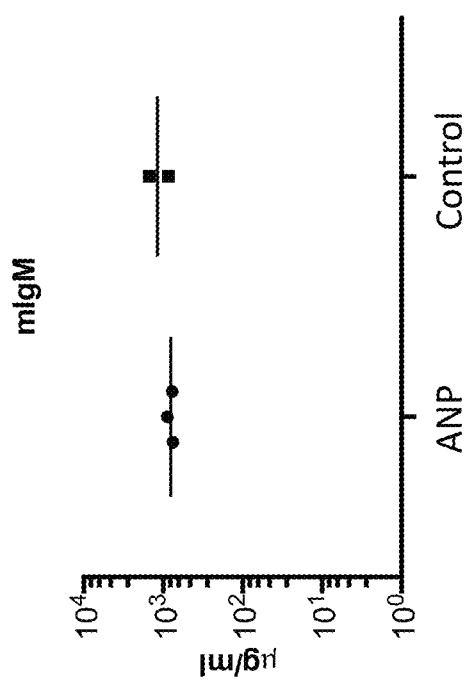

As shown in FIGS. 8A-8B, serum IgG levels measured by ELISA were comparable between ANP-$V_H$1-69 modified mice and VELOCIMMUNE® control mice. Serum IgM levels measured by ELISA were also comparable between ANP-$V_H$1-69 modified mice and VELOCIMMUNE® control mice. Both results suggest the ANP mice have normal Ab levels as compared with VELOCIMMUNE® control mice.

The retention of the anchor by antibodies was verified by Matrix-Assisted Laser Desorption Ionization-Time of Flight Mass Spectrometry (MALDI-TOF MS). Immunoglobulin isolated from mouse serum using Protein A magnetic beads (Thermo Scientific) were run under reducing conditions by SDS-PAGE gel to separate immunoglobulin heavy and light chains. Immunoglobulin heavy chains were excised and digested with Lys-C enzyme (Promega) overnight. Salts were removed from the digests with a C18 Ziptip (Millipore) according to the manufacturer's protocol. Peptides were eluted from each ziptip in 2.5 ul of 70% ACN/0.1% TFA containing 10 mg/ml a-cyano-4-hydroxycinnamic acid (CHCA) and directly applied to a Bruker Anchorchip Target (Bruker Daltonics) mixed with a-cyano-4-hydroxycinnamic acid (Protea), which was dissolved in 70% acetonitrile+ 0.1% Trifluoroacetic acid (TFA). Upon drying, each target was analyzed by Matrix-Assisted Laser Desorption Ionization-Time of Flight Mass Spectrometry (MALDI-TOF MS) on Bruker Ultraflextreme MALDI MS (Bruker Daltonics) in reflextron-positive mode.

MALDI-TOF MS suggests that the ANP-modified immunoglobulins remain intact in the serum of ANP-$V_H$1-69 modified mice (data not shown).

Example 4. Production of Antibodies in Rodents Containing Engineered Immunoglobulin Variable Region Gene Segments This example demonstrates production of antibodies in a rodent whose genome comprises an immunoglobulin heavy chain variable region that includes an engineered immunoglobulin variable region gene segment as described herein. The methods described in this example, and/or immunization methods well known in the art, can be used to immunize rodents containing an engineered immunoglobulin variable region gene segment as described herein with polypeptides or fragments thereof (e.g., peptides derived from a desired epitope), or combination of polypeptides or fragments thereof, as desired.

Briefly, cohorts of mice that include an engineered immunoglobulin variable region gene segment as described herein are challenged with an antigen of interest, e.g., a receptor of a non-immunoglobulin polypeptide of interest that binds a cognate receptor, using immunization methods known in the art. The antibody immune response is monitored by an ELISA immunoassay (i.e., serum titer).

Immunization

VELOCIMMUNE® control (n=3) and ANP-$V_H$1-69 modified (n=4) mice were immunized with a protein immunogen comprised of the extracellular domain of NPR3 fused to a C-terminal mFc tag (referred to as human NPR3 ecto-mFc) using standard immunization protocols. The mice were bled prior to the initiation of immunization and following immunogen boosts. The last bleeds prior to euthanizing the mice for antibody isolation were subjected to titer analysis on a human NPR3 protein (comprised of the extracellular domain of NPR3 fused to a C-terminal a myc-myc-hexahistidine tag; referred to as human NPR3 ecto-MMH) and engineered human NPR3 expressing cells (HEK293 cells engineered to overexpress full length human NPR3; referred to as 293/hNPR3 cells).

Anti-Serum Titer Determination

Antibody titers in serum against NPR3 were determined using ELISA. Ninety six-well microtiter plates (Pierce) were coated with the human NPR3 ecto-MMH antigen at 2 µg/mL in phosphate-buffered saline (PBS, Irvine Scientific) overnight at 4° C. Plates were washed with PBS containing 0.05% Tween-20 (PBS-T, Sigma-Aldrich) and blocked with 250 µL of 0.5% bovine serum albumin (BSA, Sigma-Aldrich) in PBS for 1 hour at room temperature. The plates were washed with PBS-T. Pre-immune and immune antisera were serially diluted three-fold in 0.5% BSA-PBS and added to the plates for 1 h at room temperature. The plates were washed and goat anti-mouse IgG-Fc-Horse Radish Peroxidase (HRP) conjugated secondary antibodies (Jackson ImmunoResearch) were added at 1:5000 dilution to the plates and incubated for 1 hour at room temperature. Plates were washed and developed using TMB/H2O2 as substrate by incubating for 15-20 min. The reaction was stopped with acid and plates read on a spectrophotometer (Victor, Perkin Elmer) at 450 nm. Antibody titers were computed using Graphpad PRISM software. The titer was defined as interpolated serum dilution factor of which the binding signal is 2-fold over background.

Antibody Titers on Cells

Anti-NPR3 antibody titers on engineered cells were determined using Meso Scale Discovery's (MSD) MULTI-ARRAY® technology. Ninety-six-well carbon electrode plates (from MSD) were coated with 40,000 cells per well of either 293/hNPR3 cells or HEK293 cells in PBS at 37° C. for 1 hour. The cell coating solution was decanted and plates blocked by incubation for 1 hour at room temperature (RT) with 150 µL of 2% bovine serum albumin (BSA, Sigma-Aldrich) in PBS followed by washing with PBS. Pre-immune and immune anti-sera were serially diluted three-fold in 1% BSA-PBS and added to the plates for 1 hour at room temperature followed by washing. Goat anti-mouse IgG-Fc ruthenium conjugated secondary antibody (Jackson ImmunoResearch and Ruthenium labeled in-house) was then added to the plates at 1 µg/mL and incubated for 1 hour at RT. MSD's 4× Read Buffer T surfactant free was diluted to 1× and 150 µL were added to each well and read on MSD SECTOR® imager instrument. Antibody titers were computed using Graphpad PRISM software. The titer was defined as interpolated serum dilution factor of which the binding signal is 2-fold over background.

Results

Figure 9:
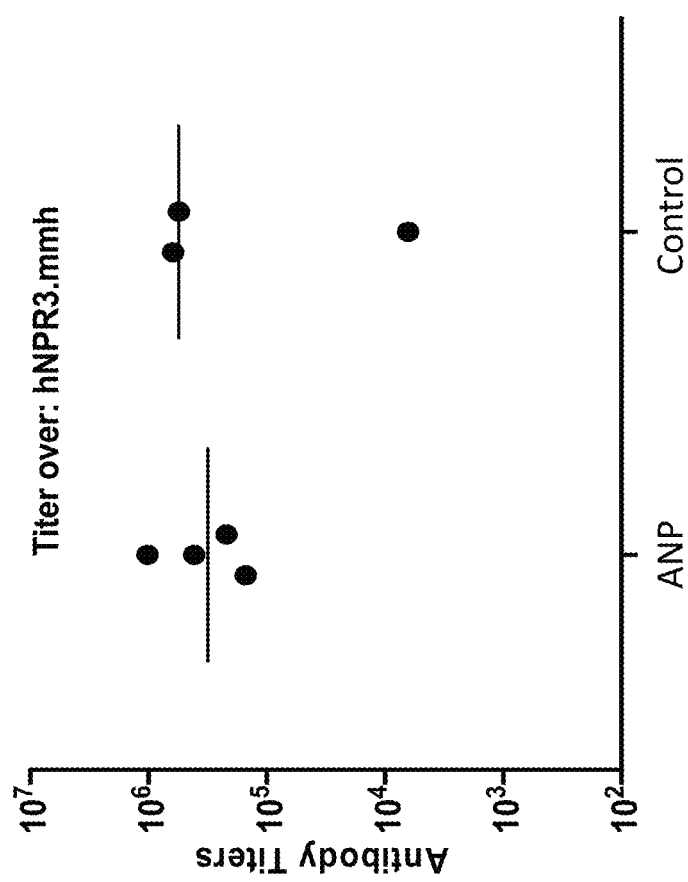
FIG. 9 shows results, in connection with a non-limiting embodiment of the invention, graphs comparing immune responses (antibody titers; y-axis) in ANP-V$_H$1-69 modified mice (ANP) or control VELOCIMMUNE® animals comprising humanized Ig loci (control) on protein antigens. Of the sera tested, 3 sera samples were from bleeds after 3rd boost while 1 is after 5th boost for ANP-V$_H$1-69 modified mice. For VELOCIMMUNE® control mice, 2 sera samples were from bleeds after 6th boost, while 1 is after 9th boost.
Figure 10:
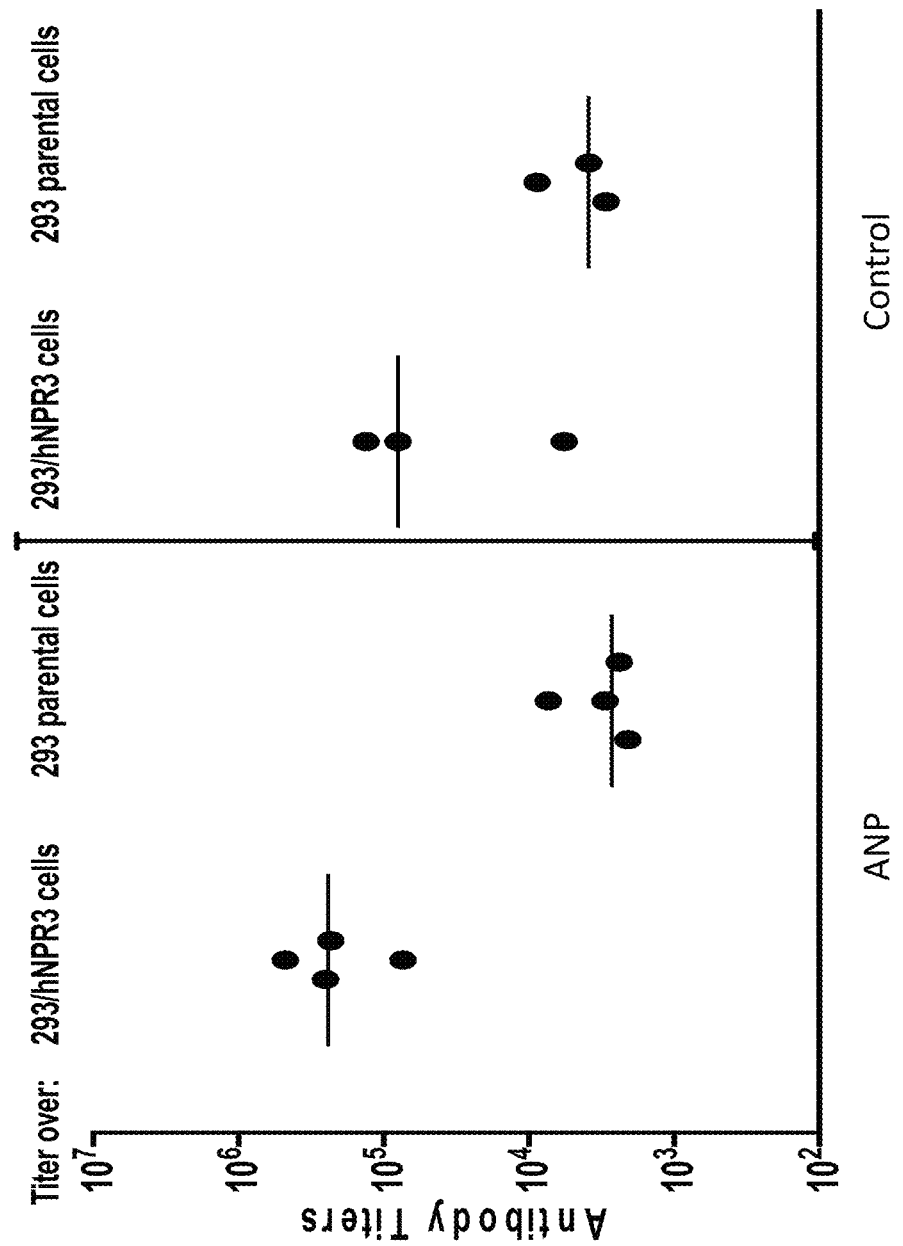
FIG. 10 shows results, in connection with a non-limiting embodiment of the invention, graphs comparing immune responses (antibody titers; y-axis) in ANP-V$_H$1-69 modified mice (ANP) or control VELOCIMMUNE® animals comprising humanized Ig loci (control) on protein antigens. Of the sera tested, 3 sera samples were from bleeds after 3rd boost while 1 is after 5th boost for ANP-V$_H$1-69 modified mice. For VELOCIMMUNE® control mice, 2 sera samples were from bleeds after 6th boost, while 1 is after 9th boost.

The humoral immune responses in VELOCIMMUNE® control and ANP-$V_H$1-69 modified mice were determined using recombinant hNPR3 protein and engineered human NPR3-expressing cells (HEK293/hNPR3) following immunization with NPR3 ecto protein immunogen. Antisera of ANP-$V_H$1-69 modified mice (n=4) showed a range of high antibody titers on hNPR3.mmh protein with an average titer of 465,625 comparable to the average titers of 394,032 for VELOCIMMUNE® control strain (n=3) (FIG. 9). The average antibody titers of ANP-$V_H$1-69 modified mice on HEK293/hNPR3 expressing cells and the parental HEK293 cells were 268,763 and 3,948 respectively, suggesting the anti-sera are specific to NPR3. Similar results were obtained for VELOCIMMUNE® control mice with average antibody titers of 72,826 and 5,219 on HEK293/hNPR3 expressing cells and parental HEK293 cells respectively (FIG. 10). These results suggest that the ANP-$V_H$1-69 modified mice are capable of mounting immune response comparable to the VELOCIMMUNE® control mouse strain.

Example 4. Isolation of Cells Expressing and/or Nucleic Acids Encoding Antibodies Produced in Rodents Containing Engineered Immunoglobulin Variable Region Gene Segment When a desired immune response is achieved, splenocytes (and/or other lymphatic tissue) are harvested and fused with mouse myeloma cells to preserve their viability and form immortal hybridoma cell lines. The hybridoma cell lines are screened (e.g., by an ELISA assay) and selected to identify hybridoma cell lines that produce antigen-specific antibodies. Hybridomas may be further characterized for relative binding affinity and isotype as desired. Using this technique several antigen-specific chimeric antibodies (i.e., antibodies possessing human variable domains and rodent constant domains) are obtained.

DNA encoding the variable regions of heavy chain and light chains may be isolated and linked to desirable isotypes (constant regions) of the heavy chain and light chain for the preparation of fully-human antibodies. Such an antibody protein may be produced in a cell, such as a CHO cell. Fully human antibodies are then characterized for relative binding affinity and/or neutralizing activity of the antigen of interest.

DNA encoding the antigen-specific chimeric antibodies or the variable domains of light and heavy chains may be isolated directly from antigen-specific lymphocytes. Initially, high affinity chimeric antibodies are isolated having a human variable region and a rodent constant region and are characterized and selected for desirable characteristics, including affinity, selectivity, epitope, etc. Rodent constant regions are replaced with a desired human constant region to generate fully-human antibodies. While the constant region selected may vary according to specific use, high affinity antigen-binding and target specificity characteristics reside in the variable region. Antigen-specific antibodies are also isolated directly from antigen-positive B cells (from immunized mice) without fusion to myeloma cells, as described in, e.g., U.S. Pat. No. 7,582,298, specifically incorporated herein by reference in its entirety. Using this method, several fully human antigen-specific antibodies (i.e., antibodies possessing human variable domains and human constant domains) are made.

Specifically, splenocytes from NPR3 immunized VELOCIMMUNE® mice or ANP-$V_H$1-69 modified mice were stained with human NPR3 extracellular domain expressed with a C-terminal human Fc tag (hNPR3 ecto-hFc) and FITC-anti-mFc as described in U.S. Pat. No. 7,582,298, incorporated herein in its entirety by reference. Single IgG positive and antigen positive B cells were isolated by fluorescence-activated cell sorting (FACS) into separate wells of a 384-well plate. RT-PCR of antibody genes from these B cells was performed according to a method described by Wang and Stollar (Journal of Immunological Methods 2000; 244: 217-225, incorporated herein by reference in its entirety). Briefly, cDNAs for each B cell were synthesized via reverse transcriptase (RT) reaction (SUPERSCIPT™ III, Invitrogen). Each resulting RT product was then split and transferred into two corresponding wells on separate 384-well plates for amplification of heavy and light chain sequences. One set of the resulting RT products was first amplified by PCR using a 5' degenerate primer specific for human IgG heavy chain variable region leader sequence and a 3' primer specific for mouse heavy chain constant region, to form an amplicon. The amplicon was subjected to a second round of PCR using a 5' degenerate primer set specific for framework 1 of human IgG heavy chain variable region sequence or a specific primer for the ANP peptide (ANP mice only) and a 3' degenerate primer set specific for framework 4 of human IgG heavy chain variable region sequence. The other set of the resulting RT products was first amplified by PCR using a 5' degenerate primer set specific for human kappa light chain variable region leader sequence and a 3' primer specific for mouse kappa light chain constant region to form an amplicon. A second round of PCR was performed on this amplicon using a 5' degenerate primer set specific for framework 1 of human kappa light chain variable region sequence and a 3' degenerate primer set specific for framework 4 of human kappa light chain variable region sequence. The heavy chain and light chain PCR products were cloned into antibody vectors containing human IgG1 heavy chain constant region and kappa light chain constant region, respectively. Recombinant hIgG1 antibodies were produced by transient transfection of CHO K1 cells for further screening.

Example 5: Primary Screening of Supernatants Isolated from CHO K1 Cells

The binding properties of a panel of anti-NPR3 monoclonal antibodies containing supernatants collected from CHO K1 transfected cells, 146 from the ANP-$V_H$1-69 modified mice and 65 from VELOCIMMUNE® control, to hNPR3-mmH were characterized, and the kinetic binding parameters and equilibrium binding constant were determined using SPR technology.

The equilibrium dissociation constant ($K_D$) for NPR3 binding to different NPR3 monoclonal antibodies (mAbs) and the dissociation rate in pH6.0 were determined using a real-time surface plasmon resonance biosensor using a Biacore 4000 instrument. All binding studies were performed in 10 mM sodium phosphate, 137 mM NaCl, 2.7 mM KCl and 0.05% v/v Surfactant Tween-20 (PBS-T), prepared at pH 7.4 (PBS-T_pH7.4) running buffer at 25° C. The Biacore CM5 sensor chip surface was first derivatized by amine coupling with anti-human Fc specific mouse mAb (REGN2567) to capture different NPR3 mAbs. Single 100 nM concentration of the ectodomain of human NPR3 expressed with a C-terminal myc-myc-6×His tag (hNPR3-MMI-1) prepared in PBS-T_pH7.4 running buffer were injected over the NPR3 mAb captured surface for 90 sec at a flow rate of 30 μL/min and their dissociation in PBS-T_pH7.4 running buffer was monitored for 90 sec. After the dissociation phase, PBS-T buffer prepared at pH6.0 (PBS-T_pH6.0) was injected for 2 min. At the end of each cycle, the NPR3 mAb captured surface was regenerated using a 12 sec injection of 20 mM phosphoric acid.

The association rate ($k_a$) and dissociation rate ($k_d$) were determined by fitting the real-time binding sensorgrams to a 1:1 binding model with mass transport limitation using Biacore 4000 evaluation software while the dissociation of hNPR3-MMH from NPR3 mAbs in PBS-T_pH6.0 was determined by fitting the dissociation curve using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\min) = \frac{\ln(2)}{60*kd}$$

The median and mean values of $K_D$ and t½ values of NPR3 mAbs isolated from VELOCIMMUNE® control and ANP-$V_H$1-69 modified mice were also calculated and provided in Table 3.

Figure 11:
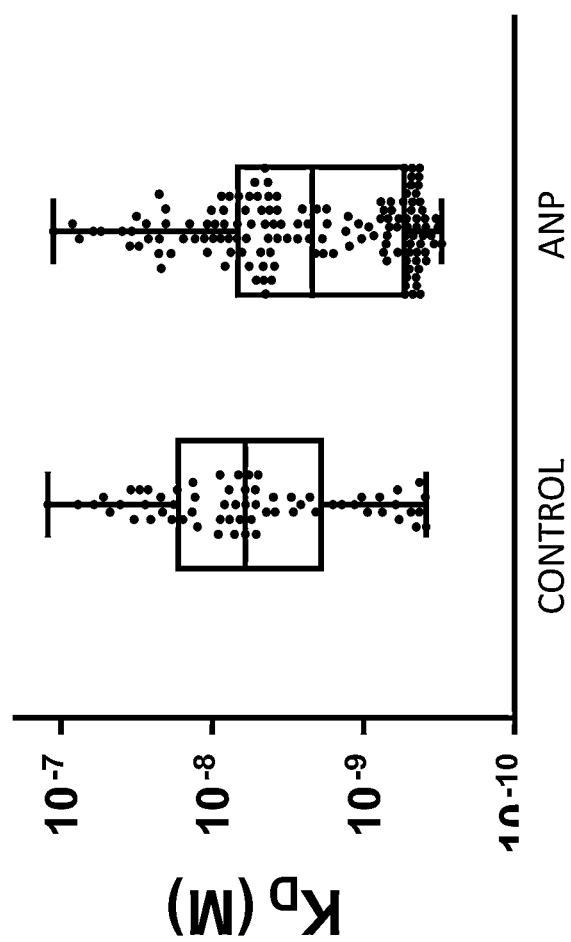
FIG. 11 shows results, in connection with a non-limiting embodiment of the invention, graphs comparing the K$_D$ values (y-axis) of hNPR3-MMH binding to NPR3 monoclonal antibodies (mAbs) isolated from in ANP-V$_H$1-69 modified mice (ANP) or control VELOCIMMUNE® animals comprising humanized Ig loci (control) on protein antigens at 25° C. using box and whisker plot.
Figure 12:
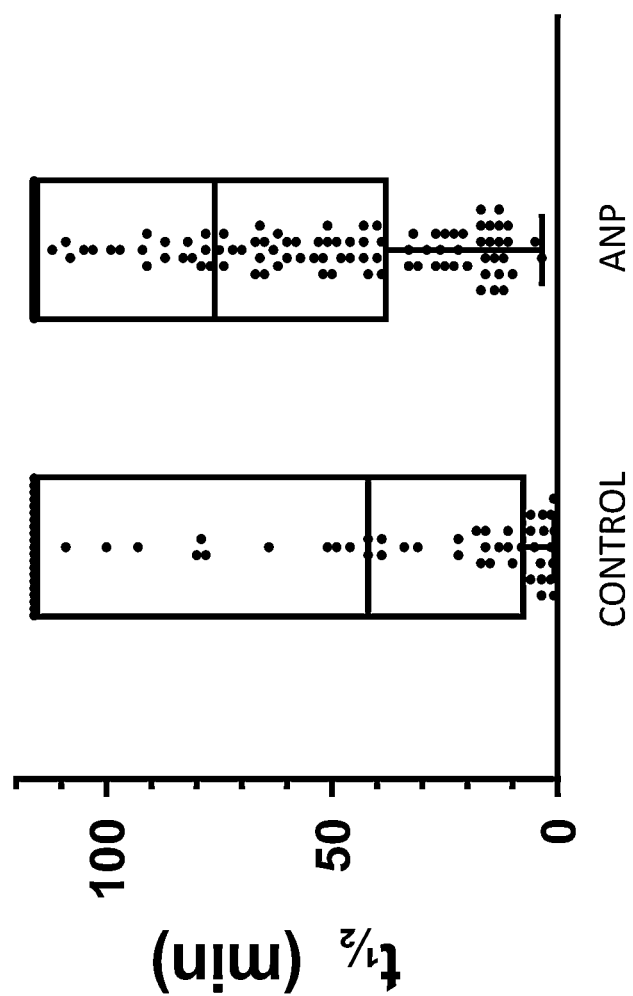
FIG. 12: shows results, in connection with a non-limiting embodiment of the invention, graphs comparing the t½ values (y-axis) of hNPR3-MMH binding to NPR3 monoclonal antibodies (mAbs) isolated from in ANP-V$_H$1-69 modified mice (ANP) or control VELOCIMMUNE® animals comprising humanized Ig loci (control) on protein antigens at 25° C. using box and whisker plot.

The $K_D$ and t½ values of NPR3 mAbs isolated from VELOCIMMUNE® control and ANP-$V_H$1-69 modified mice were compared using box and whisker plot as shown in FIGS. 11-12, respectively.

The mean and median values of $K_D$ and t½ of the groups of mAbs from ANP-$V_H$-1-69 modified and VELOCIMMUNE® control respectively are listed in Table 3, and the comparison of $K_D$ values and the t½ are shown in FIG. 11 and FIG. 12, respectively. Both ANP-$V_H$1-69 modified and VELOCIMMUNE® control mice were capable of generating antibodies in a wide affinity range, with the mean/median $K_D$ value smaller, and t½ longer, for Abs from ANP-$V_H$1-69 modified mice than from VELOCIMMUNE® control mice. These results suggest that ANP-$V_H$1-69 modified mice may generate high affinity antibodies in a higher population than VELOCIMMUNE® control mice.

TABLE 3

Median and mean $K_D$ and t½ values of hNPR3-MMH binding to NPR3 monoclonal antibodies (mAbs) isolated from VELOCIMMUNE ® control and ANP-$V_H$1-69 modified mice at 25° C.

| Mouse Strain | No of samples | Median KD (M) | Mean KD (M) | Median t½ (min) | Mean t½ (min) |
|---|---|---|---|---|---|
| ANP-$V_H$1-69 modified | 146 | 2.18E−09 | 7.85E−09 | 47.00 | 48.64 |
| VELOCIMMUNE ® control | 65 | 6.05E−09 | 1.39E−08 | 6.00 | 27.36 |

Luminex

Luminex binding assays was performed in order to determine the binding of antibodies isolated from mice immunized with NPR3 to a panel of NPR3 antigens. For this assay, antigens were amine coupled to Luminex microspheres. Microspheres for amine couple proteins were prepared as follow: approximately 10 million MicroPlex microspheres (MicroPLex Microspheres, Luminex, Cat. No. LC10000-00), were resuspended by vortexing in 500 µL of 0.1M NaPO4, pH 6.2 (activation buffer) and then centrifuged to remove the supernatant. The microspheres were resuspended in 160 µL of activation buffer and the carboxylate groups (—COOH) were activated by addition of 15 µL of 50 mg/mL of N-hydroxysuccinimide (NHS, Thermo Scientific, Cat. No. 24525) followed by addition of 15 µL of 50 mg/mL of 1-ethyl-3-[3-dimethylaminopropyl]carbodiimide (EDC, ThermoScientific, Cat. No. 22980) at 25° C. After 10 minutes, the pH of the reaction was reduced to 5.0 with the addition of 500 µL of 50 mM MES pH 5.0, and the microspheres were vortexed followed by centrifugation to remove the supernatant. The activated microspheres were immediately mixed with 500 µL of 25 µg/mL of the protein antigens [human NPR3 extracellular domain expressed with a C-terminal human Fc tag (hNPR3 ecto-hFc) and human NPR3 extracellular domain expressed with a C-terminal mouse Fc tag complexed with human ANP (hNPR3-ecto-mFc-hANP)] in 50 mM MES pH 5.0. A unique bead region was used per coupled protein/antibody. The microspheres-protein mixture was incubated for two hours at 25° C. The coupling reaction was quenched by addition of 50 µL of 1M Tris-HCl, pH 8.0 and the microspheres were vortexed, centrifuged, and washed three times with 800 uL of PBS containing 0.05% Tween20, to remove uncoupled proteins and other reaction components. Microspheres were resuspended in PBS with 2% BSA and 0.05% Na Azide at 10 million microspheres/mL.

Microspheres with amine-coupled proteins were mixed at 2700 beads/mL, then 75 µL of microspheres were plated per well on a 96 well filter plate flat bottom plate (Millipore, Cat. No: MSBVN1250) and mixed with 25 µL of supernatants containing individual anti-NPR3 antibodies. Samples and microspheres were incubated for two hours at 25° C. and then washed twice with 200 µL of PBS with 0.05% Tween 20. To detect bound antibody levels to individual microspheres, 100 µL of 2.5 µg/mL R-Phycoerythrin conjugated goat F(ab')2 anti-human kappa (Southern Biotech, Cat. No. 2063-09) in PBS with 2% BSA and 0.05% Na Azide was added then incubated for 30 minutes at 25° C. The samples were washed twice with 200 µL of PBS with 0.05% Tween 20 and resuspended in 150 µL of PBS with 0.05% Tween 20. The plates were read on a Luminex FlexMap 3D instrument with Luminex xPonent software version 4.2.

Antibodies that bound to hNPR3-ecto-hFc and hNPR3-ecto-mFc-hANP with binding signals greater than 1000, but less than 5000 and greater than 5000 are shown in Table 4. There were total of 439 samples tested: 236 samples from ANP-$V_H$1-69 modified mice and 203 samples from VELOCIMMUNE® control mice. Binding signals were measured as median fluorescence intensity (MFI). As shown in Table 4, there was a higher percentage of antibodies from the ANP-$V_H$1-69 modified mice that bound to hNPR3 ecto-hFc and the complex of hNPR3 ecto-mFc-hANP>5000 in the Luminex assay as compared with those antibodies isolated from VELOCIMMUNE® control mice.

TABLE 4

Total number of anti-NRP3 antibodies (percentage) bound to amine coupled hNPR3-ecto-hFc and hNPR3-ecto-mFc-hANP in Luminex binding assay.

| Mouse strain | Binding signal (MFI) | hNPR3-ecto-hFc | hNPR3-ecto-mFc-hANP |
|---|---|---|---|
| ANP-$V_H$1-69 modified | >5000 | 206 (87%) | 202 (86%) |
|  | >1000 | 14 (6%) | 18 (8%) |
| VELOCIMMUNE ® control | >5000 | 88 (43%) | 83 (41%) |
|  | >1000 | 14 (22%) | 50 (25%) |

Blocking Capabilities

An ELISA-based blocking assay was developed to determine the ability of anti-NPR3 antibodies to block human NPR3 binding human ANP (hANP). In this assay, the recombinant human NPR3 protein, comprising a portion of the human NPR3 extracellular domain (amino acids Gly27-Ser482) fused to the Fc portion of the mouse IgG2a at the NPR3 C-terminus (hNPR3-mFc, Seq ID or Accession #), was passively absorbed at a concentration of 2 µg/mL in PBS on a 96-well microtiter plate overnight at 4° C. Nonspecific binding sites were subsequently blocked using a 0.5% (w/v) solution of BSA in PBS for 1 hour at room temperature. After the plate was washed with PBS+ tween, anti-NPR3 antibody supernatants at 1:10 dilution or 1 µg/mL of non-binding human IgG1 isotype control antibody was added. The plate was incubated at room temperature for 1 hour followed by the addition of recombinant biotinylated hANP (biotin-hANP; Phoenix Pharmaceuticals INC, Burlingame, CA) to a final concentration of 200 pM and incubated for 1 hour. The concentration of biotin-hANP was in the dynamic range of the dose dependent binding of biotin-hANP to plate-coated hNPR3 near the EC50 value. The plate was washed and plate-bound biotin-hANP was detected with 100 ng/mL of streptavidin conjugated with horseradish peroxidase (HRP) and visualized using TMB substrate solution (BD Biosciences, San Jose, CA) according to the manufacturer's recommended procedures. Absorbance at 450 nm was measured on a Victor™ Multilabel Plate Reader (PerkinElmer™).

Percent blocking for the tested anti-NPR3 antibodies was calculated using the formula below:

$$\% \text{ Blocking} = 100 - \left( \frac{[\text{Experimental Signal}_{(tested\ anti-NPR3)} - \text{Background Signal}_{(buffer)}]}{[\text{Maximum Signal}_{(biotin-hANP\ alone)} - \text{Background Signal}_{(buffer)}]} \right) \times 100$$

Antibodies that blocked binding of biotin-hANP to hNPR3 more than or equal to 50% were classified as blockers.

The ability of the anti-NPR3 antibody supernatants from VELOCIMMUNE® control and the ANP-V$_H$1-69 modified mice to block human ANP binding to human NPR3 was evaluated using a ELISA-based blocking assay. As seen in Table 5, 338 anti-NPR3 antibody supernatants were tested for blocking human ANP binding to human NPR3, where 125 were from VELOCIMMUNE® control mice and 213 were from ANP-V$_H$1-69 modified mice. One hundred thirty-four anti-NPR3 antibody supernatants blocked hNPR3-mFc binding to biotin-hANP with a percent blockade of greater than or equal to 50%. Of the 134 blockers, 17 were isolated from VELOCIMMUNE® control mice and 117 from ANP-V$_H$1-69 modified mice, which were 14% and 55% of the number of antibodies tested from VELOCIMMUNE® control mice and ANP-V$_H$1-69 modified mice, respectively. Of the top 50 blockers, 7 were from VELOCIMMUNE® control mice and 43 from ANP-V$_H$1-69 modified mice, which accounts for 6% and 20% of the total mAbs tested from the two trains of mice, respectively.

In this experiment, the human IgG1 isotype control antibody displayed a percent blockade of 32% and was categorized as a non-blocker.

Overall, the ANP-V$_H$1-69 modified mice produced more antibodies that bound NPR3 with high specificity and blocked the recombinant NPR3 protein binding to human ANP than that of the VELOCIMMUNE® control mice.

TABLE 5

Summary of Anti-NPR3 Antibody Supernatants Blocking Human ANP binding to Human NPR3-mFc.

| Mouse Strain | Number of tested anti-NPR3 | Number of blockers (% blocking >50%) | % Blockers per strain of mice | Number of mAbs in top 50 blockers (range of % blocking) | % Blockers with the highest 50 values for % blocking from individual strain of mice |
|---|---|---|---|---|---|
| VELOCIMMUNE ® control | 125 | 17 | 14% | 7 (80%-95%) | 6% |
| ANP-V$_H$1-69 modified | 213 | 117 | 55% | 43 (80%-99%) | 20% |

The ability of anti-human NPR3 monoclonal antibodies isolated from ANP-V$_H$1-69 modified and VELOCIMMUNE® control mice immunized with NPR3 recombinant protein to bind human NPR3 (hNPR3) expressing cells was determined using electrochemiluminescence (ECL) based assay.

Briefly, HEK293 were engineered to express human NPR3 by transfecting the cells with neomycin resistant pLVXN.NPR3 expression plasmid which encodes human NPR3 (amino acids M1-A541, UniProtKB—P17342). The non-transfected HEK293 cells which showed no detectable expression of NPR3 by fluorescence activated cell sorting (FACS) with commercial atrial natriuretic peptide (ANP) were included in the experiment as a background binding control. An anti-allergen human IgG1 antibody and an anti-idiotype mouse IgG2 antibody were included as irrelevant antibody controls for binding.

Experiments were carried out according to the following procedure. The NPR3-expressing cells and the parental cells cultured in flasks were rinsed once in 1×PBS buffer without Ca2+/Mg2+ and incubated for 10 minutes at 37° C. with Enzyme Free Cell Dissociation Solution to detach cells. The cell pellets were washed once with 1×PBS with Ca2+/Mg2+ and counted with a Cellometer™ Auto T4 cell counter (Nexcelom Bioscience, Lawrence, MA). Approximately 2.0×104 HEK293/hNPR3 or HEK293 cells per well were seeded separately onto 96-well carbon electrode plates (Meso Scale Discovery, Rockville, MD) and incubated for 1 hour at 37° C. to allow the cells to adhere. Nonspecific binding sites were blocked by incubating with 2% BSA (w/v) in 1×PBS with Ca2+/Mg2+ for 1 hour at room temperature. To the plate-bound cells, anti-NPR3 antibody supernatants at a dilution of 1:10 or 0.2 m/mL of control antibodies were added followed by 1 hour incubation at room temperature. Plates were then washed to remove unbound antibodies using an AquaMax2000 plate washer with a cell washing head (MDS Analytical Technologies, Sunnyvale, CA). The plate-bound human IgG was detected with SULFO-TAG™-conjugated goat polyclonal anti-human IgG antibody specific for heavy and light chains (Jackson Immunoresearch Labs, West Grove, PA) and the plate-bound mouse IgG (the commercial NPR3 antibody and mIgG isotype control antibody) was detected with SULFO-TAG™-conjugated goat polyclonal anti-mouse IgG antibody specific for Fcγ fragment (Jackson Immunoresearch Labs, West Grove, PA) for 1 hour at room temperature. After washes, plates were developed with Read Buffer (Meso Scale Discovery, Rockville, MD) according to manufacturer's recommended procedure and luminescent signals were recorded with a SECTOR Imager 600 (Meso Scale Discovery, Rockville, MD). The ratio of binding signals on the HEK293/hNPR3 to the parental HEK293 cells was calculated and reported as an indication of the binding specificity of anti-NPR3 antibodies. Antibodies with the binding signal on HEK293/hNPR3 cells of greater than or equal to 200 RLU and binding ratio of greater than or equal to 3 were classified as specific binders and antibodies with a binding signal less than 200 RLU or binding ratio less than 3 were classified as non-specific binders or non-binders.

Results:

The ability of the anti-NPR3 antibody isolated from VELOCIMMUNE® control and the ANP-$V_H$1-69 modified mice to bind specifically to NPR3-expressing HEK293 cells was evaluated in a electrochemiluminescence based binding assay.

The experimental results are summarized in Table 6. A total of 338 anti-NPR3 antibodies in crude supernatants were tested for binding to HEK293/hNPR3 cells, of which 125 antibodies were isolated from VELOCIMMUNE® control mice and 213 antibodies from ANP-$V_H$1-69 modified mice. A total of 250 anti-NPR3 antibodies, 62 from VELOCIMMUNE® control and 188 from ANP-$V_H$1-69 modified mice, displayed binding signals greater than or equal to 200 RLU on HEK293/hNPR3 cells and ratios of bindings on HEK293/hNPR3 to parental HEK293 greater than or equal to 3, suggesting these antibodies capable of binding to NPR3 specifically. Fifty percent of anti-NPR3 antibodies from VELOCIMMUNE® control mice and in comparison, 88% from ANP-$V_H$1-69 modified mice were specific NPR3 binders. Of the top 50 specific binders, 6 antibodies were from VELOCIMMUNE® control and 44 were from ANP-$V_H$1-69 modified mice, which suggests 5% of anti-NPR3 antibody supernatants from VELOCIMMUNE® control mice and 21% of anti-NPR3 antibody supernatants from ANP-$V_H$1-69 modified mice were top binders.

In the experiment the commercial anti-hNPR3-mIgG2 antibody, included as a positive control bound specifically to the HEK293/hNPR3 cells, and both human IgG1 and mouse IgG2 isotype controls did not bind HEK293/hNPR3 cells, as expected.

Overall, the binding results using HEK293/hNPR3 cells suggest that ANP-$V_H$1-69 modified mice were capable of generating antibodies that bound specifically to hNPR3 expressing cells and the abundance of high efficacy binders may be higher of the antibodies isolated from ANP-$V_H$1-69 modified mice than from the regular VELOCIMMUNE® control mice.

TABLE 6

Summary of Anti-NPR3 Antibody Supernatants Binding to Cells Engineered to Express Human NPR3.

| Mouse Strain | Number of tested anti-NPR3 | Number of specific anti-NPR3 binders | % Of specific anti-NPR3 binders per strain of mice | Number of specific anti-NPR3 binders with top 50 cell binding ratio | % Of anti-NPR3 specific binders with top 50 cell binding ratio per total binders per strain of mice |
|---|---|---|---|---|---|
| VELOCIMMUNE® control | 125 | 62 | 50% | 6 | 5% |
| ANP-$V_H$1-69 modified mice | 213 | 188 | 88% | 44 | 21% |

Purified Antibodies

In order to assess the ability of anti-NPR3 antibodies derived from ANP-$V_H$1-69 modified mice for binding to NPR3, an engineered cell line was established in HEK293 cells (human embryonic kidney 293, ATCC) that were transfected to stably express full-length human NPR3 and subsequently sorted for high expression. The resulting cell line was named HEK293/hNPR3 High Sort (ACL #9752, Regeneron).

For the flow cytometry binding assessment, HEK293/hNPR3 High Sort cells were lifted with enzyme-free cell dissociation buffer (Millipore, cat #S-004-C), washed once and resuspended in staining buffer (1×PBS, without calcium or magnesium (Irvine Scientific, cat #9240) with 2% filtered Fetal Bovine Serum (Seradigm, cat #1500-500)) and stained with fixable green viability dye (Life Technologies, cat #L23101) before being washed again and plated in the V-bottom staining plates (Axygen Scientific, cat #P-96-450-V-C-S).

Purified antibodies isolated from ANP-$V_H$1-69 modified mice and VELOCIMMUNE® control mice, a commercial antibody (GeneTex, GTX84015), or isotype control antibodies were serially diluted in staining buffer 1:3 from 100 nM to 24.4 pM (with an additional well for staining buffer alone without test molecule) and added to the cells in the staining plate.

After an additional wash step, samples were stained with Alexa Fluor®647-tagged secondary detection antibodies [anti-human (Jackson ImmunoResearch, cat #109-607-003) and anti-mouse (Jackson ImmunoResearch, cat #115-607-003)] before fixation with CytoFix (BD Biosciences, cat #554655) fixation buffer. All samples were filtered through 96-well filter plates (Pall, cat #8027) into U-bottom read plates (Corning, cat #3799) before being run through the iQue PLUS cytometer and Mean Fluorescence Intensity (MFI) was measured for each sample. Data was gated in the iQue Forecyt® software to calculate the geometric mean of each sample in the RL1-A channel and results further analyzed using a nonlinear regression (4-parameter logistic) model in Prism® 8 software to obtain EC50 values. The maximum fold binding was calculated using the following equation:

$$\text{Fold Binding} = \frac{MFI_{geometry\ mean\ RL1-A}}{MFI_{geometry\ mean\ RL1-A,\ secondary\ antibody\ alone\ control}}$$

In this equation "$MFI_{geometric\ mean\ RL1-A}$" refers to the maximum mean fluorescence intensity (MFI) value in the RL1-A channel from cells stained with the purified antibodies. "$MFI_{geometric\ mean\ RL1-A,\ secondary\ antibody\ alone\ control}$" refers to the WI value in the RL1-A channel from cells stained with only Alexa647-tagged secondary detection antibody.

As shown in Table 7, 12 purified anti-NPR3 antibodies isolated from ANP-$V_H$1-69 modified mice expressed with the ANP tag ("+ANP"), 12 purified anti-NPR3 antibodies isolated from ANP-$V_H$1-69 modified mice expressed without the ANP tag ("−ANP"), and 8 purified anti-NPR3 antibodies isolated from VELOCIMMUNE® control mice were tested for specific binding to HEK293/hNPR3 High Sort cells by flow cytometry. Eleven of the 12 purified anti-NPR3 antibodies isolated from ANP-$V_H$1-69 modified mice expressed with the ANP tag showed specific binding to HEK293/hNPR3 cells, with fold binding values ranging from 21 to 1012 over the secondary detection antibody alone control and EC50 values ranging from 7.7 nM to >10 nM.

The 10 of the 12 purified anti-NPR3 antibodies isolated from ANP-$V_H$1-69 modified mice expressed without the ANP tag showed specific binding to HEK293/hNPR3 cells, with fold binding values ranging from 132 to 819 over the secondary detection antibody alone control and EC50 values ranging from 6.3 nM to >10 nM. All 8 of the purified anti-NPR3 antibodies isolated from VELOCIMMUNE® control mice showed specific binding to HEK293/hNPR3 cells, with fold binding values ranging from 215 to 789 over the secondary detection antibody alone control and EC50 values ranging from 2.4 nM to >10 nM. Isotype control antibodies showed no binding to HEK293/hNPR3 cells and a commercial anti-NPR3 antibody bound to HEK293/hNPR3 with 22-fold binding over the secondary detection antibody alone control and an EC50 of 7.6 nM.

TABLE 7

| Antibody | Fold Binding | EC$_{50}$ [M] |
|---|---|---|
| VELOCIMMUNE ® control Ab 1 | 609 | >1.0E−08 |
| VELOCIMMUNE ® control Ab 2 | 311 | >1.0E−08 |
| VELOCIMMUNE ® control Ab 3 | 215 | 2.4E−09 |
| VELOCIMMUNE ® control Ab 4 | 562 | 1.1E−08 |
| VELOCIMMUNE ® control Ab 5 | 629 | 1.0E−08 |
| VELOCIMMUNE ® control Ab 6 | 789 | >1.0E−08 |
| VELOCIMMUNE ® control Ab 7 | 443 | 1.1E−08 |
| VELOCIMMUNE ® control Ab 8 | 291 | 2.1E−08 |
| ANP-$V_H$1-69 modified Ab 1 − ANP | 132 | >1.0E−08 |
| ANP-$V_H$1-69 modified Ab 2 − ANP | 798 | >1.0E−08 |
| ANP-$V_H$1-69 modified Ab 3 − ANP | 689 | >1.0E−08 |
| ANP-$V_H$1-69 modified Ab 4 − ANP | 798 | 7.0E−09 |
| ANP-$V_H$1-69 modified Ab 5 − ANP | 3 | no binding |
| ANP-$V_H$1-69 modified Ab 6 − ANP | 576 | 9.1E−09 |
| ANP-$V_H$1-69 modified Ab 7 − ANP | 605 | 7.0E−09 |
| ANP-$V_H$1-69 modified Ab 8 − ANP | 819 | 9.9E−09 |
| ANP-$V_H$1-69 modified Ab 9 − ANP | 566 | 6.3E−09 |
| ANP-$V_H$1-69 modified Ab 10 − ANP | 799 | 8.7E−09 |
| ANP-$V_H$1-69 modified Ab 11 − ANP | 712 | 1.7E−08 |
| ANP-$V_H$1-69 modified Ab 12 − ANP | 14 | no binding |
| ANP-$V_H$1-69 modified Ab 1 + ANP | 330 | >5.0E−08 |
| ANP-$V_H$1-69 modified Ab 2 + ANP | 519 | 7.7E−09 |
| ANP-$V_H$1-69 modified Ab 3 + ANP | 664 | 1.2E−08 |
| ANP-$V_H$1-69 modified Ab 4 + ANP | 688 | 8.4E−09 |
| ANP-$V_H$1-69 modified Ab 5 + ANP | 7 | no binding |
| ANP-$V_H$1-69 modified Ab 6 + ANP | 549 | 1.0E−08 |
| ANP-$V_H$1-69 modified Ab 7 + ANP | 686 | 1.3E−08 |
| ANP-$V_H$1-69 modified Ab 8 + ANP | 783 | 9.5E−09 |
| ANP-$V_H$1-69 modified Ab 9 + ANP | 913 | 1.1E−08 |
| ANP-$V_H$1-69 modified Ab 10 + ANP | 1012 | >1.0E−08 |
| ANP-$V_H$1-69 modified Ab 11 + ANP | 411 | 1.5E−08 |
| ANP-$V_H$1-69 modified Ab 12 + ANP | 21 | >5.0E−08 |
| Isotype Control Ab 1 | 2 | no binding |
| Isotype Control Ab 2 | 1 | no binding |
| Commercial anti-hNPR3 Ab | 22 | 7.6E−09 |

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

What is claimed:

1. A recombinant nucleic acid molecule comprising a modified immunoglobulin (Ig) variable (V) gene segment that encodes an anchor-modified Ig polypeptide, wherein the modified Ig V gene segment comprises a nucleic acid sequence encoding the anchor between a nucleic acid sequence encoding an Ig signal peptide and a nucleic acid sequence encoding the framework region (FR) 1, complementarity determining region (CDR) 1, FR2, CDR2, FR3, and CDR3 of a germline Ig V gene segment, or a variant thereof, wherein the anchor-modified Ig polypeptide comprises, in operable linkage:

(i) the Ig signal peptide, (ii) the anchor, and (iii) the FR1, CDR1, FR2, CDR2, FR3, and CDR3 of the germline Ig V gene segment, or a variant thereof, wherein the anchor comprises a receptor binding portion of a non-immunoglobulin polypeptide of interest that binds a cognate receptor, and optionally wherein the nucleic acid molecule lacks any other Ig V gene segments.

2. The recombinant nucleic acid molecule of claim 1, wherein the Ig signal peptide is the Ig signal peptide of the germline Ig V gene segment, or the variant thereof.

3. The recombinant nucleic acid molecule of claim 1, wherein the germline Ig V gene segment, or the variant thereof is a germline Ig heavy chain variable ($V_H$) gene segment, or a variant thereof such that the modified Ig V gene segment is a modified Ig $V_H$ gene segment that comprises the nucleic acid sequence encoding the anchor between the nucleic acid sequence encoding the Ig signal peptide and the nucleic acid sequence encoding the framework region (FR) 1, complementarity determining region (CDR) 1, FR2, CDR2, FR3, and CDR3 of the germline Ig $V_H$ gene segment, or a variant thereof, and the anchor-modified Ig polypeptide comprises in operable linkage:

(i) the Ig signal peptide, (ii) the anchor, and (iii) the FR1, CDR1, FR2, CDR2, FR3, and CDR3 of the germline Ig $V_H$ gene segment, or a variant thereof.

4. The recombinant nucleic acid molecule of claim 1, wherein the germline Ig V gene segment, or the variant thereof is a germline $hV_H1$-69 gene segment, or a variant thereof, optionally wherein the Ig signal peptide comprises the sequence MDWTWRFLFVVAAATGVQS (SEQ ID NO:7).

5. The recombinant nucleic acid molecule of claim 3, comprising in operable linkage and from 5' to 3':

(I) the modified Ig $V_H$ gene segment, (II) one or a plurality of Ig heavy chain diversity ($D_H$) gene segments, and (III) one or a plurality of Ig heavy chain joining ($J_H$) gene segments.

6. The recombinant nucleic acid molecule of claim 5, wherein the one or a plurality of Ig $D_H$ gene segments of (II) comprises one, a plurality of, or all human Ig $D_H$ gene segments, and/or the one or a plurality of Ig $J_H$ gene segments of (III) comprises one, a plurality of, or all human Ig $J_H$ gene segments.

7. The recombinant nucleic acid molecule of claim 5, wherein the one or a plurality of Ig $D_H$ gene segments of (II) and the one or a plurality of Ig $J_H$ gene segments of (III) are recombined and form a rearranged Ig $D_H/J_H$ sequence such that the recombinant nucleic acid molecule comprises in operable linkage and from 5' to 3':

the modified Ig $V_H$ gene segment and the rearranged Ig $D_H/J_H$ sequence.

8. The recombinant nucleic acid molecule of claim 7, wherein the modified Ig $V_H$ gene segment and the rearranged Ig $D_H/J_H$ sequence are recombined and form a rearranged Ig $V_H/D_H/J_H$ sequence that encodes an anchor-modified Ig $V_H$ domain, wherein the anchor-modified Ig $V_H$ domain comprises in operable linkage:

(i) the Ig signal peptide, (ii) the anchor, and (iii) the FR1, complementarity determining region (CDR) 1, FR2, CDR2, FR3, CDR3, and FR4 encoded by the rearranged Ig $V_H/D_H/J_H$ sequence.

9. The recombinant nucleic acid molecule of claim 3, wherein the modified Ig $V_H$ gene segment is an unrearranged modified Ig $V_H$ gene segment.

10. The recombinant nucleic acid molecule of claim 5, further comprising a nucleic acid sequence encoding an Ig heavy chain constant region (CH), wherein the nucleic acid sequence encoding the Ig CH is downstream of and operably linked to (I) the modified Ig $V_H$ gene segment, (II) the one or a plurality of Ig $D_H$ gene segments, and (III) the one or a plurality of Ig $J_H$ gene segments.

11. The recombinant nucleic acid molecule of claim 1, wherein the germline Ig V gene segment or the variant thereof is a germline Ig light chain variable ($V_L$) gene segment or a variant thereof such that the modified Ig V gene segment is a modified Ig $V_L$ gene segment that comprises the nucleic acid sequence encoding the anchor between the nucleic acid sequence encoding the Ig signal peptide and the nucleic acid sequence encoding the framework region (FR) 1, complementarity determining region (CDR) 1, FR2, CDR2, FR3, and CDR3 of the germline Ig $V_L$ gene segment or the variant thereof, and the anchor-modified Ig polypeptide comprises in operable linkage:
(i) the Ig signal peptide,
(ii) the anchor, and
(iii) the FR1, CDR1, FR2, CDR2, FR3, and CDR3 of the germline Ig $V_L$ gene segment or a variant thereof.

12. The recombinant nucleic acid molecule of claim 11, comprising in operable linkage and from 5' to 3':
(I) the modified Ig $V_L$ gene segment, and
(II) one or a plurality of Ig light chain joining ($J_L$) gene segments.

13. The recombinant nucleic acid molecule of claim 12, wherein the modified Ig $V_L$ gene segment and the one or a plurality of Ig $J_L$ gene segments are recombined and form a rearranged Ig $VI/J_L$ sequence that encodes an anchor-modified Ig $V_L$ domain,
wherein the anchor-modified Ig $V_L$ domain comprises in operable linkage:
(i) the Ig signal peptide,
(ii) the anchor, and
(iii) the FR1, CDR1, FR2, CDR2, FR3, CDR3, and FR4 encoded by the rearranged Ig $V_L/J_L$ sequence.

14. The recombinant nucleic acid molecule of claim 12, further comprising a nucleic acid sequence encoding an Ig light chain constant region ($C_L$),
wherein the nucleic acid sequence encoding the Ig $C_L$ is downstream of and operably linked to:
(I) the modified Ig $V_L$ gene segment and
(II) the one or a plurality of Ig $J_L$ gene segments.

15. The recombinant nucleic acid molecule of claim 1, wherein the anchor comprises a linker that links the receptor binding portion of the non-immunoglobulin polypeptide of interest to the FR1, CDR1, FR2, CDR2, FR3, and CDR3 of the germline Ig V gene segment, or a variant thereof.

16. The recombinant nucleic acid molecule of claim 15, wherein the linker comprises the sequence GGGGS (SEQ ID NO:5).

17. The recombinant nucleic acid molecule of claim 1, wherein the anchor comprises the natriuretic peptide receptor (NPR) binding portion of a natriuretic peptide (NP).

18. The recombinant nucleic acid molecule of claim 17, wherein the NPR binding portion of the NP comprises the C-terminal tail of the NP.

19. The recombinant nucleic acid molecule of claim 17, wherein the NP is atrial natriuretic peptide (ANP).

20. The recombinant nucleic acid molecule of claim 1, wherein the anchor comprises the sequence NSFRY (SEQ ID NO:3).

21. The recombinant nucleic acid molecule of claim 1, comprising a sequence selected from the group consisting of the sequence set forth as SEQ ID NO:8 or a degenerate variant thereof, the sequence set forth as SEQ ID NO:10 or a degenerate variant thereof, the sequence set forth as SEQ ID NO:11 or a degenerate variant thereof, and the sequence set forth as SEQ ID NO:12 or a degenerate variant thereof.

22. A targeting vector comprising the recombinant nucleic acid molecule of claim 1, wherein the targeting vector further comprises 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule upstream of and in operable linkage to a non-human Ig CH at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof.

23. A targeting vector comprising the recombinant nucleic acid molecule of claim 1, wherein the targeting vector further comprises 5' and 3' homology arms that target a non-human Ig heavy chain locus such that upon homologous recombination between the targeting vector and the non-human Ig heavy chain locus, the targeted non-human Ig heavy chain locus comprises the recombinant nucleic acid molecule in operable linkage to a non-human Ig heavy chain regulatory sequence at the non-human Ig heavy chain locus, optionally wherein the non-human Ig heavy chain locus is an endogenous rodent Ig heavy chain locus and/or wherein the non-human Ig heavy chain locus comprises a human or humanized immunoglobulin heavy chain variable region, a deletion of endogenous Ig $V_H$, $D_H$, and/or $J_H$ gene segments, or a combination thereof.

24. A targeting vector comprising the recombinant nucleic acid molecule of claim 1, wherein the targeting vector further comprises 5' and 3' homology arms that target a non-human Ig light chain locus such that upon homologous recombination between the targeting vector and the non-human Ig light chain locus, the targeted non-human Ig light chain locus comprises the recombinant nucleic acid molecule upstream of and in operable linkage to a non-human Ig $C_L$ at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof.

25. A targeting vector comprising the recombinant nucleic acid molecule of claim 1, wherein the targeting vector further comprises 5' and 3' homology arms that target a non-human Ig light chain locus such that upon homologous recombination between the targeting vector and the non-human Ig light chain locus, the targeted non-human Ig light chain locus comprises the recombinant nucleic acid molecule in operable linkage to a non-human Ig light chain regulatory sequence at the non-human Ig light chain locus, optionally wherein the non-human Ig light chain locus is an endogenous rodent Ig light chain locus and/or wherein the non-human Ig light chain locus comprises a human or humanized immunoglobulin light chain variable region, a deletion of endogenous Ig $V_L$ and/or $J_L$ gene segments, or a combination thereof.

26. An antigen-binding protein comprising an anchor-modified Ig polypeptide encoded by the recombinant nucleic acid molecule of claim 1, optionally:
wherein the mass of each antigen-binding protein confirms the presence of the anchor-modified Ig polypeptide,
wherein the mass of each antigen-binding protein is determined by Matrix-Assisted Laser Desorption Ionization—Time of Flight Mass Spectrometry, or
wherein the mass of each antigen-binding protein confirms the presence of the anchor-modified Ig polypeptide and the mass of each antigen-binding protein is determined by Matrix-Assisted Laser Desorption Ionization—Time of Flight Mass Spectrometry.

27. The antigen-binding protein comprising the anchor-modified Ig polypeptide of claim 26 comprising an amino acid sequence set forth as SEQ ID NO:3 at its N-terminus.

* * * * *

SEQUENCE LISTING

<160> NUMBER OF SEQ ID NOS: 32

<210> SEQ ID NO 1
<211> LENGTH: 855
<212> TYPE: DNA
<213> ORGANISM: Homo sapiens

<400> SEQUENCE: 1

| | | | | | |
|---|---|---|---|---|---|
| gagacaggga | cagacgtagg | ccaagagagg | ggaaccagag | aggaaccaga | ggggagagac | 60 |
| agagcagcaa | gcagtggatt | gctccttgac | gacgccagca | tgagctcctt | ctccaccacc | 120 |
| accgtgagct | tcctcctttt | actggcattc | cagctcctag | gtcagaccag | agctaatccc | 180 |
| atgtacaatg | ccgtgtccaa | cgcagacctg | atggatttca | agaatttgct | ggaccatttg | 240 |
| gaagaaaaga | tgcctttaga | agatgaggtc | gtgcccccac | aagtgctcag | tgagccgaat | 300 |
| gaagaagcgg | gggctgctct | cagccccctc | cctgaggtgc | ctccctggac | cggggaagtc | 360 |
| agcccagccc | agagagatgg | aggtgccctc | ggcgggggcc | cctgggactc | ctctgatcga | 420 |
| tctgccctcc | taaaaagcaa | gctgagggcg | ctgctcactg | cccctcggag | cctgcggaga | 480 |
| tccagctgct | tcgggggcag | gatggacagg | attggagccc | agagcggact | gggctgtaac | 540 |
| agcttccggt | actgaagata | acagccaggg | aggacaagca | gggctgggcc | tagggacaga | 600 |
| ctgcaagagg | ctcctgtccc | ctggggtctc | tgctgcattt | tgtcatctt | gttgccatgg | 660 |
| agttgtgatc | atcccatcta | agctgcagct | tcctgtcaac | acttctcaca | tcttatgcta | 720 |
| actgtagata | aagtggtttg | atggtgactt | cctcgcctct | cccacccat | gcattaaatt | 780 |
| ttaaggtaga | acctcacctg | ttactgaaag | tggtttgaaa | gtgaataaac | ttcagcacca | 840 |
| tggacagaag | acaaa | | | | | 855 |

<210> SEQ ID NO 2
<211> LENGTH: 151
<212> TYPE: PRT
<213> ORGANISM: Homo sapiens

<400> SEQUENCE: 2

Met Ser Ser Phe Ser Thr Thr Thr Val Ser Phe Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150

```
<210> SEQ ID NO 3
<211> LENGTH: 5
<212> TYPE: PRT
<213> ORGANISM: Homo sapiens

<400> SEQUENCE: 3

Asn Ser Phe Arg Tyr
1               5

<210> SEQ ID NO 4
<211> LENGTH: 15
<212> TYPE: DNA
<213> ORGANISM: Artificial Sequence
<220> FEATURE:
<223> OTHER INFORMATION: G4S DNA sequence
<220> FEATURE:
<221> NAME/KEY: CDS
<222> LOCATION: (1)..(15)

<400> SEQUENCE: 4 ggt ggc ggc ggt agc                                              15
Gly Gly Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Gly Gly Gly Gly Ser
1               5

<210> SEQ ID NO 6
<211> LENGTH: 107
<212> TYPE: DNA
<213> ORGANISM: Homo sapiens

<400> SEQUENCE: 6
gcagctacag gtaaggggct tcctagtcct aaggctgagg aagggatcct ggtttagtta    60
aagaggattt tattcacccc tgtgtcctgt ccacaggtgt ccagtcc                 107

<210> SEQ ID NO 7
<211> LENGTH: 19
<212> TYPE: PRT
<213> ORGANISM: Homo sapiens

<400> SEQUENCE: 7

Met Asp Trp Thr Trp Arg Phe Leu Phe Val Val Ala Ala Ala Thr Gly
1               5                   10                  15

Val Gln Ser

<210> SEQ ID NO 8
<211> LENGTH: 327
<212> TYPE: DNA
<213> ORGANISM: Artificial Sequence
<220> FEATURE:
<223> OTHER INFORMATION: ANP-VH1-69 without leader
<220> FEATURE:
<221> NAME/KEY: CDS
<222> LOCATION: (1)..(327)

<400> SEQUENCE: 8 aac agc ttc cgg tac ggt ggc ggc ggt agc cag gtc cag ctg gtg cag    48
```

```
Asn Ser Phe Arg Tyr Gly Gly Gly Ser Gln Val Gln Leu Val Gln
1               5                   10                  15 tct ggg gct gag gtg aag aag cct ggg tcc tcg gtg aag gtc tcc tgc        96
Ser Gly Ala Glu Val Lys Lys Pro Gly Ser Ser Val Lys Val Ser Cys
            20                  25                  30 aag gct tct gga ggc acc ttc agc agc tat gct atc agc tgg gtg cga       144
Lys Ala Ser Gly Gly Thr Phe Ser Ser Tyr Ala Ile Ser Trp Val Arg
                35                  40                  45 cag gcc cct gga caa ggg ctt gag tgg atg gga ggg atc atc cct atc       192
Gln Ala Pro Gly Gln Gly Leu Glu Trp Met Gly Gly Ile Ile Pro Ile
        50                  55                  60 ttt ggt aca gca aac tac gca cag aag ttc cag ggc aga gtc acg att       240
Phe Gly Thr Ala Asn Tyr Ala Gln Lys Phe Gln Gly Arg Val Thr Ile
65                  70                  75                  80 acc acg gac gaa tcc acg agc aca gcc tac atg gag ctg agc agc ctg       288
Thr Thr Asp Glu Ser Thr Ser Thr Ala Tyr Met Glu Leu Ser Ser Leu
                    85                  90                  95 aga tct gag gac acg gcc gtg tat tac tgt gcg aga gac                   327
Arg Ser Glu Asp Thr Ala Val Tyr Tyr Cys Ala Arg Asp
                100                 105

<210> SEQ ID NO 9
<211> LENGTH: 109
<212> TYPE: PRT
<213> ORGANISM: Artificial Sequence
<220> FEATURE:
<223> OTHER INFORMATION: Synthetic Construct

<400> SEQUENCE: 9

Asn Ser Phe Arg Tyr Gly Gly Gly Ser Gln Val Gln Leu Val Gln
1               5                   10                  15

Ser Gly Ala Glu Val Lys Lys Pro Gly Ser Ser Val Lys Val Ser Cys
            20                  25                  30

Lys Ala Ser Gly Gly Thr Phe Ser Ser Tyr Ala Ile Ser Trp Val Arg
                35                  40                  45

Gln Ala Pro Gly Gln Gly Leu Glu Trp Met Gly Gly Ile Ile Pro Ile
        50                  55                  60

Phe Gly Thr Ala Asn Tyr Ala Gln Lys Phe Gln Gly Arg Val Thr Ile
65                  70                  75                  80

Thr Thr Asp Glu Ser Thr Ser Thr Ala Tyr Met Glu Leu Ser Ser Leu
                    85                  90                  95

Arg Ser Glu Asp Thr Ala Val Tyr Tyr Cys Ala Arg Asp
                100                 105

<210> SEQ ID NO 10
<211> LENGTH: 583
<212> TYPE: DNA
<213> ORGANISM: Artificial Sequence
<220> FEATURE:
<223> OTHER INFORMATION: ANP-VH1-69 Cas9/BHR donor

<400> SEQUENCE: 10
ctcgagcagc tacaggtaag gggcttccta gtcctaaggc tgaggaaggg atcctggttt     60
agttaaagag gatttttattc acccctgtgt cctgtccaca ggtgtccagt ccaacagctt   120
ccggtacggt ggcggcggta gccaggtcca gctggtgcag tctggggctg aggtgaagaa   180
gcctgggtcc tcggtgaagg tctcctgcaa ggcttctgga ggcaccttca gcagctatgc   240
tatcagctgg gtgcgacagg cccctggaca agggcttgag tggatgggag ggatcatccc   300
tatctttggt acagcaaact acgcacagaa gttccagggc agagtcacga ttaccacgga   360
```

```
cgaatccacg agcacagcct acatggagct gagcagcctg agatctgagg acacggccgt    420
gtattactgt gcgagagaca cagtgtgaaa acccacatcc tgagagtgac aaaaaccctg    480
agggcgccgg cggaattcaa gcttcctagg cgccggcgag aaggcagctg tgccgggctg    540
aggagatgac aggggttatt aggtttaagg ctgtttactc gag                     583

<210> SEQ ID NO 11
<211> LENGTH: 19726
<212> TYPE: DNA
<213> ORGANISM: Mus musculus

<400> SEQUENCE: 11
aagcttatct ctctgttgct cagactcatc taggaatttc agaaatttct gttctagcat     60
ctcttccagc ttttgtctcc aaccctcatt ctcttcttc ttttttttt taaattatat     120 gttctctgtc tttttaaaaa acttttaaa attaggtatt tatgtcattt acatttccaa    180
tgctatccca aaagtcccac ccacgctccc aacccacta tcccaccac ccactcccac    240 ttcttggccc tggcattcac agtgtactga acatataaa gtttgcacaa ccaatgggcc    300
tctctttcca ctgatggccg actaggccat cttctgatac atatgcagct agagacacga    360
gattctgggg gtactggtta gttcatattg ttgttccacc tataggggttg cagatccttt   420 tagctccttg ggtactttct ctagctcctc cattgggggc cctgtgatcc atccaatagc   480
tgactgtgag catccacttc tgtgtttgct aggccccaga tagtctcaca agagacagct   540
atatctgggt cctttcagca aaatcttgct agtgtatgca acgtgtcag agtttggaag     600 ctgattatgg gatggatccc cggatatggc attctctagt tggttcatcc ttttgtctca   660
gctccaaact ttgtctctgt aactccttcc atgggtgttt tgttcccagt tctaaggagg   720
ggcaaagtat ccacactttg gtcttcattc ttcttgagtt tcatgtgttt tgcaaattgt   780
atcttatatc ttgggtattc taagtttctg ggctaatatc cacttatcag tgagtacaca   840
ttgtgtgagt tcttttgtga ttgggttacc tcactcagta tgatgccctc caggtccatc   900
catttgccta ggaatttcat aaattcattc tttttaatag ctcagtagta ctccattgtg   960
tagatgtacc cattttctg tattcattcc tctgttgagg ggcatctggg ttcttttccag  1020 cttctggcta ttataaataa ggctgctatg aacatagtgg agcatgtgac cttcttaccg  1080
gttgggacat cttctggata tatgcccagg agaggtattg ctggatcttc cggtagtact  1140
atgtccaatt ttctgaggaa ctgacaaact gatttccaga gtggttagta ccagcttgca  1200
atcccaccaa caatgagagg agtgttcgtc tttctccaca tcctcaccag catgctgctg  1260
tcacctgaat ttttgatgct tagccattct gactggtgtg aggtggaatc tcagggttgt  1320
tttgatttgt atttccctga tgattaagga tgctgaacat tttctcaggt gcttctcagc   1380
cattcagtat tctttaggtg agaattcttt gtttagctct aagccccatt tttttaatgg  1440
ggttatttga ttttctggag tccaccttct tgagttttt tttccatttt ttattacata  1500
atttcctcaa ttacatttcc aatgctatcc caaaagtccc ccatacctc ccccccccaa   1560 ttccctaccc accccttccc attttttttgg ccctggcgtt ccctgtact ggggcatata   1620 aagtttgtgt gtccaatggg cttctctttc cagtgatggc tgactaggcc atcttttgat  1680
acatatgcag ctagagtcaa gagctcccgg gtactggtta gttcataatg ttgttccacc  1740
tatagggttg cagatccctt tagcttcttg ggtactttct ctagctcctc cattgggagc  1800
cctgtgatcc atccaatagc tgactgtgag catccacttc tgtgtttgct aggccccggc  1860
```

```
atagtctcac aagagacagc tacatctggg tccttttgat aaaatcttgc tagtgtatgc    1920
aagggtgtca gcatttggaa gctgattatg gggtggatcc ctggatatgg cagtctctac    1980
atggtccatc cttttgtctc agctccaaac tttgtctctg taacttcttc catgagtgtt    2040
ttgttcccaa ttctaaggag gggcatagtg tccacacttc attcttcatt cttcttgagt    2100
ttcatgtgtt tagcaaattg tatcttatat cttgggtatc ctaggttttg ggctaatatc    2160
cacttatcag tgagtacata ttgtgtgagt tcctttgtaa atgtgttacc tcactcagga    2220
tgacgccctc caggtccatc catttggcta ggaatttcat aaattcattc tttttaatag    2280
ctgagtagta ctccattgtg taaatgtacc catttttctg tactcattcc tctgttgagg    2340
ggcatctggg ttctttatag gttctggcta ttataaataa ggttgctatg aacatagtgg    2400
agcatgtgtc cttcttaccg gttgagacat cttctggata tatgcccagg cgaggtattg    2460
ctggatcctc cggtagtact atgtccaatt ttctgaggaa ctgccagact gatttccaga    2520
gtggttgtac aagcctgcac tctcaccaac aatggaggag tgttcctctt tctccacatc    2580
cacgccagca tctgctgtca cctgaatttt tgatcttagc cattctgact ggtgtgaggt    2640
ggaatctcag ggttgttttg atttgcattt ccctgatgat taaggatgtt gaacattttt    2700
ttcaggtgct tctctgccat tcggtattcc tcaggtgaga attctttgtt cagttctgag    2760
ccccattttt taatggggtt atttgatttt ctgaagtcca ccttcttgag ttctttatat    2820
atgttggata ttagtcccct atctgattta cgataggtaa agatcctttc ccaatctgtt    2880
ggtggtcttt ttctcttatt gacggtgtct tttgccttgc agaaactttg gagtgagttc    2940
tttatatata ttggatatta gtcccctatc tgatttagga taggtaaaga tccttttccca   3000 atctgttggt gaccttttg tcttattgac ggtgtctttt gccttgcaga atctttgcaa    3060
ttttatgagg tcgcatttgt caattctcga tcttacagca caagtcattg ctgttctgtt    3120
caggaatttt tcctctgtgc ccatatcttc gaggctttta cctgctttct cctctatatg    3180
tttgagtgtc tctggtttaa tgtggagttc cttaatccac ttagatttga ccttagtaca    3240
aggagatagg aatggatcaa ttcgcattct tctacatgat aaccgctagt tgtgccagca    3300
ccatttgttg ataatgctgt cttttttcca ctggatggtt tttgctccct tgtctaagat    3360
caagtgacca taggtgtgtg ggttcatttc tgggtcttca attctatttc attggtctac    3420
ttgtctgttg ttataccagt accatgcaga ttttatcaca attgctctgt agtagagttt    3480
taggtcaggc atggtgatta caccagaggt ttttttatc cttgagcaga gttttttgcta   3540 tcctaggttt tgtgttattt cagatgaatt tgcagattgc cctttccagt tcgttgaaga    3600
attgagttgg aattttgatg gggattgcat tgaatctgta gattgctttg gcaatatagc    3660
catttttact atattgatcc tgccaatcca tgagcatggg agatctttcc atcttctcaa    3720
atcttcttta atttctttct tcagagactt gaagttcttg tcatacagat ctttcacttc    3780
cttagttaga gtcacgctaa ggtattttat attatttgtg actattgaga agggtgttgt    3840
ttccctaatt tctttctcag cctgtttatc ctttgtgtac agaaaagcca ttgacttgtg    3900
ttagttaatc tcatatccag ctacttcact gaagcggttt atcaggttta ggagttctct    3960
ggtgtaattt ttagggtcac tcatatatac tatcatatca tctgcaaaaa gtgacatttt    4020
gacttcttcc tttccaattt gtatcccctt gatctccttt tgttgtcgaa ttgctctggc    4080
aaggacatca agtactatat tgaataggta gggagaaaat cggcacccct gtctagtccc    4140
tgattttagt aggattgctt caagtttctc accattact ttgatgttgg ctactggttt     4200
gctgttgaat gctttttatc atgtttaggt atgggccttg aattcctgat ctttccaaga    4260
```

```
cttttatcat gaaagggtgt tggattttgt caaatgcttt ctccagcctt tcattctgag    4320
gttgtgtctg tcttttccc tgagatgggg ttcctgtaag cagcaaaatg ttgggtcctg    4380
tttgtgtagc ccgtctgtta ttctatgtct ttttattggg gagttgagtc cattgatatt    4440
aagatatatt aaggaaaagt aattgttgct tcctattatt tttgttttta aagttggcat    4500
tctgttcttg tggctgtctt cttttaggtt tgttgaagga ttcctttctt gcttttccta    4560
ggtcgtggtt tccatccttg tattcatttt ttttctgtta ttatcctttg aaggactgga    4620
ttcatggata gataatgtgt gaatttggtt ttgtcttgga atacttttgt ttctccatct    4680
acggtaattg agagtttggc tgggtatagt agcctgggct ggcaattgtg ttgtcttagt    4740
gtctatataa tgtctgtcca ggatcttctg gctttcatag tctgtggtga aaaatctggt    4800
gtaattctga taggcttgcc tttatatgtt acttgaattt tcacttact gcttttaata    4860 ttctttcttt atttagtgca tttgttgttc tgattattat gtgtcgggag gaatttcttt    4920
tctggtccag tctatttgga gttctgtagg cttcttgtat gttcacgggc atctctttct    4980
ttaggtttgg gaagttttct tctataattt tgttgaagat atttgctggc ccttcaagtt    5040
gaaaatgttc attctcatct actcctatta ttcgtatggt tggtcttctc attgtgtcct    5100
ggatttcctg gatgttttga gttaggatct ttttgcattt tccattttct ttgattgttg    5160
tgcagatgtt ctctatggaa tcttctgcac ctgatattct ctcttccatc tcttgtagtc    5220
tgttgctgat gctcgcatct atggttccag atttctttcc tagggtttct atctccagtg    5280
ttgccccact ttgggttttc tgtatagtgt ctacttccct ttttagatct agtatggttt    5340
tgttcatttc catcacctgt ttgggtgtgt tttcctgttt ttctttaaag acttgcaact    5400
ctttagcaga gttctcctgt atttaagtga gttattaaag tccttcttga tgtccagtac    5460
cataattgtg agatatgcct ttaaatccaa gtctaggttt tgggtgtgt tggggtgccc    5520 tggactggct gagttgggag tgctgcattc tgatgatggt gagtggtctt ggtttctgct    5580
agtaagattc ttacatctgc ctttcgccat ctggtaatct ctggagtcag ttgttaaagt    5640
tgtctctggt taaagcttgt tcctctcgtg attctgttat tctcttccag cagacctggg    5700
agactagctc tttcctgagt ttcagtggtc agagcactct ctgcaggcag gatttcctct    5760
ttcagggaag gtgcacagat atctggtgtt cagatttgcc tcctggcaga agatgatggc    5820
ctgaaacagg acctgtccca gaagctgtta gcttctgtag tcaacactgt cacctgtgca    5880
gactagtctc ggtggagtcc gggaaccaag atgtctcctg cagatgctct ggcattccct    5940
tctgggccgt gtgatcacct ctcctctggc agggaaggtg ccctggtgtc tggaacccga    6000 aaaggggggct gcctcagaag ctctgtggct actgcctgtc ccagaagctg ttagcttctg    6060
tagtccacac tctcacctgt gcagactagt cttggtggag tctgggaacc aagatgtctc    6120
ccgcagatgc tccagccatt ctcctctttc tgttgcttat tttgacctat gaaatcctgg    6180
acatatagtt ctagtgttgc ttgtaatctc ttttctaagc caaggaattt tttttatcta    6240
gggcacaatc ttttgagaag acatattaaa tcaagagaat aaatattgca agaccaataa    6300
atgataaggt atctatttc tttaaatcca tcgctgtcaa accattcaaa atatcctcac    6360
ataaagccaa aaagatattt attgtgtttc ccatcttagt tgagttcaag tcaatatttt    6420
ggtgccattt tgttgcagta aatctctaac acaaatatgc ctgggcaatg aaaacacaac    6480
tcagttaata tgaatacaga ttgttcagat ctaccactac actaccatct tcttcatcta    6540
agagacccct tagaacttgc agtttctcca ggccttgtgc ttctgcgctg cttttcttct    6600
```

```
tcttcctctt ctacattgct tctctcataa acctacttct ttttttccct ccttctgttc      6660
catcttccct tttatctgcc caatcattag ctctccttta ttttacaaat taaggtgtga      6720
agccggtttc taggaaatca cctgagtgct gacttgttcc ttgttcagag ccacgcacag      6780
gagaacagaa ttaacatcaa atataattat ccccagggct atccacaaca cgtgcatcct      6840
ataagatcac cacggactaa tgctggtctt caattacaac ataaacaaca aaaacccac       6900 atatatgtgg aaacaaatcg aactatacaa agaatcaatg aaaccaggag cttgttcttt      6960
gagaaaaatc aacaagatag ataaacccct agccagacta accagagggc acagagacag      7020
tatccaaatt aataaagtca gaaatgaaag gaagacataa caatgaaata tatcttaaaa      7080
taattaatct gtttgtagac tattagcagt tgaaaatatt aaaatcatgt tctacaaacg      7140
tggaattatt attgataatt ttctcactgt gcttgaaatt agcatttttct taatgtttaa     7200 cttcaaagag ttttttgctat tttgaaatat taaacatata cttactgata aaataatttc     7260
cctcctaaca acactgataa tcttttttta agtaaactga ttattagaca atgtacacag      7320
atatataatg tgttttaaat actctcccac tgtcaggtgg tatcatatag ggcctttgaa      7380
tatattttta aatgtattat ttgtaatatt ttatggtctc tcctatgctt atttctgaaa      7440
gaatattttg tatgttttga aacaatttag tatttaacat tagatatagg atcctcagtt      7500
atggatagta ttaaatattc attaatgata tttttaaggt ataaaaggat atgaatataa      7560
aagtttaaca aattttatgt attatttgat tctaaaaata ctcaatatta ttaatatgtt      7620
tgatgtttaa aatgcattta aataataaaa acatttaaaa aaataaaatc aagaaatgag      7680
gttctaagca gaggtcaagg aaaatgagga atagaaaaat agtaaaaatc aatatgtcca      7740
tttattcaag gaaagctcct acatagacat tgcaccagat tagcaaatat tatggtcctc      7800
atattagttt aagttaggag actatgctta tgttatctat ttacattcta aggagcctag      7860
acatttgtga atggattaca ttataagagg aggatgtcta cttaagtagg catgaacgcc      7920
tgtgcattgc accctatgag ttccatcagc attccatgat tggagtatga agaacagcat      7980
tatagacatt acccagaacc ttagtggttc tagaatgcca agataaaaca atctaacctt      8040
ctggatagta gggataaatg ttcctatatc atcagaattc actggtgccc tgaggatgtt      8100
accctgctaa ctgacaattc acaggacatc acatggattc tgataagttg cagaaaagag      8160
gagatgcatt caattggtcc tcctccttct aagctgcaat attaggtgca tccaatttgt      8220
gaacttcaat ttagattaca atagacatga ataatctgaa ttcatgtagt acatattttt      8280
gttttaatat gagttaccat tgttcagaaa attaaataca catgatcaca tattcctaca      8340
tagtgctgtt agttttttcac atctctggga caatattcca aatatctcct tcattagtga     8400
aaatatcaac tactgtaaag cttagctaac atgcctttgc aggaataaga acatcctgga      8460
ttgaaagcta cacagggaga tgtaaaactt tctaagcaca cacattctcc atccattagg      8520
atcatggtcc atgagatttt tctctctctc ttcttcccat taaatgcatg tacatgcagg      8580
ttgggaaaca gattgtgttg cagaatacat ttgcttgatt tccacttcct tctcaatgca      8640
aatatttttg aagtgttaat tttgctgtga gtaccacagt ggttcttgct ctttctgttg      8700
actcctgtct gtgaatgttc caggaattca cacatggaca cacgtggggc tgcatctgag      8760
ctccagactc actgttgtcc ttctgtcctc agctgctctg gcccaggcac agcctcgtga      8820
attcaacaaa gaccctgatc tctcttgttt cacctcatt acaaatggga actgttagag       8880
gtggacccaa ctgcatttcc atgaggaaag cacatgagtt tgagagggtc gttgatgata      8940
aggtagaaac aactttaatt cataggctga gatatcagtc atcacctcca gataaacaag      9000
```

```
agccatttct tcctgcatct gagccctgta agcacactag ctttaggaat atgttactgc   9060
tgaagtcaga ttgggcaact tcatagtata caatagaaaa tctacctgca gatgagttca   9120
gaaccagcag ggggcacaat ggggccaaga atccctagca gagagatgtg gtgtgtgtgc   9180
aggggactct gcatcctctg tggtttcctt tcttaactta catgtacctg tagtgattga   9240
catgtaacgt ttccacgctc aaacactgtg aagatacttt gctaaacact tcaaagattt   9300
atgttttctt gatgtgtgca tgtgtgtatt cttttttgtt tttagacaca gggtttctct   9360
gtgtagtcct ggctgccctg gaactcactc tgtagaccag gctggcctcg aactcagaaa   9420
tctgcctgct tctgcctccc aagtgctgaa gttaaagaca tgtgccacca ttgcctggcc   9480
atgtgtgtat tcttgatgca ctcttctgtt gacagataca cagtttattt ccataattta   9540
tttattgtga tggtgctgca ataatcactt atgtacaaat gtttctgaag tatatttagt   9600
tttggtcatt tgggtgatta tttttttctt tctagtatat agcattttgg aaaggtagat   9660
attaattgta tgtatgggaa ggaggctgta aattctaata acttagctgc ttttgaaatt   9720
tgtcctcaat tctatcatcc ttgtaaccac cttaaatcca tctattagcc ttgtcacaag   9780
tgagccactg tctcaggctg caaatctttt tatagattag gtcgtgatgt tacatccaca   9840
gcctctgcac aatgctcagg ggtgggatat gggatgaatt ccctcagaca gcattaggac   9900
ttggatctca gcagactgat tcttgaccca aatgtctctt cttctctagc aggagtaagt   9960
ccttatctaa gatgtactct gctcatgaat atgcaaatca attgagtcta tggtggtaaa   10020
tatagggatg tctacacccc tcaaaaactt aagatcactg tcgtcttcac agtcacagga   10080
gtacacagga catcaccatg tgttggagct gtatcatcct cttcctgtta gcaacagctg   10140
cacgtaaggg gcttacagta gcaggcttga ggtctggcca tacactcatg tgacaatgac   10200
atccactctg tccttcccTT cacaggtgtg cactcccagg tccagctgca gcagtctggg   10260
gctgagctgg tgaggcctgg ggcctcagtg aagatttcct gcaaggcttt tggctacacc   10320
ttcacaaacc atcatataaa ctgggtgaag cagaggcctg gacagggcct ggactggatt   10380
ggatatatta atccttataa tgattatact agctacagaa ccagaagttc aagggcaagg   10440
ccacattgac tgtagacaaa tcctccagca cagcctatat ggagcttagc agcctgacat   10500
ctgaggactc tgcagtctat tactgtgcaa gacacagtgc tacaaacaca tcctgagtgt   10560
gtcagaaacc ctggaggaga agcaagcaga gctggaatgg agatgacaga aagattatca   10620
tttagacttg ctcagaaaga gaaattttga atgcccatt attgcctctt ccttacagta   10680
ctatagtgcc tgttttttgtt gacattttca aactaatttc caaagtcact accacaattt   10740
acaatcacat aaaaagcaag caaggataac attattttct gtgcttactt gccatttata   10800
ttcttgctta ttctcatctc actgaggtca tattgggaca ttaaatttct ggggttactt   10860
tttattaaaa attttcatt attcattcac tttacatcct tctagtcttc ctctcacaca   10920
tgccctatcc cttctcctc tgagaggatg gagccctccc tacccctcgta tccccttacc   10980 caggcacatc aagtgtctgc agtactagga atattctctg tcaatgctgc cagacaaggc   11040
agacaagtta ggggatcagg attcacagga aggcaacagc ttgagggaca gcccccactg   11100
aagttattgg tggattcaca tgaagactga gttgcacatc tgctacatat attcagggt   11160 cctatttaca gctcaagtag actcttgttg gtggtttagt ctcttagaac cccaagtgtc   11220
caggttagtt gactctgtgg gtcttccttt ggagttccta tccctcccag atccctcagt   11280
tcttctccca actcttccat aagacacccg taggtccatc caatgtttgg ttttgggttt   11340
```

-continued

```
ttctgcatct gcttcagtca gctgctgggt ggagcatctc tgaggataat tatgagaagc   11400
tcttatgtgc aagcataaca ggatatcatt attagtgtca gggactggtg cttggccatg   11460
ggatgggtct caagtttggt cagttatttg gccattccca cagtctctga taatctttgt   11520
ccctgcattt cttgtagaca ggaaaaatat tgggttgaaa gttttgtggg tgggttggcg   11580
tctctattgc tccactgggc ttctttctgg atataggagt ttgcctcttc aggttccata   11640
ttcccaaagt agtgtgtcac actaaggtca ctcccataca gagggacact cattctcttg   11700
ccacgtctct gtccaccttc attggacctg aggttcctga atcatacaga actgcatgtg   11760
tgcaaccaca cagaacaagg ctatctatca gaggcctacc ataccaggac catcaaggtt   11820
caccttactc ccaatactga ctacaaaaag aacatcaagg accaatgcag tctatatgga   11880
taaacacact tgaaagaaca caaacaagat tgagggcaac atgacacctc caaagcatac   11940
ctaaccgagt acagcatgcc ctggatatcc taacacaatc aaaacacaag aaagttacct   12000
taaatccagt cttataaagg tgatgaaggc ctttaaatag gaaatgaatt aatccttagg   12060
ataatacagg acaatacatt cgaacagata gaggtcttta ggaggaaaga aataaatccc   12120
tcaaagacat acatgaaaat acaattaaac aggtgaaagt aataactaca atggtgtaag   12180
acctaaaaat ggaaatagaa gcaataaagt aacacaaact tagaatcttg aaggtggaaa   12240
acctagagaa caggaatact agatgcaagg atgatatctt ctaggtccat ccatttgctt   12300
gcacaattta tcatgtcctt gcttttaata gttgaacagt atttcattgt ttaaatgaac   12360
cacatgttct gtctccattc tctggatgag ggggtgagca agttttcca cattctggct   12420 attacaaata gagctgctat gaacctagta gaaaacatat cctgtgtatg gtggagagtt   12480
ttggagtata tcaccaagag tgttatagct gggtcttcat gtagaactat tcctaatttt   12540
ctgagaaatc ccaagtcaga tttctagaat ggttgttcaa gtgttcactc caaccatcaa   12600
tggaggactg ttttccttgc cagcatgtgc tgtattttga gtttttgatc ctagccagtt   12660
ttatcctgca tttcacactt agatatggac tatggtacag gacagagaga aaccaacctt   12720
ctactcacca ggatattcta cctgctacca atttatttat ttatttattt atttatttat   12780
ttatttattt atttatttat attagagaac aacaccatgc agtttagaag aagtactaag   12840
acgtcagtga tgttatactg tgcctaacct tgcattgtac aatctcagct ttcaggtaag   12900
acagtgcatg actcttatgc agtgccaact gttttctgat tgtatttatg gtctattgcc   12960
taggaatgac ctcctctcaa ataaacatgg tcaaagccc atggcctgag atgacagagc    13020
ccctagtaga ccctagttgt atttctgaag tttagatatc ataatgactt ataaatactt   13080
atgtttatac aatagattag agctgctctc agccatgacc aaggagcttc tgtgttcaat   13140
gaataatgat tgatgcagac attcgtgagt ggtcaaagtg gtgagaatga ttagagagtc   13200
ctcagccaca caagcgttaa tgatatgaac tttccaatat attaactgta ttaatgaata   13260
aatgcagaca tcatatgaga tctcattagt agttcttagg tattgcattt ttatatacaa   13320
ttatgcatat cagtacatta tagtgtataa aggaaattgt ctagcataat agagaaaaat   13380
aggacagtca agaaacaaaa gagtagaaat tatgggtgaa atatgcagtg tgaaatattt   13440
acatgaaaat tttaaccata tgtaaaattg ttattttgt ttttcagaat gagtttgctc    13500
attctttgac attttattc ctgtgtgaaa tatatcagga tcatatgtat cccattctga    13560
tggtctgact tccactggga atttccaata tatctcttcc aactaactga ccagtttctt   13620
tttttcttat tttctctctt tctcgttttg ttttgctttg ttttgttttt caagacaggg   13680
tttctctgtg tagctctggc tgtcctggaa ctcactttgt agatcaggct ggcttcgagc   13740
```

```
tcataaatcc acttgcctct gcctcctgag tgctgggatt aaaggagtgg ctaccacgcc   13800
cggctagttt ttttttttct tataagaaca acatttactg gatggtcact tacatattca   13860
gaggttcagt caattattat caaggcagaa gcatggcagt ggtccagtag tcatggcact   13920
ggggaaggag ctgagagatc tacatcttgc tccaaaggga aagaggaata gtctgacttc   13980
catgtgtttc agaggagggt ttcatttccc accccacag tgacacactt cctccaacac    14040
ggccacacct cctaatattg ccactcttgg atcaagcata ttcacaccac aaaggaaagt   14100
ttagagataa acattaagaa aattaatgaa gtcattttat cttatatgct caacatgact   14160
agtacttaaa accataattt tacatgtaca atatttcatg gcataacata ttttttatat   14220
ttttattaga tattttcttt atttatattt caaatgtgat acccttccc aattcccctc    14280 caaaatccc ctatgccttc ccctcatagc cagctcccaa acccacccac tcctgctttc    14340
tggtcctggc attcccctat actggggcat aaaaccttca caggaccaag tgcctcttct   14400
ccattgatgg ccaattaggc catcctctgc tacatatgca gctagagcca tgagttccac   14460
catgtgtttt ctttgattgg tggtttagtt ccagggagct ctgggggtat tggttagttc   14520
atattgttcc tcctatgggg ctgcaaaccc tttcagcccc ttgggtattt tttctagctc   14580
cttcattggg gaccctgtgc tccatccaat ggatgagtga gcctccactt ttgtatttgt   14640
caggaactgg cagagtctct caggagacaa ttatatcagg ctcctgtcag caaaatctcg   14700
ttggcatctg caatagtgtc tgggtttggt ggttgtttat gggatggatt tctgggtggg   14760
gcagtctctg gattgtcatt cctttagtct ctgcttccac ctttgtcttt gtaactccat   14820
ccatgggtat tttgttcccc cttcaaagaa ggatcaaaat atccacactt tagtcttcct   14880
tcttcttgag tctcatgtgt ttttcaaatt gtatcttggg tattctgagc ttctaggcta   14940
atatccactt atcagtgagt gattatcatg tctgttcttt tgtgattgag ttacctcact   15000
tagcatgata tcctccaggt ctatccattt gtctaagaat ttcataaagt cattgtcttt   15060
aatagctgca tcgtactcaa ttgtgtaaat gcaccacatt ttctttatcc attcctctgt   15120
tgagggacac ttggttttc ccagcttctg gttattataa ataaggctgc tatgaacata   15180
gtggaacatg tgtccttagt acatgttgga acatcttctg ggtatatgcc caggagtggt   15240
attgctggat cttctggtgg tactatgtcc aaattttgg ggaaccatca aactgatttc    15300
ctgagtggtt gtacaagctt gcaatccac accagcaata gtggaatgtt catctttgtc    15360
caagtccttg ccagcatctg ctgtcacctg agttttgat cttagccatt cttactggtg    15420
tgaggtggaa tctggggtt gttttgattt gcatttccct gatgtttaag ggttttgaac    15480
atttttaggt gcttattaga catttggtat tcctcagttt agaaatcttt gtttagctct   15540
gtaccacatt tttgaatagg gttatttggt tttctggagt ctaacttctt gagttctttg   15600
tacatattgg atattagccc tctatcagat ttagaattag taaggatctt tccccaaact   15660
gttggtggtt cttttgtctt attgacagtg tactttgcct tagagaagct ttgcaattt     15720 atgaggtccc atttgtcaat tcttgatctt atagtacaag ccattggtct tttgttcagg   15780
aattttcccc atgtgtccat atgttcaagg catttcccca ctttctccac tacaagtttt   15840
agtgtctctg gttttatgtg gaggtccttg atccacttag atttgagctt tgtacaagga   15900
gataagaatg gatagattca cattcttcta catgctctct gccagttgag ctagcaccat   15960
ttgttgaaaa tgctgtctttt ttttttcccc actggatggt ttttagctct tttggccaag   16020
atcaagtgac cattggtgtg tgggttcatt tcttggtctt caattctagt tcactgactt   16080
```

```
acctgtttgt cactgtacaa ggaccatgca gcttttttca caattgctct gtagtacagc    16140
ttgaggtctg ggatggtgat tctaccagag agattctttt actgttgtga ataattttg     16200
ctatcatagg atatttttt  atttcagatg aatttacaaa ttgctctttc taactctgtg    16260
aacaattgag ttggaatttt gattgtgatt gctttgaata ctcaagatat aatttacaaa    16320
acacatgaaa cttaacaagg actactaaag tgcagatact tcgatccttc ttagaagggg    16380
gaacaaaata cccatagatg gagttacaga gacaaagttc ggagcagaga ctataggaac    16440
gaccatccag aggtccacct ggggatccat catgtaaaca accacccaaa acagacacta    16500
ttgtggatgc caagaagaac ttgctgacag gagtctgata tagctgtctc ttgagaggct    16560
ctgccagggc ctcagaaagt ggaggctcac agccatccat tggatggagc acagggtccc    16620
caatgaagga gctagagaaa gtactcaagg agctgaaggg gtttgcagcc ccataggagg    16680
aacaacaata tgaactaacc agtaccccca gagctccctg ggactaaacc accaatcaaa    16740
gaaaacacat ggaggagctt gaagctcttg ctgcatttat agcagaggat ggcctagatg    16800
gtcatcaatg ggaggagagg tcaatggtcc tgggaaggtt ccatgcccca gtataggga    16860
atgccagggc caggaagcag gagtgggtgg gctgggatc agggaggggg agatgatagg     16920
gcattttcag tggggaaact aggaaagagg ataacatttta aaatataaat aaagaaaata   16980
tctaattaaa aaggattacc tatgtgcatg ggagctcatg agcagcaggg gtcactctaa    17040
ggccaataat ccacatagag cgatgagctg tgtgtgaaca ggactctgta tcctctgtgg    17100
tttcctttct taagtgtatt aactgatctg tccagctgtg attgacatgt gatgtctcca    17160
tgctcaagcc cagtaaagat tctctgttaa ataccttaca gacttatgtt tacttgtttt    17220
tatttgcttt tcatattttt ttaaaaagtc atacaatgta ttctaataac tcattctccc    17280
atctccaatt tattcaagt ttttcttaac tcatccaacc acacactttt taattctgat     17340
aaagcacccc ccccccaaa aaaaaccca accaaccaaa aaaaaaaaa gccaaggaat       17400
ttaaaggggg attgaaagca aataaaaact aaacaaaaaa gtaaaaacta cacacacaca    17460
cacacacaca cacacacaca cacacacaca cacacactca cacacacaca cacacaccac   17520
acacacacac acccatgcac gaacacacac acacacacac acacacacac acacacacac   17580
acacacacac acacatggaa tccagtaaaa ccacaactct ttacccatga tacacaggaa    17640
aatataagtc aaacaaacag aatggaagaa ggtggtatta taaaaatgtc tgcacaaata    17700
ccattaagtt catttttcttg ttggctacca actgctaagc ctgtctccct tgattaattg   17760
tgcttatcat cccctatgaa ctccattgga ggacactaat ttttccttct gtctccagga    17820
attgaagtgt tgcagaactc tcagtagctt tatttacctg cacaatacag cctctaatcc    17880
aaccagtgaa aattaccaca tgagagactt ccaaatgaaa gaacaggtaa agttgtctac    17940
tggcaagctt agtaatatca tgtaaatgcc ttagaattta atgacatatg tcatcctctg    18000
aggttaataa atccattttg gtgcatatat accctgaact caccactaac ataatacaac    18060
aattaaaaaa ttccaacatg gatgcagagg aatccctgag ggacatttgt tgatttgtga    18120
gcacaatata attattttt  gggggggaaa tgtctgaatg ttaactcttt accagtgata    18180
atctattcta ttaatgtgta cataggtagc actaattaaa atcactgtgt tatcaggtaa    18240
tgaaacagag gaagtaggat gctgggaaac agactttttgg aaggtcccaa gggaaaccac   18300
agggacctag tggtgataga ttatggtgag agtcctgaga gtggtcatag attatagcat    18360
atttcatatg caattgaaaa tttcaaagaa tgaaaatcct tatgaaatat agaaataaca    18420
actttactta tgtacatata cttcatagta caatttttac actgtgcata tttctcctgt    18480
```

| | |
|---|---|
| aacatctggt tcctcctatt ttcctttatt ctcctagaca atttcactga tacaatctca | 18540 |
| tgttttgta taaatagttg tatataacta ttaaatacat aagctgttaa tgagtcttca | 18600 |
| ttaatgtctg tgatttttt attgtcttaa ttaatactat tatctctaat tgcatccaca | 18660 |
| ttttcaaaag caatgtaaat ttcttactca tttctgttca aaaacttctg ttgttgtatc | 18720 |
| attaccatgc cttagtgata aaatcctttc ttgacacatc tatagctatt gctataattt | 18780 |
| agttattgat gatcctcctg caataatcat tgataggtaa atattttaag cacttttact | 18840 |
| tttagtcatt ttagtgagat ttgaagtagt atataacctg ttggaaaggc aaatattaat | 18900 |
| tccatatatg tgaaagaaga cgctaaaact aaaaacatta gccactttta gatatcttct | 18960 |
| ccttcttctt cttcttcttc ttcttcttct tcttcttctt cttcttcttc ttcttcttct | 19020 |
| tcttcttctt cttcttttct tcttcttctt ctccttctcc ttcttcttct ccttctcctt | 19080 |
| ctcctcttcc tcctccttcc ttccttcctt ccttccttcc ttccttcctt ccttccttcc | 19140 |
| ttccttcctt ccttccttcc ttccttcctt ccttccttcc ttccttcctt ccttccttcc | 19200 |
| ttcctttctt tctttctttc tttctttctt tctttctttc tttctttctt tctttctttc | 19260 |
| tttctttctt tctttctttc tttctttctt ctcctcctcc ttcttttttcc ttctccttcc | 19320 |
| ccttcacctt cccccttcctt cctctttccc ttcccccttct ccttctcctc aatctacaat | 19380 |
| ctgttaacat attaacatgt cccagagtag agcaacagac tcaggtcaaa catctactga | 19440 |
| gaaatttgcc catgtagtta acatctacag catctgtcta gggggttacaa aaagtctatg | 19500 |
| ggatacaatt cctcagaaag gaataggatt tggacctgag catactgctg cctaacacat | 19560 |
| gaaatggcag ttcttctcca gctggactag gtccttaact aagaaatgca ctgctcatga | 19620 |
| atatgcaaat tacccaagtc tatggcagta aatacagaga tgtccacacc ctgaagacaa | 19680 |
| cctatgaaca atgttctctc cacagtccct gaagacactg attcta | 19726 |

<210> SEQ ID NO 12
<211> LENGTH: 7928
<212> TYPE: DNA
<213> ORGANISM: Mus musculus

<400> SEQUENCE: 12

| | |
|---|---|
| ctgagcattg cagactaatc ttggatattt gtccctgagg gagccggctg agagaagttg | 60 |
| ggaaataaac tgtctaggga tctcagagcc tttaggacag attatctcca catctttgaa | 120 |
| aaactaagaa tctgtgtgat ggtgttggtg gagtccctgg atgatgggat agggactttg | 180 |
| gaggctcatt tgagggagat gctaaaacaa tcctatggct ggagggatag ttggggctgt | 240 |
| agttggagat tttcagttttt tagaataaaa gtattagctg cggaatatac ttcaggacca | 300 |
| cctctgtgac agcatttata cagtatccga tgcataggga caaagagtgg agtggggcac | 360 |
| tttctttaga tttgtgagga atgttccaca ctagattgtt taaaacttca tttgttggaa | 420 |
| ggagagctgt cttagtgatt gagtcaaggg agaaaggcat ctagcctcgg tctcaaaagg | 480 |
| gtagttgctg tctagagagg tctggtggag cctgcaaaag tccagctttc aaaggaacac | 540 |
| agaagtatgt gtatggaata ttagaagatg ttgcttttac tcttaagttg gttcctagga | 600 |
| aaaatagtta aatactgtga ctttaaaatg tgagagggtt ttcaagtact cattttttta | 660 |
| aatgtccaaa attcttgtca atcagtttga ggtcttgttt gtgtagaact gatattactt | 720 |
| aaagtttaac cgaggaatgg gagtgaggct ctctcataac ctattcagaa ctgactttta | 780 |
| acaataataa attaagtttc aaatattttt aaatgaattg agcaatgttg agttggagtc | 840 |

```
aagatggccg atcagaacca gaacacctgc agcagctggc aggaagcagg tcatgtggca    900
aggctatttg gggaagggaa aataaaacca ctaggtaaac ttgtagctgt ggtttgaaga    960
agtggttttg aaacactctg tccagcccca ccaaaccgaa agtccaggct gagcaaaaca   1020
ccacctgggt aatttgcatt tctaaaataa gttgaggatt cagccgaaac tggagaggtc   1080
ctcttttaac ttattgagtt caaccttttta attttagctt gagtagttct agtttcccca   1140
aacttaagtt tatcgacttc taaaatgtat ttagaattca ttttcaaaat taggttatgt   1200
aagaaattga aggactttag tgtctttaat ttctaatata tttagaaaac ttcttaaaat   1260
tactctatta ttcttccctc tgattattgg tctccattca attcttttcc aatacccgaa   1320
gcatttacag tgactttgtt catgatcttt tttagttgtt tgttttgcct tactattaag   1380
actttgacat tctggtcaaa acggcttcac aaatctttt caagaccact ttctgagtat   1440
tcatttagg agaaagactt ttttttaaa tgaatgcaat tatctagact tatttcagtt   1500
gaacatgctg gttggtggtt gagaggacac tcagtcagtc agtgacgtga agggcttcta   1560
agccagtcca catgctctgt gtgaactccc tctggccctg cttattgttg aatgggccaa   1620
aggtctgaga ccaggctgct gctgggtagg cctggacttt gggtctccca cccagacctg   1680
ggaatgtatg gttgtggctt ctgccaccca tccacctggc tgctcatgga ccagccagcc   1740
tcggtggctt tgaaggaaca attccacaca aagactctgg acctctccga aaccaggcac   1800
cgcaaatggt aagccagagg cagccacagc tgtggctgct gctcttaaag cttgtaaact   1860
gtttctgctt aagagggact gagtcttcag tcattgcttt aggggagaa agagacattt   1920
gtgtgtcttt tgagtaccgt tgtctgggtc actcacattt aactttcctt gaaaaactag   1980
taaaagaaaa atgttgcctg ttaaccaata atcatagagc tcatggtact ttgaggaaat   2040
cttagaaagc gtgtatacaa ttgtctggaa ttatttcagt taagtgtatt agttgaggta   2100
ctgatgctgt ctctacttca gttatacatg tgggtttgaa ttttgaatct attctggctc   2160
ttcttaagca gaaaatttag ataaaatgga tacctcagtg gttttaatg gtgggtttaa   2220
tatagaagga atttaaattg gaagctaatt tagaatcagt aaggagggac ccaggctaag   2280
aaggcaatcc tgggattctg gaagaaaaga tgttttttagt tttatagaa aacactacta   2340
cattcttgat ctacaactca atgtggttta atgaatttga agttgccagt aaatgtactt   2400
cctggttgtt aaagaatggt atcaaaggac agtgcttaga tccgaggtga gtgtgagagg   2460
acagggcctg gggtatggat acgcagaagg aaggccacag ctgtacagaa ttgagaaaga   2520
atagagacct gcagttgagg ccagcaggtc ggctggacta actctccagc cacagtaatg   2580
acccagacag agaaagccag actcataaag cttgctgagc aaaattaagg gaacaaggtt   2640
gagagccta gtaagcgagg ctctaaaaag cacagctgag ctgagatggg tgggcttctc   2700
tgagtgcttc taaaatgcgc taaactgagg tgattactct gaggtaagca aagctgggct   2760
tgagccaaaa tgaagtagac tgtaatgaac tggaatgagc tgggccgcta agctaaacta   2820
ggctggctta accgagatga gccaaactgg aatgaacttc attaatctag gttgaataga   2880
gctaaactct actgcctaca ctggactgtt ctgagctgag atgagctggg gtgagctcag   2940
ctatgctacg ctgtgttggg gtgagctgat ctgaaatgag atactctgga gtagctgaga   3000
tggggtgaga tggggtgagc tgagctgggc tgagctagac tgagctgagc tagggtgagc   3060
tgagctgggt gagctgagct aagctggggt gagctgagct gagcttggct gagctagggt   3120
gagctgggct gagctggggt gagctgagct gagctggggt aagctgggat gagctggggt   3180
gagctgagct gagctggagt gagctgagct gggctgagct ggggtgagct gggctgagct   3240
```

```
gggctgagct gggctgagct ggggtgagct gagctggggt gagctgagct gagctggggt    3300
gagctgagct gagctggggt gagctggggt gagctgagct ggggtgagct gagctgagct    3360
ggggtgagct gagctggggt gagctgagct gagctggggt gagctgagct gagctgagct    3420
gagctgagct ggggtgagct gagctgagct gagctggggt gagctggggt gagctgagct    3480
gagctggagt gagctgagct ggggtgagct ggggtgagct ggggtgagct ggggtgagct    3540
gagctgagct gagctgagct ggggtgagct gagctgagct ggggtgagct gagctggggt    3600
gagctgggct gagctgagct gagctgagct gagctgagct gagctgagct gagctgagct    3660
gagctgagct gagctgagct gagctgagct gagctggggt gagctgagct gagctgggct    3720
gagctggggt gagctgggct gagctggggt gagctgggct gagctggggt gagctgagct    3780
ggggtgagct gagctgagct ggggtgagct gagctgagct ggggtgagct gagctgagct    3840
ggggtgagct gagctgagct gagctggggt gagctgagct gagctggggt gagcagggct    3900
gagctggggt gagctgagct gagctggggt gagctgggct gagctgggct gagctgagct    3960
gagctgggct gagctgggct gagctgggct gagctgggct gagctgggct gagctggggt    4020
gagctgagct ggggtgagct ggggtgagct gagctggggt gagctgagct ggggtgagct    4080
gagctgagct ggggtgagct gagctggggt gagctgagct gagctggggt gagctgagct    4140
gagctggggt gagctgagct agggtgaact gggctggagtg agctggagtg agctgagctg    4200
aggtgaactg gggtgagccg ggatgttttg agttgagctg gggtaagatg agctgaactg    4260
gggtaaactg ggatgagctg tgatgagcgg agctggattg aactgagctg tgtgagctga    4320
gctggggtca gctgagcaag agtgagtaga gctggctggc cagaaccaga atcaattagg    4380
ctaagtgagc cagattgtgc tgggatcagc tgtactcaga tgagctggga tgaggtaggc    4440
tgggatgagc tgggctagct gacatggatt atgtgaggct gagctagcat gggctggcct    4500
agctgatgag ctaagcttga atgagcgggg ctgagctgga ctcagatgtg ctagactgag    4560
ctgtactgga tgatctggtg tagggtgatc tggactcaac tgggctggct gatgggatgc    4620
gccaggttga actaggctca gataagttag gctgagtagg gcctggttga gatggttcgg    4680
gatgagctgg gaaaagatgg actcggacca tgaactgggc tgagctgggt tgggagacca    4740
tgaattgagc tgaactgagt gcagctggga taaactgggt tgagctaaga atagactacc    4800
tgaattgtgc caaactcggc tgggatcaat tggaaattat caggatttag atgagccgga    4860
ctaaactatg ctgagctgga ctggttggat gtgttgaact ggcctgctgc tgggctggca    4920
tagctgagtt gaacttaaat gaggaaggct gagcaaggct agcctgcttg catagagctg    4980
aactttagcc tagcctgagc tggaccagcc tgagctgagt aggtctaaac tgagttaaaa    5040
atcaacaggg ataatttaac agctaattta acaagcctga ggtctgagat tgaatgagca    5100
gagctgggat gaactgaatg agtttcacca ggcctggacc agttaggcta ggacctcgtt    5160
ctatagaggc agactgtgtg ctacagtgga gtttcaagat gattccatga gtcctccccg    5220
cccccaacat aacccacctt cctcctaccc tacacgcctg tctggtgtgt aaatcccagc    5280
tttgtgtgct gatacagaag cctgagcccc tccccacct ccacctacct attactttgg    5340
gatgagaata gttctcccag ccagtgtctc agagggaagc caagcaggac aggcccaagg    5400
ctacttgaga agccaggatc taggcctctc cctgagaacg ggtgttcatg ccctagagt    5460 tggctgaagg gccagatcca cctactctag aggcatctct ccctgtctgt gaaggcttcc    5520
aaagtcacgt tcctgtggct agaaggcagc tccatagccc tgctgcagtt tcgtcctgta    5580
```

```
taccaggttc acctactacc atatctagcc ctgcctgcct taagagtagc aacaaggaaa    5640
tagcagggtg tagagggatc tcctgtctga caggaggcaa aagacagat tcttacccct    5700 ccatttctct tttatccctc tctggtcctc agagagtcag tccttcccaa atgtcttccc    5760
cctcgtctcc tgcgagagcc ccctgtctga taagaatctg gtggccatgg gctgcctggc    5820
ccgggacttc ctgcccagca ccatttcctt cacctggaac taccagaaca acactgaagt    5880
catccagggt atcagaacct tcccaacact gaggacaggg ggcaagtacc tagccacctc    5940
gcaggtgttg ctgtctccca agagcatcct tgaaggttca gatgaatacc tggtatgcaa    6000
aatccactac ggaggcaaaa acaaagatct gcatgtgccc attccaggta agaaccaaac    6060
cctcccagca ggggtgccca ggcccaggca tggcccagag ggagcagcgg ggtggggctt    6120
aggccaagct gagctcacac cttgaccttt cattccagct gtcgcagaga tgaaccccaa    6180
tgtaaatgtg ttcgtcccac cacgggatgg cttctctggc cctgcaccac gcaagtctaa    6240
actcatctgc gaggccacga acttcactcc aaaaccgatc acagtatcct ggctaaagga    6300
tgggaagctc gtggaatctg gcttcaccac agatccggtg accatcgaga acaaaggatc    6360
cacaccccaa acctacaagg tcataagcac acttaccatc tctgaaatcg actggctgaa    6420
cctgaatgtg tacacctgcc gtgtggatca caggggtctc accttcttga agaacgtgtc    6480
ctccacatgt gctgccagtg agtggcctgg gctaagccca atgcctagcc ctcccagatt    6540
agggaagtcc tcctacaatt atggccaatg ccacccagac atggtcattt gctccttgaa    6600
ctttggctcc ccagagtggc caaggacaag aatgagcaat aggcagtaga ggggtgagaa    6660
tcagctggaa ggaccagcat cttcccttaa gtaggtttgg gggatggaga ctaagctttt    6720
ttccaacttc acaactagat atgtcataac ctgacacagt gttctcttga ctgcaggtcc    6780
ctccacagac atcctaacct tcaccatccc ccctcctttt gccgacatct tcctcagcaa    6840
gtccgctaac ctgacctgtc tggtctcaaa cctggcaacc tatgaaaccc tgaatatctc    6900
ctgggcttct caaagtggtg aaccactgga accaaaatt aaaatcatgg aaagccctcc    6960
caatggcacc ttcagtgcta agggtgtggc tagtgtttgt gtggaagact ggaataacag    7020
gaaggaattt gtgcgtactg tgactcacag ggatctgcct tcaccacaga agaaattcat    7080
ctcaaaaccc aatggtaggt atccccccctt cccttcccct ccaattgcag gacccttcct    7140
gtacctcata gggagggcag gtcctcttcc accctatcct cactactgtc ttcatttaca    7200
gaggtgcaca acatccacc tgctgtgtac ctgctgccac cagctcgtga gcaactgaac    7260
ctgagggagt cagccacagt cacctgcctg gtgaagggct tctctcctgc agacatcagt    7320
gtgcagtggc ttcagagagg gcaactcttg ccccaagaga agtatgtgac cagtgccccg    7380
atgccagagc ctgggggcccc aggcttctac tttacccaca gcatcctgac tgtgacagag    7440
gaggaatgga actccggaga gacctatacc tgtgttgtag gccacgaggc cctgccacac    7500
ctggtgaccg agaggaccgt ggacaagtcc actggtaaac ccacactgta caatgtctcc    7560
ctgatcatgt ctgacacagg cggcacctgc tattgaccat gctagcgctc aaccaggcag    7620
gccctgggtg tccagttgct ctgtgtatgc aaactaacca tgtcagagtg agatgttgca    7680
ttttataaaa attagaaata aaaaaaatcc attcaaacgt cactggtttt gattatacaa    7740
tgctcatgcc tgctgagaca gttgtgtttt gcttgctctg cacacaccct gcatacttgc    7800
ctccaccctg gccctccctc taccttgcca gtttcctcct tgtgtgtgaa ctcagtcagg    7860
cttacaacag acagagtatg aacatgcgat tcctccagct acttctagat atatggctga    7920
aagcttgc                                                            7928
```

```
<210> SEQ ID NO 13
<211> LENGTH: 4
<212> TYPE: PRT
<213> ORGANISM: Artificial Sequence
<220> FEATURE:
<223> OTHER INFORMATION: GLSG

<400> SEQUENCE: 13

Gly Leu Ser Gly
1

<210> SEQ ID NO 14
<211> LENGTH: 6
<212> TYPE: PRT
<213> ORGANISM: Artificial Sequence
<220> FEATURE:
<223> OTHER INFORMATION: linker - GGGGS

<400> SEQUENCE: 14

Gly Leu Ser Gly Ser Gly
1               5

<210> SEQ ID NO 15
<211> LENGTH: 8
<212> TYPE: PRT
<213> ORGANISM: Artificial Sequence
<220> FEATURE:
<223> OTHER INFORMATION: linker - GLSGLSGS

<400> SEQUENCE: 15

Gly Leu Ser Gly Leu Ser Gly Ser
1               5

<210> SEQ ID NO 16
<211> LENGTH: 10
<212> TYPE: PRT
<213> ORGANISM: Artificial Sequence
<220> FEATURE:
<223> OTHER INFORMATION: GLSGLSGLSG linker

<400> SEQUENCE: 16

Gly Leu Ser Gly Leu Ser Gly Leu Ser Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: GLSGGSGLSG

<400> SEQUENCE: 17

Gly Leu Ser Gly Gly Ser Gly Leu Ser Gly
1               5                   10

<210> SEQ ID NO 18
<211> LENGTH: 20
<212> TYPE: DNA
<213> ORGANISM: Artificial Sequence
<220> FEATURE:
<223> OTHER INFORMATION: 5' detect VH1-69 FR3

<400> SEQUENCE: 18
acagaagttc cagggcagag                                             20
```

```
<210> SEQ ID NO 19
<211> LENGTH: 21
<212> TYPE: DNA
<213> ORGANISM: Artificial Sequence
<220> FEATURE:
<223> OTHER INFORMATION: 3' up detect spec

<400> SEQUENCE: 19
tgtccactgg gttcgtgcct t                                                    21

<210> SEQ ID NO 20
<211> LENGTH: 21
<212> TYPE: DNA
<213> ORGANISM: Artificial Sequence
<220> FEATURE:
<223> OTHER INFORMATION: 5' down detect spec

<400> SEQUENCE: 20
cagtatcagc ccgtcatact t                                                    21

<210> SEQ ID NO 21
<211> LENGTH: 19
<212> TYPE: DNA
<213> ORGANISM: Artificial Sequence
<220> FEATURE:
<223> OTHER INFORMATION: 3' VH1-69 overlap detect

<400> SEQUENCE: 21
taacccctgt catctcctc                                                       19

<210> SEQ ID NO 22
<211> LENGTH: 23
<212> TYPE: DNA
<213> ORGANISM: Artificial Sequence
<220> FEATURE:
<223> OTHER INFORMATION: 5' DNA Target(PAM)

<400> SEQUENCE: 22
ggatcctggt ttagttaaag agg                                                  23

<210> SEQ ID NO 23
<211> LENGTH: 42
<212> TYPE: RNA
<213> ORGANISM: Artificial Sequence
<220> FEATURE:
<223> OTHER INFORMATION: 5' VH1-69 Cas9 crRNA

<400> SEQUENCE: 23
ggauccuggu uuaguuaaag guuuuagagc uaugcuguuu ug                             42

<210> SEQ ID NO 24
<211> LENGTH: 23
<212> TYPE: DNA
<213> ORGANISM: Artificial Sequence
<220> FEATURE:
<223> OTHER INFORMATION: 3' DNA Target(PAM)

<400> SEQUENCE: 24
gacaaaaacc ctgagggaga agg                                                  23

<210> SEQ ID NO 25
<211> LENGTH: 42
<212> TYPE: RNA
<213> ORGANISM: Artificial Sequence
<220> FEATURE:
<223> OTHER INFORMATION: 3 VH1-69 Cas9 crRNA
```

```
<400> SEQUENCE: 25
gacaaaaacc cugagggaga guuuuagagc uaugcuguuu ug                    42

<210> SEQ ID NO 26
<211> LENGTH: 19
<212> TYPE: DNA
<213> ORGANISM: Artificial Sequence
<220> FEATURE:
<223> OTHER INFORMATION: 5' up detect VH1-69

<400> SEQUENCE: 26
ctgtgaaata ccctgcctc                                              19

<210> SEQ ID NO 27
<211> LENGTH: 21
<212> TYPE: DNA
<213> ORGANISM: Artificial Sequence
<220> FEATURE:
<223> OTHER INFORMATION: 3' up detect spec

<400> SEQUENCE: 27
tgtccactgg gttcgtgcct t                                           21

<210> SEQ ID NO 28
<211> LENGTH: 21
<212> TYPE: DNA
<213> ORGANISM: Artificial Sequence
<220> FEATURE:
<223> OTHER INFORMATION: 5' down detect spec

<400> SEQUENCE: 28
cagtatcagc ccgtcatact t                                           21

<210> SEQ ID NO 29
<211> LENGTH: 20
<212> TYPE: DNA
<213> ORGANISM: Artificial Sequence
<220> FEATURE:
<223> OTHER INFORMATION: 3'down detect M1116(h70)

<400> SEQUENCE: 29 cccccctcttg ctctctttct                                            20

<210> SEQ ID NO 30
<211> LENGTH: 80
<212> TYPE: DNA
<213> ORGANISM: Artificial Sequence
<220> FEATURE:
<223> OTHER INFORMATION: VH1-69 MreI del Joiner Oligo

<400> SEQUENCE: 30
gtgaaaaccc acatcctgag agtgacaaaa accctgaggg agaaggcagc tgtgccgggc   60
tgaggagatg acagggttta                                             80

<210> SEQ ID NO 31
<211> LENGTH: 20
<212> TYPE: DNA
<213> ORGANISM: Artificial Sequence
<220> FEATURE:
<223> OTHER INFORMATION: 5' detect VH1-69 FR3

<400> SEQUENCE: 31
acagaagttc cagggcagag                                             20
```

```
<210> SEQ ID NO 32
<211> LENGTH: 20
<212> TYPE: DNA
<213> ORGANISM: Artificial Sequence
<220> FEATURE:
<223> OTHER INFORMATION: 3'down detect M1116(h70)

<400> SEQUENCE: 32
ccccctcttg ctctctttct                                                   20
```

UNITED STATES PATENT AND TRADEMARK OFFICE
CERTIFICATE OF CORRECTION

PATENT NO. : 12,371,475 B2
APPLICATION NO. : 17/555616
DATED : July 29, 2025
INVENTOR(S) : Jason Mastaitis et al.

Page 1 of 1

It is certified that error appears in the above-identified patent and that said Letters Patent is hereby corrected as shown below:

In the Claims

Claim 10, Line 3; Column 134, Line 52:
heavy chain constant region (CH),
Should be:
--heavy chain constant region ($C_H$),--

Claim 10, Line 4; Column 134, Line 53:
wherein the nucleic acid sequence encoding the Ig CH is
Should be:
--wherein the nucleic acid sequence encoding the Ig $C_H$ is--

Claim 13, Line 4; Column 135, Line 17:
rearranged Ig VI/$J_L$ sequence
Should be:
--rearranged Ig $V_L$/$J_L$ sequence--

Claim 22, Line 9; Column 135, Line 66:
human Ig CH at the non-human Ig heavy chain locus,
Should be:
--human Ig $C_H$ at the non-human Ig heavy chain locus,--

Signed and Sealed this
Eleventh Day of November, 2025

John A. Squires
*Director of the United States Patent and Trademark Office*